US011046649B2

(12) United States Patent
Lewis et al.

(10) Patent No.: US 11,046,649 B2
(45) Date of Patent: *Jun. 29, 2021

(54) COMPOUNDS USEFUL AS INHIBITORS OF INDOLEAMINE 2,3-DIOXYGENASE AND/OR TRYPTOPHAN DIOXYGENASE

(71) Applicant: Board of Regents, The University of Texas System, Austin, TX (US)

(72) Inventors: Richard T. Lewis, Missouri City, TX (US); Matthew Hamilton, Missouri City, TX (US); Philip Jones, Houston, TX (US); Alessia Petrocchi, Houston, TX (US); Naphtali Reyna, Arlington, TX (US); Timothy McAfoos, Pearland, TX (US); Jason Bryant Cross, Pearland, TX (US); Michael J. Soth, Sugar Land, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/514,382

(22) Filed: Jul. 17, 2019

(65) Prior Publication Data

US 2020/0024236 A1     Jan. 23, 2020

Related U.S. Application Data

(60) Provisional application No. 62/699,510, filed on Jul. 17, 2018.

(51) Int. Cl.
| | |
|---|---|
| C07D 215/233 | (2006.01) |
| C07D 401/14 | (2006.01) |
| A61K 31/47 | (2006.01) |
| C07D 235/08 | (2006.01) |
| A61K 31/4184 | (2006.01) |
| C07D 401/12 | (2006.01) |
| A61K 31/4709 | (2006.01) |
| A61K 31/4439 | (2006.01) |
| C07D 403/12 | (2006.01) |
| C07D 471/04 | (2006.01) |
| A61K 31/437 | (2006.01) |
| A61K 31/506 | (2006.01) |
| C07D 413/12 | (2006.01) |
| A61K 31/423 | (2006.01) |
| C07D 417/12 | (2006.01) |
| A61K 31/428 | (2006.01) |
| A61K 31/497 | (2006.01) |
| A61K 31/501 | (2006.01) |
| A61K 31/433 | (2006.01) |
| A61K 31/4245 | (2006.01) |
| C07D 487/04 | (2006.01) |
| A61K 31/519 | (2006.01) |
| C07D 405/14 | (2006.01) |
| A61K 45/06 | (2006.01) |

(52) U.S. Cl.
CPC ...... *C07D 215/233* (2013.01); *A61K 31/4184* (2013.01); *A61K 31/423* (2013.01); *A61K 31/428* (2013.01); *A61K 31/4245* (2013.01); *A61K 31/433* (2013.01); *A61K 31/437* (2013.01); *A61K 31/4439* (2013.01); *A61K 31/47* (2013.01); *A61K 31/4709* (2013.01); *A61K 31/497* (2013.01); *A61K 31/501* (2013.01); *A61K 31/506* (2013.01); *A61K 31/519* (2013.01); *A61K 45/06* (2013.01); *C07D 235/08* (2013.01); *C07D 401/12* (2013.01); *C07D 401/14* (2013.01); *C07D 403/12* (2013.01); *C07D 405/14* (2013.01); *C07D 413/12* (2013.01); *C07D 417/12* (2013.01); *C07D 471/04* (2013.01); *C07D 487/04* (2013.01)

(58) Field of Classification Search
CPC .................................................. C07D 215/233
See application file for complete search history.

(56) References Cited

U.S. PATENT DOCUMENTS

| | | | |
|---|---|---|---|
| 4,177,280 | A | 12/1979 | Berkoz |
| 5,705,511 | A | 1/1998 | Hudkins |
| 2004/0077617 | A1 | 4/2004 | Bennani |
| 2007/0078156 | A1 | 4/2007 | Fletcher |
| 2009/0306408 | A1 | 12/2009 | Yasuhara |
| 2012/0046292 | A1 | 2/2012 | Kawano |
| 2019/0365718 | A1 | 12/2019 | Lewis |

FOREIGN PATENT DOCUMENTS

| | | |
|---|---|---|
| CN | 102532144 | 7/2012 |
| WO | 2000018770 | 4/2000 |
| WO | 2004005252 | 1/2004 |
| WO | 2006005185 | 1/2006 |
| WO | 2006091905 | 8/2006 |
| WO | 2006122150 | 11/2006 |
| WO | 2007075598 | 7/2007 |

(Continued)

OTHER PUBLICATIONS

McMahon et al. (2000).*
Pinedo et al. (2000).*
U.S. Appl. No. 16/478,076, filed Jul. 3, 2017.*
Creary, X., "Cyclopropyl Triflates. Neighboring-Group and Solvent Effects", J Am Chem Soc., 98 (21):6608-13, (1976).
Dounay, A. et al., "Challenges and Opportunities in the Discovery of New Therapeutics Targeting the Kynurenine Pathway", J Med Chem., 58(22):8762-82, (2015).

(Continued)

*Primary Examiner* — Paul V Ward
(74) *Attorney, Agent, or Firm* — Dennis A. Bennett; Lauren L. Stevens; John Desper

(57) ABSTRACT

The present invention relates to bicyclic compounds and compositions and methods which may be useful as inhibitors of IDO1, IDO2, and TDO for the treatment or prevention of diseases such as cancer.

23 Claims, No Drawings

(56) References Cited

FOREIGN PATENT DOCUMENTS

| WO | 2007095050 | 8/2007 |
|---|---|---|
| WO | 2008036642 | 3/2008 |
| WO | 2008036643 | 3/2008 |
| WO | 2008036652 | 3/2008 |
| WO | 2008036653 | 3/2008 |
| WO | 2008058178 | 5/2008 |
| WO | 2009073620 | 6/2009 |
| WO | 2009127669 | 10/2009 |
| WO | 2009132238 | 10/2009 |
| WO | 2010005958 | 1/2010 |
| WO | 2011056652 | 5/2011 |
| WO | 2012064943 | 5/2012 |
| WO | 2012068067 | 5/2012 |
| WO | 2012142237 | 10/2012 |
| WO | 2013062680 | 5/2013 |
| WO | 2013069765 | 5/2013 |
| WO | 2013107164 | 7/2013 |
| WO | 2014009295 | 1/2014 |
| WO | 2014081689 | 5/2014 |
| WO | 2014150646 | 9/2014 |
| WO | 2014150677 | 9/2014 |
| WO | 2014159248 | 10/2014 |
| WO | 2015002918 | 1/2015 |
| WO | 2015007249 | 1/2015 |
| WO | 2015031295 | 3/2015 |
| WO | 2015070766 | 5/2015 |
| WO | 2015082499 | 6/2015 |
| WO | 2015086512 | 6/2015 |
| WO | 2015086526 | 6/2015 |
| WO | 2015091889 | 6/2015 |
| WO | 2015119944 | 8/2015 |
| WO | 2015150097 | 10/2015 |
| WO | 2015173764 | 11/2015 |
| WO | 2015188085 | 12/2015 |
| WO | 2016024233 | 2/2016 |
| WO | 2016026772 | 2/2016 |
| WO | 2016027241 | 2/2016 |
| WO | 2016037026 | 3/2016 |
| WO | 2016041489 | 3/2016 |
| WO | 2016051181 | 4/2016 |
| WO | 2016059412 | 4/2016 |
| WO | 2016071283 | 5/2016 |
| WO | 2016071293 | 5/2016 |
| WO | 2016073738 | 5/2016 |
| WO | 2016073770 | 5/2016 |
| WO | 2016073774 | 5/2016 |
| WO | 2016161269 | 10/2016 |
| WO | 2016161279 | 10/2016 |
| WO | 2016161286 | 10/2016 |
| WO | 2016161960 | 10/2016 |
| WO | 2016210414 | 12/2016 |
| WO | 2017051353 | 3/2017 |
| WO | 2017051354 | 3/2017 |
| WO | 2017139414 | 8/2017 |
| WO | 2017192811 | 11/2017 |
| WO | 2017192815 | 11/2017 |
| WO | 2017192844 | 11/2017 |
| WO | 2018039512 | 3/2018 |
| WO | 2018136437 | 7/2018 |
| WO | 2018136887 | 7/2018 |
| WO | 2020018670 | 1/2020 |

OTHER PUBLICATIONS

Guillemin, G. et al., "Accumulation of an Endogenous Tryptophan-Derived Metabolite in Colorectal and Breast Cancers", PLoS One, 10(4):e0122046/1-e0122046/9, (2015).
International Application No. PCT/US2018/013914; International Preliminary Report on Patentability, dated Aug. 1, 2019; 14 pages.
International Application No. PCT/US2018/013914; International Search Report and Written Opinion of the International Searching Authority, dated Jul. 6, 2018; 9 pages.
International Application No. PCT/US2019/046449; International Search Report and Written Opinion of the International Searching Authority, dated Sep. 10, 2019; 10 pages.
Jendralla, H., "Desaminierung von N(6endoMethylbicyclo[3.1.0]hex6exoyl)und N (6endoMethylbicyclo[3.1.0]hex2en6exoyl)Nnitrosoharnstoff. Versuchte nicht photochemische Erzeugung von transCyclohexenDerivaten", Chemische Berichte, 113(11):3585-96, (1980).
Kaplan, L. et al., "Photosolvation of Benzene. Mechanism of Formation of Bicyclo[3.1.0]hex-3-en-2-yl and of bicyclo[3.1.0]hex-2-en-6-yl Derivatives", J Am Chem Soc., 94(24):8638-40, (1972).
Koblish, H. et al., "Hydroxyamidine Inhibitors of Indoleamine-2,3-dioxygenase Potently Suppress Systemic Tryptophan Catabolism and the Growth of IDO-Expressing Tumors", Molecular Cancer Therapeutics, 9(2):489-98, (2010).
Lim, C. et al., "Involvement of the Kynurenine Pathway in the Pathogenesis of Parkinson's Disease", Progress in Neurobiology, 155:76-95, (2017).
Liu, X. et al., "Selective Inhibition of IDO1 Effectively Regulates Mediators of Antitumor Immunity", Blood, 115(17):3520-30, (2010).
Maleki Vareki, S. et al., "IDO Downregulation Induces Sensitivity to Pemetrexed, Gemcitabine, FK866, and Methoxyamine in Human Cancer Cells", PLoS One, 10(11):e0143435/1-e0143435/22, (2015).
PubChem Substance record for SID 103905401, Kinome_3406 (5-Phenylimidazo[1,5-a]pyridin-3-amine), Available date: Jan. 6, 2011, pp. 1-6., https://pubchem.ncbi.nlm.nih.gov/substance/103905401.
Pubchem. CID 280183. Mar. 26, 2005, pp. 1-7. Retrieved from the Internet <URL: https://pubchem.ncbi.nlm.nih.gov/compound/280183>; p. 2, formula.
Pubchem. CID 57266349. Jun. 15, 2012, pp. 1-8. Retrieved from the Internet <URL: https:llpubchem.ncbi.nlm.nih.gov/compound/57266349>; p. 2, formula.
Pubmed Compound Summay for CID 12013505, [(1S,5R)-6-Bicyclo[3.1.0]hexanyl]-phenylmethanone, US National Library of Medecine, Feb. 7, 2007, p. 1-10; https://pubchem.ncbi.nlm.nih.gov/compound/12013505.
Qian, S. et al., "IDO as a Drug Target for Cancer Immunotherapy: Recent Developments in IDO Inhibitors Discovery", RSC Advances, 6(9):7575-81, (2016).
Röhrig, U. et al., "Challenges in the Discovery of Indoleamine 2,3-Dioxygenase 1 (IDO1) Inhibitors", J Med Chem., 58(24):9421-37, (2015).
Yeung, A. et al., "Role of Indoleamine 2,3-Dioxygenase in Health and Disease", Clinical Science, 129(7):601-72, (2015).
Zhai, L. et al., "Molecular Pathways: Targeting IDO1 and Other Tryptophan Dioxygenases for Cancer Immunotherapy", Clin Cancer Res, 21(24):5427-33, (2015).
Zhai, L. et al., "The Role of IDO in Brain Tumor Immunotherapy", A Journal of Neuro-Oncology, 123(3): 395-403, (2015).
Arai, S. et al., "Asymmetric Cyclopropanation Reaction Under Phase-Transfer Catalyzed Conditions", Tetrahedron Lett., 40(22):4215-8, (1999).
Horie, H. et al., "Nickel-catalyzed Cycloaddition of $\alpha,\beta,\gamma,\delta$-unsaturated Ketones With Alkynes", Angew Chem Int Ed Engl., 50(38):8956-9, (2011).
Reutrakul, V. et al., "A Rapid Entry to Functionalized Cyclohexanes and Cyclopentanes via a One-Pot Multicomponent Annulations", J Sci Soc Thailand, 22(1):83-7, (1996).
Wessig, P. et al., "A New Photochemical Route to Cyclopropanes", Angew Chem Int Ed Engl., 40(6):1064-5, (2001).
Zhao, G. et al., "Photochemical Studies on Exo-bicyclo[2.1.1]hexyl and Bicyclo[3.1.0]hexyl Aryl Ketones: Two Approaches for Synthesis of Enantiomerically Enriched Cyclopentene Derivatives", Tetrahedron, 65(48):9952-5, (2009).
International Application No. PCT/US2019/042211; International Preliminary Report on Patentability, dated Jan. 28, 2021; 8 pages.
Banker, G. et al., "Modern Pharmaceutics", 3rd Ed., pp. 451 & 596, (1996).
U.S. Appl. No. 16/478,076; Non-Final Office Action, dated Nov. 19, 2020; 23 pages.
Vippagunta, S. et al., "Crystalline Solids", Adv Drug Deliv Rev., 48(1):3-26, (2001).

(56) References Cited

OTHER PUBLICATIONS

Wolff, M., "Burger's Medicinal Chemistry and Drug Discovery", 5th Ed., vol. 1, 975-77, (1995).

* cited by examiner

COMPOUNDS USEFUL AS INHIBITORS OF INDOLEAMINE 2,3-DIOXYGENASE AND/OR TRYPTOPHAN DIOXYGENASE

This application claims the benefit of priority of U.S. Provisional Application No. 62/699,510, filed Jul. 17, 2018, the disclosure of which is hereby incorporated by reference as if written herein in its entirety.

Disclosed herein are new bicyclic compounds and compositions and their application as pharmaceuticals for the treatment of disease. Methods of inhibition of indoleamine 2,3-dioxygenase and/or tryptophan dioxygenase activity in a human or animal subject are also provided for the treatment of diseases such as cancer.

Indoleamine 2,3-dioxygenase (IDO1 and IDO2) and tryptophan dioxygenase (TDO) belong to a family of heme-containing enzymes that mediate the degradation of the essential amino acid L-tryptophan (L-TRP) to N-formylkynurenine. This is the first and rate-limiting step of L-TRP oxidation in the kynurenine (KYN) pathway. Although IDO1, IDO2 and TDO all catalyse the same biochemical reaction, they share limited structural similarity. TDO is a homotetrameric enzyme with high substrate specificity for L-TRP, whilst IDO1 is a monomeric enzyme which recognises a broader range of substrates including L- and D-TRP, serotonin and tryptamine. IDO2 shares 43% sequence identity with IDO1 but is much less effective in catabolizing L-TRP. In healthy patients, TDO is primarily expressed in the liver, and lower levels of the enzyme are also present in the brain. In contrast, IDO1 is ubiquitous in the body, including in the placenta, lung, small and large intestines, colon, spleen, liver, kidney, stomach and brain. IDO2 is expressed in a subset of the tissues that express IDO1, primarily in the kidney, as well as in the epididymis, testis, liver, ovary, uterus, and placenta (Dounay et al., J. Med. Chem. (2015) 58:8762-8782).

The KYN pathway is thought to regulate immune responses to prevent excessive immune activity and immunopathology. For example, IDO1 is believed to play a role in the protection of the foetus from rejection by the mother's immune system (Munn et al., Science (1998) 281:1191-1193), and is implicated in allergies, in autoimmunity, and in tolerance to allografts (Lovelace et al., Neuropharmacology (2017) 112:373-388).

The catabolism of L-TRP by IDO1, IDO2 and/or TDO, and the production of L-TRP derived metabolites such as KYN, has also been identified as an important immune effector pathway in tumour cells to escape potential immune responses, for example by suppressing antigen-specific T-cells and natural killer T-cells, while inducing the formation of regulatory T-cells which suppress immune cells (Qian et al., RSC Adv. (2016) 6:7575-7581). The generation of KYN and its metabolites, including quinolic acid (QUIN), also affects the synthesis of the coenzyme nicotinamide adenine dinucleotide (NAD$^+$). NAD$^+$ plays an important role in DNA replication, and hence cell division, as well as in DNA repair, redox signalling, and mitochondrial function, all of which may be involved in cancer cell proliferation (Bostian et al., Chem. Res. Toxicol. (2016) 29:1369-1380).

IDO1, IDO2 and/or TDO are expressed by many human tumours. The degree of IDO1 expression in tumour cells is known to correlate with clinical prognosis (e.g. overall survival and progression-free survival) and increased IDO1 levels have been linked with tumour cell resistance to immunotherapy, radiation therapy, and chemotherapy agents. Tumour cell resistance is often accompanied by increased metastasis, due to the suppression of the patient's immune response to the invading cancer cells. In particular, in vitro experiments have demonstrated the role of IDO1 in tumour chemoresistance to a variety of agents including cisplatin, olaparib, paclitaxel, pemetrexed, gemcitabine, and gamma radiation (Vareki et al., PLOS ONE (2015) 10(11), e0143435/1-22).

Aberrant KYN signalling has also been associated with a number of neurological diseases or disorders such as Alzheimer's disease, amyotrophic lateral sclerosis, Huntington's disease, multiple sclerosis and Parkinson's disease (Bostian, 2016). The interaction between immune activation and the metabolism of L-TRP via the kynurenine pathway has also been shown to be involved in neuropsychological diseases or disorders such as schizophrenia, anorexia and depression, including depressive and anxiety symptoms in the early puerperium (Lovelace, 2017).

Inhibitors of IDO1, IDO2 and/or TDO are also believed to have utility in the treatment of cataracts; infectious diseases where the immune system is compromised (e.g. influenza virus, peritonitis, sepsis, *Chlamydia trachomatis*, human immunodeficiency virus (HIV) and HIV-associated neurological disorders (HAND)); and autoimmune disorders such as arthritis, rheumatoid arthritis or multiple sclerosis (Lovelace, 2017).

A number of structurally-diverse inhibitors of IDO1, IDO2 and/or TDO have recently been developed. These include indoximod (NLG8189), which is being evaluated in clinical studies for metastatic breast cancer, metastatic melanoma, non-small cell lung cancer, primary malignant brain tumours, metastatic pancreatic cancer, as well as metastatic prostate cancer; epacadostat (INCB024360), which is being evaluated in clinical studies in gynaecological and peritoneal cancers, melanoma, malignant solid tumour, lymphoma, breast, lung, and renal cell cancers; and GDC-0919 (NLG919), which is being evaluated in trials for the treatment of advanced-stage solid tumours.

However, there remains a need for new inhibitors of IDO1, IDO2 and/or TDO, especially inhibitors having high potency, high selectivity and/or beneficial in vivo properties such as pharmacokinetic properties. This need is met by the present invention.

The present inventors have discovered a family of compounds which are useful as inhibitors of IDO1, IDO2 and/or TDO, especially IDO1. These compounds are suitable for use in pharmaceutical compositions as well as in medical treatments in which the KYN pathway needs to be modulated. In particular, the compounds of the invention are suitable for use in the treatment of cancers, immune system regulatory disorders and neurological disorders.

Without wishing to be bound by theory, the inventors postulate that compounds of the present disclosure may inhibit IDO1, IDO2 and/or TDO apoprotein, i.e. before incorporation of the heme cofactor. Such inhibition may prevent the formation of functional protein and offer advantages over other classes of inhibitors which bind directly to the heme moiety in the holoprotein.

Novel compounds and pharmaceutical compositions, certain of which have been found to inhibit IDO1, IDO2 and/or TDO have been discovered, together with methods of synthesizing and using the compounds including methods for the treatment of diseases mediated by IDO1, IDO2 and/or TDO in a patient by administering the compounds.

DETAILED DESCRIPTION

Provided herein is Embodiment 1: a compound having structural Formula (I):

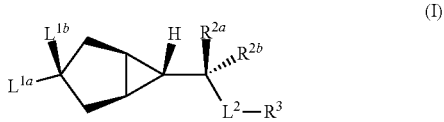

or a salt or tautomer thereof, wherein:
either $L^{1a}$ is $L^1$-$R^1$ and $L^{1b}$ is H, or $L^{1a}$ is H and $L^{1b}$ is $L^1$-$R^1$;
either $R^{2a}$ is $R^2$ and $R^{2b}$ is H, or $R^{2a}$ is H and $R^{2b}$ is $R^2$;
$L^1$ is chosen from a bond, —O—, —N($R^5$)—, C($R^{5a}$)($R^{5b}$)—, and —S—;
$L^2$ is chosen from —C(O)NH—, —C(N$R^4$)NH—, —NHC(O)—, —NHC(N$R^4$)—, —N($R^4$)C($R^6$)—, and —C($R^6$)N($R^4$)—,
or $L^2$ is

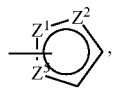

or $L^2$ is chosen from

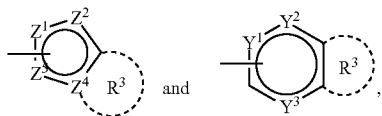

forming a bicyclic ring system with $R^3$ when $R^3$ is cyclic;
$Y^1$, $Y^2$, $Y^3$, $Z^1$, $Z^2$, and $Z^5$ are independently chosen from CH, C($R^9$), N, NH, N($R^9$), O, and S;
$Z^4$ is chosen from C and N;
$R^1$ is H or is chosen from alkyl, aryl, cycloalkyl, heteroaryl, and heterocycloalkyl, any of which is optionally substituted with one or more $R^7$ groups;
$R^2$ is H or is chosen from alkyl, aryl, cycloalkyl, heteroaryl, and heterocycloalkyl, any of which is optionally substituted with one or more $R^8$ groups;
$R^3$ is H or is chosen from alkyl, cycloalkyl, heterocycloalkyl, aryl, heteroaryl, (aryl)aryl, (aryl)heteroaryl, (heteroaryl)aryl, (heteroaryl)heteroaryl, (aryl)cycloalkyl, (heteroaryl)-cycloalkyl, (cycloalkyl)aryl, and (heterocycloalkyl)aryl, any of which is optionally substituted with one or more $R^9$ groups;
$R^4$ is H or is chosen from alkyl, cycloalkyl, heterocycloalkyl, aryl, and heteroaryl, any one of which is optionally substituted with one or more $R^{10}$ groups;
or $R^3$ and $R^4$, together with the intervening atoms, form a first heteroaryl ring, which is optionally fused with a second aryl or heteroaryl ring to form a bicyclic heteroaryl system, said first heteroaryl ring or bicyclic heteroaryl system is optionally substituted with one or more $R^{10}$ groups;
each $R^5$, $R^{5a}$, and $R^{5b}$ is independently H or is chosen from alkyl, cycloalkyl, heterocycloalkyl, aryl, and heteroaryl;

$R^6$ is chosen from $CF_3$, $CF_2CF_3$, and $CF_2CH_3$;
each $R^7$, $R^8$, $R^9$, and $R^{10}$ is independently chosen from halo, haloalkyl, hydroxy, alkyl, amino, $C_{3-6}$cycloalkyl, hydroxyalkyl, alkoxy, alkoxyalkyl, cyano, cyanoalkyl, NHC(O)$R^{11}$, NHS(O)$_2R^{12}$, NHC(O)NH$R^{12}$, C(O)O$R^{12}$, S(O)$_2$NH$R^{12}$, $C_{3-6}$cycloalkyl optionally substituted with one or two $R^{11}$, $C_{3-6}$heterocycloalkyl optionally substituted with one or two $R^{11}$, phenyl optionally substituted with one or two $R^{11}$, and 5-6 membered heteroaryl optionally substituted with one or two $R^{11}$;
each $R^{11}$ is independently chosen from halo, haloalkyl, hydroxy, alkyl, amino, $C_{3-6}$cycloalkyl, alkoxy, hydroxyalkyl, alkoxyalkyl, cyanoalkyl, and cyano; and
$R^{12}$ is chosen from H and alkyl.

Certain compounds disclosed herein may possess useful IDO1 and/or IDO2 inhibiting activity, and may be used in the treatment or prophylaxis of a disease or condition in which IDO1 and/or IDO2 plays an active role. Thus, in a broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting IDO1 and/or IDO2. Other embodiments provide methods for treating an IDO1 and/or IDO2-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the inhibition of IDO1 and/or IDO2.

Certain compounds disclosed herein may possess useful TDO inhibiting activity, and may be used in the treatment or prophylaxis of a disease or condition in which TDO plays an active role. Thus, in a broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting TDO. Other embodiments provide methods for treating a TDO-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the inhibition of TDO.

In certain embodiments, $L^{1a}$ is $L^1$-$R^1$ and $L^{1b}$ is H.
In certain embodiments, $L^{1a}$ is H and $L^{1b}$ is $L^1$-$R^1$.
In certain embodiments, $R^{2a}$ is $R^2$ and $R^{2b}$ is H.
In certain embodiments, $R^{2a}$ is H and $R^{2b}$ is $R^2$.
In certain embodiments, $R^1$ is chosen from aryl and heteroaryl, either one of which is optionally substituted with one or more $R^7$ groups.
In certain embodiments, $R^1$ is chosen from monocyclic and bicyclic aryl, either one of which is optionally substituted with one or more $R^7$ groups.
In certain embodiments, $R^1$ is bicyclic aryl, and is optionally substituted with one or more $R^7$ groups.
In certain embodiments, $R^1$ is chosen from monocyclic and bicyclic heteroaryl, either one of which is optionally substituted with one or more $R^7$ groups.
In certain embodiments, $R^1$ is bicyclic heteroaryl, and is optionally substituted with one or more $R^7$ groups.

In certain embodiments, R¹ is chosen from indol-1-yl, indazol-1-yl, and benzo[d]imidazol-1-yl, any one of which is optionally substituted with one or more R⁷ groups.

In certain embodiments, R¹ is benzo[d]imidazol-1-yl, and is optionally substituted with one or more R⁷ groups.

In certain embodiments, R¹ is 5,6-difluorobenzo[d]imidazol-1-yl.

In certain embodiments, R¹ is chosen from quinolin-4-yl and isoiquinolin-4-yl, either one of which is optionally substituted with one or more R⁷ groups.

In certain embodiments, R¹ is quinolin-4-yl, and is optionally substituted with one or more R⁷ groups.

In certain embodiments, R¹ is 6-fluoroquinolin-4-yl.

In certain embodiments, L² is

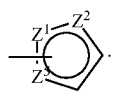

In certain embodiments, L² is

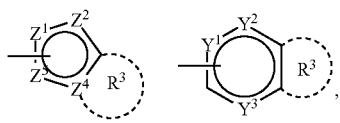

forming a bicyclic ring system with R³ when R³ is cyclic.

In certain embodiments, L² is

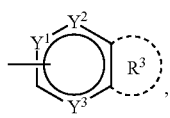

forming a bicyclic ring system with R³ when R³ is cyclic.

In certain embodiments, L² and R³ combine to form a bicyclic ring system chosen from benzo[d]imidazolyl, imidazopyridinyl, benzothiazolyl, benzooxazolyl, triazolopyridinyl, pyrazolopyridinyl, quinazolinonyl, and imidazopyridazinyl, any one of which is optionally substituted with one or more R⁹ groups.

In certain embodiments, L² and R³ combine to form a bicyclic ring system chosen from benzo[d]imidazol-2-yl, 1H-imidazo[4,5-b]pyridin-2-yl, imidazo[1,5-a]pyridin-3-yl, benzo[d]thiazol-2-yl, benzo[d]oxazol-2-yl, [1,2,4]triazolo[4,3-a]pyridin-3-yl, 1H-pyrazolo-[4,3-b]pyridin-1-yl, 1H-pyrazolo[4,3-b]pyridin-3-yl, 1H-pyrazolo[3,4-b]pyridin-1-yl, 1H-pyrazolo[3,4-b]pyridin-3-yl, imidazo[1,5-b]pyridazin-5-yl, imidazo[1,5-b]pyridazin-7-yl, and imidazo[1,2-b]pyridazine-2-yl.

In certain embodiments, L² and R³ combine to form a benzo[d]imidazolyl, which is optionally substituted with one or more R⁹ groups.

In certain embodiments, L² is —C(O)NH—.

In certain embodiments, L² is —NHC(O)—.

In certain embodiments, R² is H or is chosen from alkyl and cycloalkyl, either of which is optionally substituted with one or more R⁸ groups.

In certain embodiments, R² is H or is chosen from alkyl and cycloalkyl.

In certain embodiments, R² is chosen from $C_{1-4}$alkyl and $C_{3-6}$cycloalkyl.

In certain embodiments, R² is chosen from methyl, ethyl, and cyclopropyl.

In certain embodiments, R³ is cycloalkyl, and is optionally substituted with one or more R⁹ groups.

In certain embodiments, R³ is chosen from cyclobutyl, bicyclo[1.1.1]pentan-1-yl, bicyclo[2.1.1]hexan-1-yl, bicyclo[2.2.1]heptan-1-yl, and bicyclo[2.2.2]octan-1-yl, and is optionally substituted with one or more R⁹ groups.

In certain embodiments, R³ is bicyclo[1.1.1]pentan-1-yl, and is optionally substituted with one or more R⁹ groups.

In certain embodiments, R³ is chosen from

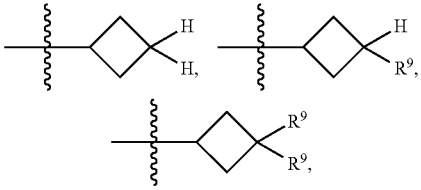

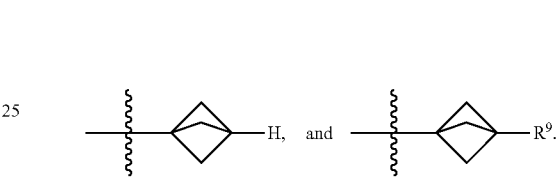

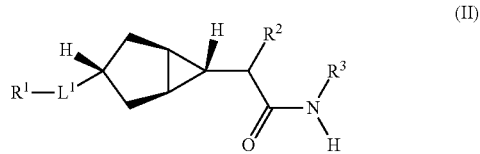

In certain embodiments, R³ is chosen from phenyl and monocyclic heteroaryl, either of which is optionally substituted with one or more R⁹ groups.

In certain embodiments, R³ is chosen from phenyl, pyridinyl, pyridazinyl, pyrimidinyl, and pyrazinyl, any of which is optionally substituted with one or more R⁹ groups.

In certain embodiments, R³ is chosen from pyrrolyl, pyrazolyl, imidazolyl, and 1,2,4-triazolyl.

Provided herein is Embodiment 2: a compound having structural Formula (II):

or a salt or tautomer thereof, wherein:
L¹ is chosen from a bond, —O—, —N(R⁵)—, C(R⁵ᵃ)(R⁵ᵇ)—, and —S—;
R¹ is H or is chosen from alkyl, aryl, cycloalkyl, heteroaryl, and heterocycloalkyl, any of which is optionally substituted with one or more R⁷ groups;
R² is H or is chosen from alkyl, cycloalkyl, and heterocycloalkyl, any one of which is optionally substituted with one or more R⁸ groups;
R³ is H or is chosen from alkyl, cycloalkyl, heterocycloalkyl, aryl, heteroaryl, (aryl)aryl, (aryl)heteroaryl, (heteroaryl)aryl, (heteroaryl)heteroaryl, aryl(cycloalkyl), and heteroaryl(cycloalkyl), any of which is optionally substituted with one or more R⁹ groups;
each R⁵, R⁵ᵃ, and R⁵ᵇ is independently H or is chosen from alkyl, cycloalkyl, heterocycloalkyl, aryl, and heteroaryl; and
each R⁷, R⁸, and R⁹ is independently chosen from halo, haloalkyl, hydroxy, alkyl, amino, $C_{3-6}$cycloalkyl, hydroxyalkyl, alkoxy, alkoxyalkyl, cyano, cyanoalkyl, NHC(O)R$^{11}$, NHS(O)$_2$R$^{12}$, NHC(O)NHR$^{12}$, C(O)OR$^{12}$, S(O)$_2$NHR$^{12}$, C$_{3-6}$cycloalkyl optionally substituted with one or two R$^{11}$, C$_{3-6}$heterocycloalkyl optionally substituted with one or two R$^{11}$, phenyl optionally substituted with one or two R$^{11}$, and 5-6 membered heteroaryl optionally substituted with one or two R$^{11}$;

each R$^{11}$ is independently chosen from halo, haloalkyl, hydroxy, alkyl, amino, C$_{3-6}$cycloalkyl, hydroxyalkyl, alkyl, alkoxy, and cyano; and R$^{12}$ is chosen from H and alkyl.

Provided herein is Embodiment 3: a compound having structural Formula (III):

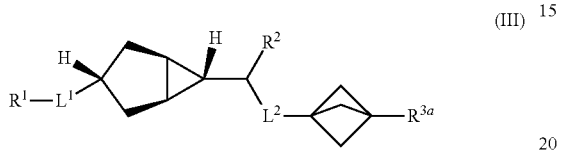

(III)

or a salt or tautomer thereof, wherein:

L$^1$ is chosen from a bond, —O—, —N(R$^5$)—, C(R$^{5a}$)(R$^{5b}$)—, and —S—;

L$^2$ is chosen from —C(O)O—, —C(O)NH—, —C(NR$^4$)NH—, —NHC(O)—, —NHC(O)NH—, —NHC(NR$^4$)—, —N(R$^4$)C(R$^6$)—, and —C(R$^6$)N(R$^4$)—;

R$^1$ is H or is chosen from alkyl, aryl, cycloalkyl, heteroaryl, and heterocycloalkyl, any of which is optionally substituted with one or more R$^7$ groups;

R$^2$ is H or is chosen from alkyl, aryl, cycloalkyl, heteroaryl, and heterocycloalkyl, any of which is optionally substituted with one or more R$^8$ groups;

R$^{1a}$ is chosen from H, halo, hydroxy, alkoxy, and cyano, or is chosen from aryl or heteroaryl, either of which is optionally substituted with one or more R$^9$ groups;

R$^4$ is H or is chosen from alkyl, cycloalkyl, heterocycloalkyl, aryl, and heteroaryl, any one of which is optionally substituted with one or more R$^{10}$ groups;

each R$^5$, R$^{5a}$, and R$^{5b}$ is independently H or is chosen from alkyl, cycloalkyl, heterocycloalkyl, aryl, and heteroaryl;

R$^6$ is chosen from CF$_3$, CF$_2$CF$_3$, and CF$_2$CH$_3$; and each R$^7$, R$^8$, R$^9$, and R$^{10}$ is independently chosen from halo, haloalkyl, hydroxy, alkyl, amino, C$_{3-6}$cycloalkyl, hydroxyalkyl, alkoxy, alkoxyalkyl, cyano, cyanoalkyl, NHC(O)R$^{11}$, NHS(O)$_2$R$^{12}$, NHC(O)NHR$^{12}$, C(O)OR$^{12}$, S(O)$_2$NHR$^{12}$, C$_{3-6}$cycloalkyl optionally substituted with one or two R$^{11}$, C$_{3-6}$heterocycloalkyl optionally substituted with one or two R$^{11}$, phenyl optionally substituted with one or two R$^{11}$, and 5-6 membered heteroaryl optionally substituted with one or two R$^{11}$;

each R$^{11}$ is independently chosen from halo, haloalkyl, hydroxy, alkyl, amino, C$_{3-6}$cycloalkyl, hydroxyalkyl, alkyl, alkoxy, and cyano; and R$^{12}$ is chosen from H and alkyl.

Provided herein is Embodiment 4: a compound having structural Formula (IV):

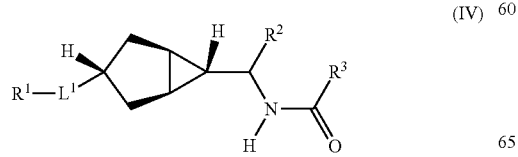

(IV)

or a salt or tautomer thereof, wherein:

L$^1$ is chosen from a bond, —O—, —N(R$^5$)—, C(R$^{5a}$)(R$^{5b}$)—, and —S—;

R$^1$ is H or is chosen from alkyl, aryl, cycloalkyl, heteroaryl, and heterocycloalkyl, any of which is optionally substituted with one or more R$^7$ groups;

R$^2$ is H or is chosen from alkyl, aryl, cycloalkyl, heteroaryl, and heterocycloalkyl, any of which is optionally substituted with one or more R$^8$ groups;

R$^3$ is H or is chosen from alkyl, cycloalkyl, heterocycloalkyl, aryl, heteroaryl, (aryl)aryl, (aryl)heteroaryl, (heteroaryl)aryl, (heteroaryl)heteroaryl, aryl(cycloalkyl), and heteroaryl(cycloalkyl), any of which is optionally substituted with one or more R$^9$ groups;

each R$^5$, R$^{5a}$, and R$^{5b}$ is independently H or is chosen from alkyl, cycloalkyl, heterocycloalkyl, aryl, and heteroaryl;

each R$^7$, R$^8$, and R$^9$ is independently chosen from halo, haloalkyl, hydroxy, alkyl, amino, C$_{3-6}$cycloalkyl, hydroxyalkyl, alkoxy, alkoxyalkyl, cyano, cyanoalkyl, NHC(O)R$^{11}$, NHS(O)$_2$R$^{12}$, NHC(O)NHR$^{12}$, C(O)OR$^{12}$, S(O)$_2$NHR$^{12}$, C$_{3-6}$cycloalkyl optionally substituted with one or two R$^{11}$, C$_{3-6}$heterocycloalkyl optionally substituted with one or two R$^{11}$, phenyl optionally substituted with one or two R$^{11}$, and 5-6 membered heteroaryl optionally substituted with one or two R$^{11}$;

each R$^{11}$ is independently chosen from halo, haloalkyl, hydroxy, alkyl, amino, C$_{3-6}$cycloalkyl, hydroxyalkyl, alkyl, alkoxy, and cyano; and R$^{12}$ is chosen from H and alkyl.

Provided herein is Embodiment 5: a compound having structural Formula (V):

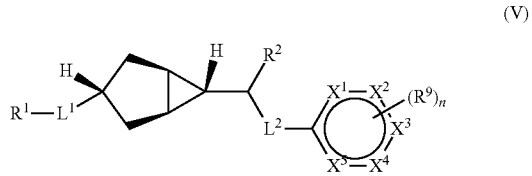

(V)

or a salt or tautomer thereof, wherein:

n is 0, 1, or 2;

X$^1$ is chosen from C(R$^{9a}$), N, O, and S;

X$^2$ is chosen from C(R$^{9b}$), N, O, and S;

X$^3$ is chosen from C(R$^{9c}$), N, O, and S;

X$^4$ is chosen from C(R$^{9d}$), N, O, and S;

X$^5$ is chosen from a bond, C(R$^{9e}$), N, O, and S;

L$^1$ is chosen from a bond, —O—, —N(R$^5$)—, C(R$^{5a}$)(R$^{5b}$)—, and —S—;

L$^2$ is chosen from —C(O)NH—, —C(NR$^4$)NH—, —NHC(O)—, —NHC(NR$^4$)—, —N(R$^4$)C(R$^6$)—, and —C(R$^6$)N(R$^4$)—, or L$^2$ is

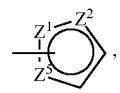

or L² is chosen from

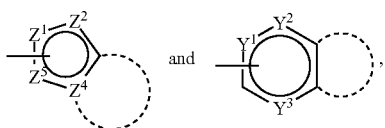

forming, as shown, a bicyclic ring system with

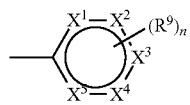

(which, for clarity, is a type of R³);
- R¹ is H or is chosen from alkyl, aryl, cycloalkyl, heteroaryl, and heterocycloalkyl, any of which is optionally substituted with one or more R⁷ groups;
- R² is H or is chosen from alkyl, aryl, cycloalkyl, heteroaryl, and heterocycloalkyl, any of which is optionally substituted with one or more R⁸ groups;
- R⁴ is H or is chosen from alkyl, cycloalkyl, heterocycloalkyl, aryl, and heteroaryl, any one of which is optionally substituted with one or more R¹⁰ groups;
- each R⁵, R⁵ᵃ, and R⁵ᵇ is independently H or is chosen from alkyl, cycloalkyl, heterocycloalkyl, aryl, and heteroaryl;
- R⁶ is chosen from CF₃, CF₂CF₃, and CF₂CH₃;
- R⁹ᵃ, R⁹ᵇ, R⁹ᶜ, R⁹ᵈ, and R⁹ᵉ are independently chosen from H, alkyl, halo, haloalkyl, hydroxy, amino, C₃₋₆cycloalkyl, hydroxyalkyl, alkoxy, and cyano;
- each R⁷, R⁸, R⁹, and R¹⁰ is independently chosen from halo, haloalkyl, hydroxy, alkyl, amino, hydroxyalkyl, alkoxy, alkoxyalkyl, cyano, cyanoalkyl, NHC(O)R¹¹, NHS(O)₂R¹², NHC(O)NHR¹², C(O)OR¹², S(O)₂NHR¹², C₃₋₆cycloalkyl optionally substituted with one or two R¹¹, C₃₋₆heterocycloalkyl optionally substituted with one or two R¹¹, phenyl optionally substituted with one or two R¹¹, and 5-6 membered heteroaryl optionally substituted with one or two R¹¹;
- each R¹¹ is independently chosen from halo, haloalkyl, hydroxy, alkyl, amino, C₃₋₆cycloalkyl, hydroxyalkyl, alkyl, alkoxy, and cyano; and
- R¹² is chosen from H and alkyl.

Provided herein is Embodiment 6: a compound having structural Formula (VI):

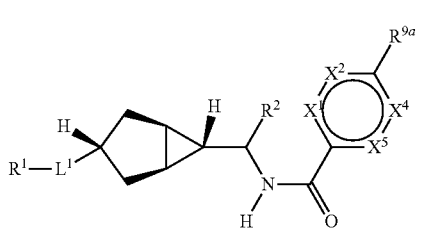

or a salt or tautomer thereof, wherein:
- X¹, X², and X⁴ are independently chosen from CH and N;
- X⁵ is chosen from a bond, CH and N;
- at most two of X¹, X², X⁴, and X are N;

L¹ is chosen from a bond, —O—, —N(R⁵)—, C(R⁵ᵃ)(R⁵ᵇ)—, and —S—;
- R¹ is H or is chosen from alkyl, aryl, cycloalkyl, heteroaryl, and heterocycloalkyl, any of which is optionally substituted with one or more R⁷ groups;
- R² is H or is chosen from alkyl, aryl, cycloalkyl, heteroaryl, and heterocycloalkyl, any of which is optionally substituted with one or more R⁸ groups;
- each R⁵, R⁵ᵃ, and R⁵ᵇ is independently H or is chosen from alkyl, cycloalkyl, heterocycloalkyl, aryl, and heteroaryl;
- R⁹ᵃ is chosen from H, alkyl, halo, haloalkyl, hydroxy, amino, C₃₋₆cycloalkyl, hydroxyalkyl, alkoxy, and cyano;
- each R⁷, R⁸, R⁹, and R¹⁰ is independently chosen from halo, haloalkyl, hydroxy, alkyl, amino, hydroxyalkyl, alkoxy, alkoxyalkyl, cyano, cyanoalkyl, NHC(O)R¹¹, NHS(O)₂R¹², NHC(O)NHR¹², C(O)OR¹², S(O)₂NHR¹², C₃₋₆cycloalkyl optionally substituted with one or two R¹¹, C₃₋₆heterocycloalkyl optionally substituted with one or two R¹¹, phenyl optionally substituted with one or two R¹¹, and 5-6 membered heteroaryl optionally substituted with one or two R¹¹;
- each R¹¹ is independently chosen from halo, haloalkyl, hydroxy, alkyl, amino, C₃₋₆cycloalkyl, hydroxyalkyl, alkyl, alkoxy, and cyano; and
- R¹² is chosen from H and alkyl.

Provided herein is Embodiment 7: a compound having structural Formula (VII):

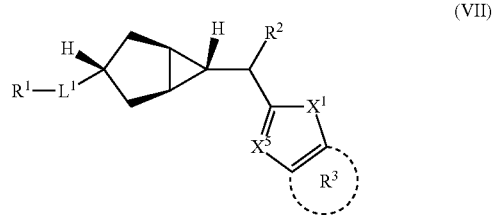

or a salt or tautomer thereof, wherein:
- L¹ is chosen from a bond, —O—, —N(R⁵)—, C(R⁵ᵃ)(R⁵ᵇ)—, and —S—;
- X¹ is chosen from NH, NR⁹, O, and S;
- X⁵ is chosen from CH, CR⁹, and N;
- R¹ is H or is chosen from alkyl, aryl, cycloalkyl, heteroaryl, and heterocycloalkyl, any of which is optionally substituted with one or more R⁷ groups;
- R² is H or is chosen from alkyl, aryl, cycloalkyl, heteroaryl, and heterocycloalkyl, any of which is optionally substituted with one or more R⁸ groups;
- R³ is chosen from cycloalkyl, heterocycloalkyl, aryl, and heteroaryl, any of which is optionally substituted with one or more R⁹ groups; and each R⁵, R⁵ᵃ, and R⁵ᵇ is independently H or is chosen from alkyl, cycloalkyl, heterocycloalkyl, aryl, and heteroaryl;
- each R⁷, R⁸, and R⁹ is independently chosen from halo, haloalkyl, hydroxy, alkyl, amino, C₃₋₆cycloalkyl, hydroxyalkyl, alkoxy, alkoxyalkyl, cyano, cyanoalkyl, NHC(O)R¹¹, NHS(O)₂R¹², NHC(O)NHR¹², C(O)OR¹², S(O)₂NHR¹², C₃₋₆cycloalkyl optionally substituted with one or two R¹¹, C₃₋₆heterocycloalkyl optionally substituted with one or two R¹¹, phenyl optionally substituted with one or two R¹¹, and 5-6 membered heteroaryl optionally substituted with one or two R¹¹;

each R[11] is independently chosen from halo, haloalkyl, hydroxy, alkyl, amino, C$_{3-6}$cycloalkyl, hydroxyalkyl, alkyl, alkoxy, and cyano; and R[12] is chosen from H and alkyl.

Provided herein is Embodiment 8: a compound having structural Formula (VIII):

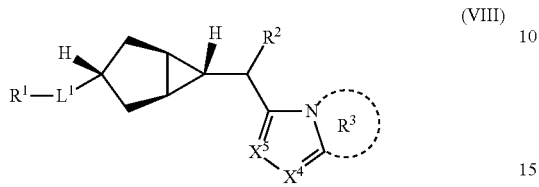

(VIII)

or a salt or tautomer thereof, wherein:

L[1] is chosen from a bond, —O—, —N(R[5])—, C(R[5a])(R[5b])—, and —S—;

X[4] and X[5] are independently chosen from CH, CR[9], and N;

R[1] is H or is chosen from alkyl, aryl, cycloalkyl, heteroaryl, and heterocycloalkyl, any of which is optionally substituted with one or more R[7] groups;

R[2] is H or is chosen from alkyl, cycloalkyl, and heterocycloalkyl, any one of which is optionally substituted with one or more R[8] groups;

R[3] is H or is chosen from cycloalkyl, heterocycloalkyl, aryl, and heteroaryl, any one of which is optionally substituted with one or more R[9] groups;

each R[5], R[5a], and R[5b] is independently H or is chosen from alkyl, cycloalkyl, heterocycloalkyl, aryl, and heteroaryl;

each R[7], R[8], and R[9] independently chosen from halo, haloalkyl, hydroxy, alkyl, amino, C$_{3-6}$cycloalkyl, hydroxyalkyl, alkoxy, alkoxyalkyl, cyano, cyanoalkyl, NHC(O)R[11], NHS(O)$_2$R[12], NHC(O)NHR[12], C(O)OR[12], S(O)$_2$NHR[12], C$_{3-6}$cycloalkyl optionally substituted with one or two R[11], C$_{3-6}$heterocycloalkyl optionally substituted with one or two R[11], phenyl optionally substituted with one or two R[11], and 5-6 membered heteroaryl optionally substituted with one or two R[11];

each R[11] is independently chosen from halo, haloalkyl, hydroxy, alkyl, amino, C$_{3-6}$cycloalkyl, hydroxyalkyl, alkyl, alkoxy, and cyano; and R[12] is chosen from H and alkyl.

Provided herein is Embodiment 9: a compound having structural Formula (IX):

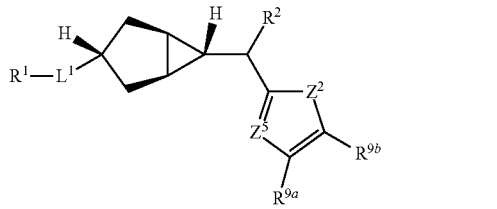

(IX)

or a salt or tautomer thereof, wherein:

L[1] is chosen from a bond, —O—, —N(R[5])—, C(R[5a])(R[5b])—, and —S—;

Z[2] is chosen from NH, NR[9], O, and S;

Z[5] is chosen from CH, C(R[9]), and N;

R[1] is aryl or heteroaryl, and is optionally substituted with one or more R[7] groups;

R[2] is H or is chosen from alkyl, cycloalkyl, and heterocycloalkyl, any one of which is optionally substituted with one or more R[8] groups;

R[3] is H or is chosen from alkyl, cycloalkyl, heterocycloalkyl, aryl, and heteroaryl, any one of which is optionally substituted with one or more R[9] groups;

each R[5], R[5a], and R[5b] is independently H or is chosen from alkyl, cycloalkyl, heterocycloalkyl, aryl, and heteroaryl;

each R[7] and R[8] is independently chosen from alkyl, C$_{3-6}$cycloalkyl, halo, hydroxy, alkoxy, and cyano;

R[9a] and R[9b] are independently chosen from H, alkyl, C$_{3-6}$cycloalkyl, halo, hydroxy, alkoxy, and cyano, or R[9a] and R[9b], together with the intervening atoms, combine to form an aryl or heteroaryl ring, which is optionally substituted with one or more R[9] groups; and each R[9] is independently chosen from alkyl, C$_{3-6}$cycloalkyl, halo, hydroxy, alkoxy, and cyano.

Provided herein is Embodiment 10: a compound having structural Formula (X):

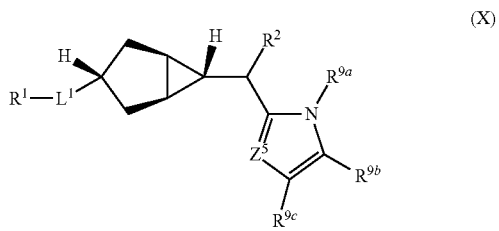

(X)

or a salt or tautomer thereof, wherein:

L[1] is chosen from a bond, —O—, —N(R[5])—, C(R[5a])(R[5b])—, and —S—;

Z[5] is chosen from CH, C(R[9]), and N;

R[1] is aryl or heteroaryl, and is optionally substituted with one or more R[7] groups;

R[2] is H or is chosen from alkyl, cycloalkyl, and heterocycloalkyl, any one of which is optionally substituted with one or more R[8] groups;

R[3] is H or is chosen from alkyl, cycloalkyl, heterocycloalkyl, aryl, and heteroaryl, any one of which is optionally substituted with one or more R[9] groups;

each R[5], R[5a], and R[5b] is independently H or is chosen from alkyl, cycloalkyl, heterocycloalkyl, aryl, and heteroaryl;

each R[7] and R[8] is independently chosen from alkyl, C$_{3-6}$cycloalkyl, halo, hydroxy, alkoxy, and cyano;

R[9a] and R[9b] are independently chosen from H, alkyl, C$_{3-6}$cycloalkyl, halo, hydroxy, alkoxy, and cyano, or R[9a] and R[9b], together with the intervening atoms, combine to form a heteroaryl ring, which is optionally substituted with one or more R[9] groups; and each R[9] is independently chosen from alkyl, C$_{3-6}$cycloalkyl, halo, hydroxy, alkoxy, and cyano.

Provided herein is Embodiment 11: a compound having structural Formula (XI):

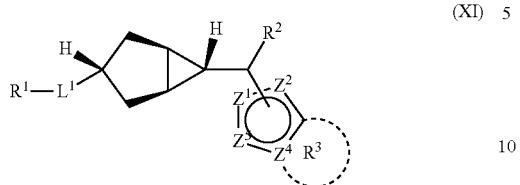

(XI)

or a salt or tautomer thereof, wherein:
L$^1$ is chosen from a bond, —O—, —N(R$^5$)—, C(R$^{5a}$)(R$^{5b}$)—, and —S—;
Z$^1$, Z$^2$, and Z$^5$ are independently chosen from CH, C(R$^9$), NH, NR$^9$, O, and S;
Z$^4$ is chosen from C and N;
R$^1$ is H or is chosen from alkyl, aryl, cycloalkyl, heteroaryl, and heterocycloalkyl, any of which is optionally substituted with one or more R$^7$ groups;
R$^2$ is H or is chosen from alkyl, cycloalkyl, and heterocycloalkyl, any one of which is optionally substituted with one or more R$^8$ groups;
R$^3$ is chosen from cycloalkyl, heterocycloalkyl, aryl, and heteroaryl, any of which is optionally substituted with one or more R$^9$ groups;
each R$^5$, R$^{5a}$, and R$^{5b}$ is independently H or is chosen from alkyl, cycloalkyl, heterocycloalkyl, aryl, and heteroaryl;
each R$^7$, R$^8$, and R$^9$ is independently chosen from halo, haloalkyl, hydroxy, alkyl, amino, C$_{3-6}$cycloalkyl, hydroxyalkyl, alkoxy, alkoxyalkyl, cyano, cyanoalkyl, NHC(O)R$^{11}$, NHS(O)$_2$R$^{12}$, NHC(O)NHR$^{12}$, C(O)OR$^{12}$, S(O)$_2$NHR$^{12}$, C$_{3-6}$cycloalkyl optionally substituted with one or two R$^{11}$, C$_{3-6}$heterocycloalkyl optionally substituted with one or two R$^{11}$, phenyl optionally substituted with one or two R$^{11}$, and 5-6 membered heteroaryl optionally substituted with one or two R$^{11}$;
each R$^{11}$ is independently chosen from halo, haloalkyl, hydroxy, alkyl, amino, C$_{3-6}$cycloalkyl, hydroxyalkyl, alkyl, alkoxy, and cyano; and
R$^{12}$ is chosen from H and alkyl.

Provided herein is Embodiment 12: a compound having structural Formula (XII):

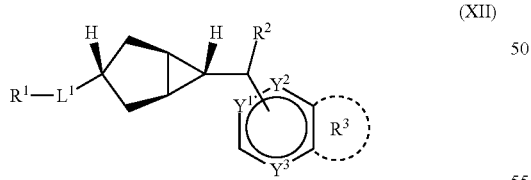

(XII)

or a salt or tautomer thereof, wherein:
L$^1$ is chosen from a bond, —O—, —N(R$^5$)—, C(R$^{5a}$)(R$^{5b}$)—, and —S—;
Y$^1$, Y$^2$, and Y$^3$ are independently chosen from CH, C(R$^9$), NH, NR$^9$, O, and S;
R$^1$ is H or is chosen from alkyl, aryl, cycloalkyl, heteroaryl, and heterocycloalkyl, any of which is optionally substituted with one or more R$^7$ groups;
R$^2$ is H or is chosen from alkyl, cycloalkyl, and heterocycloalkyl, any one of which is optionally substituted with one or more R$^8$ groups;
R$^3$ is chosen from cycloalkyl, heterocycloalkyl, aryl, and heteroaryl, any of which is optionally substituted with one or more R$^9$ groups;
each R$^5$, R$^{5a}$, and R$^{5b}$ is independently H or is chosen from alkyl, cycloalkyl, heterocycloalkyl, aryl, and heteroaryl;
each R$^7$, R$^8$, and R$^9$ is independently chosen from halo, haloalkyl, hydroxy, alkyl, amino, C$_{3-6}$cycloalkyl, hydroxyalkyl, alkoxy, alkoxyalkyl, cyano, cyanoalkyl, NHC(O)R$^{11}$, NHS(O)$_2$R$^{12}$, NHC(O)NHR$^{12}$, C(O)OR$^{12}$, S(O)$_2$NHR$^{12}$, C$_{3-6}$cycloalkyl optionally substituted with one or two R$^{11}$, C$_{3-6}$heterocycloalkyl optionally substituted with one or two R$^{11}$, phenyl optionally substituted with one or two R$^{11}$, and 5-6 membered heteroaryl optionally substituted with one or two R$^{11}$;
each R$^{11}$ is independently chosen from halo, haloalkyl, hydroxy, alkyl, amino, C$_{3-6}$cycloalkyl, hydroxyalkyl, alkyl, alkoxy, and cyano; and
R$^{12}$ is chosen from H and alkyl.

The disclosure provides the further embodiments:

Embodiment 13

The compound of any one of Embodiments 1, 2, 4, and 6, wherein R$^3$ is chosen from cycloalkyl and heterocycloalkyl, either of which is optionally substituted with one or more R$^9$ groups.

Embodiment 14

The compound of Embodiment 13, wherein R$^3$ is chosen from bicycloalkyl and heterobicycloalkyl, either of which is optionally substituted with one or more R$^9$ groups.

Embodiment 15

The compound of Embodiment 14, wherein R$^3$ is chosen from bicyclo[1.1.1]pentane, bicyclo[2.1.1]hexane, bicyclo[2.2.1]heptane, and bicyclo[2.2.2]octane, any of which is optionally substituted with one or two R$^9$ groups.

Embodiment 16

The compound of Embodiment 15, wherein R$^3$ is chosen from bicyclo[1.1.1]pentane.

Embodiment 17

The compound of any one of 1, 2, and 4, wherein R$^3$ is H or is chosen from cycloalkyl, heterocycloalkyl, aryl, heteroaryl, any of which is optionally substituted with one or more R$^9$ groups;

Embodiment 18

The compound of any one of Embodiments 1, 2, 4, 7, 8, 11, and 12, wherein R$^3$ is chosen from aryl and heteroaryl, either one of which is optionally substituted with one or more R$^9$ groups.

Embodiment 19

The compound of Embodiment 18, wherein R$^3$ is a 6-membered aryl or heteroaryl, either one of which is optionally substituted with one or more R$^9$ groups.

Embodiment 20

The compound of Embodiment 19, wherein $R^3$ is chosen from phenyl, pyridinyl, pyridazinyl, pyrimidinyl, and pyrazinyl, any one of which is optionally substituted with one or more $R^9$ groups.

Embodiment 21

The compound of Embodiment 3, wherein $R^{1a}$ is H.

Embodiment 22

The compound of Embodiment 3, wherein $R^{1a}$ is chosen from H, halo, hydroxy, alkoxy, and cyano, or is chosen from aryl or heteroaryl, either of which is optionally substituted with one or more $R^9$ groups.

Embodiment 23

The compound of Embodiment 3, wherein $R^{1a}$ is chosen from H, halo, hydroxy, alkoxy, and cyano.

Embodiment 24

The compound of Embodiment 3, wherein $R^{1a}$ is chosen from aryl or heteroaryl, either of which is optionally substituted with one or more $R^9$ groups.

Embodiment 25

The compound of any one of Embodiments 1-20, wherein $L^1$ is a bond.

Embodiment 26

The compound of any one of Embodiments 1-20, wherein $L^1$ is —O—.

Embodiment 27

The compound of any one of Embodiments 1-20, wherein $L^1$ is —$NR^5$—.

Embodiment 28

The compound of any one of Embodiments 1-27, wherein $R^1$ is benzo[d]imidazol-1-yl, and is substituted with one or more $R^7$ groups.

Embodiment 29

The compound of Embodiment 11, wherein $L^2$ and $R^3$ combine to form a bicyclic ring system chosen from benzo[d]imidazolyl, imidazopyridinyl, benzothiazolyl, benzooxazolyl, triazolopyridinyl, pyrazolopyridinyl, quinazolinonyl, and imidazopyridazinyl, any one of which is optionally substituted with one or more $R^9$ groups.

Embodiment 29

The compound of Embodiment 28, wherein $R^1$ is 5,6-difluoro benzo[d]imidazol-1-yl.

Embodiment 30

The compound of any one of Embodiments 1-27, wherein $R^1$ is quinolin-4-yl, and is substituted with one or more $R^7$ groups.

Embodiment 31

The compound of Embodiment 30, wherein $R^1$ is 6-fluoroquinolin-4-yl.

Embodiment 32

The compound of any one of Embodiments 1-31, wherein $R^2$ is chosen from H, alkyl, and cycloalkyl.

Embodiment 33

The compound of Embodiment 32, wherein $R^2$ is chosen from H, methyl, ethyl, and cyclopropyl.

Embodiment 34

The compound of Embodiment 18, wherein $R^3$ is a bicyclic aryl or heteroaryl, either one of which is optionally substituted with one or more $R^9$ groups.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound chosen from the Examples disclosed herein.

The present invention also relates to a method of inhibiting at least one function of a target chosen from IDO1, IDO2 and TDO comprising the step of contacting said target with a compound as described herein. The cell phenotype, cell proliferation, activity of said target, change in biochemical output produced by active target, expression of target, or binding of target with a natural binding partner may be monitored. Such methods may be modes of treatment of disease, biological assays, cellular assays, biochemical assays, or the like.

Also provided herein is a method of treatment of a disease mediated by IDO1, IDO2 and/or TDO comprising the administration of a therapeutically effective amount of a compound as disclosed herein, or a salt thereof, to a patient in need thereof.

In certain embodiments, the disease is cancer.

In certain embodiments, the disease is a cancer chosen from head and neck cancer, breast cancer, prostate cancer, ovarian cancer, endometrial cancer, colon cancer, lung cancer, bladder cancer, pancreatic cancer, brain tumour, gynecological cancer, peritoneal cancer, skin cancer, thyroid cancer, oesophageal cancer, cervical cancer, gastric cancer, liver cancer, stomach cancer, renal cell cancer, biliary tract cancer, hematologic cancer, and blood cancer.

In certain embodiments, the disease is a neurological disease or disorder.

In certain embodiments, the disease is a neurological disease or disorder chosen from Alzheimer's disease, amyotrophic lateral sclerosis, Huntington's disease, multiple sclerosis, Parkinson's disease, and HIV-associated neurological disorders (HAND).

In certain embodiments, the disease is a neuropsychological disease.

In certain embodiments, the disease is a neuropsychological disease or disorder chosen from schizophrenia, anorexia, depression, and anxiety.

In certain embodiments, the disease is an autoimmune disease or disorder.

In certain embodiments, the disease is an autoimmune disease or disorder chosen from arthritis, rheumatoid arthritis, and multiple sclerosis.

In certain embodiments, the disease is an infection.

In certain embodiments, the disease is an infection chosen from influenza virus infection, peritonitis, sepsis, *Chlamydia trachomatis* infection, and human immunodeficiency virus (HIV).

In certain embodiments, the disease is a cataract.

In certain embodiments, the disease is a vascular disease.

Also provided herein is a compound as disclosed herein for use as a medicament.

Also provided herein is a compound as disclosed herein for use as a medicament for the treatment of a disease mediated by IDO1, IDO2 and/or TDO.

Also provided is the use of a compound as disclosed herein as a medicament.

Also provided is the use of a compound as disclosed herein as a medicament for the treatment of a disease mediated by IDO1, IDO2 and/or TDO.

Also provided is a compound as disclosed herein for use in the manufacture of a medicament for the treatment of a mediated disease mediated by.

Also provided is the use of a compound as disclosed herein for the treatment of a disease mediated by IDO1, IDO2 and/or TDO.

Also provided herein is a method of inhibition of a target chosen from IDO1, IDO2 and TDO comprising contacting said target with a compound as disclosed herein, or a salt thereof.

Also provided herein is a method for achieving an effect in a patient comprising the administration of a therapeutically effective amount of a compound as disclosed herein, or a salt thereof, to a patient, wherein the effect is chosen from cognition enhancement.

In certain embodiments, the disease mediated by IDO1, IDO2 and/or TDO is cancer.

Also provided is a method of modulation of a function of IDO1, IDO2 and/or TDO in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the pharmaceutical composition is formulated for parenteral administration.

In certain embodiments, the pharmaceutical composition is formulated for intravenous administration.

In certain embodiments, the pharmaceutical composition is formulated for intramuscular administration.

In certain embodiments, the pharmaceutical composition is formulated for subcutaneous administration.

In certain embodiments, the oral pharmaceutical composition is chosen from a tablet and a capsule.

Abbreviations and Definitions

Terms

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. As such, it includes primary, secondary, and tertiary amido groups. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3C$(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. As such, it includes primary, secondary, and tertiary amino groups. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$=derived from benzene. Examples include benzothiophene and benzo[d]imidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, alone or in combination, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cyclic" as used herein in reference to a chemical group means forming a ring or ring system. Cyclic groups include both non-aromatic cyclic (cycloaliphatic) groups such as cycloalkyl and heterocycloalkyl, and aromatic groups such as aryl and heteroaryl.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzo[d]imidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom (noncarbon atom) as a ring member, wherein each said heteroatom may be independently chosen from N, O, and S. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocycloalkyl also includes bridged or spirocyclic systems. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S—.

The term "sulfinyl," as used herein, alone or in combination, refers to S(O)—.

The term "sulfonyl," as used herein, alone or in combination, refers to —S(O)$_2$—.

The term "N-sulfonamido" refers to a RS(O)$_2$NR'— group with R and R' as defined herein.

The term "S-sulfonamido" refers to a —S(O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3$CS(O)$_2$NR— group with X is a halogen and R as defined herein.

The term "trihalomethanesulfonyl" refers to a $X_3$CS(O)$_2$— group where X is a halogen.

The term "trihalomethoxy" refers to a $X_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, C(O)$CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N (R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof; the mixture may be racemic (having approximately equal amounts of enantiomers) or have one enantiomer (or diastereomer) is present in an enantiomeric excess of at least about 5%, 10%, 25%, 40%, 70%, 80%, 90%, 95%, 97%, 98% or 99%, e.g. about 100%. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are encompassed by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

Isotopically-enriched compounds are also within the scope of the present disclosure. As used herein, an "isotopically-enriched compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. In certain embodiments, the isotopically-enriched compound, is a deuterated compound, i.e., a compound which has one or more hydrogen atoms replaced by deuterium.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The compounds of the invention are useful as inhibitors of IDO1, IDO2 and/or TDO. In particular, compounds of the invention are useful as inhibitors of IDO1. Assays for determining the inhibitory activity of compounds against IDO1 (e.g. against mouse or human IDO1, or a fragment thereof having catalytic activity) are known in the art and are also set out in the following Examples. The activity values listed below may, for example, be determined according to an assay as disclosed herein.

In certain embodiments, compounds of the invention have an $IC_{50}$ value (e.g. an inhibitory activity against IDO1 in a cell-based assay) of less than 10 µM, less than 5 µM, less than 2 µM, less than 1 µM, less than 500 nM, less than 200 nM, less than 100 nM, less than 75 nM, less than 50 nM, less than 40 nM, less than 30 nM, less than 25 nM, less than 20 nM, less than 15 nM, less than 10 nM, less than 8 nM, less than 6 nM, less than 5 nM, less than 4 nM, less than 3 nM, less than 2.5 nM, or less than 2 nM.

The compounds of the invention may be selective for IDO1 and/or IDO2 over TDO. In particular, the compounds of the invention may be selective for IDO1 over TDO. Assays for determining the selectivity of a compound for IDO1 (or IDO2) over TDO are known in the art and are illustrated in the following Examples.

In embodiments, the compounds of the invention are selective for IDO1 over TDO by a value of at least 100 times, at least 200 times, at least 500 times, at least 1000 times, at least 2000 times, at least 5000 times or at least 10000 times. By "selective" is meant that the concentration of compound which results in 50% maximal inhibition ($IC_{50}$) of TDO is at least the stated factor more than the concentration of compound which results in 50% maximal inhibition of IDO1. Thus, a compound having an $IC_{50}$ value of 10 nM against IDO1, and having an IC50 value of 20 µM against TDO, is selective for IDO1 over TDO by a value of 2000 times.

The phrase "therapeutically effective" or "effective" when used to modify an amount of a drug is intended to qualify the amount of active ingredients used in the treatment of a disease or disorder or on the effecting of a clinical endpoint. An "effective amount" or "therapeutically effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc.

The term "therapeutically acceptable" or "pharmaceutically acceptable" refers to those compounds (or salts, prodrugs, tautomers, zwitterionic forms, etc.) or formulations thereof which are suitable for use in contact with the tissues of patients without undue toxicity, irritation, and allergic response, are commensurate with a reasonable benefit/risk ratio, and are effective for their intended use.

As used herein, reference to "treatment" of a patient is intended, in certain embodiments, to include arresting or reducing the development of the disease or its clinical symptoms; and/or relieving the disease, i.e. causing regression of the disease or its clinical symptoms; and/or complete protection from disease, for example as in the case of prevention of infection with a pathogen, or may involve prevention of disease progression. Prevention of a disease may not mean complete foreclosure of any effect related to the disease at any level, but instead may mean prevention of the symptoms of a disease to a clinically significant or detectable level. Prevention of diseases may also mean prevention of progression of a disease to a later stage of the disease.

A patient "with" or "having" a disease is one who has been diagnosed with or is predisposed to the disease. A patient may also be referred to being "at risk of having" a disease because of a history of disease in their family lineage, because of the presence of genetic mutations associated with the disease, or due to the presence of predisposing factors in their life or lifestyle. A patient at risk of a disease has not yet developed all or some of the characteristic pathologies of the disease.

The term "patient" is generally synonymous with the term "subject" and includes all mammals including humans. Examples of patients include humans, livestock such as cattle, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions, either spontaneous or enzymatic, to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

In certain embodiments, the salts may include hydrochloride, hydrobromide, sulfonate, citrate, tartrate, phosphonate, lactate, pyruvate, acetate, succinate, oxalate, fumarate, malate, oxaloacetate, methanesulfonate, ethanesulfonate, p-toluenesulfonate, benzenesulfonate and isethionate salts of compounds disclosed herein. A salt of a compound can be made by reacting the appropriate compound in the form of the free base with the appropriate acid.

Pharmaceutical Compositions

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Oral Administration

The compounds of the present disclosure may be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, powders, or granules, solutions or suspensions in an aqueous liquid or a non-aqueous liquid, or as an oil-in-water liquid emulsion or a water-in-oil liquid emulsion. The active ingredient may also be presented as a bolus, electuary or paste.

In a tablet or capsule dosage form the amount of drug present may be from about 0.05% to about 95% by weight, more typically from about 2% to about 50% by weight of the dosage form.

In addition, tablets or capsules may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet or capsule, may be present in amounts from about 0.1% to about 3% by weight, and include polysorbate 80, sodium dodecyl sulfate, talc and silicon dioxide.

Suitable lubricants, for use in a tablet or capsule, may be present in amounts from about 0.1% to about 5% by weight, and include calcium, zinc or magnesium stearate, sodium stearyl fumarate and the like.

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with a liquid diluent. Dyes or pigments may be added to tablets for identification or to characterize different combinations of active compound doses.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Parenteral Administration

Compounds of the present disclosure may be administered directly into the blood stream, muscle, or internal organs by injection, e.g., by bolus injection or continuous infusion. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods. The formulations may be presented in unit-dose or multi-dose containers, for example sealed ampoules and vials.

Most parenteral formulations are aqueous solutions containing excipients, including salts, buffering, suspending, stabilizing and/or dispersing agents, antioxidants, bacteriostats, preservatives, and solutes which render the formulation isotonic with the blood of the intended recipient, and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions. Compositions for parenteral administration may be formulated as immediate or modified release, including delayed or sustained release. Compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Topical Administration

Compounds of the present disclosure may be administered topically (for example to the skin, mucous membranes, ear, nose, or eye) or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Typically, the active ingredient for topical administration may comprise from 0.001% to 10% w/w (by weight) of the formulation. In certain embodiments, the active ingredient may comprise as much as 10% w/w; less than 5% w/w; from 2% w/w to 5% w/w; or from 0.1% to 1% w/w of the formulation.

Compositions for topical administration may be formulated as immediate or modified release, including delayed or sustained release.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

(Optional—the following section describes topical formulations in detail)

Gels for topical or transdermal administration may comprise, generally, a mixture of volatile solvents, nonvolatile solvents, and water. In certain embodiments, the volatile solvent component of the buffered solvent system may include lower (C1-C6) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or *arachis* oil.

Creams, ointments or pastes are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, *arachis*, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Rectal, Buccal, and Sublingual Administration

Suppositories for rectal administration of the compounds of the present disclosure can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Administration by Inhalation

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Other carrier materials and modes of administration known in the pharmaceutical art may also be used. Pharmaceutical compositions of the invention may be prepared by any of the well-known techniques of pharmacy, such as effective formulation and administration procedures. Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, route of administration, route of administration, rate of excretion, drug combination, the precise disorder being treated, and the severity of the indication or condition being treated. In addition, the route of administration may vary depending on the condition and its severity. The above considerations concerning effective formulations and administration procedures are well known in the art and are described in standard textbooks.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

Methods of Treatment and Indications for Use

The compounds described herein, and pharmaceutical compositions thereof, are useful in therapy, in particular in the therapeutic treatment of IDO1, IDO2 and/or TDO mediated conditions in a subject, and especially in the therapeutic treatment of IDO1 mediated conditions in a subject.

Disclosed herein is a method for treating an IDO1, IDO2 and/or TDO mediated condition (e.g. an IDO1 mediated condition) in a subject, the method comprising administering to the subject an effective amount of a compound as defined herein, e.g. a compound of formula (I). Also provided is a compound as defined herein, e.g. a compound of formula (I), for use in a method of treating an IDO1, IDO2 and/or TDO mediated condition (e.g. an IDO1 mediated condition) in a subject. Further provided is the use of a compound as defined herein, e.g. a compound characterised by formula (I), in the manufacture of a medicament for use in a method of treating an IDO1, IDO2 and/or TDO mediated condition (e.g. an IDO1-mediated condition) in a subject.

The KYN pathway has been implicated in a number of conditions, including: cancers; neurological and neuropsychological diseases and disorders; autoimmune diseases and disorders; infections; and cataracts.

In embodiments, the IDO1, IDO2 and/or TDO mediated condition (e.g. the IDO1 mediated condition) is selected from a cancer; a neurological or neuropsychological disease or disorder; an autoimmune disease or disorder; an infection; a cataract; and a vascular disease.

In certain embodiments, the IDO1, IDO2 and/or TDO mediated condition (e.g. the IDO1 mediated condition) is characterised by the overexpression of IDO1, IDO2 and/or TDO, respectively (e.g. by the overexpression of IDO1).

In certain embodiments, the treatment of the IDO1, IDO2 and/or TDO mediated condition (e.g. the IDO1 mediated condition) comprises administering a compound of the invention in combination with another therapeutic intervention for said condition. The other therapeutic intervention may be performed before, during and/or after administering the compound of the invention.

Cancers

Overexpression of IDO1, IDO2 and/or TDO occurs in a significant number of cancer types, including breast cancer, prostate cancer, colon cancer, colorectal carcinoma, head and neck carcinoma, glioblastoma, astrocytoma, lung carcinoma, bladder carcinoma, hepatocarcinoma, lymphocytic leukaemia, melanoma, mesothelioma, neuroblastoma, and brain tumour. For example, the deregulation of IDO1 in tumour cells has been shown to be linked to the cancer suppressive gene bridging integrator 1 (Bin1), which is a down-regulator of IDO1. Clinical observations suggest that high expression levels of IDO1 and loss or attenuation of Bin1 are frequent in a number of cancers including advanced breast cancer, prostate cancer, melanoma, astrocytoma, neuroblastoma, lymphocytic leukaemia and colon cancer.

Furthermore, metabolites of KYN such as QUIN affect the biosynthesis of $NAD^+$, which may be involved in cancer cell proliferation. For example, in glioblastoma multiforme, genotoxic anticancer drugs such as temozolomide (TMZ), hydroxyurea, procarbazine, cisplatin, and nitrosamines, such as carmustine, lomustine, and nimustine, in combination with radiation are used to kill tumour cells which remain following surgery. However, the effectiveness of these drugs can be weakened by the tolerance of the tumour cells to DNA repair/damage. It is thought that modulation of the KYN pathway can enhance genotoxic treatment by diminishing the ability of the cancer cells to repair damaged DNA and/or to bypass the cytotoxic effects of DNA damage. Thus, treatment with a compound as defined herein in combination with immunotherapy, radiation therapy and/or chemotherapy is expected to enhance the efficacy of said therapy.

Accordingly, in one embodiment the IDO1, IDO2 and/or TDO mediated condition (e.g. the IDO1 mediated condition) is a cancer. In certain embodiments, the cancer is associated with low levels of L-TRP. In certain embodiments, the tumour microenvironment is depleted in L-TRP (e.g. below normal levels). In certain embodiments, the cancer is associated with high levels of L-TRP metabolites, e.g. KYN and/or QUIN. In certain embodiments, the concentration of said L-TRP metabolites in cells of the tumour are above normal levels for cells of that tissue type. In certain embodiments, the cancer is associated with overexpression of IDO1, IDO2 and/or TDO, e.g. overexpression of IDO1.

In certain embodiments the cancer is selected from head and neck cancer, breast cancer (e.g. metastatic breast cancer), prostate cancer (e.g. metastatic prostate cancer), ovarian cancer, endometrial cancer, colon cancer, lung cancer (e.g. non small cell lung cancer), bladder cancer, pancreatic cancer (e.g. metastatic pancreatic cancer), brain tumour (e.g.

primary malignant brain tumour), gynecological cancer, peritoneal cancer, skin cancer, thyroid cancer, oesophageal cancer, cervical cancer, gastric cancer, liver cancer, stomach cancer, renal cell cancer, biliary tract cancer, hematologic cancer, and blood cancer. In certain embodiments, the cancer is selected from colorectal carcinoma, large intestinal colon carcinoma, head and neck carcinoma, lung carcinoma, lung adenocarcinoma, bladder carcinoma, Barret's adenocarcinoma, renal carcinoma, and hepatocarcinoma. In certain embodiments, the cancer is selected from glioblastoma, astrocytoma, melanoma (e.g. metastatic melanoma), mesothelioma, neuroblastoma, histiocytic lymphoma, and lymphocytic leukaemia. In certain embodiments, the cancer is a solid tumour (e.g. a malignant solid tumour) which may be an advanced-stage solid tumour.

In certain embodiments, the treatment of said IDO1, IDO2 and/or TDO mediated condition (e.g. said IDO1 mediated condition) as disclosed herein comprises administering a compound of the invention in combination with another therapeutic intervention for said condition. The other therapeutic intervention may be performed before, during and/or after administering the compound of the invention. Thus, in certain embodiments the subject is receiving (or has received, or will receive) said another therapeutic intervention for said IDO1, IDO2 and/or TDO mediated condition.

In certain embodiments, said another therapeutic intervention is immunotherapy, radiation therapy and/or chemotherapy. In certain embodiments, said another therapeutic intervention is immunotherapy. In certain embodiments, said another therapeutic intervention is radiation therapy. In certain embodiments, said another therapeutic intervention is chemotherapy. In certain embodiments, said another therapeutic intervention comprises radiation therapy and further comprises treatment with immunotherapy and/or with chemotherapy.

In certain embodiments, said radiotherapy comprises treatment with gamma radiation.

In certain embodiments, said immunotherapy comprises treatment with an immunotherapeutic agent selected from therapeutic antibodies. In certain embodiments, the therapeutic antibody is a humanised monoclonal antibody. In certain embodiments, said immunotherapy comprises treatment with an immunotherapeutic agent selected from vaccines. In certain embodiments, the vaccine is a gene therapy vaccine.

In certain embodiments, said chemotherapy comprises treatment with a chemotherapeutic agent selected from alkylating agents, alkyl sulfonates, aziridines, ethylenimines and methylamelamines, nitrogen mustards, nitrosureas, bisphosphonates, purine analogs, pyrimidine analogs, taxoids, platinum analogs, anti-hormonal agents, aromatase inhibitors, antiandrogens, protein kinase inhibitors, lipid kinase inhibitors, antisense oligonucleotides, ribozymes, anti-retroviral protease inhibitors, anti-angiogenic agents, and topoisomerase 1 inhibitors.

In certain embodiments, said cancer is partially or totally resistant to treatment with at least one chemotherapeutic and/or immunotherapeutic agent (e.g. as defined herein).

In certain embodiments, administration of the compounds as disclosed herein can treat subjects diagnosed as having said cancer or being at risk of developing said cancer. In certain embodiments, administration of compounds as disclosed herein improves prognosis, reduces angiogenesis, reduces the catabolism of L-TRP, decreases growth of malignant cells, and/or prevents or reduces tumour progression.

Neurological and Neuropsychological Diseases and Disorders

IDO1 is present in numerous cell types within the body, in particular in microglia, the macrophage-like cells located in the central nervous system. Expression of IDO1 is induced by proinflammatory cytokines and molecules, in particular by interferon gamma (IFN-$\gamma$) and, to a lesser extent, by IFN-$\alpha$, IFN-$\beta$, interleukines, and tumor necrosis factors (TNF). TDO is present in small amount in the brain, where its expression is induced by corticosteroids and glucagon.

Increased levels of KYN, and its metabolites, have been observed in a number of neurological and neuropsychological diseases and disorders including Alzheimer's disease, amyotrophic lateral sclerosis, Huntington's disease, multiple sclerosis, and Parkinson's disease (Bostian, 2016; Lovelace, 2017). Decreasing the production of neurotoxic metabolites of KYN, which include QUIN and 3-hydroxykynurenine, may reduce neuronal loss and atrophy in various neurological disorders and diseases. Furthermore, the interaction between immune activation and the metabolism of L-TRP (which is a precursor of serotonin) via the KYN pathway is implicated in neuropsychological diseases and disorders such as schizophrenia, anorexia, and depression, including depressive and anxiety symptoms in the early puerperium (Lovelace, 2017).

Accordingly, in one embodiment, the IDO1 IDO2 and/or TDO mediated condition (e.g. the IDO1 mediated condition) is a neurological or neuropsychological disease or disorder. In certain embodiments, said condition is a neurological disease or disorder. In other embodiments, said condition is a neuropsychological disease or disorder.

In certain embodiments, the neurological or neuropsychological disease or disorder is associated with low levels of L-TRP. In certain embodiments, the cerebrospinal fluid and/or the serum of the subject is depleted in L-TRP (e.g. below normal levels). In certain embodiments, the neurological or neuropsychological disease or disorder is associated with high levels of L-TRP metabolites, e.g. KYN, QUIN and/or 3-hydroxykynurenine. In certain embodiments, the concentration of said L-TRP metabolites in microglia of the subject are above normal levels. In certain embodiments, the neurological or neuropsychological disease or disorder is associated with overexpression of IDO1, IDO2 and/or TDO, e.g. overexpression of IDO1.

In certain embodiments, the neurological disease or disorder is selected from Alzheimer's disease, amyotrophic lateral sclerosis, Huntington's disease, multiple sclerosis, Parkinson's disease, and HAND. In certain embodiments, the neuropsychological disease or disorder is selected from schizophrenia, anorexia, depression, and anxiety (e.g. depressive and anxiety symptoms in the early puerperium).

Autoimmune Diseases and Disorders

Catabolism of L-TRP may prevent normal proliferation in various cell types, and may increase the susceptibility of cells to apoptosis. In particular, antigen-specific T-cells have been shown to be susceptible to L-TRP deprivation. In addition, L-TRP catabolism leads to the formation of metabolites which have been shown to increase apoptosis of helper T-cells and natural killer T-cells. Further, KYN induces the formation of regulatory T-cells which may suppress immune cells. Furthermore, L-TRP levels in rheumatoid arthritis patients have been shown to be lower than in healthy patients, this may be due to overexpression of IDO1.

Accordingly, in one embodiment, the IDO1 IDO2 and/or TDO mediated condition (e.g. the IDO1 mediated condition) is an autoimmune disease or disorder.

In certain embodiments, the autoimmune disease or disorder is associated with low levels of L-TRP. In certain embodiments, the serum of the subject is depleted in L-TRP (e.g. below normal levels). In certain embodiments, the autoimmune disease or disorder is associated with high levels of L-TRP metabolites, e.g. KYN, QUIN and/or 3-hydroxykynurenine. In certain embodiments, the autoimmune disease or disorder is associated with overexpression of IDO1, IDO2 and/or TDO, e.g. overexpression of IDO1.

In certain embodiments, the autoimmune disease or disorder is selected from arthritis, rheumatoid arthritis, and multiple sclerosis.

Infections

Antigen-specific T-cells have been shown to be susceptible to L-TRP deprivation. In addition, L-TRP catabolism leads to the formation of metabolites which have been shown to increase apoptosis of helper T-cells and natural killer T-cells. Further, KYN induces the formation of regulatory T-cells which may suppress immune cells. Thus, IDO1, IDO2 and/or TDO may influence the progression of infectious diseases in which the immune system is compromised.

In particular, HIV infections may be caused by $CD4^+$ T-cell depletion, combined with chronic immune activation and inflammation responses. Elevated levels of KYN metabolites and IFN-γ are commonly found in HIV patients, and catabolism of L-TRP may be a factor in HIV disease progression, through immune suppression and/or the generation of neurotoxic KYN metabolites. Elevated levels of KYN neurotoxic metabolites such as QUIN in HIV infected patients have also been linked to the progression of HAND. Those KYN metabolites may be produced in the central nervous system, possibly by microglia, in response to peripheral immune and inflammatory signals.

IDO1 activity is elevated in sepsis and has been associated with disease severity. Further, IDO1 activity has been shown to correlate with hypotension in cases of human septic shock. In this regard, KYN is thought to be a vasodilator which may contribute to the hypotension observed in septic shock.

Accordingly, In certain embodiments the infection is selected from influenza virus infection, peritonitis, sepsis, *Chlamydia trachomatis* infection, and HIV.

In certain embodiments, the infection is associated with low levels of L-TRP. In certain embodiments, the plasma of the subject is depleted in L-TRP (e.g. below normal levels). In certain embodiments, the infection is associated with high levels of L-TRP metabolites, e.g. KYN, QUIN and/or 3-hydroxykynurenine. In certain embodiments, the plasma of the subject has a ratio of KYN to L-TRP above normal levels. In certain embodiments, the infection is associated with overexpression of IDO1, IDO2 and/or TDO, e.g. overexpression of IDO1.

In certain embodiments, the treatment of said infection comprises administering a compound of the invention in combination with another therapeutic intervention for said infection. Said another therapeutic intervention may be performed before, during and/or after administering the compound of the invention. Thus, in certain embodiments the subject is receiving (or has received, or will receive) said another therapeutic intervention for said infection.

In certain embodiments, the infection is a viral infection and said another therapeutic intervention is treatment with an antiviral agent. In certain embodiments, the infection is HIV infection and said another therapeutic intervention is treatment with an antiretroviral agent. In certain embodiments, the infection is a bacterial infection and said another therapeutic intervention is treatment with an antibacterial agent.

Other Conditions

The KYN pathway has also been implicated in other conditions. For example, elevated lenticular levels of IDO1 and KYN metabolites have been observed in association with cataracts. IDO1 activity has also been shown to correlate with carotid artery intima/media thickness, which is an early marker of atherosclerosis (a leading cause of cardiovascular diseases). Elevated levels of KYN have also been associated with the risk of acute myocardial infarction.

Accordingly, in one embodiment, the IDO1 IDO2 and/or TDO mediated condition (e.g. the IDO1 mediated condition) is a cataract. In certain embodiments, the cataract is age related, or is associated with diabetes in the subject.

In another embodiment, the IDO1, IDO2 and/or TDO mediated condition (e.g. the IDO1 mediated condition) is a vascular disease. In certain embodiments, the vascular disease is a cardiovascular disease. In certain embodiments, the IDO1, IDO2 and/or TDO mediated condition (e.g. the IDO1 mediated condition) is atherosclerosis. In certain embodiments, the IDO1 IDO2 and/or TDO mediated condition (e.g. the IDO1 mediated condition) is myocardial infarction, in particular acute myocardial infarction.

Combinations and Combination Therapy

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

For use in cancer and neoplastic diseases an IDO1, IDO2, or TDO inhibitor may be optimally used together with one or more of the following non-limiting examples of anti-cancer agents:

1) inhibitors or modulators of a protein involved in one or more of the DNA damage repair (DDR) pathways such as:
   a. PARP1/2, including, but not limited to: olaparib, niraparib, rucaparib;
   b. checkpoint kinase 1 (CHK1), including, but not limited to: UCN-01, AZD7762, PF477736, SCH900776, MK-8776, LY2603618, V158411, and EXEL-9844;

c. checkpoint kinase 2 (CHK2), including, but not limited to: PV1019, NSC 109555, and VRX0466617;
d. dual CHK1/CHK2, including, but not limited to: XL-844, AZD7762, and PF-473336;
e. WEE1, including, but not limited to: MK-1775 and PD0166285;
f. ATM, including, but not limited to KU-55933,
g. DNA-dependent protein kinase, including, but not limited to NU7441 and M3814; and
h. Additional proteins involved in DDR;

2) Inhibitors or modulators of one or more immune checkpoints, including, but not limited to:
a. PD-1 inhibitors such as nivolumab (OPDIVO), pembrolizumab (KEYTRUDA), pidilizumab (CT-011), and AMP-224 (AMPLIMMUNE);
b. PD-L1 inhibitors such as Atezolizumab (TECENTRIQ), Avelumab (Bavencio), Durvalumab (Imfinzi), MPDL3280A (Tecentriq), BMS-936559, and MEDI4736;
c. anti-CTLA-4 antibodies such as ipilimumab (YERVOY) and CP-675,206 (TREMELIMUMAB);
d. inhibitors of T-cell immunoglobulin and mucin domain 3 (Tim-3);
e. inhibitors of V-domain Ig suppressor of T cell activation (Vista);
f. inhibitors of band T lymphocyte attenuator (BTLA);
g. inhibitors of lymphocyte activation gene 3 (LAG3); and
h. inhibitors of T cell immunoglobulin and immunoreceptor tyrosine-based inhibitory motif domain (TIGIT);

3) telomerase inhibitors or telomeric DNA binding compounds;

4) alkylating agents, including, but not limited to: chlorambucil (LEUKERAN), oxaliplatin (ELOXATIN), streptozocin (ZANOSAR), dacarbazine, ifosfamide, lomustine (CCNU), procarbazine (MATULAN), temozolomide (TEMODAR), and thiotepa;

5) DNA crosslinking agents, including, but not limited to: carmustine, chlorambucil (LEUKERAN), carboplatin (PARAPLATIN), cisplatin (PLATIN), busulfan (MYLERAN), melphalan (ALKERAN), mitomycin (MITOSOL), and cyclophosphamide (ENDOXAN);

6) anti-metabolites, including, but not limited to: cladribine (LEUSTATIN), cytarbine, (ARA-C), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), and raltitrexed;

7) antimitotics, which are often plant alkaloids and terpenoids, or derivateves thereof including but limited to: taxanes such as docetaxel (TAXITERE), paclitaxel (ABRAXANE, TAXOL), vinca alkaloids such as vincristine (ONCOVIN), vinblastine, vindesine, and vinorelbine (NAVELBINE);

8) topoisomerase inhibitors, including, but not limited to: amsacrine, camptothecin (CTP), genisten, irinotecan (CAMPTOSAR), topotecan (HYCAMTIN), doxorubicin (ADRIAMYCIN), daunorubicin (CERUBIDINE), epirubicin (ELLENCE), ICRF-193, teniposide (VUMON), mitoxantrone (NOVANTRONE), and etoposide (EPOSIN);

9) DNA replication inhibitors, including, but not limited to: fludarabine (FLUDARA), aphidicolin, ganciclovir, and cidofovir;

10) ribonucleoside diphosphate reductase inhibitors, including, but not limited to: hydroxyurea;

11) transcription inhibitors, including, but not limited to: actinomycin D (dactinomycin, COSMEGEN) and plicamycin (mithramycin);

12) DNA cleaving agents, including, but not limited to: bleomycin (BLENOXANE), idarubicin, 13) cytotoxic antibiotics, including, but not limited to: actinomycin D (dactinomycin, COSMEGEN), 14) aromatase inhibitors, including, but not limited to: aminoglutethimide, anastrozole (ARIMIDEX), letrozole (FEMARA), vorozole (RIVIZOR), and exemestane (AROMASIN);

15) angiogenesis inhibitors, including, but not limited to: genistein, sunitinib (SUTENT), and bevacizumab (AVASTIN);

16) anti-steroids and anti-androgens, including, but not limited to: aminoglutethimide (CYTADREN), bicalutamide (CASODEX), cyproterone, flutamide (EULEXIN), nilutamide(NILANDRON);

17) tyrosine kinase inhibitors, including, but not limited to: imatinib (GLEEVEC), erlotinib (TARCEVA), lapatininb (TYKERB), sorafenib (NEXAVAR), and axitinib (INLYTA);

18) mTOR inhibitors, including, but not limited to: everolimus, temsirolimus (TORISEL), and sirolimus;

19) monoclonal antibodies, including, but not limited to: trastuzumab (HERCEPTIN) and rituximab (RITUXAN);

20) apoptosis inducers such as cordycepin;

21) protein synthesis inhibitors, including, but not limited to: clindamycin, chloramphenicol, streptomycin, anisomycin, and cycloheximide;

22) antidiabetics, including, but not limited to: metformin and phenformin;

23) antibiotics, including, but not limited to:
a. tetracyclines, including, but not limited to: doxycycline;
b. erythromycins, including, but not limited to: azithromycin;
c. glycylglycines, including, but not limited to: tigecyline;
d. antiparasitics, including, but not limted to: pyrvinium pamoate;
e. beta-lactams, including, but not limited to the penicillins and cephalosporins;
f. anthracycline antibiotics, including, but not limited to: daunorubicin and doxorubicin;
g. other antibiotics, including, but not limited to: chloramphenicol, mitomycin C, and actinomycin;

24) antibody therapeutical agents, including, but not limited to: muromonab-CD3, infliximab (REMICADE), adalimumab (HUMIRA), omalizumab (XOLAIR), daclizumab (ZENAPAX), rituximab (RITUXAN), ibritumomab (ZEVALIN), tositumomab (BEXXAR), cetuximab (ERBITUX), trastuzumab (HERCEPTIN), ADCETRIS, alemtuzumab (CAMPATH-1H), Lym-1 (ONCOLYM), ipilimumab (YERVOY), vitaxin, bevacizumab (AVASTIN), and abciximab (REOPRO); and 25) other agents, such as *Bacillus* Calmette-Guérin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPO- GEN); fludrocortisone (FLORINEF); goserelin (ZOLADEX); interferon; leucovorin; leuprolide (LUPRON); levamisole; lonidamine; mesna; metformin; mitotane (o,p'-DDD, LYS ODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Compound Synthesis

Compounds of the present disclosure can be prepared using methods illustrated in general synthetic schemes and experimental procedures detailed below. General synthetic schemes and experimental procedures are presented for purposes of illustration and are not intended to be limiting. Starting materials used to prepare compounds of the present disclosure are commercially available or can be prepared using routine methods known in the art.

List of Abbreviations

Ac$_2$O=acetic anhydride; AcCl=acetyl chloride; AcOH=acetic acid; AIBN=azobisisobutyronitrile; aq.=aqueous; Bu$_3$SnH=tributyltin hydride; CD$_3$OD=deuterated methanol; CDCl$_3$=deuterated chloroform; CDI=1,1'-Carbonyldiimidazole; DBU=1,8-diazabicyclo[5.4.0]undec-7-ene; DCM=dichloromethane; DEAD=diethyl azodicarboxylate; DIBAL-H=di-iso-butyl aluminium hydride; DIEA=DIPEA=N,N-diisopropylethylamine; DMAP=4-dimethylaminopyridine; DMF=N,N-dimethylformamide; DMSO-d6=deuterated dimethyl sulfoxide; DMSO=dimethyl sulfoxide; DPPA=diphenylphosphoryl azide; EDC.HCl=EDCI.HCl=1-ethyl-3-(3-dimethylaminopropyl)carbodiimide hydrochloride; Et$_2$O=diethyl ether; EtOAc=ethyl acetate; EtOH=ethanol; h=hour; HATU=2-(1H-7-azabenzotriazol-1-yl)-1,1,3,3-tetramethyl uronium hexafluorophosphate methanaminium; HMDS=hexamethyldisilazane; HOBT=1-hydroxybenzotriazole; i-PrOH=isopropanol; LAH=lithium aluminium hydride; LiHMDS=Lithium bis(trimethylsilyl)amide; MeCN=acetonitrile; MeOH=methanol; MP-carbonate resin=macroporous triethylammonium methylpolystyrene carbonate resin; MsCl=mesyl chloride; MTBE=methyl tertiary butyl ether; MW=microwave irradiation; n-BuLi=n-butyllithium; NaHMDS=Sodium bis(trimethylsilyl)amide; NaOMe=sodium methoxide; NaOtBu=sodium t-butoxide; NBS=N-bromosuccinimide; NCS=N-chloro-succinimide; NMP=N-Methyl-2-pyrrolidone; Pd(Ph$_3$)$_4$=tetrakis(triphenylphosphine)-palladium(O); Pd$_2$(dba)$_3$=tris(dibenzylideneacetone)dipalladium(O); PdCl$_2$(PPh$_3$)$_2$=bis(triphenylphosphine)palladium(II) dichloride; PG=protecting group; prep-HPLC=preparative high-performance liquid chromatography; PyB op=(benzotriazol-1-yloxy)-tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; t-BuOH=tert-butanol; T3P=Propylphosphonic Anhydride; TBS=TBDMS=tert-butyldimethylsilyl; TBSC1=TBDMSC1=tert-butyldimethylchlorosilane; TEA=Et$_3$N=triethylamine; TFA=trifluoroacetic acid; TFAA=trifluoroacetic anhydride; THF=tetrahydrofuran; Tot=toluene; TsCl=tosyl chloride; XPhos=2-dicyclohexylphosphino-2',4',6'-triisopropylbiphenyl.

General Synthetic Methods for Preparing Compounds

The following general procedures can be use to practice the present invention. Details for performing the general procedures are disclosed in the synthesis of example compounds.

| General Procedure | Transformation |
|---|---|
| A | Toluenesulfonate ester from alcohol using toluenesulfonyl chloride |
| B | Cyclopropanation from alkene and diazoacetate ester |
| C | Ether from displacement of a sulfonate ester with an alcoxide |
| D | Weinreb amide from a carboxylic ester and N,O-dimethyl hydroxylamine |
| E | Alkyl ketone from a Weinreb ester and an alkyl Grignard |
| F | Alkene formation from methoxymethyl triphenylphosphorane |
| G | Carboxaldehyde from hydrolysis of a vinyl ether |
| H | Carboxylic acid from oxidation of a carboxaldehyde |
| I | Amide from coupling of a carboxylic acid and an amine using T3P |
| J | Methyl ketone from reaction of a carboxylic acid with methyllithium |
| K | Methyl ester from Fischer esterification of a carboxylic acid |
| L | Methanesulfonate ester from an alcohol using methanesulfonyl chloride |
| M | Carboxylic acid from LiOH hydrolysis of a carboxylate ester |
| N | Amide from condensation of an arylamine anion with an ester |
| O | Amide from coupling of a carboxylic acid and an amine using HATU |
| P | Benzo[d]imidazole formation from dehydration of (2-amino)aryl amide |
| Q | Amide from coupling of a carboxylic acid and an amine using PyBroP |
| R | Aryl boronate from Miyaura borylation of an aryl halide |
| S | Biaryl fromi Suzuki coupling of an aryl boronate and aryl halide |
| T | Methyl ester from esterification of a carboxylic acid with silyl deprotection |

The following schemes can be used to practice the present invention.

SCHEME I

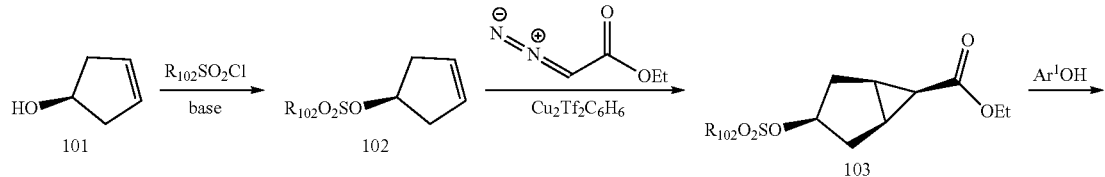

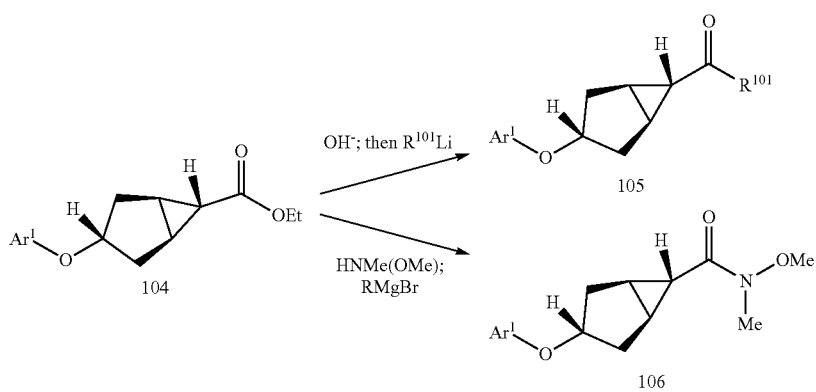

Scheme I can be used in the synthesis of compounds disclosed herein. A cycloalkenol such as cyclopent-3-en-1-ol 101 can be activated by formation of a sulfonate ester 102 (for example, $8^{101}$=Me or toluene) by using, for example, either General Procedure A or General Procedure L. Cyclopropanation with a carbenoid, by using, for example, General Procedure B, produces bicyclo compound 103. The sulfonate ester can be displaced in a Williamson ether synthesis, by using, for example, General Procedure C, to give ether 104, which in turn is converted to ketone 105 via an organolithium (variant Ia: General Procedure J) or a Weinreb amide 106 (variant Ib: General Procedure D).

SCHEME II

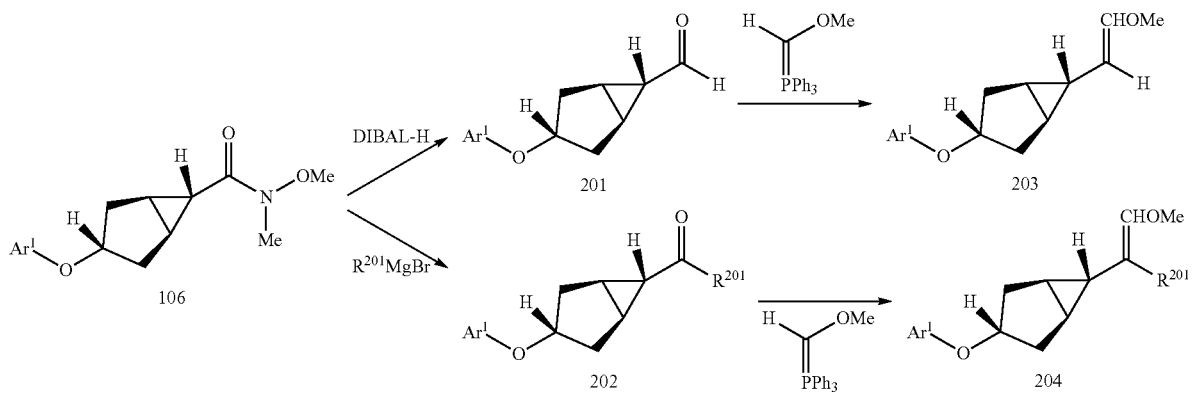

Scheme II can be used to convert Weinreb amide 106 to alkenes. Reduction of 106 affords aldehyde 201; alternatively, 106 can be converted to ketone 202, using, for example, General Procedure E. Conversion of aldehyde 201 and ketone 202, using, for example, General Procedure F, affords enol ethers 203 and 204, respectively. (For purposes of successive schemes, 203 can be considered as a special case of 204, for which $R^{201}$=H.)

301, which can be oxidized to carboxylic acid 302, using, for example, General Procedure H. Coupling of the carboxylic acid with amine 303, using, for example, General Procedure I, General Procedure O, or General Procedure Q, provides amide 304. If desired, the diastereomers of 304 can be separated at this stage, to afford 304a and 304b.

Variations of Scheme III use different amide coupling conditions. Variant IIIa: General Procedure I; Variant IIIb: General Procedure O; and Variant IIIc: General Procedure P.

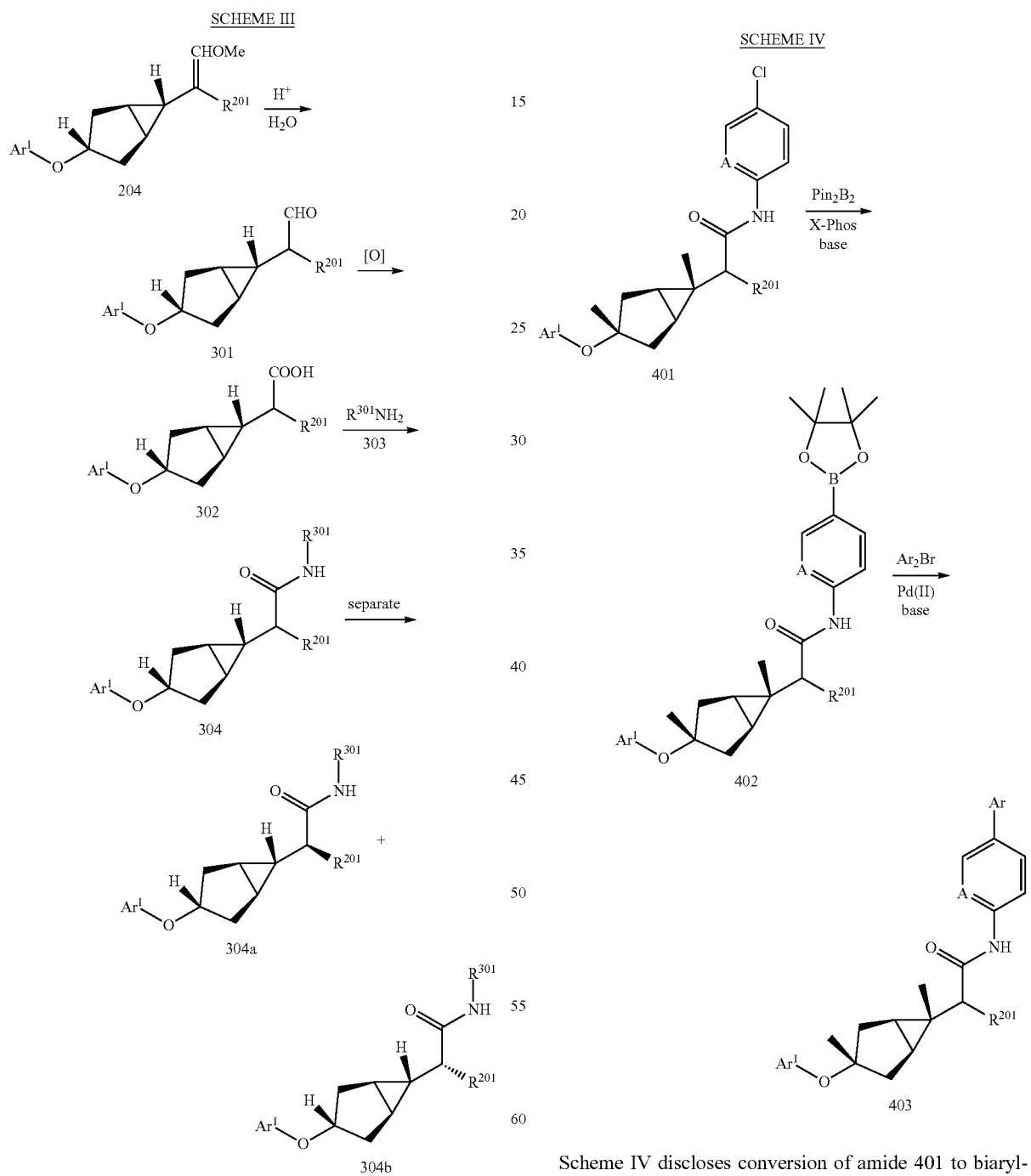

Scheme III can be used to convert enol ether 204 to carboxylic acid derivatives. Hydrolysis of the enol ether, using, for example, General Procedure G, provides aldehyde Scheme IV discloses conversion of amide 401 to biaryl-type compounds. Amide 401 can be synthesized from Scheme II, using 4-chloroaniline (A=CH), 2-amino-5-chloropyridine (A=N), or a similar aryl compound. Conversion to the arylboronate 402 is accomplished by metal-catalyzed substitution of the chlorine, by using, for example, the Miyaura borylation of General Procedure R. Arylboronate can in turn be converted to a biaryl 403 by means of coupling with an aryl halide, by using, for example, the Suzuki coupling of General Procedure S.

SCHEME V

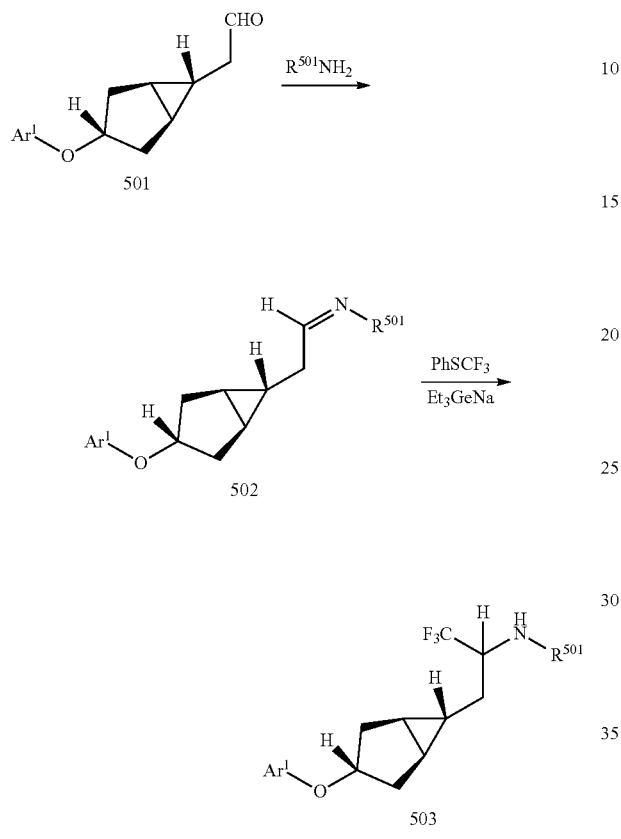

Scheme V discloses manipulation of aldehyde 501 (equivalent to compound 301, with $R^{201}$=H) to provide a trifluoromethyl group. Aldehyde 501 is converted to imine 502, which in turn is reacted under established conditions (Tetrahedron Lett. 1997, 3443-3446) to give the substituted compound 503.

SCHEME VI

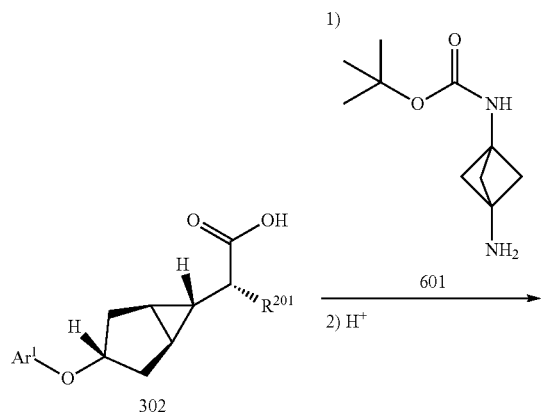

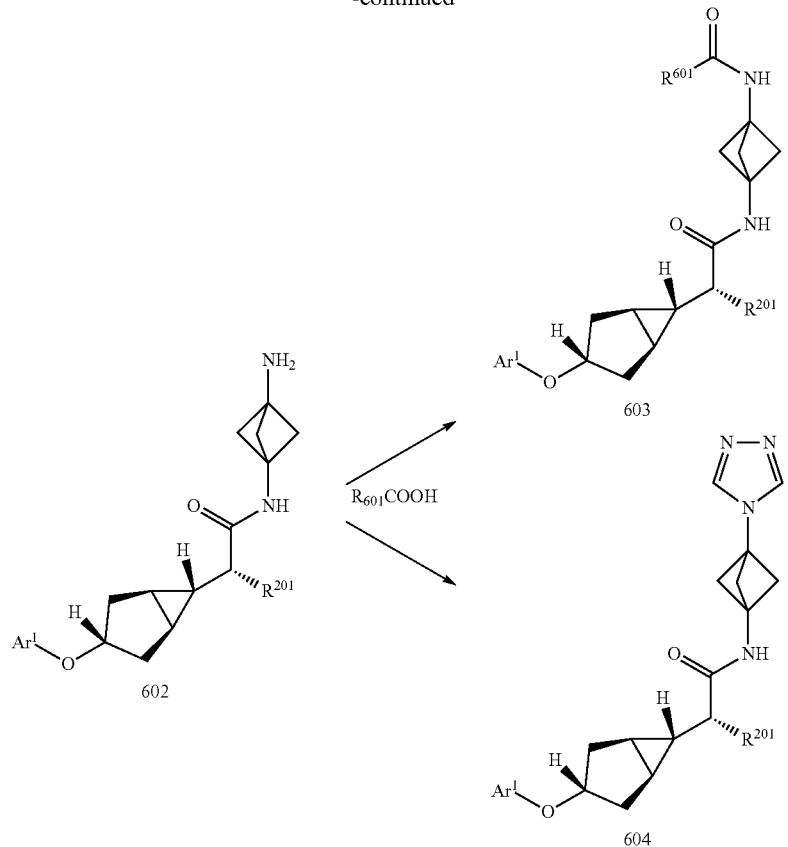

Scheme VI can be used to introduce alkyl, cycloalkyl, and heterocycloalkyl moieties. Carboxylic acid 302 can be derived from Scheme II. A single isomer of 302 is shown in Scheme VI; however, the synthesis can be carried out with either isomer, or a mixture of isomers. Reaction of a suitable monoprotected diamine, such as mono-Boc protected bicyclo diamine 601, followed by deprotection, can provide amide 602. Any one of General Procedure I, General Procedure O, or General Procedure Q can be used for synthesis of the amide. The newly deprotected amine group can be converted to various functionalities, including the acyl group of 603, and the heterocycle of 604.

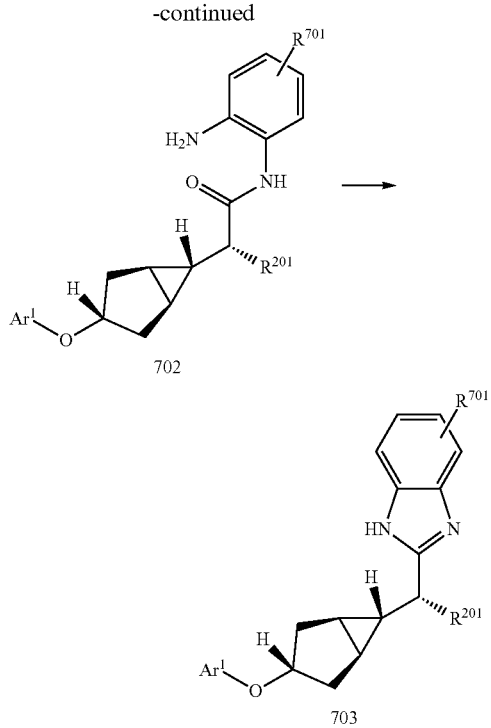

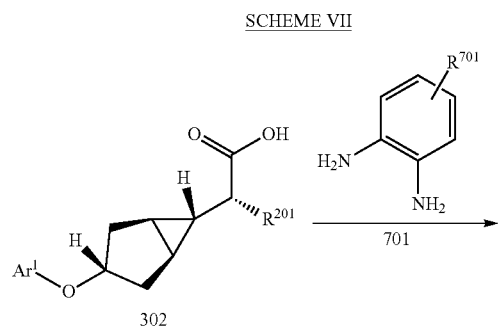

Scheme VII can be used to provide benzo[d]imidazole compounds. Carboxylic acid 302 is coupled with a suitable 1,2-diaminoaryl compound 701 to form amide 702. Dehydrative ring closure provides benzo[d]imidazole 703, using, for example, General Procedure P.

to provide amide 902. If desired, the diastereomers of 304 can be separated at this stage, to afford 902a and 902b (not shown).

SCHEME VIII

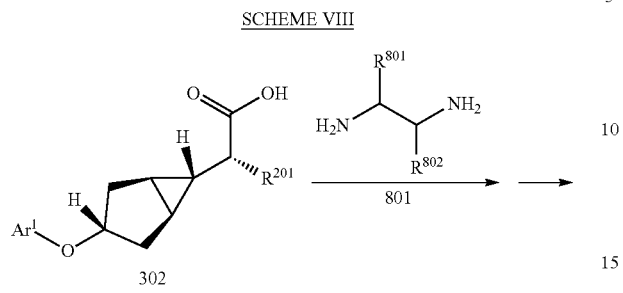

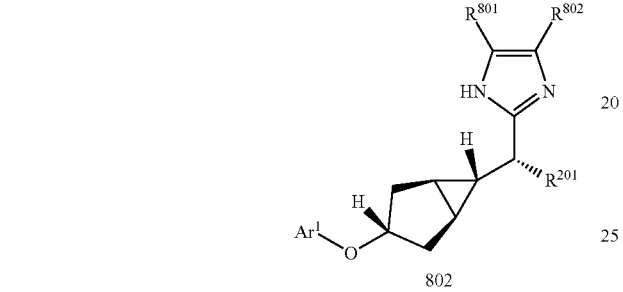

Scheme VIII can be used to provide imidazole compounds. Carboxylic acid 302 is coupled with a suitable ethylenediamine compound 801 to form an amide (not shown), which forms benzo[d]imidazole 702 on dehydrative ring closure, using, for example, General Procedure P.

SCHEME IX

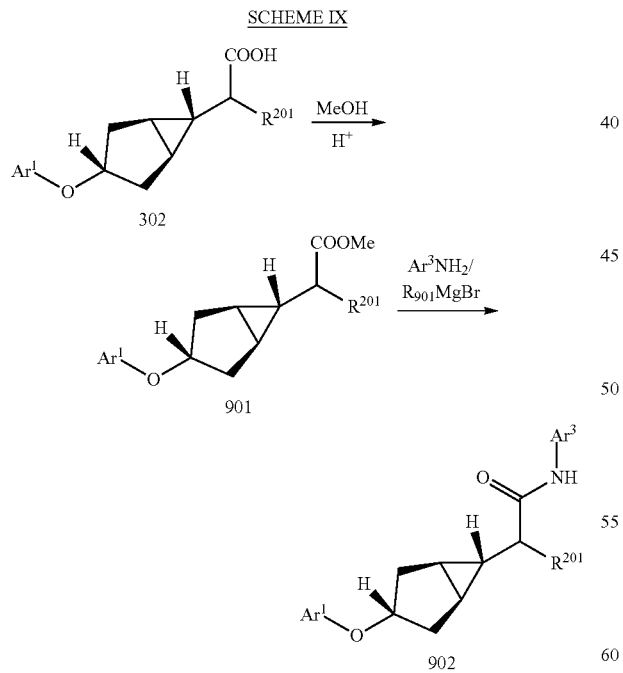

Scheme IX provides an alternative method for amide synthesis. Carboxylic acid 302 is converted to the corresponding methyl ester 901, by using, for example, General Procedure K. The ester can then be reacted with the anion of an arylamine, by using, for example, General Procedure N,

SCHEME X

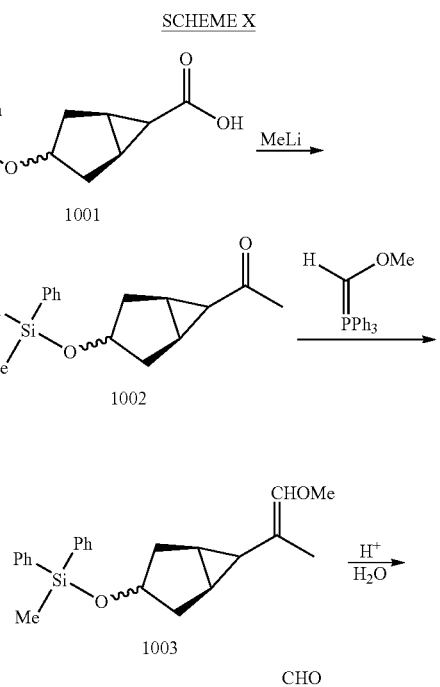

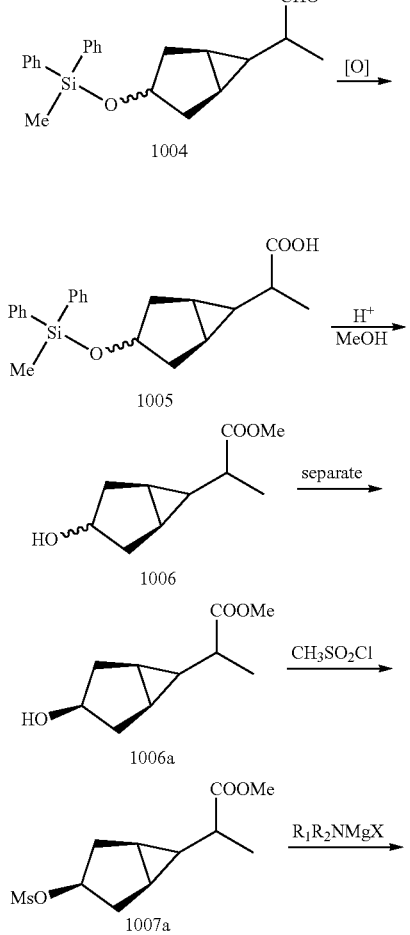

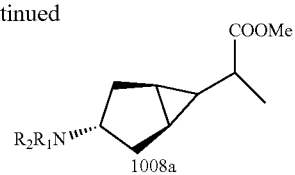

An alternative sequence for preparation of the compounds in this disclosure is presented above. A silyl protected ether such as 1001 is reacted to form the methyl ketone, by using, for example, General Procedure J. The ketone 1002, in turn, is reacted with a Wittig reagent, using, for example, General Procedure F, to give enol ether 1003. Hydrolysis of the enol ether, by using, for example, General Procedure G, gives aldehyde 1005, which in turn is oxidized, by using, for example, General Procedure H. Exposure to methanol under acidic conditions both accomplishes Fischer esterification of the carboxylic acid, and deprotection of the silyl ether, in General Procedure T. At this point, isomers at the secondary hydroxyl of 1006 can be separated. For convenience, the single isomer is designated as 1006a. The active methanesulfonate ("mesylate") ester 1007a is formed, by using, for example, General Procedure L. The mesylate group is then displaced by an amine anion, for example, the amine anion formed upon reaction of an amine with a Grignard reagent. Compound 1008a, which is formed under these conditions, can be carried forth by any of the Schemes disclosed elsewhere.

The invention is further illustrated by the following examples.

Example 1

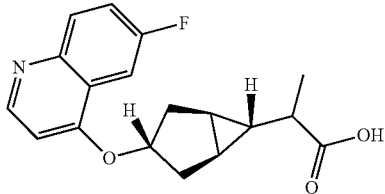 [SMILES: CC(C(=O)O)[C@H]1[C@@H]2C[C@@H](Oc3ccnc4ccc(F)cc34)C[C@@H]21]

2-((1R,3s,5S,6r)-3-((6-fluoroquinolin-4-yl)oxy)bicyclo[3.1.0]hexan-6-yl)propanoic acid General Procedure A, for preparation of tosylates, is exemplified in the following reaction.

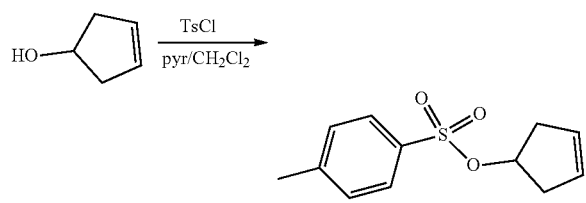

Cyclopent-3-en-1-yl 4-methylbenzenesulfonate

To a solution of cyclopent-3-ene-1-ol (70.2 g, 835 mmol) in pyridine (150 mL) and DCM (300 ml) cooled at 4° C. under $N_2$ atm was added slowly with stirring 4-toluenesulfonyl chloride (175 g, 918 mmol). The mixture was then stirred under $N_2$ atm at this temperature for 1 h, then stood in cold room at 4° C. for 48 h. Most of the dichloromethane was evaporated at reduced pressure. The mixture was diluted with EtOAc/Hexane (20%, 600 ml) and washed with water (5×) and brine. The aqueous phases were back extracted with EtOAc/hexanes (20%, 1×400 ml), the organic layers combined, dried over $MgSO_4$, and then filtered through a short plug (3 cm×11 cm) of silica (washed with a further 1000 ml 20% EtOAc/Hexane). The solvent was evaporated at reduced pressure to give a colorless oil. The residual solvent in the crude product was azeotroped with hexanes then twice with toluene. The resulting colorless oil was further dried by azeotroping once with hexanes and then crystallizing by diluting with an equal volume of hexane and heating at 50° C. The resulting biphasic mixture of colorless oil and solids in hexanes was allowed to age at RT overnight. The solid was removed by filtration and washed with cold hexanes and then dried in-vacuum to give the title compound (173 g, 727 mmol, 87%).

$^1$H NMR (CHLOROFORM-d) δ: 7.79 (d, J=7.9 Hz, 2H), 7.34 (d, J=7.9 Hz, 2H), 5.65 (s, 2H), 5.11-5.24 (m, 1H), 2.59-2.67 (m, 2H), 2.48-2.55 (m, 2H), 2.45 (s, 3H).

General Procedure B, for cyclopropanation of alkenes, is exemplified in the following reaction.

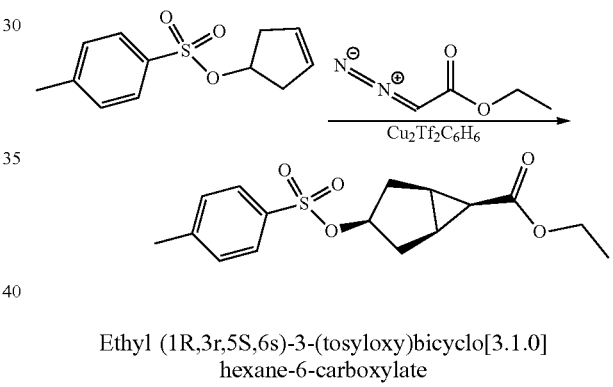

Ethyl (1R,3r,5S,6s)-3-(tosyloxy)bicyclo[3.1.0]hexane-6-carboxylate

To a flask containing the product from the previous step (60.45 g, 254 mmol) in DCM (100 mL) was added, under nitrogen, a solution of copper(I) triflate.0.5 benzene complex (1.03 g) and (4S,4'S)-2,2'-(propane-2,2-diyl)bis(4-isopropyl-4,5-dihydrooxazole) (1 ml) in DCM (10 mL) prepared under $N_2$ and ultrasonication to give a green solution. Ethyl diazoacetate (20 mL containing 13-20 wt % DCM and diluted 1:0.5 with DCM) was added dropwise via syringe pump at a rate of 9 mL/h over ~3.5 h. A further 30 mL of ethyl diazoacetate (undiluted) was then added at a rate of 8 mL/h (for the first 12 mL added) then slowed to 4 mL/h (for remaining 18 ml), with provision for venting the $N_2$ gas that was generated by the reaction. Following completion of addition, the reaction was stirred overnight. To the reaction was then added ethyl diazoacetate (20 mL containing 13-20 wt % DCM and diluted 1:0.5 with DCM) at a rate of 4 mL/h, then again stirred RT overnight. Total quantity of ethyl diazoacetate added was 70 mL containing 13-20 wt % DCM. The solvent was then removed at reduced pressure, the residue taken up in 10% EtOAc/Hexanes, passed through pad of silica gel (15 cm high×10.5 cm diameter). The diethyl fumarate (or maleate) (colorless liquid) was eluted from the plug with 10% EtOAc/Hexanes. A mixture of fumarate and starting olefin (colorless oil 21 g) followed by a mixture of isomers of the desired product were eluted with 20% EtOAc/hexanes. The desired isomer of the product was crystalized from Et₂O/Hexane to give the title compound (41 g, 126 mmol, 50%) as colorless crystalline solid (rods). If desired, the product can be further purified by flash chromatography.

¹H NMR (600 MHz, DMSO-d₆) δ ppm 1.10-1.20 (m, 3H) 1.52-1.58 (m, 1H) 1.71-1.78 (m, 2H) 1.82-1.91 (m, 2H) 2.03-2.13 (m, 2H) 2.38-2.45 (m, 3H) 3.93-4.04 (m, 2H) 4.60-4.74 (m, 1H) 7.42-7.55 (m, 2H) 7.73-7.85 (m, 2H).

General Procedure C, for Williamson ether synthesis, is exemplified in the following reaction.

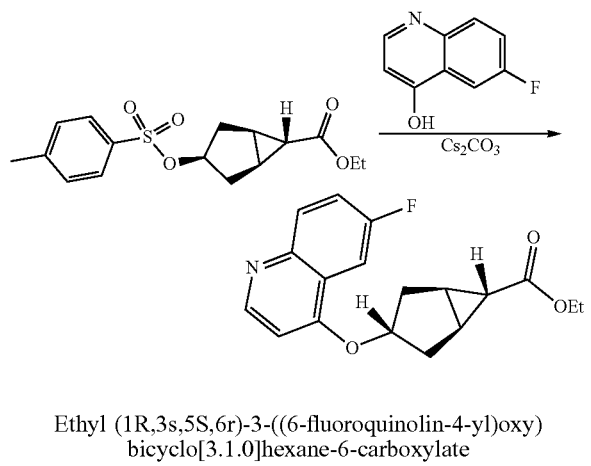

Ethyl (1R,3s,5S,6r)-3-((6-fluoroquinolin-4-yl)oxy)bicyclo[3.1.0]hexane-6-carboxylate To a solution of the product from the previous step (8.0 g, 24.66 mmol) in NMP (40 ml) were added 6-fluoroquinolin-4-ol (4.22 g, 25.9 mmol) and Cs₂CO₃ (9.64 g, 29.6 mmol) and the resulting mixture was stirred at RT 3 days under N₂. The solution was added to ice/cold water and stirred until ice melted and brown precipitate formed. The mixture was filtered, the solid washed with ice/cold water, and dried under vacuum to give the title compound (5.86 g, 18.6 mmol, 75%).

MS (ES⁺) $C_{18}H_{18}FNO_3$ requires: 315, found: 316 [M+H]⁺.

General Procedure D, for Weinreb amide synthesis, is exemplified in the following reaction.

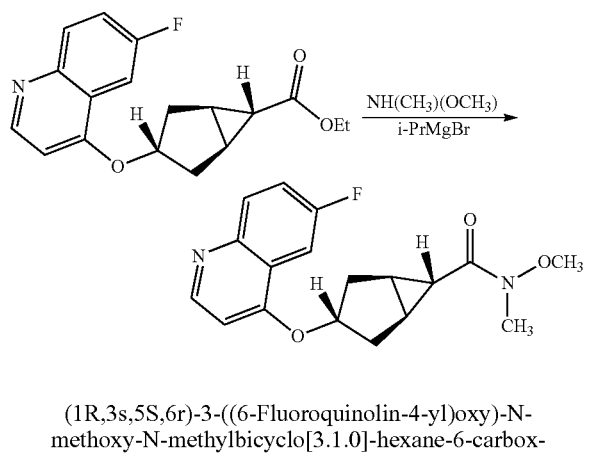

(1R,3s,5S,6r)-3-((6-Fluoroquinolin-4-yl)oxy)-N-methoxy-N-methylbicyclo[3.1.0]-hexane-6-carboxamide To a suspension of the product from the previous step (3.97 g, 12.6 mmol) in THF (21 ml) was added N,O-dimethylhydroxylamine hydrochloride (2.46 g, 25.2 mmol) and the resulting mixture was sonicated for 1 min and stirred at RT for 5 min then cooled to −13° C. in an acetone ice bath. To the cooled reaction was added dropwise over 20 mins, isopropyl magnesium chloride (2M, 34.6 ml, 69.2 mmol) and during the addition the temp was kept between −10 to −15° C. After the addition the reaction was stirred at −10 to −15° C. for 1 hr. The reaction was slowly and portion wise poured into a stirring mixture of ice and saturated NH₄Cl (500 ml, total). The mixture was stirred for 1 h and then extracted with EtOAc/DCM mixture (200/100 ml) and DCM (2×200 ml). The organic layers combined, dried over MgSO₄, filtered, and concentrated to give the title compound (3.89 g, 11.8 mmol, 94% yield) as a white-to-light yellow solid.

MS (ES⁺) $C_{18}H_{19}FN_2O_3$ requires: 330, found: 331[M+H]⁺.

General Procedure E, for synthesis of a methyl ketone from a Weinreb amide, is exemplified in the following reaction.

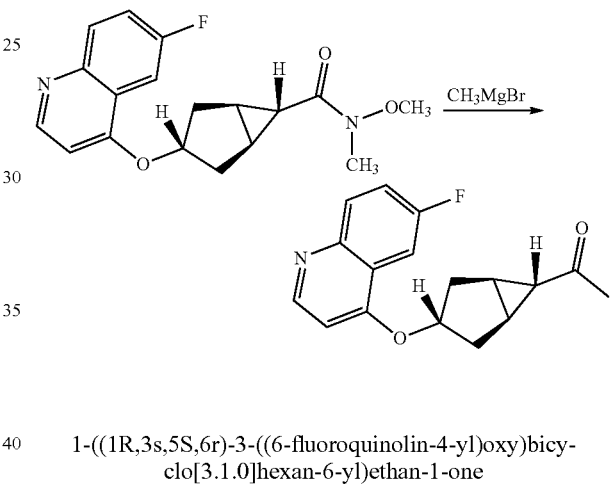

1-((1R,3s,5S,6r)-3-((6-fluoroquinolin-4-yl)oxy)bicyclo[3.1.0]hexan-6-yl)ethan-1-one To a cooled −78° C. solution of the product from the previous step (3.89 g, 11.8 mmol) in THF (47.1 ml) was added methyl magnesium bromide (5.89 ml, 17.66 mmol) dropwise and the resulting mixture was stirred at −78° C. for 15 min, then at RT overnight. The reaction was poured into mixture of ice and saturated NH₄Cl and stirred until ice melted. The mixture was extracted with EtOAc (3×200 ml). The organic layers were washed with brine, combined, dried over MgSO4, filtered, and concentrated to give the title compound (3.34 g, 11.7 mmol, 99% yield).

MS (ES⁺) $C_{17}H_{16}FNO_2$ requires: 285, found: 286 [M+H]⁺.

General Procedure F, for Wittig synthesis of a vinyl ether, is exemplified in the following reaction.

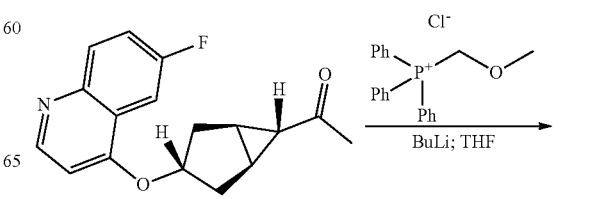

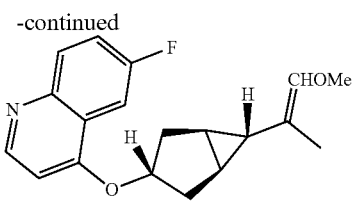

6-Fluoro-4-(((1R,3s,5S,6r)-6-((E)-1-methoxyprop-1-en-2-yl)bicyclo[3.1.0]hexan-3-yl)oxy)quinoline To a cooled −78° C. solution of (methoxymethyl)triphenylphosphonium chloride (6.42 g, 18.73 mmol) in THF (30 ml) was added n-butyllithium (2.5M in THF, 7.02 ml, 17.6 mmol) dropwise over 8 min. The reaction was stirred at −78° C. for 25 min and then at 0° C. for 30 min. To the reaction was added the product from the previous step (3.34 g, 11.71 mmol) dissolved in THF (10 ml), and the reaction was stirred at 0° C. for 10 min then at RT. The reaction was poured into a mixture of ice and saturated NH$_4$Cl (300 ml) and the resulting mixture was extracted with EtOAc (3×150 ml). The organic layers were washed with brine, combined, dried over MgSO$_4$, filtered, concentrated, and purified by flash chromatography (30 to 100% EtOAc in Hexanes) to give the title compound (2.83 g, 9.03 mmol, 77% yield) as a yellow, viscous oil.

MS (ES$^+$) C$_{19}$H$_{20}$FNO$_2$ requires: 313, found: 314 [M+H]$^+$.

General Procedure G, for hydrolysis of a vinyl ether, is exemplified in the following reaction.

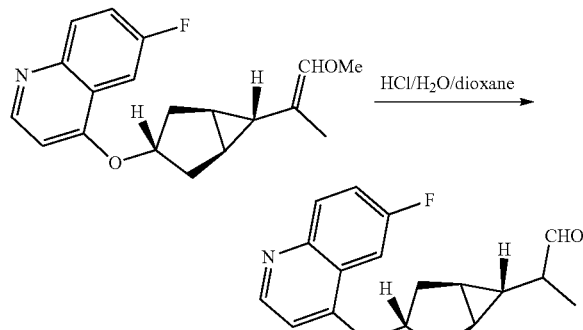

2-((1R,3s,5S,6r)-3-((6-fluoroquinolin-4-yl)oxy)bicyclo[3.1.0]hexan-6-yl)propanal To a solution of the product from the previous step (2.8 g, 8.9 mmol) in THF (40 ml) and H$_2$O (10.00 ml) was added HCl (4M in dioxane, 1.6 ml, 17.9 mmol) and the resulting mixture was stirred at 70° C. for 2 h. The reaction was diluted with EtOAc (150 ml) and water (250 ml) and the mixture neutralized with saturated NaHCO$_3$. The resulting mixture was mixed, the organic layer separated, and the aqueous layer extracted with EtOAc (2×150 ml). The organic layers were washed with brine, combined, dried over MgSO$_4$, filtered, concentrated, dissolved in minimal DCM and purified by flash chromatography (30 to 100% EtOAc in Hexanes) to give the title compound (2.1 g, 7.02 mmol, 79% yield).

MS (ES$^+$) C$_{18}$H$_{18}$FNO$_2$ requires: 299, found: 300 [M+H]$^+$.

General Procedure H, for oxidation of an aldehyde, is exemplified in the following reaction.

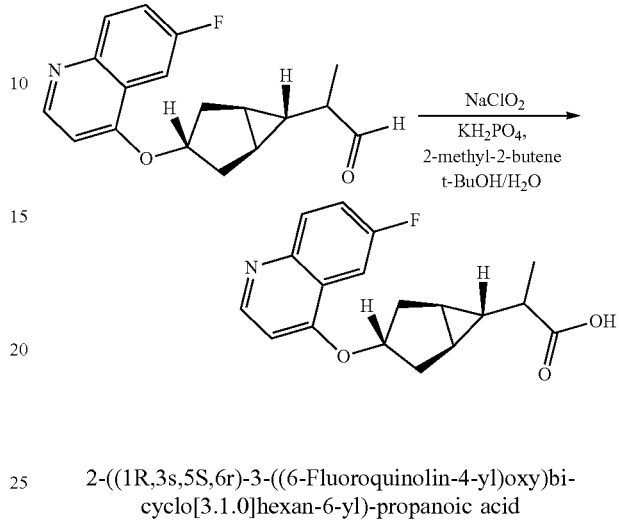

2-((1R,3s,5S,6r)-3-((6-Fluoroquinolin-4-yl)oxy)bicyclo[3.1.0]hexan-6-yl)-propanoic acid To a cooled 0° C. solution of the product from the previous step (2.1 g, 7.02 mmol) in t-BuOH (26.3 ml) and 2-methyl-2-butene (3.7 ml, 35 mmol) was added dropwise a freshly prepared solution of KH$_2$PO$_4$ (1.9 g, 14 mmol) and NaClO$_2$ (1.3 g, 14 mmol) in H$_2$O (8.8 ml). The resulting mixture was stirred at 0° C. for 0.5 h, ice bath change and then allowed to warm to RT overnight. The reaction mixture was diluted with water (150 ml), filtered, the precipitate rinsed with water and hexanes and dried in vacuo to give the title compound as a white solid (0.75 g). The filtrate was extracted with DCM (3×75 ml), the organic extracts combined, washed with brine, dried over MgSO$_4$, filtered, and concentrated to give the desired product (1 g). The precipitate and the extracted solid were combined to give the title compound (1.93 g, 6.23 mmol, 87% yield) as a white solid.

MS (ES$^+$) C$_{18}$H$_{18}$FNO$_3$ requires: 315, found: 316 [M+H]$^+$. $^1$H NMR (600 MHz, DMSO-d$_6$) δ ppm 0.69-0.85 (m, 1H), 1.06-1.17 (m, 3H), 1.22-1.43 (m, 2H), 1.61-1.74 (m, 1H), 1.90-2.04 (m, 2H), 2.39-2.50 (m, 2H), 4.80-4.96 (m, 1H), 7.04-7.14 (m, 1H), 7.57-7.69 (m, 1H), 7.70-7.79 (m, 1H), 7.93-8.04 (m, 1H), 8.61-8.72 (m, 1H), 11.42-12.86 (m, 1H).

Example 2

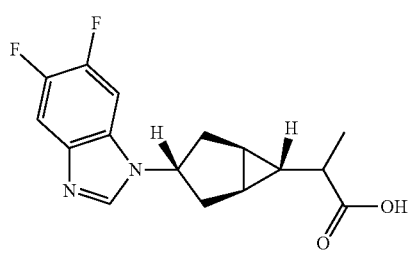 [SMILES: CC(C(=O)O)[C@H]1[C@@H]2C[C@@H](n3cnc4cc(F)c(F)cc43)C[C@@H]21]

2-((1R,3R5S,6r)-3-(5,6-difluoro-1H-benzo[d]imidazol-1-yl)-bicyclo[3.1.0]hexan-6-yl)propanoic acid General Procedure J, for synthesis of a methyl ketone directly from a carboxylic acid, is exemplified in the following reaction.

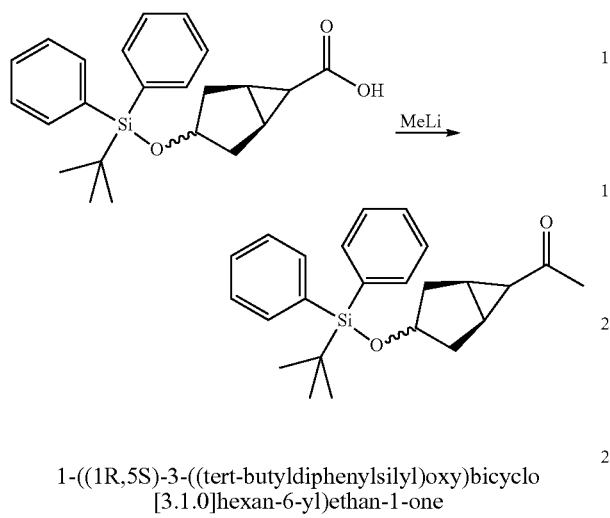

1-((1R,5S)-3-((tert-butyldiphenylsilyl)oxy)bicyclo[3.1.0]hexan-6-yl)ethan-1-one

To a solution of (1R,5S)-3-((tert-butyldiphenylsilyl)oxy)bicyclo[3.1.0]hexane-6-carboxylic acid (27.2 g, 71.5 mmol) in THF (75 ml) was added methyllithium (1.6M Et$_2$O) (115 ml, 184 mmol) and the resulting mixture was stirred at 0° C. for 5 min then RT overnight. Reaction was poured into an ice cold HCl (0.5M solution) and the mixture was diluted with EtOAc (50 mL) and the phases were separated. The aqueous layer was extracted with EtOAc (2×50 mL). The combined organic layers were washed with brine (30 mL), combined, dried over MgSO$_4$, filtered and concentrated. The residue was purified via silica gel chromatography (0-10% EtOAc in Hexanes) to give the title compound (18 g, 47.5 mmol, 66.5% yield) as a colorless oil. NMR data confirmed the desired materials.

MS (ES+) C$_{24}$H$_{30}$O$_2$Si requires: 378, found: 391 [M+Na]$^+$.

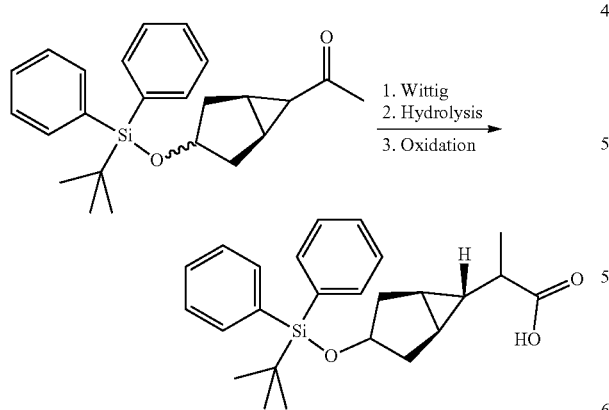

2-((1R,5S,6r)-3-((tert-butyldiphenylsilyl)oxy)bicyclo[3.1.0]hexan-6-yl)propanoic acid The title compound was obtained by the procedure set forth in Schemes II and III.

General Procedure K, for methyl ester formation and silyl ether deprotection, is exemplified in the following reaction.

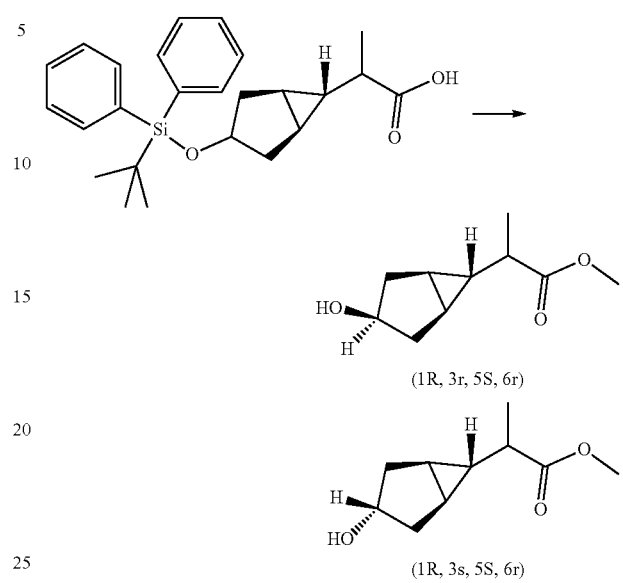

Methyl 2-((1R,3r,5S,6r)-3-hydroxybicyclo[3.1.0]hexan-6-yl)propanoate

To a solution of 2-((1R,5S,6r)-3-((tert-butyldiphenylsilyl)oxy)bicyclo[3.1.0]hexan-6-yl)propanoic acid (18.7 g, 45.8 mmol) in MeOH (458 ml) cooled in an ice bath was added sulfuric acid (25 ml, 458 mmol) slowly and the resulting mixture was stirred at 65° C. for 1.5 hr. The reaction was cooled in an ice bath and neutralized by the slow addition of TEA (65 ml, 467 mmol). The reaction was concentrated, diluted with EtOAc (200 ml) and with water (500 ml) and brine (200 ml), and the phases were separated. The aqueous layer was extracted twice with EtOAc (200 ml/ea.), the organic layers were combined, dried over MgSO$_4$, filtered and concentrated, to give crude material (viscous oil/semi-solid, 17 g). The crude was dissolved in minimal DCM, loaded onto a silica gel plug and purified by flash chromatography (10 to 80% EtOAc in hexanes) to give the title compound (3.02 g, 16.39 mmol, 35.8% yield) as a clear light yellow oil. Also obtained was the (1R,3r,5S,6r) isomer (1.4 g, 7.60 mmol, 16.60% yield) as a clear light yellow oil.

MS (ES$^+$) C$_{10}$H$_{16}$O$_3$ requires: 184, found: 185 [M+H]$^+$, 207 [M+Na]$^+$.

General Procedure L, for synthesis of a methanesulfonyl ester, is exemplified below.

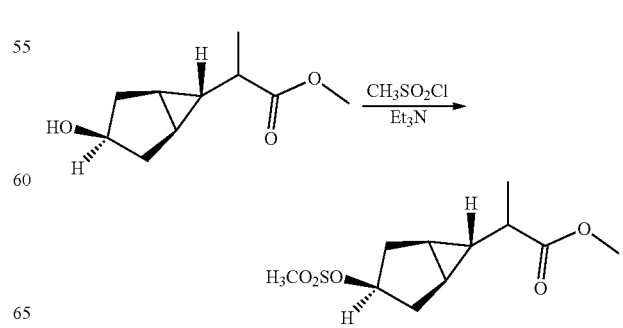

Methyl 2-((1R,3r,5S,6r)-3-((methylsulfonyl)oxy)bicyclo[3.1.0]hexan-6-yl)-propanoate To a cooled 0° C. solution of methyl 2-((1R,3r,5S,6r)-3-hydroxybicyclo[3.1.0]-hexan-6-yl)propanoate (3.02 g, 16.4 mmol) in DCM (54.6 ml) was added TEA (4.6 ml, 33 mmol) and Ms-Cl (1.9 ml, 24.6 mmol) dropwise and the resulting mixture was stirred at 0° C. 0.5 h and then at RT for 3 hr. The reaction was poured into an ice/0.5M HCl mixture and the mixture stirred until most of the ice melted. The mixture was extracted with EtOAc (3×). The organics were washed with brine, combined, dried over MgSO₄, and concentrated to give the title compound (4.02 g, 15.32 mmol, 93% yield) as a clear viscous liquid. MS (ES⁺) $C_{11}H_{18}O_5S$ requires: 262, found: 263 [M+H]⁺, 285 [M+Na]⁺.

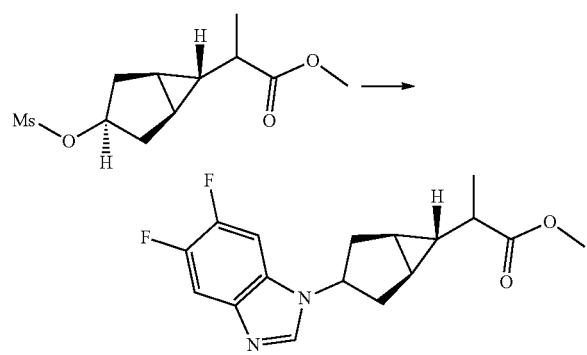

Methyl 2-((1R,5S,6r)-3-(5,6-difluoro-1H-benzo[d]imidazol-1-yl)-bicyclo[3.1.0]-hexan-6-yl)propanoate The title compound was synthesized from the preceding compound by a procedure similar to General Procedure C. MS (ES⁺) $C_{17}H_{18}F_2N_2O_2$ requires: 320, found: 321 [M+H]⁺.

General Procedure M, for LiOH hydrolysis of an ester, is exemplified in the following reaction.

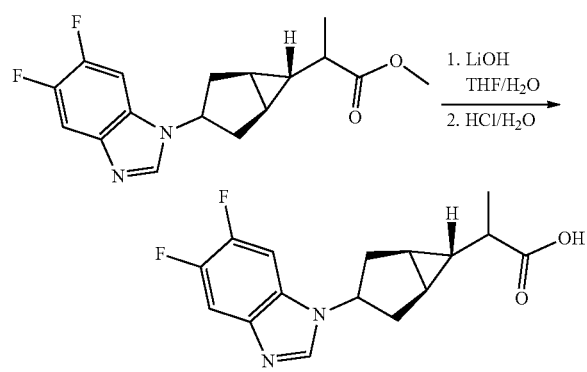

2-((1R,5S,6r)-3-(5,6-difluoro-1H-benzo[d]imidazol-1-yl)bicyclo[3.1.0]hexan-6-yl)-propanoic acid To a solution of methyl 2-((1R,5S,6r)-3-(5,6-difluoro-1H-benzo[d]-imidazol-1-yl)bicyclo[3.1.0]hexan-6-yl)propanoate (from the synthesis of the Example 1 compound) (2.17 g, 6.77 mmol) in THF (7.3 ml) were added H₂O (2.4 ml) and then LiOH 2M (6.8 ml, 13.6 mmol) and the resulting mixture was stirred at room temperature. The reaction was diluted with water (50 ml), neutralized by the addition of HCl 1M (13.5 ml, 13.5 mmol) and stirred for 1.5 h at room temperature. The mixture was filtered and the resulting precipitate was washed with water (5×20 ml) and hexanes (5×) to give the title compound (1.82 g, 5.96 mmol, 88% yield) as a white solid. MS (ES⁺) $C_{16}H_{16}F_2N_2O_2$ requires: 306, found: 307 [M+H]⁺.

Example 3

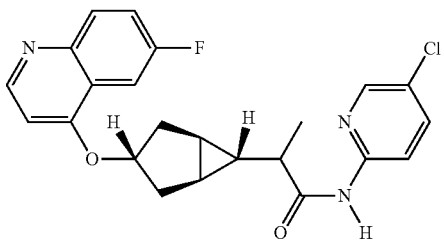 [SMILES: CC(C(=O)Nc1ccc(Cl)cn1)[C@H]1[C@@H]2C[C@@H](Oc3ccnc4ccc(F)cc34)C[C@@H]21]

N-(5-chloropyridin-2-yl)-2-((1R,3s,5S,6r)-3-((6-fluoroquinolin-4-yl)oxy)-bicyclo[3.1.0]hexan-6-yl)propanamide General Procedure I, for amide coupling with T3P, is exemplified in the following reaction.

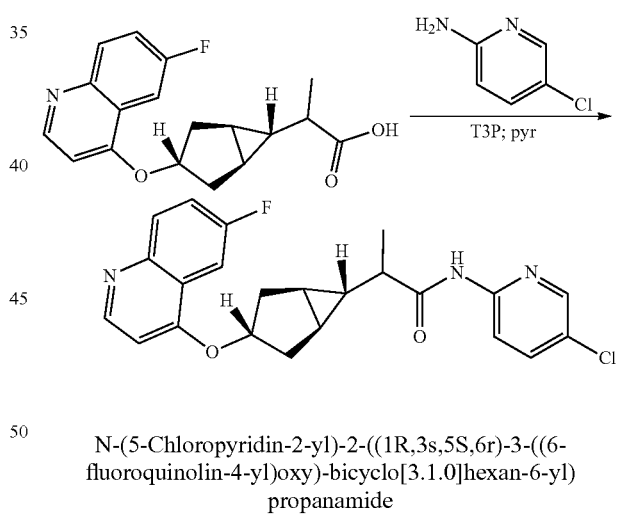

N-(5-Chloropyridin-2-yl)-2-((1R,3s,5S,6r)-3-((6-fluoroquinolin-4-yl)oxy)-bicyclo[3.1.0]hexan-6-yl)propanamide To a suspension of the Example 1 compound (20 mg, 0.063 mmol) in EtOAc (254 μl) were added 5-chloropyridin-2-amine (8.31 mg, 0.070 mmol), pyridine (15.39 μl, 0.190 mmol), T3P 50% in EtOAc (76 μl, 0.127 mmol) and the resulting mixture was stirred at 65° C. overnight. The reaction was mixed with EtOAc (2 ml) and saturated NaHCO₃. The layers were separated, the aqueous layer was extracted with EtOAc (1×2 ml). The organic layers were combined, washed with brine, dried over Na₂SO₄, decanted, concentrated, and purified by flash chromatography (0 to 100% of 90:10:1 DCM:MeOH:NH₄OH in DCM) to give the title compound (25 mg, 0.059 mmol, 93% yield) as a white solid.

MS (ES+) C23H21ClFN3O2 requires: 426, found: 427 [M+H]+. 1H NMR (600 MHz, DMSO-d6) δ ppm 0.84-0.91 (m, 1H) 1.14-1.20 (m, 3H) 1.23-1.58 (m, 2H) 1.88-2.03 (m, 3H) 2.34-2.50 (m, 2H) 4.80-4.94 (m, 1H) 7.07-7.14 (m, 1H) 7.59-7.66 (m, 1H) 7.71-7.77 (m, 1H) 7.88-7.93 (m, 1H) 7.96-8.03 (m, 1H) 8.16-8.23 (m, 1H) 8.33-8.40 (m, 1H) 8.62-8.68 (m, 1H) 10.42-10.57 (m, 1H).

Example 4

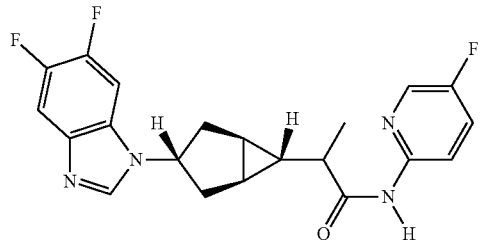 [SMILES: CC(C(=O)Nc1ccc(F)cn1)[C@H]1[C@@H]2C[C@@H](n3cnc4cc(F)c(F)cc43)C[C@@H]21]

2-((1R,3s,5S,6r)-3-(5,6-difluoro-1H-benzo[d]imidazol-1-yl)bicyclo[3.1.0]hexan-6-yl)-N-(5-fluoropyridin-2-yl)propanamide General Procedure N, for Grignard amidation of an ester, is exemplified in the following reaction.

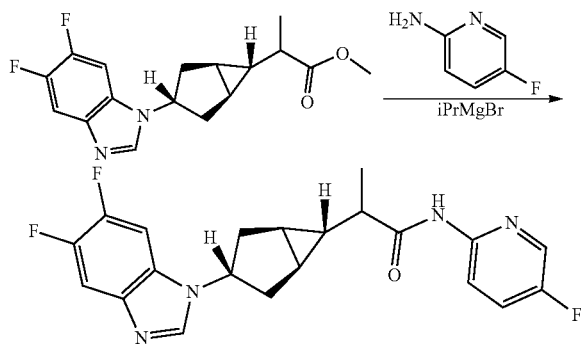

2-((1R,3s,5S,6r)-3-(5,6-difluoro-1H-benzo[d]imidazol-1-yl)bicyclo[3.1.0]hexan-6-yl)-N-(5-fluoropyridin-2-yl)propanamide To a cooled 0° C. solution of 5-fluoropyridin-2-amine (14 mg, 0.13 mmol) in THF (0.25 ml) were added isopropyl magnesium chloride (0.062 ml, 0.13 mmol). The resulting mixture was stirred at 0° C. for 5 min and then 10 min at room temperature. To the dark red/black reaction was added methyl 2-((1R,3s,5S,6r)-3-(5,6-difluoro-1H-benzo[d]imidazol-1-yl)bicyclo[3.1.0]hexan-6-yl)propanoate (20 mg, 0.062 mmol) dissolved in THF (0.25 ml) dropwise and the reaction stirred at room temperature overnight. To the reaction was added more amino pyridine (14 mg that was prepared the same way). Upon completion the reaction was quenched with saturated NH4Cl, and extracted with EtOAc (3×). The organic layers were combined, washed with brine, dried over MgSO4, filtered, concentrated, and purified by flash chromatography (0 to 100% of 90:10:1 DCM:MeOH: NH4OH in DCM) to give the title compound (15.4 mg, 0.038 mmol, 61.6% yield) as a light brown solid.

MS (ES+) C21H19F3N4O requires: 400, found: 401 [M+H]+. 1H NMR (600 MHz, DMSO-d6) δ ppm 1.15-1.22 (m, 4H) 1.25-1.61 (m, 2H) 1.94-2.36 (m, 5H) 4.59-4.72 (m, 1H) 7.68 (dd, J=10.95, 7.55 Hz, 1H) 7.74 (td, J=8.78, 2.83 Hz, 1H) 7.90 (dd, J=11.14, 7.37 Hz, 1H) 8.20 (dd, J=9.06, 4.15 Hz, 1H) 8.32 (d, J=3.02 Hz, 1H) 8.43 (s, 1H) 10.47 (s, 1H).

Example 5

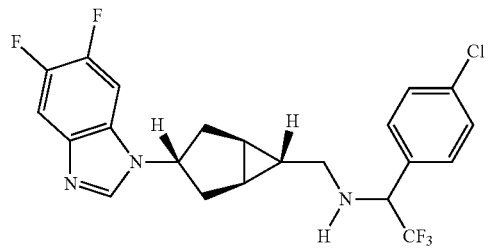 [SMILES: Fc1cc2ncn([C@H]3C[C@@H]4[C@@H](CNC(c5ccc(Cl)cc5)C(F)(F)F)[C@@H]4C3)c2cc1F]

1-(4-chlorophenyl)-N-((1R,3s,5S,6r)-3-(5,6-difluoro-1H-benzo[d]imidazol-1-yl)-bicyclo[3.1.0]hexan-6-yl)methyl)-2,2,2-trifluoroethan-1-amine

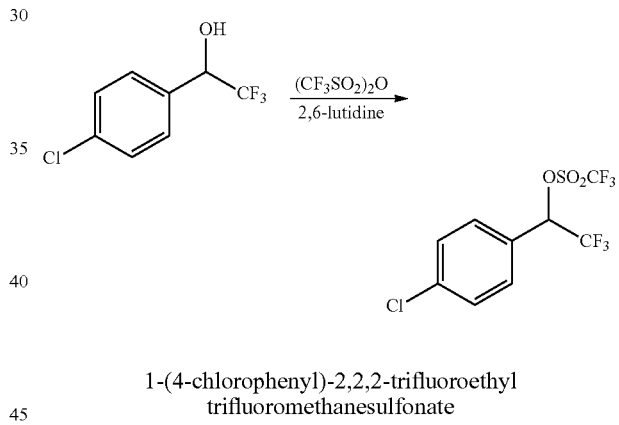

1-(4-chlorophenyl)-2,2,2-trifluoroethyl trifluoromethanesulfonate

To a cooled 0° C. solution of 1-(4-chlorophenyl)-2,2,2-trifluoroethan-1-ol (461 mg, 2.19 mmol) and 2,6-lutidine (0.41 mL, 3.5 mmol) in c-hexanes (11 mL) was added trifluoromethanesulfonic anhydride (0.56 mL, 3.3 mmol). The resulting mixture was stirred at 0° C. for 1.5 h. H2O (10 mL) and hexanes (10 mL) were added, and the layers were separated. The aqueous phase was extracted with hexanes (5 mL), the combined organic layers were washed with 1M HCl, dried over Na2SO4, filtered and concentrated under reduced pressure, to afford the title compound, which was used without further purification.

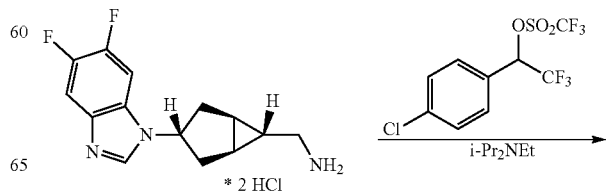

-continued

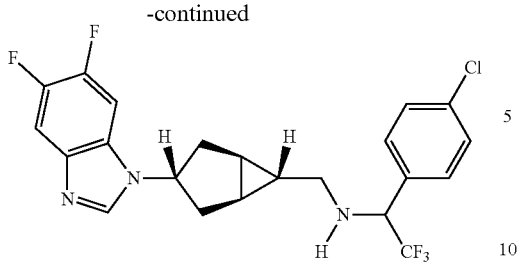

1-(4-chlorophenyl)-N-((1R,3s,5S,6r)-3-(5,6-difluoro-1H-benzo[d]imidazol-1-yl)-bicyclo[3.1.0]hexan-6-yl)methyl)-2,2,2-trifluoroethan-1-amine To a solution of ((1R,5S)-3-(5,6-difluoro-1H-benzo[d]imidazol-1-yl)bicyclo[3.1.0]hexan-6-yl)methanamine dihydrochloride (33 mg, 0.097 mmol) in DCM (973 μl) were added i-Pr$_2$NEt (85 μl, 0.49 mmol) and the product from the previous step (50 mg, 0.146 mmol) and the resulting mixture was stirred at 25° C. for 5 days. The volatiles were removed under reduced pressure and the residue was purified via silica gel chromatography (0-10% MeOH in DCM with 2% TEA to give the title compound (10 mg, 0.022 mmol, 22% yield) as a yellow liquid.

Mass: MS (ES$^+$) $C_{22}H_{19}ClF_5N_3$ requires: 455, found: 456 [M+H]$^+$.

Example 6

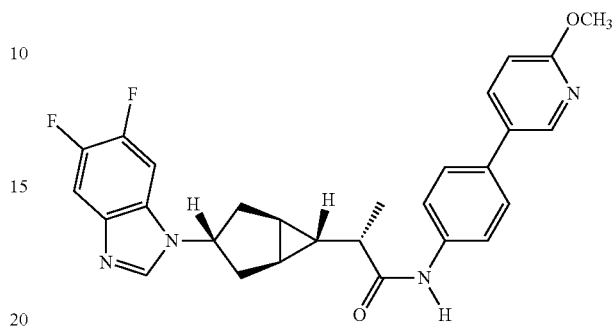

(S)-2-((1R,3R,5S,6r)-3-(5,6-difluoro-1H-benzo[d]imidazol-1-yl)bicyclo[3.1.0]hexan-6-yl)-N-(4-(6-methoxypyridin-3-yl)phenyl)propanamide General Procedure R, for Miyaura borylation of an aryl halide, is exemplified in the following reaction.

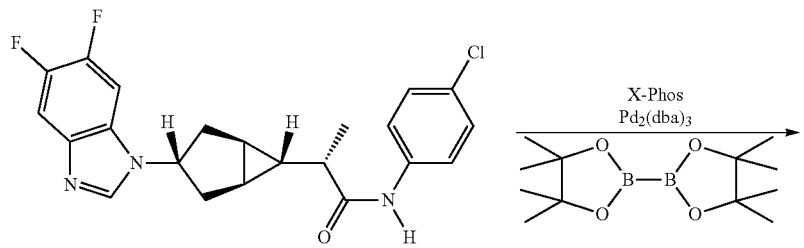

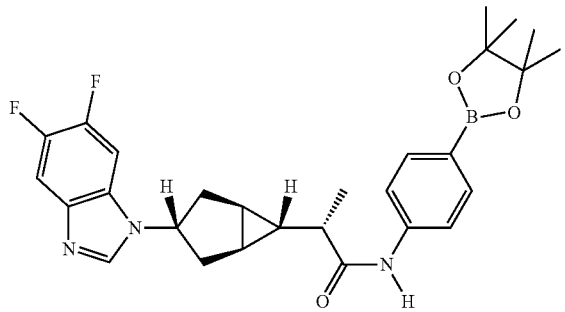

(S)-2-((1R,3R,5S,6r)-3-(5,6-difluoro-1H-benzo[d]imidazol-1-yl)bicyclo[3.1.0]-hexan-6-yl)-N-(4-(4,4,5,5-tetramethyl-1,3,2-dioxaborolan-2-yl)phenyl)propanamide To a vial containing the Example 5 compound (1.0 g, 2.42 mmol), KOAc (474 mg, 4.83 mmol), X-Phos (115 mg, 0.242 mmol), 4,4,4',4',5,5,5',5'-octamethyl-2,2'-bi(1,3,2-dioxaborolane) (1.23 g, 4.83 mmol), and Pd$_2$(dba)$_3$ (111 mg, 0.121 mmol) was added dioxane (previously degassed with N2, 5 ml). The reaction was heated in a dry block at 90° C. for 3 h, and room temperature overnight. The reaction mixture was filtered through CELITE® and the filtrate was diluted with DCM and washed with water, saturated NaHCO$_3$, and brine, dried over MgSO$_4$, filtered and concentrated. The crude was purified by flash chromatography (0-100% EtOAc in hexanes) to give the title compound as a white solid.

Mass: MS (ES$^+$) C$_{28}$H$_{32}$BF$_2$N$_3$O$_3$ requires: 507, found: 508 [M+H]$^+$.

General Procedure S, for Suzuki coupling of an aryl boronate with an aryl halide, is exemplified in the following reaction.

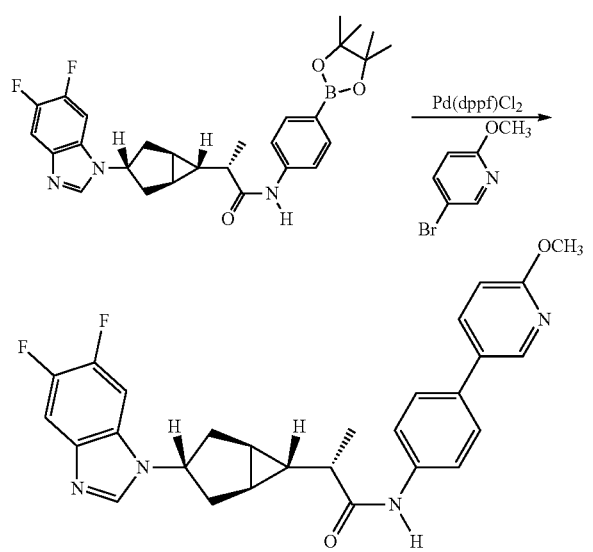

(S)-2-((1R,3R,5S,6r)-3-(5,6-difluoro-1H-benzo[d]imidazol-1-yl)bicyclo[3.1.0]-hexan-6-yl)-N-(4-(6-methoxypyridin-3-yl)phenyl)propanamide To a vial containing 5-bromo-2-methoxypyridine (9.6 mg, 0.051 mmol) and Pd(dppf)Cl$_2$ (3.2 mg, 0.0039 mmol) was added the product from the previous step (20 mg, 0.039 mmol) dissolved in DMF (0.4 ml) and Na$_2$CO$_3$ (2M, 0.039 ml, 0.079 mmol). The vial was purged with N$_2$, sealed, and heated in a dry block at 80° C. overnight. The reaction was filtered and purified by mass-triggered preparative HPLC (Mobile phase: A=0.1% TFA/H$_2$O, B=0.1% TFA/MeCN; Gradient: B=10-90%; 12 min; Column: C18) to afford the title compound as a bis(trifluoroacetate) salt (13.3 mg, 0.0186 mmol, 47%) as a white solid.

Mass: MS (ES$^+$) C$_{28}$H$_{26}$F$_2$N$_4$O$_2$ requires: 488, found: 489 [M+H]$^+$. $^1$H NMR (600 MHz, DMSO-d$_6$) δ ppm 1.15-1.29 (m, 4H) 1.31-1.63 (m, 2H) 1.80-1.93 (m, 1H) 2.14-2.43 (m, 4H) 3.85-3.93 (s, 3H) 4.65-4.82 (m, 1H) 6.86-6.94 (m, 1H) 7.57-7.65 (m, 2H) 7.72-7.76 (m, 2H) 7.78-7.85 (m, 1H) 7.95-8.02 (m, 1H) 8.05-8.15 (m, 1H) 8.44-8.50 (m, 1H) 8.82-8.96 (m, 1H) 9.82-9.94 (m, 1H).

Example 7

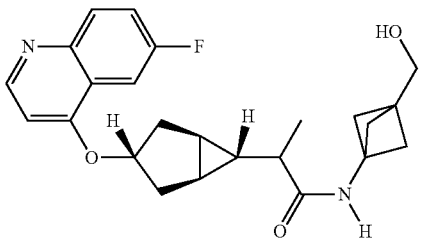 [SMILES: CC(C(=O)NC12CC(CO)(C1)C2)[C@H]1[C@@H]2C[C@@H](Oc3ccnc4ccc(F)cc34)C[C@@H]21]

2-((1R,3s,5S,6r)-3-((6-fluoroquinolin-4-yl)oxy)bicyclo[3.1.0]hexan-6-yl)-N-(3-(hydroxy-methyl)bicyclo[1.1.1]pentan-1-yl)propanamide General Procedure O, for HATU coupling, is exemplified in the following reaction.

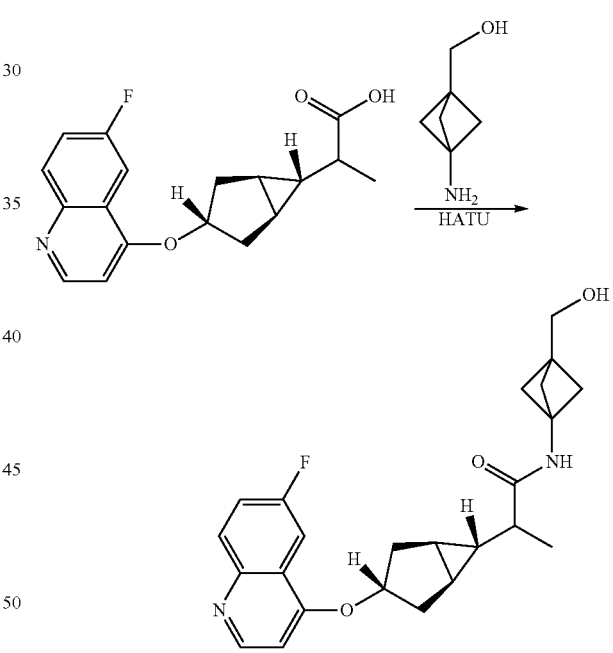

To a vial containing 2-((1R,3s,5S,6r)-3-((6-fluoroquinolin-4-yl)oxy)bicyclo[3.1.0]hexan-6-yl)propanoic acid (50 mg, 0.16 mmol) was added DCM (1.3 ml), DIEA (83 µl, 0.48 mmol), and (3-aminobicyclo[1.1.1]pentan-1-yl)methanol (20 mg, 0.17 mmol) followed by HATU (181 mg, 0.476 mmol). The reaction was stirred at room temperature overnight, diluted with DCM and washed with NaHCO$_3$ and brine, concentrated, and purified by mass-triggered preparative HPLC (Mobile phase: A=0.1% TFA/H$_2$O, B=0.1% TFA/MeCN; Gradient: B=10-90%; 12 min; Column: C18) to give the title compound, as its TFA salt (54.2 mg, 0.103 mmol, 65%) as a white solid.

Mass: MS (ES$^+$) C$_{24}$H$_{27}$FN$_2$O$_3$ requires: 410, found: 411 [M+H]$^+$.

Example 8

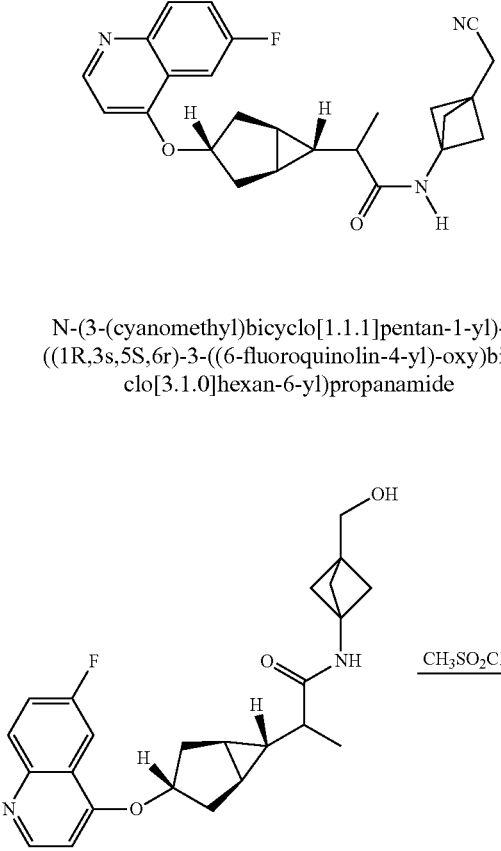

N-(3-(cyanomethyl)bicyclo[1.1.1]pentan-1-yl)-2-((1R,3s,5S,6r)-3-((6-fluoroquinolin-4-yl)-oxy)bicyclo[3.1.0]hexan-6-yl)propanamide (3-(2-((1R,3s,5S,6r)-3-((6-fluoroquinolin-4-yl)oxy)bicyclo[3.1.0]hexan-6-yl)-propanamido)bicyclo[1.1.1]pentan-1-yl)methyl methanesulfonate The title compound was synthesized from 2-((1R,3s,5S,6r)-3-((6-fluoroquinolin-4-yl)oxy)bicyclo[3.1.0]hexan-6-yl)-N-(3-(hydroxymethyl)bicyclo[1.1.1]pentan-1-yl)propanamide by general procedure L.

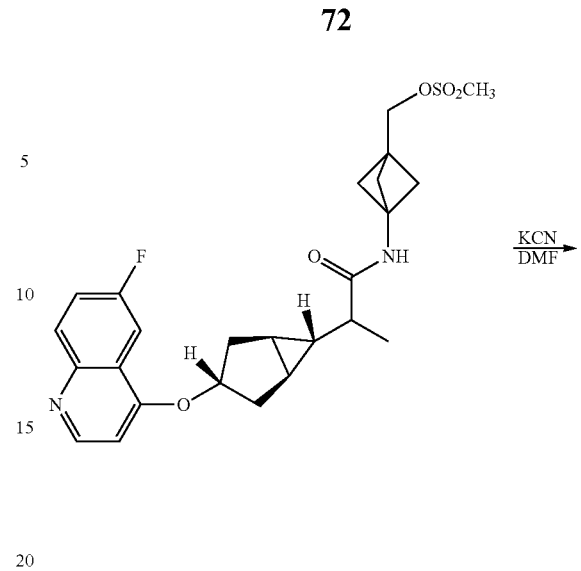

N-(3-(cyanomethyl)bicyclo[1.1.1]pentan-1-yl)-2-((1R,3s,5S,6r)-3-((6-fluoro-quinolin-4-yl)oxy)bicyclo[3.1.0]hexan-6-yl)propanamide The title compound was prepared from the previous compound using General Procedure C, using KCN in DMF, and purified by mass-triggered preparative HPLC (Mobile phase: A=0.1% TFA/H$_2$O, B=0.1% TFA/MeCN; Gradient: B=10-90%; 12 min; Column: C18) to give the title compound as a TFA salt as a white solid.

Mass: MS (ES$^+$) C$_{25}$H$_{26}$FN$_3$O$_2$ requires: 419, found: 420 [M+H]$^+$.

Example 9

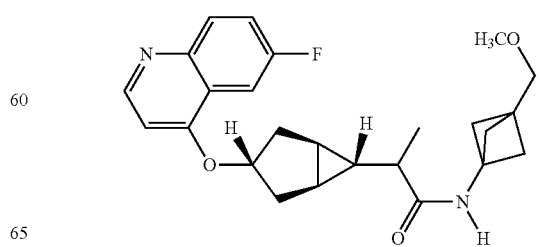

73

2-((1R,3s,5S,6r)-3-((6-fluoroquinolin-4-yl)oxy)bicyclo[3.1.0]hexan-6-yl)-N-(3-(methoxymethyl)bicyclo[1.1.1]pentan-1-yl)propanamide

74 tert-Butyl (3-(2-((1R,3s,5S,6r)-3-((6-fluoroquinolin-4-yl)oxy)bicyclo[3.1.0]hexan-6-yl)-propanamido)bicyclo[1.1.1]pentan-1-yl)carbamate

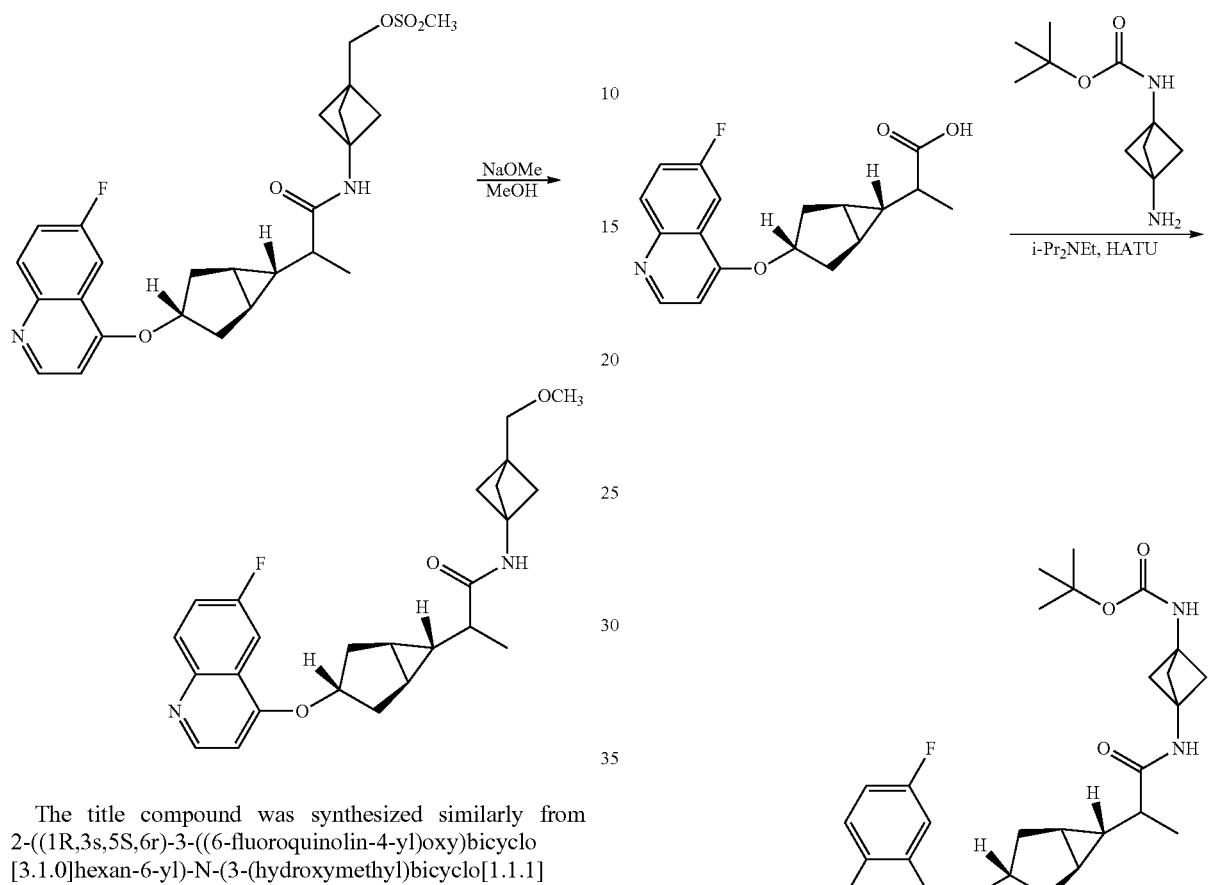

The title compound was synthesized similarly from 2-((1R,3s,5S,6r)-3-((6-fluoroquinolin-4-yl)oxy)bicyclo[3.1.0]hexan-6-yl)-N-(3-(hydroxymethyl)bicyclo[1.1.1]pentan-1-yl)propanamide by general procedures L and C (using NaOMe in MeOH, 60° C.) and purified by mass-triggered preparative HPLC (Mobile phase: A=0.1% TFA/$H_2O$, B=0.1% TFA/MeCN; Gradient: B=10-90%; 12 min; Column: C18) to give 2-((1R,3s,5S,6r)-3-((6-fluoroquinolin-4-yl)oxy)bicyclo[3.1.0]hexan-6-yl)-N-(3-(methoxymethyl)bicyclo[1.1.1]pentan-1-yl)propanamide-TFA salt. Mass: MS (ES$^+$) $C_{25}H_{29}FN_2O_3$ requires: 424, found: 425 [M+H]$^+$.

Example 10

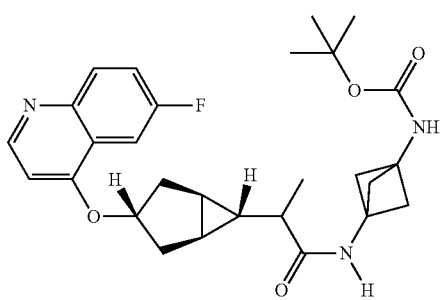 [SMILES: CC(C(=O)NC12CC(NC(=O)OC(C)(C)C)(C1)C2)[C@H]1[C@@H]2C[C@@H](Oc3ccnc4ccc(F)cc34)C[C@@H]21]

tert-Butyl (3-(2-((1R,3s,5S,6r)-3-((6-fluoroquinolin-4-yl)oxy)bicyclo[3.1.0]hexan-6-yl)propanamido)bicyclo[1.1.1]pentan-1-yl)carbamate To a vial containing the Example 1 compound (150 mg, 0.476 mmol) was added DCM (4 ml), DIEA (250 µl, 1.43 mmol), and tert-butyl (3-aminobicyclo[1.1.1]pentan-1-yl)carbamate (103 mg, 0.524 mmol), followed by HATU (543 mg, 1.43 mmol) and stirred at room temperature overnight. The reaction was diluted with water and DCM. The phases separated and the resulting precipitate in the organic layer was filtered off and washed with DCM. The solid was dissolved in MeOH/DCM mixtures and reconcentrated to give the title compound (120 mg, 0.242, 50%) as a white solid. Additional desired product was isolated from the DCM washings that was concentrated and purified by flash chromatography (0 to 100% 90:10:1 DCM:MeOH:NH$_4$OH in DCM) to give more of the desired product as a white solid (70 mg, 0.141, 29%).

Mass: MS (ES$^+$) $C_{28}H_{34}FN_3O_4$ requires: 495, found: 496 [M+H]$^+$.

Example 11

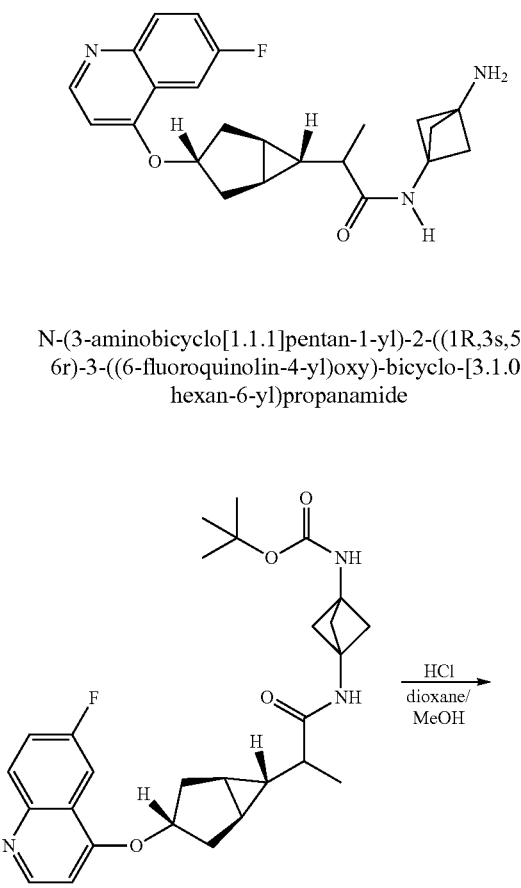

N-(3-aminobicyclo[1.1.1]pentan-1-yl)-2-((1R,3s,5S, 6r)-3-((6-fluoroquinolin-4-yl)oxy)-bicyclo-[3.1.0] hexan-6-yl)propanamide To a vial at 0° C. containing the Example 10 compound (46 mg, 0.093 mmol) dissolved in MeOH (200 μl) was added dropwise HCl 4M in dioxane (232 μl, 0.929 mmol) and was removed from the ice bath and stirred at room temperature until complete. The reaction was concentrated to give N-(3-aminobicyclo[1.1.1]pentan-1-yl)-2-((1R,3s,5S,6r)-3-((6-fluoroquinolin-4-yl)oxy)bicyclo[3.1.0]hexan-6-yl)propanamide-2 HCl salt (yield assumed quantitative) as an off-white solid and used as is. Mass: MS (ES+) $C_{23}H_{26}FN_3O_2$ requires: 395, found: 396 [M+H]+.

Example 12

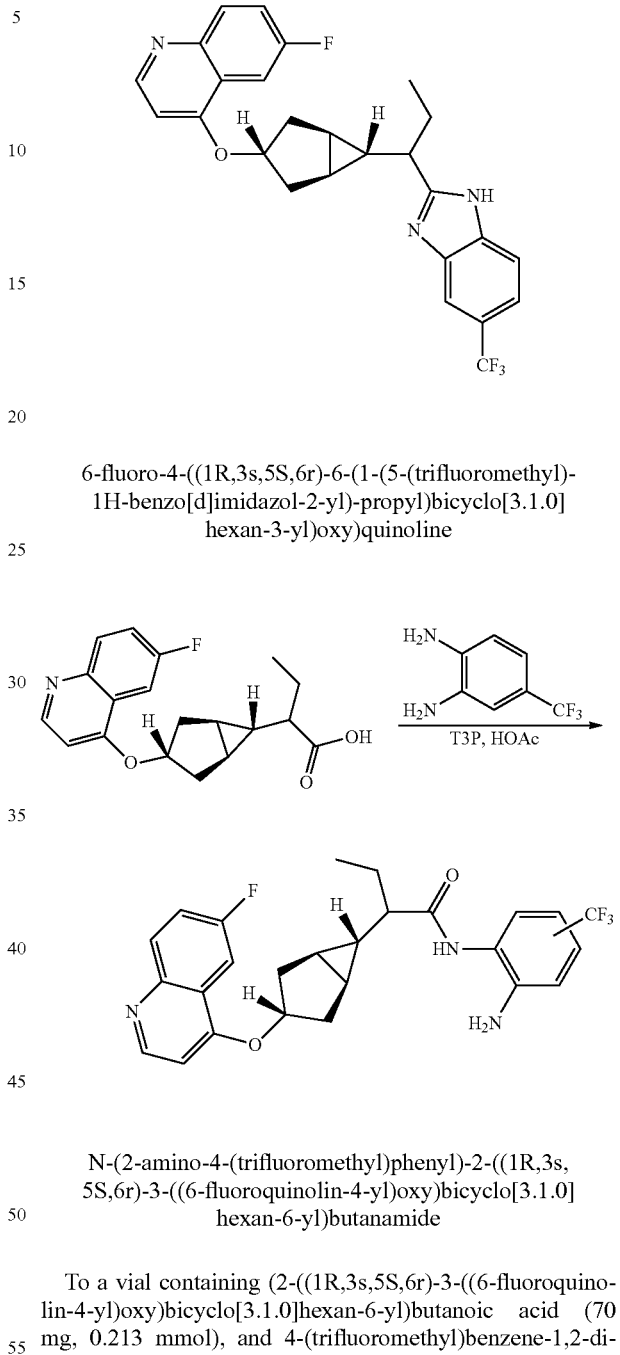

6-fluoro-4-((1R,3s,5S,6r)-6-(1-(5-(trifluoromethyl)-1H-benzo[d]imidazol-2-yl)-propyl)bicyclo[3.1.0] hexan-3-yl)oxy)quinoline N-(2-amino-4-(trifluoromethyl)phenyl)-2-((1R,3s, 5S,6r)-3-((6-fluoroquinolin-4-yl)oxy)bicyclo[3.1.0] hexan-6-yl)butanamide To a vial containing (2-((1R,3s,5S,6r)-3-((6-fluoroquinolin-4-yl)oxy)bicyclo[3.1.0]hexan-6-yl)butanoic acid (70 mg, 0.213 mmol), and 4-(trifluoromethyl)benzene-1,2-diamine (41.2 mg, 0.234 mmol) was added EtOAc (250 μL), pyridine (86 μL, 1.063 mmol) followed by T3P 50% in EtOAc (253 μL, 0.425 mmol) and the resulting mixture was stirred at 65° C. overnight. The reaction was diluted with EtOAc and quenched with saturated NaHCO₃. The layers separated, aqueous layer extracted with EtOAc (2×), organic layers combined, dried over MgSO₄, decanted, and purified by flash chromatography (0 to 100% of 90:10:1 DCM: MeOH:NH₄OH in DCM) to give (21.7 mg, 0.045 mmol, 21% yield) as a brown solid.

MS (ES+) $C_{26}H_{25}F_4N_3O_2$ requires: 487, found: 488 [M+H]+.

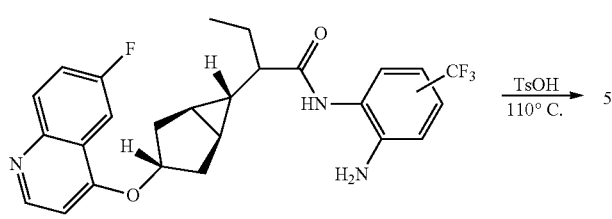

6-Fluoro-4-(((1R,3s,5S,6r)-6-(1-(6-(trifluoromethyl)-1H-benzo[d]imidazol-2-yl)-propyl)bicyclo[3.1.0] hexan-3-yl)oxy)quinoline The product from the previous step was suspended in toluene (200 µL) and pTsOH (50 mg, 0.263 mmol) was added and the reaction heated in a dry block at 110° C. overnight. The reaction was diluted with EtOAc, washed with saturated NaHCO$_3$ and brine. The aqueous layers were extracted with EtOAc (1×). The organic layers combined, dried over Na$_2$SO$_4$, decanted, concentrated and purified by flash chromatography (0 to 100% of 90:10:1 DCM:MeOH:NH$_4$OH in DCM) to give the title compound as a light brown solid.

MS (ES$^+$) C$_{26}$H$_{23}$F$_4$N$_3$O requires: 469, found: 470[M+H]$^+$.

$^1$H NMR (600 MHz, DMSO-d$_6$) δ ppm 0.84-0.91 (m, 3H) 1.01-1.07 (m, 1H) 1.37-1.47 (m, 2H) 1.84-1.97 (m, 3H) 1.99-2.06 (m, 1H) 2.18-2.25 (m, 1H) 2.32-2.38 (m, 1H) 2.53-2.59 (m, 1H) 4.81-4.93 (m, 1H) 7.05-7.11 (m, 1H) 7.41-7.52 (m, 1H) 7.60-7.65 (m, 1H) 7.71-7.81 (m, 2H) 7.91 (s, 1H) 7.96-8.02 (m, 1H) 8.60-8.74 (m, 1H) 12.49-12.66 (m, 1H).

Example 13

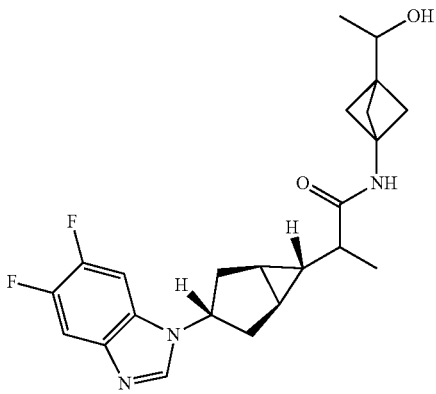 [SMILES: CC(C(=O)NC12CC(C(C)O)(C1)C2)[C@H]1[C@@H]2C[C@@H](n3cnc4cc(F)c(F)cc43)C[C@@H]21]

2-((1R,3s,5S,6r)-3-(5,6-difluoro-1H-benzo[d]imidazol-1-yl)bicyclo[3.1.0]hexan-6-yl)-N-(3-(1-hydroxyethyl)bicyclo[1.1.1]pentan-1-yl)propanamide

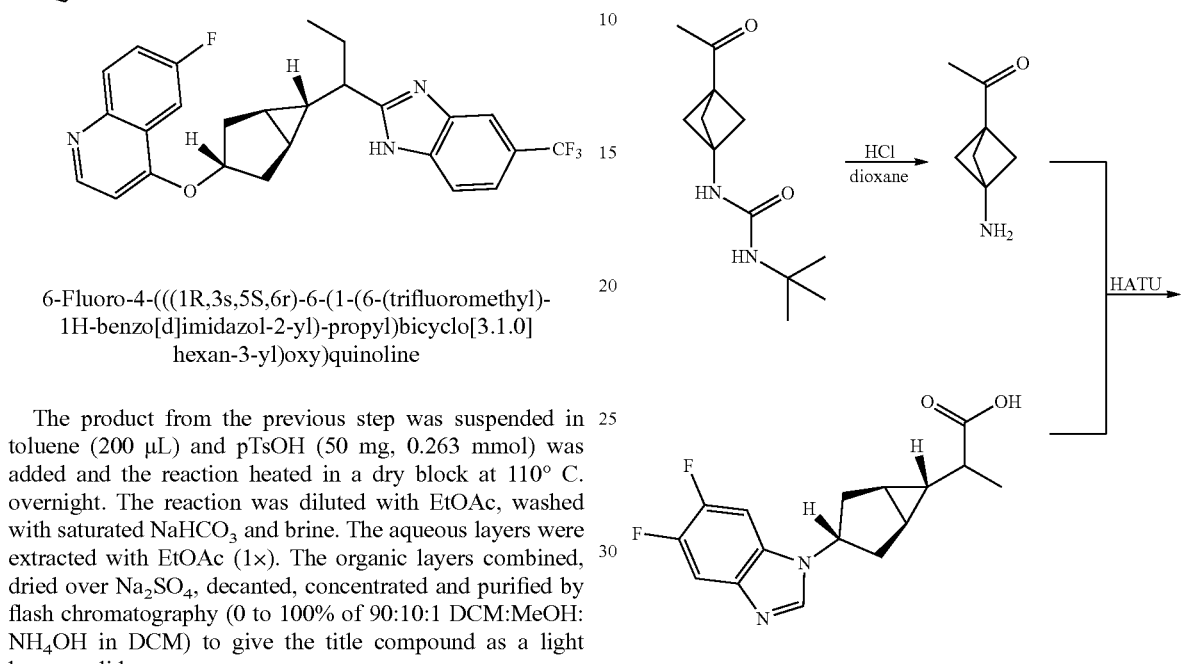

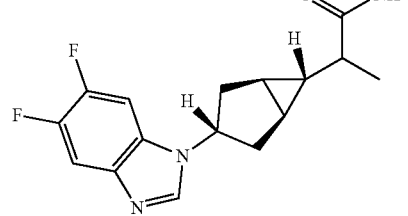

1-(3-Aminobicyclo[1.1.1]pentan-1-yl)ethan-1-one

To a vial containing tert-butyl (3-acetylbicyclo[1.1.1]pentan-1-yl)carbamate (50 mg, 0.22 mmol) dissolved in dioxane (1.1 ml) and cooled to 0° C. was added HCl 4M in dioxane (61 µl, 0.24 mmol) dropwise. The reaction was stirred at 0° C. for 10 min and allowed to warm to room temperature overnight. The reaction was concentrated to give the title compound, which was used without further purification.

N-(3-acetylbicyclo[1.1.1]pentan-1-yl)-2-((1R,3s,5S,6r)-3-(5,6-difluoro-1H-benzo[d]imidazol-1-yl)bicyclo[3.1.0]hexan-6-yl)propanamide To a vial containing the product from the previous step (27.8 mg, 0.22 mmol) dissolved in DCM (1.6 ml) was added DIEA (211 µl, 1.21 mmol) and 2-((1R,3s,5S,6r)-3-(5,6-difluoro-1H-benzo[d]imidazol-1-yl)bicyclo[3.1.0]hexan-6-yl)propanoic acid (62 mg, 0.21 mmol) followed by HATU (153 mg, 0.40 mmol). The reaction was stirred at room temperature overnight. The reaction was diluted with DCM, washed with water and brine. The aqueous layers were extracted with DCM, the organic layers combined, dried over $Na_2SO_4$, and decanted to give the title compound.

Mass: MS (ES$^+$) $C_{23}H_{25}F_2N_3O_2$ requires: 413, found: 415 [M+H]$^+$.

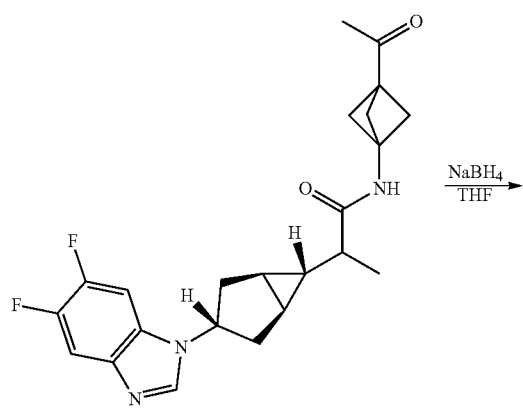

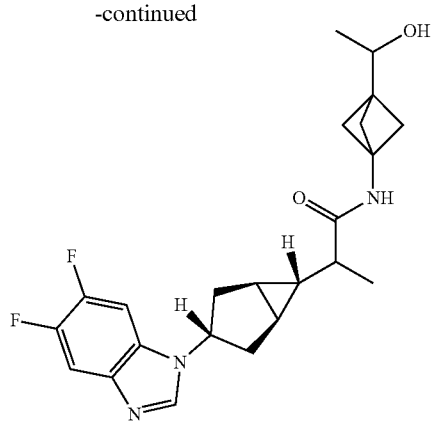

2-((1R,3s,5S,6r)-3-(5,6-difluoro-1H-benzo[d]imidazol-1-yl)bicyclo[3.1.0]hexan-6-yl)-N-(3-(1-hydroxyethyl)bicyclo[1.1.1]pentan-1-yl)propanamide To a vial containing the product from the previous step (50 mg, 0.12 mmol) dissolved in THF 0.6 ml) and cooled to 0° C. was added NaBH$_4$.(31 mg, 0.83 mmol). The reaction was stirred at 0° C. for 2 h, quenched by addition to mixture of cold 1:1 1M HCl:brine and liquid extracted with DCM (2×). The organic layers combined, washed with brine, dried over $Na_2SO_4$, decanted, and concentrated. The mixture was dissolved in MeOH (0.3 ml) and concentrated HCl (100 µl) was added. The solution was stirred at room temperature for 2 hr. The reaction was purified by mass-triggered preparative HPLC (Mobile phase: A=0.1% TFA/H$_2$O, B=0.1% TFA/MeCN; Gradient: B=10-90%; 12 min; Column: C18) to give the title compound (11 mg, 0.027 mmol, 22%) as a white solid.

Mass: MS (ES$^+$) $C_{23}H_{27}F_2N_3O_2$ requires: 415, found: 416 [M+H]$^+$.

The invention is further illustrated by the following examples. All IUPAC names were generated using CambridgeSoft's ChemDraw 10.0.

TABLE 1

Example compounds 12-151.

| Ex. | Structure | IUPAC Name | MWt | Notes |
|---|---|---|---|---|
| 14 | 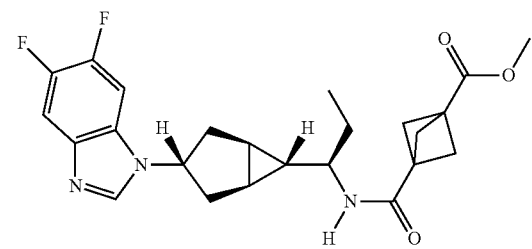 [SMILES: CC[C@@H](NC(=O)C12CC(C(=O)OC)(C1)C2)[C@H]1[C@@H]2C[C@@H](n3cnc4cc(F)c(F)cc43)C[C@@H]21] | Methyl 3-(((R)-1-((1R,3S,5S,6r)-3-(5,6-difluoro-1H-benzo[d]imidazol-1-yl)bicyclo[3.1.0]hexan-6-yl)propyl)carbamoyl)bicyclo[1.1.1]pentane-1-carboxylate | 444 | (1) |

TABLE 1-continued

Example compounds 12-151.

| Ex. | Structure | IUPAC Name | MWt | Notes |
|---|---|---|---|---|
| 15 | 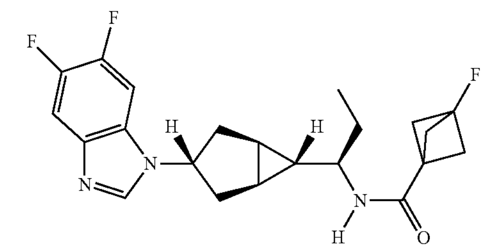 [SMILES: CC[C@@H](NC(=O)C12CC(F)(C1)C2)[C@H]1[C@@H]2C[C@@H](n3cnc4cc(F)c(F)cc43)C[C@@H]21] | N-((R)-1-((1R,3S,5S,6r)-3-(5,6-difluoro-1H-benzo[d]-imidazol-1-yl)bicyclo-[3.1.0]hexan-6-yl)propyl)-3-fluorobicyclo[1.1.1]-pentane-1-carboxamide | 404 | (1) |
| 16 | 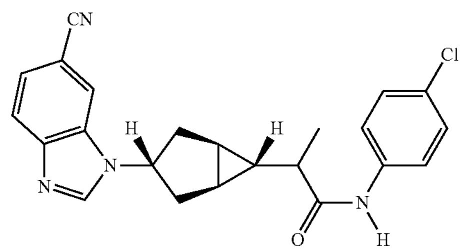 [SMILES: CC(C(=O)Nc1ccc(Cl)cc1)[C@H]1[C@@H]2C[C@@H](n3cnc4ccc(C#N)cc43)C[C@@H]21] | N-(4-chlorophenyl)-2-((1R,3s,5S,6r)-3-(6-cyano-1H-benzo[d]imidazol-1-yl)bicyclo[3.1.0]hexan-6-yl)-propanamide | 404 | |
| 17 | 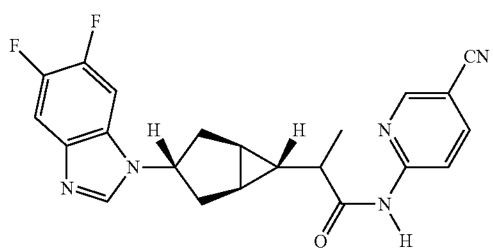 | N-(5-cyanopyridin-2-yl)-2-((1R,3s,5S,6r)-3-(5,6-difluoro-1H-benzo[d]-imidazol-1-yl)bicyclo-[3.1.0]hexan-6-yl)-propanamide | 408 | (2) |
| 18 | 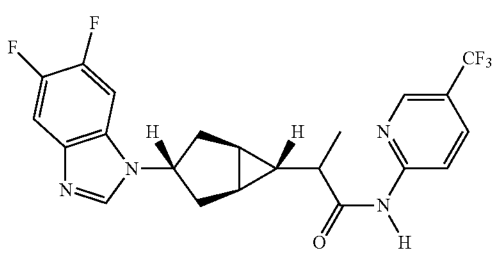 [SMILES: CC(C(=O)Nc1ccc(C(F)(F)F)cn1)[C@H]1[C@@H]2C[C@@H](n3cnc4cc(F)c(F)cc43)C[C@@H]21] | 2-((1R,3s,5S,6r)-3-(5,6-difluoro-1H-benzo[d]-imidazol-1-yl)bicyclo-[3.1.0]hexan-6-yl)-N-(5-(trifluoromethyl)pyridin-2-yl)propanamide | 451 | (2) |
| 19 | 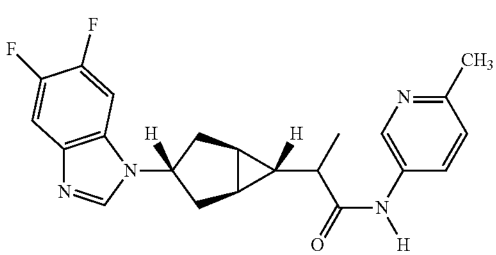 [SMILES: Cc1ccc(NC(=O)C(C)[C@H]2[C@@H]3C[C@@H](n4cnc5cc(F)c(F)cc54)C[C@@H]32)cn1] | 2-((1R,3s,5S,6r)-3-(5,6-difluoro-1H-benzo[d]-imidazol-1-yl)bicyclo-[3.1.0]hexan-6-yl)-N-(6-methylpyridin-3-yl)-propanamide | 397 | (2) |
| 20 | 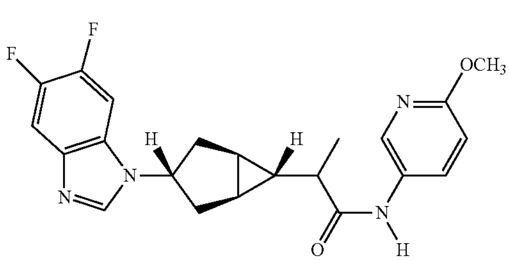 [SMILES: COc1ccc(NC(=O)C(C)[C@H]2[C@@H]3C[C@@H](n4cnc5cc(F)c(F)cc54)C[C@@H]32)cn1] | 2-((1R,3s,5S,6r)-3-(5,6-difluoro-1H-benzo[d]-imidazol-1-yl)bicyclo-[3.1.0]hexan-6-yl)-N-(6-methoxypyridin-3-yl)-propanamide | 413 | (2) |

TABLE 1-continued

Example compounds 12-151.

| Ex. | Structure | IUPAC Name | MWt | Notes |
|---|---|---|---|---|
| 21 | 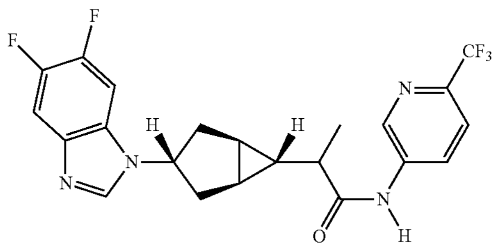 | 2-((1R,3s,5S,6r)-3-(5,6-difluoro-1H-benzo[d]-imidazol-1-yl)bicyclo-[3.1.0]hexan-6-yl)-N-(6-(trifluoromethyl)pyridin-3-yl)propanamide | 451 | (2) |
| 22 | 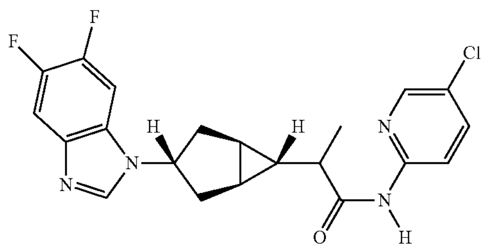 [SMILES: CC(C(=O)Nc1ccc(Cl)cn1)[C@H]1[C@@H]2C[C@@H](n3cnc4cc(F)c(F)cc43)C[C@@H]21] | N-(5-chloropyridin-2-yl)-2-((1R,3s,5S,6r)-3-(5,6-difluoro-1H-benzo[d]-imidazol-1-yl)bicyclo-[3.1.0]hexan-6-yl)-propanamide | 417 | (2) |
| 23 | 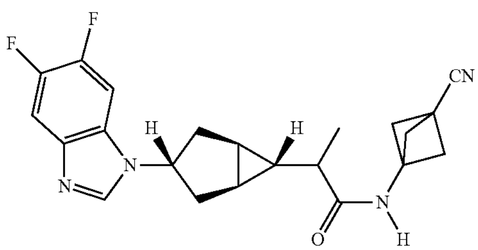 [SMILES: CC(C(=O)NC12CC(C#N)(C1)C2)[C@H]1[C@@H]2C[C@@H](n3cnc4cc(F)c(F)cc43)C[C@@H]21] | N-(3-cyanobicyclo-[1.1.1]pentan-1-yl)-2-((1R,3s,5S,6r)-3-(5,6-difluoro-1H-benzo[d]-imidazol-1-yl)bicyclo-[3.1.0]hexan-6-yl)-propanamide | 397 | (1) |
| 24 | 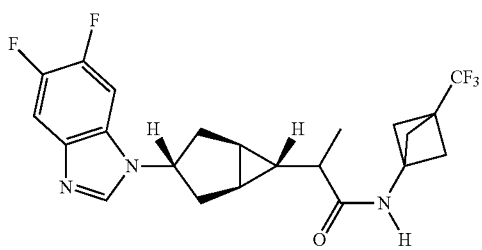 [SMILES: CC(C(=O)NC12CC(C(F)(F)F)(C1)C2)[C@H]1[C@@H]2C[C@@H](n3cnc4cc(F)c(F)cc43)C[C@@H]21] | 2-((1R,3s,5S,6r)-3-(5,6-difluoro-1H-benzo[d]-imidazol-1-yl)bicyclo-[3.1.0]hexan-6-yl)-N-(3-(trifluoromethyl)bicyclo[1.1.1]pentan-1-yl)-propanamide | 440 | (1) |
| 25 | 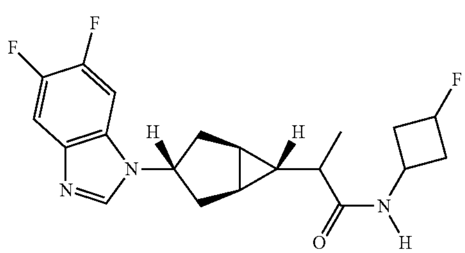 [SMILES: CC(C(=O)NC1CC(F)C1)[C@H]1[C@@H]2C[C@@H](n3cnc4cc(F)c(F)cc43)C[C@@H]21] | 2-((1R,3s,5S,6r)-3-(5,6-difluoro-1H-benzo[d]-imidazol-1-yl)bicyclo-[3.1.0]hexan-6-yl)-N-(3-fluorocyclobutyl)-propanamide | 378 | (1) |
| 26 | 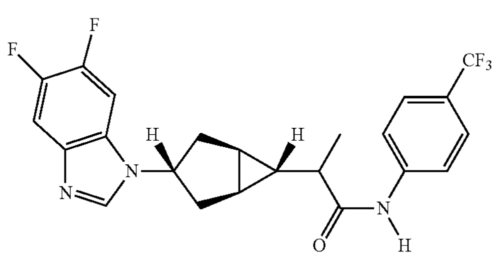 | 2-((1R,3s,5S,6r)-3-(5,6-difluoro-1H-benzo[d]-imidazol-1-yl)bicyclo-[3.1.0]hexan-6-yl)-N-(4-(trifluoromethyl)phenyl)-propanamide | 450 | (2) |

TABLE 1-continued

Example compounds 12-151.

| Ex. | Structure | IUPAC Name | MWt | Notes |
|---|---|---|---|---|
| 27 | 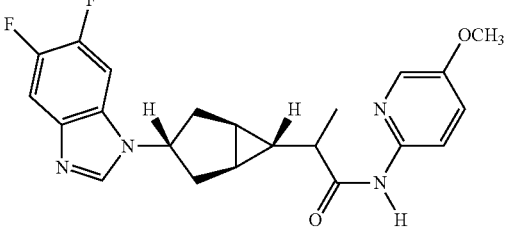 | 2-((1R,3s,5S,6r)-3-(5,6-difluoro-1H-benzo[d]-imidazol-1-yl)bicyclo-[3.1.0]hexan-6-yl)-N-(5-methoxypyridin-2-yl)-propanamide | 413 | (2) |
| 28 | 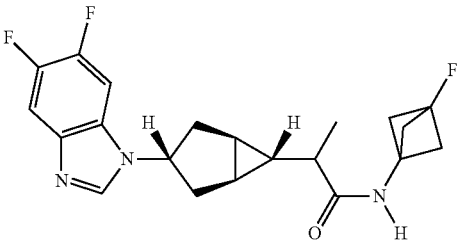 [SMILES: CC(C(=O)NC12CC(F)(C1)C2)[C@H]1[C@@H]2C[C@@H](n3cnc4cc(F)c(F)cc43)C[C@@H]21] | 2-((1R,3s,5S,6r)-3-(5,6-difluoro-1H-benzo[d]-imidazol-1-yl)bicyclo-[3.1.0]hexan-6-yl)-N-(3-fluorobicyclo[1.1.1]pentan-1-yl)propanamide | 390 | (1) |
| 29 | 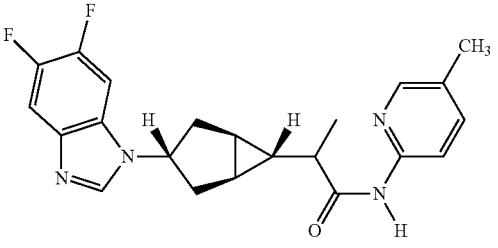 [SMILES: Cc1ccc(NC(=O)C(C)[C@H]2[C@@H]3C[C@@H](n4cnc5cc(F)c(F)cc54)C[C@@H]32)nc1] | 2-((1R,3s,5S,6r)-3-(5,6-difluoro-1H-benzo[d]-imidazol-1-yl)bicyclo-[3.1.0]hexan-6-yl)-N-(5-methylpyridin-2-yl)-propanamide | 397 | (2) |
| 30 | 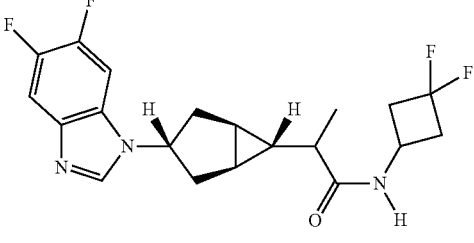 | 2-((1R,3s,5S,6r)-3-(5,6-difluoro-1H-benzo[d]-imidazol-1-yl)bicyclo-[3.1.0]hexan-6-yl)-N-(3,3-difluorocyclobutyl)-propanamide | 396 | (1) |
| 31 | 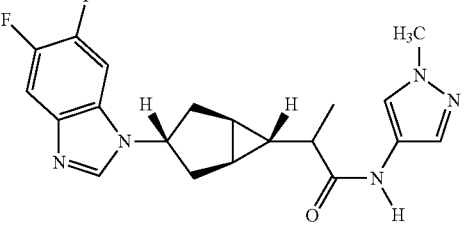 | 2-((1R,3s,5S,6r)-3-(5,6-difluoro-1H-benzo[d]-imidazol-1-yl)bicyclo-[3.1.0]hexan-6-yl)-N-(1-methyl-1H-pyrazol-4-yl)-propanamide | 386 | (2) |
| 32 | 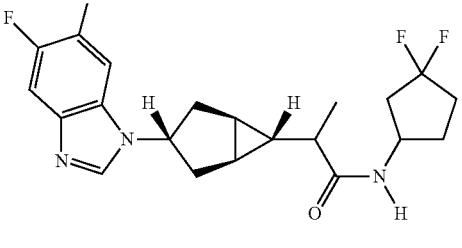 | 2-((1R,3s,5S,6r)-3-(5,6-difluoro-1H-benzo[d]-imidazol-1-yl)bicyclo-[3.1.0]hexan-6-yl)-N-(3,3-difluorocyclopentyl)-propanamide | 410 | (1) |

TABLE 1-continued

Example compounds 12-151.

| Ex. | Structure | IUPAC Name | MWt | Notes |
|---|---|---|---|---|
| 33 | 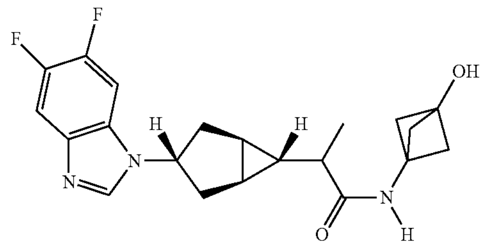 [SMILES: CC(C(=O)NC12CC(O)(C1)C2)[C@H]1[C@@H]2C[C@@H](n3cnc4cc(F)c(F)cc43)C[C@@H]21] | 2-((1R,3s,5S,6r)-3-(5,6-difluoro-1H-benzo[d]-imidazol-1-yl)bicyclo-[3.1.0]hexan-6-yl)-N-(3-hydroxybicyclo[1.1.1]-pentan-1-yl)propanamide | 388 | (3) |
| 34 | 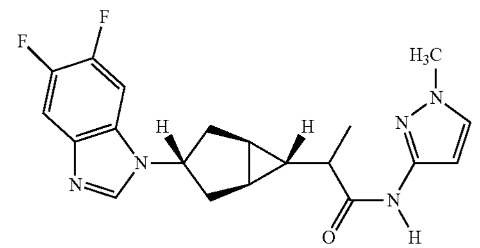 [SMILES: CC(C(=O)Nc1ccn(C)n1)[C@H]1[C@@H]2C[C@@H](n3cnc4cc(F)c(F)cc43)C[C@@H]21] | 2-((1R,3s,5S,6r)-3-(5,6-difluoro-1H-benzo[d]-imidazol-1-yl)bicyclo-[3.1.0]hexan-6-yl)-N-(1-methyl-1H-pyrazol-3-yl)-propanamide | 386 | (2) |
| 35 | 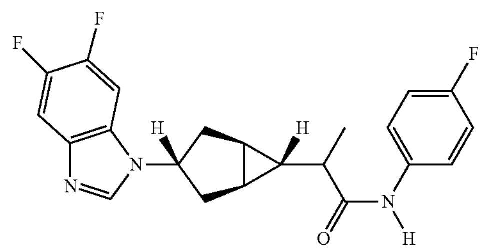 [SMILES: CC(C(=O)Nc1ccc(F)cc1)[C@H]1[C@@H]2C[C@@H](n3cnc4cc(F)c(F)cc43)C[C@@H]21] | 2-((1R,3s,5S,6r)-3-(5,6-difluoro-1H-benzo[d]-imidazol-1-yl)bicyclo-[3.1.0]hexan-6-yl)-N-(4-fluorophenyl)propanamide | 400 | (2) |
| 36 | 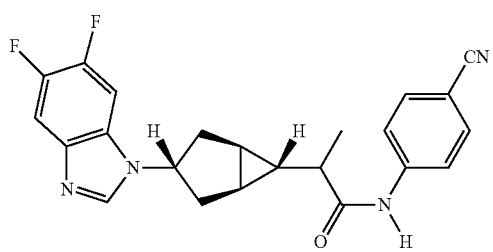 [SMILES: CC(C(=O)Nc1ccc(C#N)cc1)[C@H]1[C@@H]2C[C@@H](n3cnc4cc(F)c(F)cc43)C[C@@H]21] | N-(4-cyanophenyl)-2-((1R,3s,5S,6r)-3-(5,6-difluoro-1H-benzo[d]-imidazol-1-yl)bicyclo-[3.1.0]hexan-6-yl)-propanamide | 407 | (2) |
| 37 | 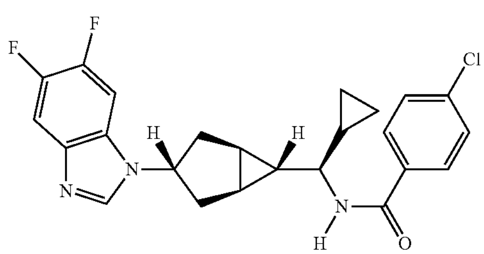 [SMILES: O=C(N[C@H](C1CC1)[C@H]1[C@@H]2C[C@@H](n3cnc4cc(F)c(F)cc43)C[C@@H]21)c1ccc(Cl)cc1] | 4-chloro-N-((R)-cyclopropyl((1R,3s,5S,6r)-3-(5,6-difluoro-1H-benzo[d]-imidazol-1-yl)-bicyclo[3.1.0]hexan-6-yl)methyl)benzamide | 442 | (4) |
| 38 | 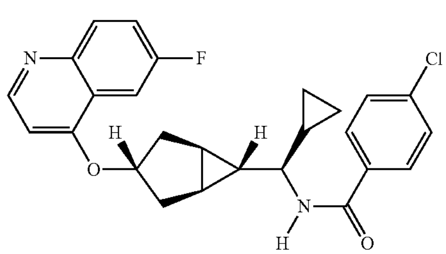 [SMILES: O=C(N[C@H](C1CC1)[C@H]1[C@@H]2C[C@@H](Oc3ccnc4ccc(F)cc34)C[C@@H]21)c1ccc(Cl)cc1] | 4-chloro-N-((R)-cyclopropyl((1R,3s,5S,6r)-3-((6-fluoroquinolin-4-yl)oxy)-bicyclo[3.1.0]hexan-6-yl)-methyl)benzamide | 451 | (4) |

TABLE 1-continued

Example compounds 12-151.

| Ex. | Structure | IUPAC Name | MWt | Notes |
|---|---|---|---|---|
| 39 | 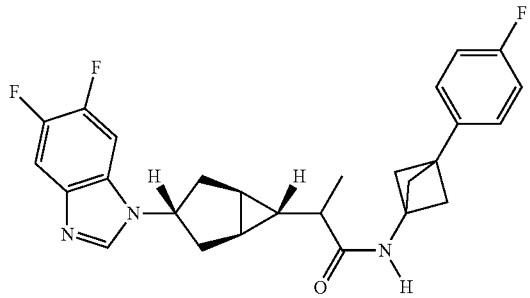 [SMILES: CC(C(=O)NC12CC(c3ccc(F)cc3)(C1)C2)[C@H]1[C@@H]2C[C@@H](n3cnc4cc(F)c(F)cc43)C[C@@H]21] | 2-((1R,3s,5S,6r)-3-(5,6-difluoro-1H-benzo[d]-imidazol-1-yl)bicyclo-[3.1.0]hexan-6-yl)-N-(3-(4-fluorophenyl)bicyclo-[1.1.1]pentan-1-yl)-propanamide | 466 | (1) |
| 40 | 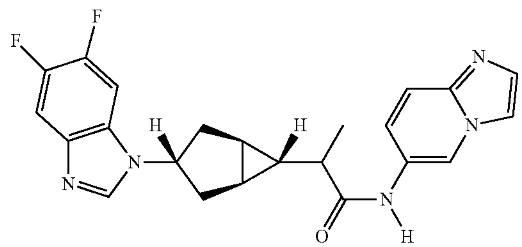 [SMILES: CC(C(=O)Nc1ccc2nccn2c1)[C@H]1[C@@H]2C[C@@H](n3cnc4cc(F)c(F)cc43)C[C@@H]21] | 2-((1R,3s,5S,6r)-3-(5,6-difluoro-1H-benzo[d]-imidazol-1-yl)bicyclo-[3.1.0]hexan-6-yl)-N-(imidazo[1,2-a]pyridin-6-yl)propanamide | 422 | (1) |
| 41 | 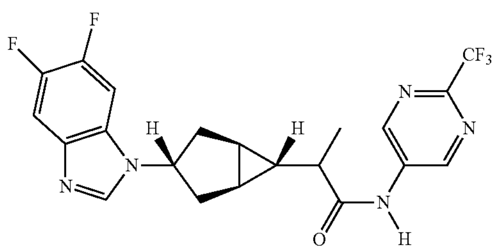 [SMILES: CC(C(=O)Nc1cnc(C(F)(F)F)nc1)[C@H]1[C@@H]2C[C@@H](n3cnc4cc(F)c(F)cc43)C[C@@H]21] | 2-((1R,3s,5S,6r)-3-(5,6-difluoro-1H-benzo[d]-imidazol-1-yl)bicyclo-[3.1.0]hexan-6-yl)-N-(2-(trifluoromethyl)pyrimidin-5-yl)propanamide | 452 | (1) |
| 42 | 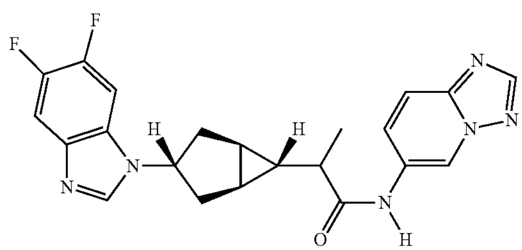 [SMILES: CC(C(=O)Nc1ccc2ncnn2c1)[C@H]1[C@@H]2C[C@@H](n3cnc4cc(F)c(F)cc43)C[C@@H]21] | N-([1,2,4]triazolo[1,5-a]-pyridin-6-yl)-2-((1R,3s,5S,6r)-3-(5,6-difluoro-1H-benzo[d]-imidazol-1-yl)bicyclo-[3.1.0]hexan-6-yl)-propanamide | 423 | (1) |
| 43 | 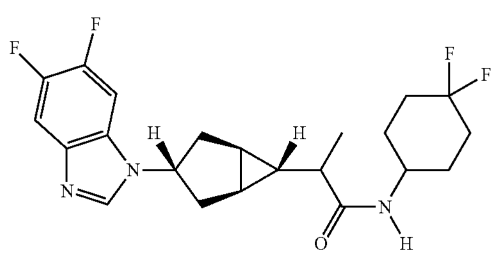 [SMILES: CC(C(=O)NC1CCC(F)(F)CC1)[C@H]1[C@@H]2C[C@@H](n3cnc4cc(F)c(F)cc43)C[C@@H]21] | 2-((1R,3s,5S,6r)-3-(5,6-difluoro-1H-benzo[d]-imidazol-1-yl)bicyclo-[3.1.0]hexan-6-yl)-N-(4,4-difluorocyclohexyl)-propanamide | 424 | (1) |
| 44 | 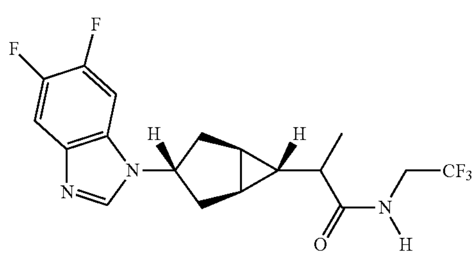 [SMILES: CC(C(=O)NCC(F)(F)F)[C@H]1[C@@H]2C[C@@H](n3cnc4cc(F)c(F)cc43)C[C@@H]21] | 2-((1R,3s,5S,6r)-3-(5,6-difluoro-1H-benzo[d]-imidazol-1-yl)bicyclo-[3.1.0]hexan-6-yl)-N-(2,2,2-trifluoroethyl)-propanamide | 388 | (1) |

TABLE 1-continued

Example compounds 12-151.

| Ex. | Structure | IUPAC Name | MWt | Notes |
|---|---|---|---|---|
| 45 | 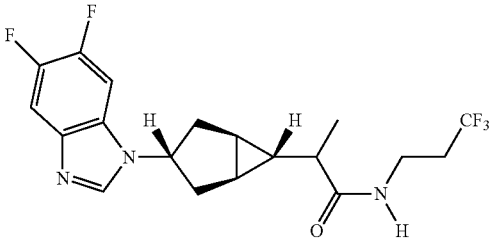 [SMILES: CC(C(=O)NCCC(F)(F)F)[C@H]1[C@@H]2C[C@@H](n3cnc4cc(F)c(F)cc43)C[C@@H]21] | 2-((1R,3s,5S,6r)-3-(5,6-difluoro-1H-benzo[d]-imidazol-1-yl)bicyclo-[3.1.0]hexan-6-yl)-N-(3,3,3-bifluoropropyl)-propanamide | 402 | (1) |
| 46 | 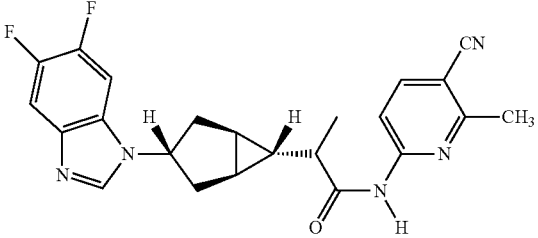 [SMILES: Cc1nc(NC(=O)C(C)[C@H]2[C@@H]3C[C@@H](n4cnc5cc(F)c(F)cc54)C[C@@H]32)ccc1C#N] | (R)-N-(5-cyano-6-methyl-pyridin-2-yl)-2-((1R,3s,5S,6r)-3-(5,6-difluoro-1H-benzo[d]-imidazol-1-yl)bicyclo-[3.1.0]hexan-6-yl)-propanamide | 422 | (1) |
| 47 | 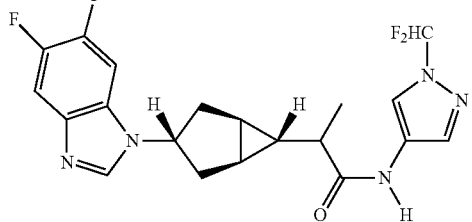 | 2-((1R,3s,5S,6r)-3-(5,6-difluoro-1H-benzo[d]-imidazol-1-yl)bicyclo-[3.1.0]hexan-6-yl)-N-(1-(difluoromethyl)-1H-pyrazol-4-yl)propanamide | 422 | (1) |
| 48 | 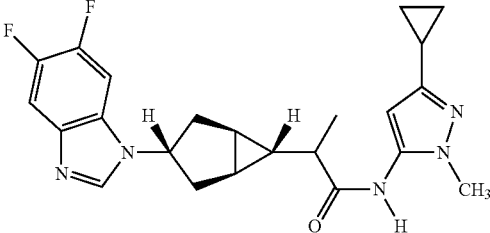 [SMILES: CC(C(=O)Nc1cc(C2CC2)nn1C)[C@H]1[C@@H]2C[C@@H](n3cnc4cc(F)c(F)cc43)C[C@@H]21] | N-(3-cyclopropyl-1-methyl-1H-pyrazol-5-yl)-2-((1R,3s,5S,6r)-3-(5,6-difluoro-1H-benzo[d]-imidazol-1-yl)bicyclo-[3.1.0]hexan-6-yl)-propanamide | 426 | (1) |
| 49 | 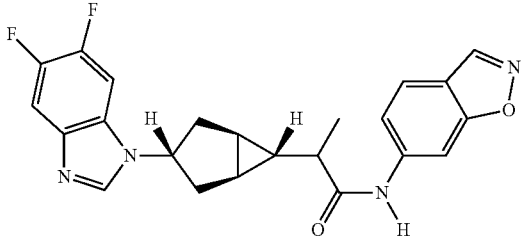 [SMILES: CC(C(=O)Nc1ccc2cnoc2c1)[C@H]1[C@@H]2C[C@@H](n3cnc4cc(F)c(F)cc43)C[C@@H]21] | N-(benzo[d]isoxazol-6-yl)-2-((1R,3s,5S,6r)-3-(5,6-difluoro-1H-benzo[d]-imidazol-1-yl)-bicyclo[3.1.0]hexan-6-yl)propanamide | 423 | (1) |
| 50 | 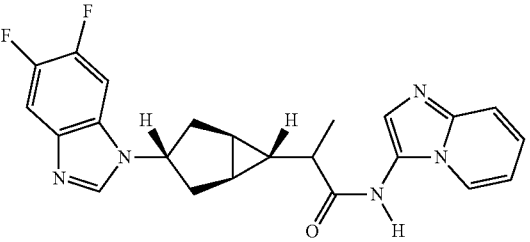 [SMILES: CC(C(=O)Nc1cnc2ccccn12)[C@H]1[C@@H]2C[C@@H](n3cnc4cc(F)c(F)cc43)C[C@@H]21] | 2-((1R,3s,5S,6r)-3-(5,6-difluoro-1H-benzo[d]-imidazol-1-yl)bicyclo-[3.1.0]hexan-6-yl)-N-(imidazo[1,2-a]pyridin-3-yl)propanamide | 422 | (1) |

TABLE 1-continued

Example compounds 12-151.

| Ex. | Structure | IUPAC Name | MWt | Notes |
|---|---|---|---|---|
| 51 | 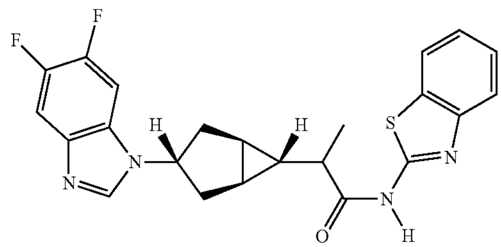 [SMILES: CC(C(=O)Nc1nc2ccccc2s1)[C@H]1[C@@H]2C[C@@H](n3cnc4cc(F)c(F)cc43)C[C@@H]21] | N-(benzo[d]thiazol-2-yl)-2-((1R,3s,5S,6r)-3-(5,6-difluoro-1H-benzo[d]-imidazol-1-yl)bicyclo-[3.1.0]hexan-6-yl)-propanamide | 439 | (1) |
| 52 | 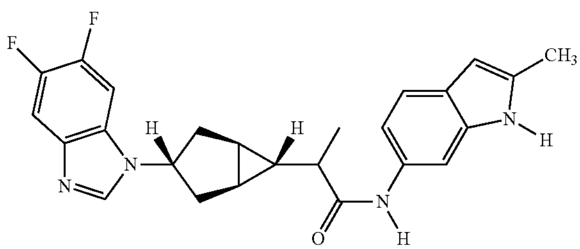 [SMILES: Cc1cc2ccc(NC(=O)C(C)[C@H]3[C@@H]4C[C@@H](n5cnc6cc(F)c(F)cc65)C[C@@H]43)cc2[nH]1] | 2-((1R,3s,5S,6r)-3-(5,6-difluoro-1H-benzo[d]-imidazol-1-yl)bicyclo-[3.1.0]hexan-6-yl)-N-(2-methyl-1H-indol-6-yl)-propanamide | 435 | (1) |
| 53 | 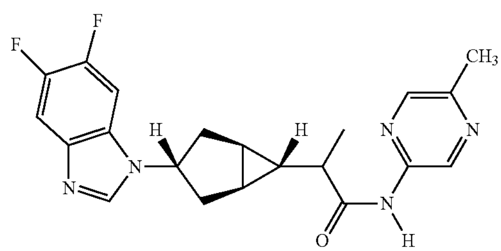 [SMILES: Cc1cnc(NC(=O)C(C)[C@H]2[C@@H]3C[C@@H](n4cnc5cc(F)c(F)cc54)C[C@@H]32)cn1] | 2-((1R,3s,5S,6r)-3-(5,6-difluoro-1H-benzo[d]-imidazol-1-yl)bicyclo-[3.1.0]hexan-6-yl)-N-(5-methylpyrazin-2-yl)-propanamide | 398 | (1) |
| 54 | 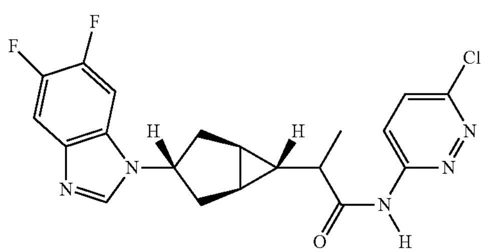 [SMILES: CC(C(=O)Nc1ccc(Cl)nn1)[C@H]1[C@@H]2C[C@@H](n3cnc4cc(F)c(F)cc43)C[C@@H]21] | N-(6-chloropyridazin-3-yl)-2-((1R,3s,5S,6r)-3-(5,6-difluoro-1H-benzo[d]-imidazol-1-yl)-bicyclo[3.1.0]hexan-6-yl)-propanamide | 418 | (1) |
| 55 | 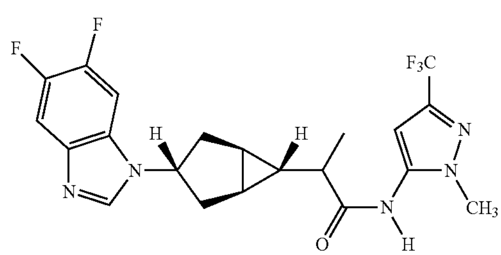 [SMILES: CC(C(=O)Nc1cc(C(F)(F)F)nn1C)[C@H]1[C@@H]2C[C@@H](n3cnc4cc(F)c(F)cc43)C[C@@H]21] | 2-((1R,3s,5S,6r)-3-(5,6-difluoro-1H-benzo[d]-imidazol-1-yl)bicyclo-[3.1.0]hexan-6-yl)-N-(1-methyl-3-(trifluoromethyl)-1H-pyrazol-5-yl)-propanamide | 454 | (1) |
| 56 | 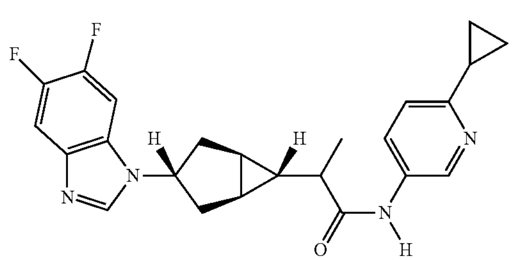 [SMILES: CC(C(=O)Nc1ccc(C2CC2)nc1)[C@H]1[C@@H]2C[C@@H](n3cnc4cc(F)c(F)cc43)C[C@@H]21] | N-(6-cyclopropylpyridin-3-yl)-2-((1R,3s,5S,6r)-3-(5,6-difluoro-1H-benzo[d]-imidazol-1-yl)bicyclo-[3.1.0]hexan-6-yl)-propanamide | 423 | (1) |

TABLE 1-continued

Example compounds 12-151.

| Ex. | Structure | IUPAC Name | MWt | Notes |
|---|---|---|---|---|
| 57 | 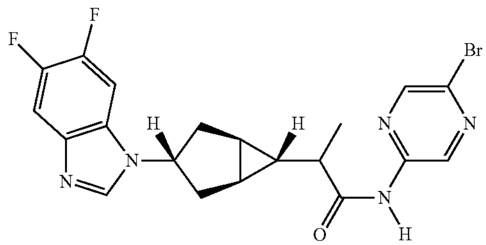 [SMILES: CC(C(=O)Nc1cnc(Br)cn1)[C@H]1[C@@H]2C[C@@H](n3cnc4cc(F)c(F)cc43)C[C@@H]21] | N-(5-bromopyrazin-2-yl)-2-((1R,3s,5S,6r)-3-(5,6-difluoro-1H-benzo[d]-imidazol-1-yl)bicyclo-[3.1.0]hexan-6-yl)-propanamide | 463 | (1) |
| 58 | 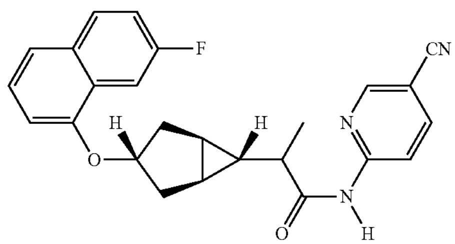 [SMILES: CC(C(=O)Nc1ccc(C#N)cn1)[C@H]1[C@@H]2C[C@@H](Oc3cccc4ccc(F)cc34)C[C@@H]21] | N-(5-cyanopyridin-2-yl)-2-((1R,3s,5S,6r)-3-((6-fluoroquinolin-4-yl)oxy)-bicyclo[3.1.0]hexan-6-yl)-propanamide | 417 | (1) |
| 59 | 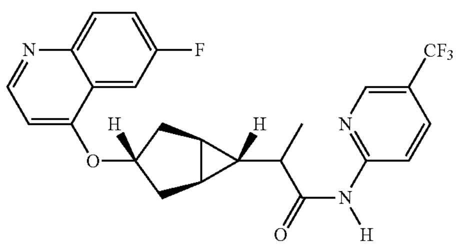 [SMILES: CC(C(=O)Nc1ccc(C(F)(F)F)cn1)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(5-(trifluoromethyl)-pyridin-2-yl)propanamide | 460 | (1) |
| 60 | 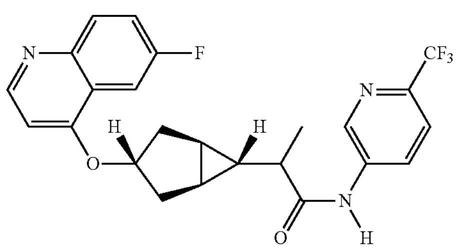 [SMILES: CC(C(=O)Nc1ccc(C(F)(F)F)nc1)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(6-(trifluoromethyl)-pyridin-3-yl)propanamide | 460 | (1) |
| 61 | 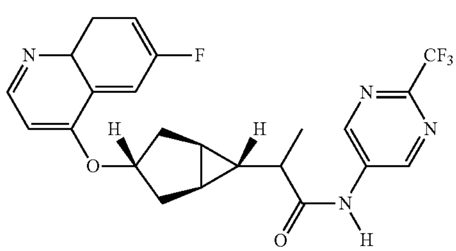 [SMILES: CC(C(=O)Nc1cnc(C(F)(F)F)nc1)[C@H]1[C@@H]2C[C@@H](OC3=CC=NC4CC=C(F)C=C34)C[C@@H]21] | 2-((1R,3s,5S,6r)-3-((6-fluoro-8,8a-dihydro-quinolin-4-yl)oxy)bicyclo-[3.1.0]hexan-6-yl)-N-(2-(trifluoromethyl)pyrimidin-5-yl)propanamide | 461 | (1) |
| 62 | 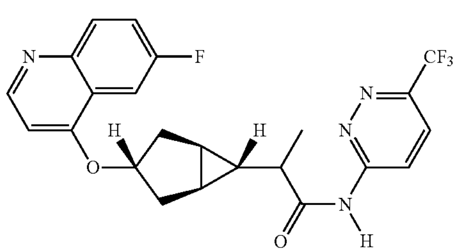 | 2-((1R,3s,5S,6r)-3-((6-fluoroquinolin-4-yl)oxy)-bicyclo[3.1.0]hexan-6-yl)-N-(6-(trifluoromethyl)-pyridazin-3-yl)-propanamide | 461 | (1) |

TABLE 1-continued

Example compounds 12-151.

| Ex. | Structure | IUPAC Name | MWt | Notes |
|---|---|---|---|---|
| 63 | 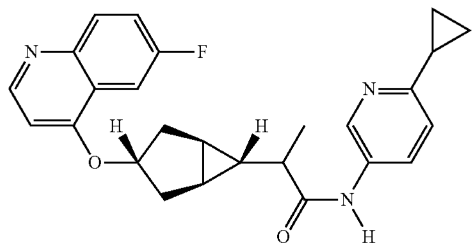 [SMILES: CC(C(=O)Nc1ccc(C2CC2)nc1)[C@H]1[C@@H]2C[C@@H](Oc3ccnc4ccc(F)cc34)C[C@@H]21] | N-(6-cyclopropylpyridin-3-yl)-2-((1R,3s,5S,6r)-3-((6-fluoroquinolin-4-yl)oxy)-bicyclo[3.1.0]hexan-6-yl)propanamide | 432 | (1) |
| 64 | 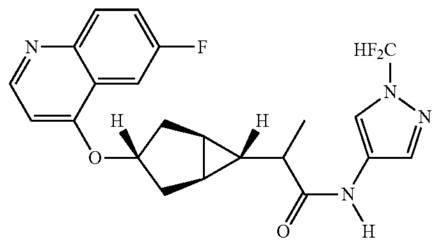 | N-(1-(difluoromethyl)-1H-pyrazol-4-yl)-2-((1R,3s,5S,6r)-3-((6-fluoroquinolin-4-yl)oxy)-bicyclo[3.1.0]hexan-6-yl)-propanamide | 431 | (1) |
| 65 | 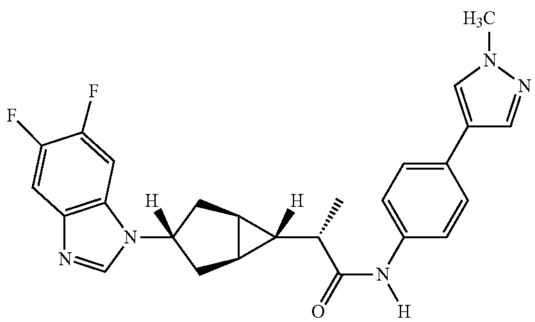 [SMILES: C[C@H](C(=O)Nc1ccc(-c2cnn(C)c2)cc1)[C@H]1[C@@H]2C[C@@H](n3cnc4cc(F)c(F)cc43)C[C@@H]21] | (S)-2-((1R,3R,5S,6r)-3-(5,6-difluoro-1H-benzo[d]-imidazol-1-yl)-bicyclo[3.1.0]hexan-6-yl)-N-(4-(1-methyl-1H-pyrazol-4-yl)phenyl)-propanamide | 462 | (5) |
| 66 | 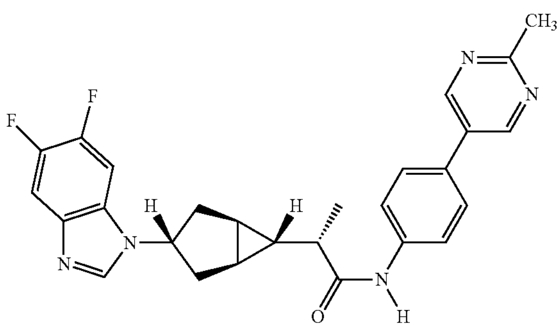 [SMILES: Cc1ncc(-c2ccc(NC(=O)[C@@H](C)[C@H]3[C@@H]4C[C@@H](n5cnc6cc(F)c(F)cc65)C[C@@H]43)cc2)cn1] | (S)-2-((1R,3R,5S,6r)-3-(5,6-difluoro-1H-benzo[d]-imidazol-1-yl)bicyclo-[3.1.0]hexan-6-yl)-N-(4-(2-methylpyrimidin-5-yl)-phenyl)propanamide | 474 | (5) |
| 67 | 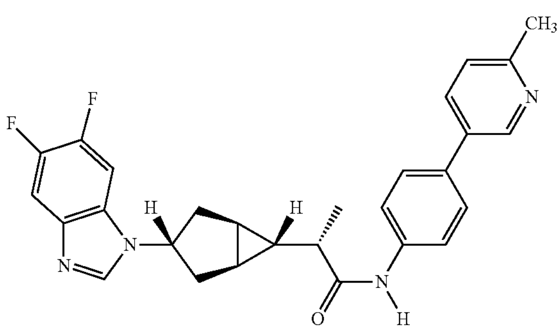 | (S)-2-((1R,3R,5S,6r)-3-(5,6-difluoro-1H-benzo[d]-imidazol-1-yl)-bicyclo[3.1.0]hexan-6-yl)-N-(4-(6-methylpyridin-3-yl)phenyl)propanamide | 473 | (5) |

TABLE 1-continued

Example compounds 12-151.

| Ex. | Structure | IUPAC Name | MWt | Notes |
|---|---|---|---|---|
| 68 | 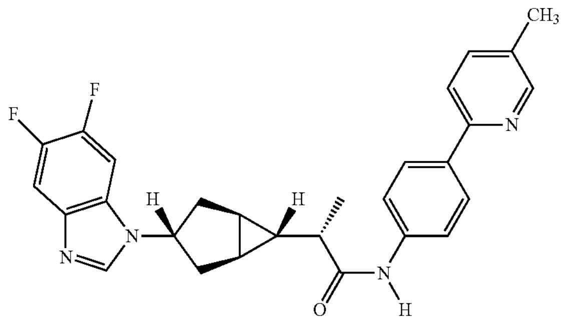 [SMILES: Cc1ccc(-c2ccc(NC(=O)[C@@H](C)[C@H]3[C@@H]4C[C@@H](n5cnc6cc(F)c(F)cc65)C[C@@H]43)cc2)nc1] | (S)-2-((1R,3R,5S,6r)-3-(5,6-difluoro-1H-benzo[d]-imidazol-1-yl)-bicyclo[3.1.0]hexan-6-yl)-N-(4-(5-methylpyridin-2-yl)phenyl)propanamide | 527 | (5) |
| 69 | 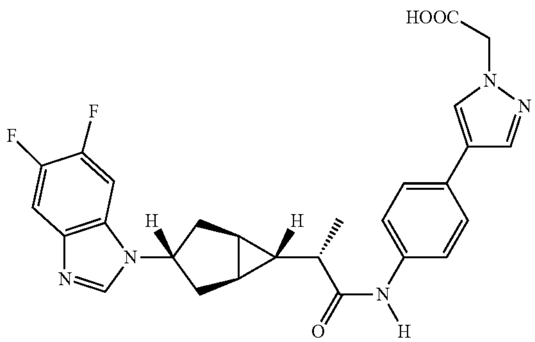 [SMILES: C[C@H](C(=O)Nc1ccc(-c2cnn(CC(=O)O)c2)cc1)[C@H]1[C@@H]2C[C@@H](n3cnc4cc(F)c(F)cc43)C[C@@H]21] | 2-(4-(4-((S)-2-((1R,3R,5S,6r)-3-(5,6-difluoro-1H-benzo[d]-imidazol-1-yl)bicyclo-[3.1.0]hexan-6-yl)-propanamido)phenyl)-1H-pyrazol-1-yl)acetic acid | 506 | (5) |
| 70 | 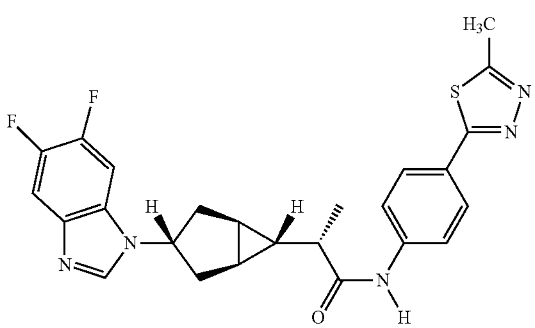 [SMILES: Cc1nnc(-c2ccc(NC(=O)[C@@H](C)[C@H]3[C@@H]4C[C@@H](n5cnc6cc(F)c(F)cc65)C[C@@H]43)cc2)s1] | (S)-2-((1R,3R,5S,6r)-3-(5,6-difluoro-1H-benzo[d]-imidazol-1-yl)bicyclo-[3.1.0]hexan-6-yl)-N-(4-(5-methyl-1,3,4-thiadiazol-2-yl)phenyl)propanamide | 480 | (5) |
| 71 | 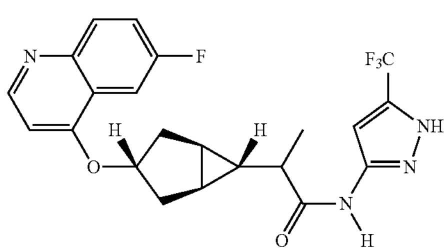 [SMILES: CC(C(=O)Nc1cc(C(F)(F)F)[nH]n1)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(5-(trifluoromethyl)-1H-pyrazol-3-yl)propanamide | 449 | (1) |
| 72 | 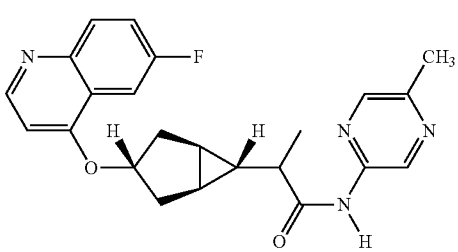 [SMILES: Cc1cnc(NC(=O)C(C)[C@H]2[C@@H]3C[C@@H](Oc4ccnc5ccc(F)cc45)C[C@@H]32)cn1] | 2-((1R,3s,5S,6r)-3-((6-fluoroquinolin-4-yl)oxy)-bicyclo[3.1.0]hexan-6-yl)-N-(5-methylpyrazin-2-yl)-propanamide | 407 | (1) |

TABLE 1-continued

Example compounds 12-151.

| Ex. | Structure | IUPAC Name | MWt | Notes |
|---|---|---|---|---|
| 73 | 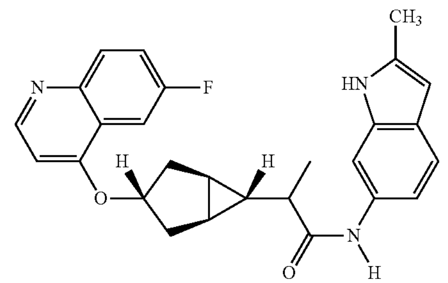 [SMILES: Cc1cc2ccc(NC(=O)C(C)[C@H]3[C@@H]4C[C@@H](Oc5ccnc6ccc(F)cc56)C[C@@H]43)cc2[nH]1] | 2-((1R,3s,5S,6r)-3-((6-fluoroquinolin-4-yl)oxy)-bicyclo[3.1.0]hexan-6-yl)-N-(2-methyl-1H-indol-6-yl)propanamide | 444 | (1) |
| 74 | 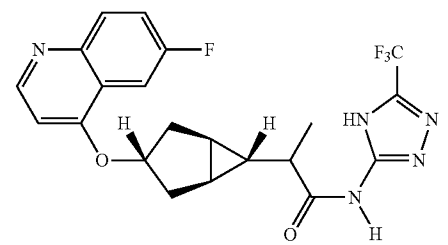 [SMILES: CC(C(=O)Nc1nnc(C(F)(F)F)[nH]1)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(5-(trifluoromethyl)-4H-1,2,4-triazol-3-yl)-propanamide | 450 | (1) |
| 75 | 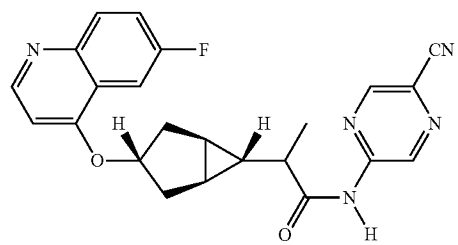 [SMILES: CC(C(=O)Nc1cnc(C#N)cn1)[C@H]1[C@@H]2C[C@@H](Oc3ccnc4ccc(F)cc34)C[C@@H]21] | N-(5-cyanopyrazin-2-yl)-2-((1R,3s,5S,6r)-3-((6-fluoroquinolin-4-yl)oxy)-bicyclo[3.1.0]hexan-6-yl)-propanamide | 418 | (1) |
| 76 | 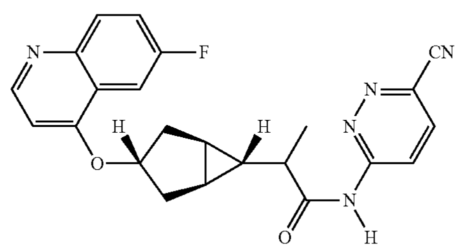 [SMILES: CC(C(=O)Nc1ccc(C#N)nn1)[C@H]1[C@@H]2C[C@@H](Oc3ccnc4ccc(F)cc34)C[C@@H]21] | N-(6-cyanopyridazin-3-yl)-2-((1R,3s,5S,6r)-3-((6-fluoroquinolin-4-yl)oxy)-bicyclo[3.1.0]hexan-6-yl)-propanamide | 418 | (1) |
| 77 | 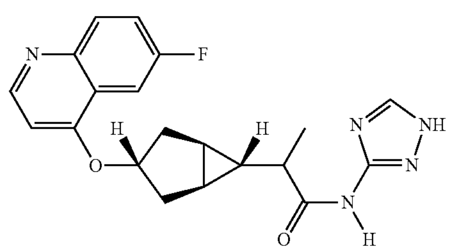 [SMILES: CC(C(=O)Nc1nc[nH]n1)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(1H-1,2,4-triazol-3-yl)-propanamide | 382 | (1) |
| 78 | 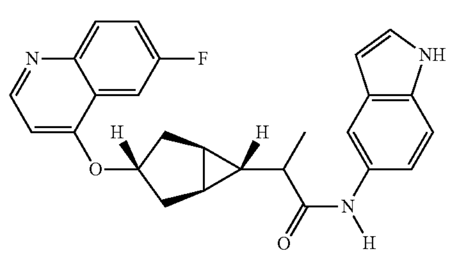 [SMILES: CC(C(=O)Nc1ccc2[nH]ccc2c1)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(1H-indol-5-yl)-propanamide | 430 | (1) |

TABLE 1-continued

Example compounds 12-151.

| Ex. | Structure | IUPAC Name | MWt | Notes |
|---|---|---|---|---|
| 79 | 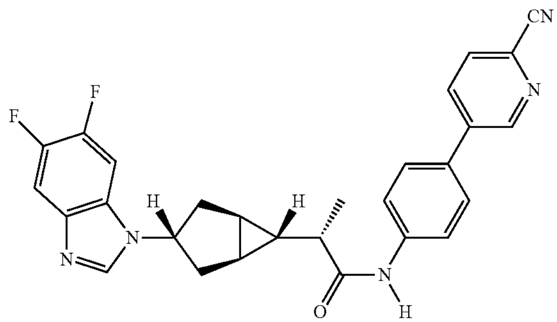 [SMILES: C[C@H](C(=O)Nc1ccc(-c2ccc(C#N)nc2)cc1)[C@H]1[C@@H]2C[C@@H](n3cnc4cc(F)c(F)cc43)C[C@@H]21] | (S)-N-(4-(6-cyanopyridin-3-yl)phenyl)-2-((1R,3R,5S,6r)-3-(5,6-difluoro-1H-benzo[d]-imidazol-1-yl)bicyclo-[3.1.0]hexan-6-yl)-propanamide | 484 | (5) |
| 80 | 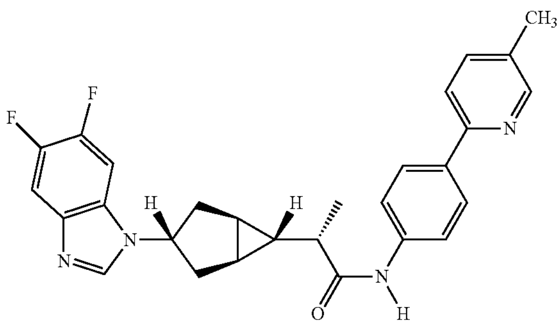 [SMILES: Cc1ccc(-c2ccc(NC(=O)[C@@H](C)[C@H]3[C@@H]4C[C@@H](n5cnc6cc(F)c(F)cc65)C[C@@H]43)cc2)nc1] | (S)-2-((1R,3R,5S,6r)-3-(5,6-difluoro-1H-benzo[d]-imidazol-1-yl)bicyclo-[3.1.0]hexan-6-yl)-N-(4-(5-methylpyridin-2-yl)-phenyl)propanamide | 473 | (5) |
| 81 | 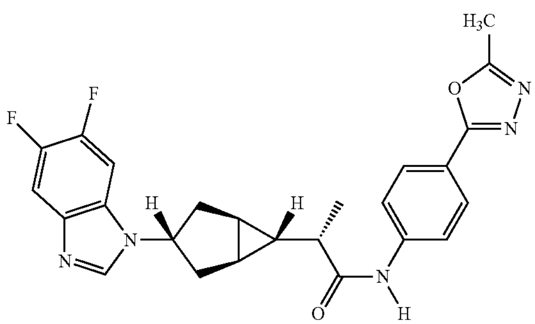 [SMILES: Cc1nnc(-c2ccc(NC(=O)[C@@H](C)[C@H]3[C@@H]4C[C@@H](n5cnc6cc(F)c(F)cc65)C[C@@H]43)cc2)o1] | (S)-2-((1R,3R,5S,6r)-3-(5,6-difluoro-1H-benzo[d]-imidazol-1-yl)-bicyclo[3.1.0]hexan-6-yl)-N-(4-(5-methyl-1,3,4-oxadiazol-2-yl)phenyl)-propanamide | 464 | (5) |
| 82 | 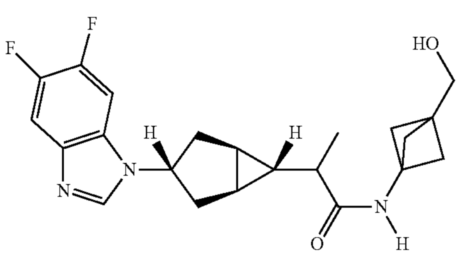 [SMILES: CC(C(=O)NC12CC(CO)(C1)C2)[C@H]1[C@@H]2C[C@@H](n3cnc4cc(F)c(F)cc43)C[C@@H]21] | 2-((1R,3s,5S,6r)-3-(5,6-difluoro-1H-benzo[d]-imidazol-1-yl)bicyclo-[3.1.0]hexan-6-yl)-N-(3-(hydroxymethyl)bicyclo-[1.1.1]pentan-1-yl)-propanamide | 402 | (7) |
| 83 | 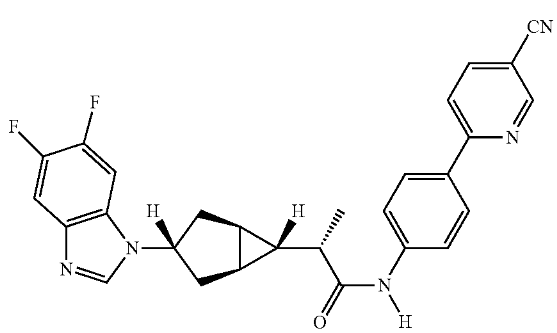 [SMILES: C[C@H](C(=O)Nc1ccc(-c2ccc(C#N)cn2)cc1)[C@H]1[C@@H]2C[C@@H](n3cnc4cc(F)c(F)cc43)C[C@@H]21] | (S)-N-(4-(5-cyanopyridin-2-yl)phenyl)-2-((1R,3R,5S,6r)-3-(5,6-difluoro-1H-benzo[d]-imidazol-1-yl)bicyclo-[3.1.0]hexan-6-yl)-propanamide | 484 | (5) |

TABLE 1-continued

Example compounds 12-151.

| Ex. | Structure | IUPAC Name | MWt | Notes |
| --- | --- | --- | --- | --- |
| 84 | 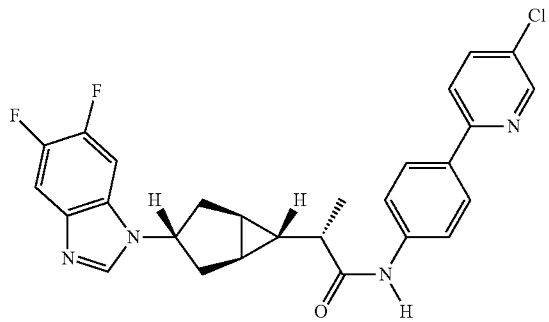 [SMILES: C[C@H](C(=O)Nc1ccc(-c2ccc(Cl)cn2)cc1)[C@H]1[C@@H]2C[C@@H](n3cnc4cc(F)c(F)cc43)C[C@@H]21] | (S)-N-(4-(5-chloropyridin-2-yl)phenyl)-2-((1R,3R,5S,6r)-3-(5,6-difluoro-1H-benzo[d]imidazol-1-yl)bicyclo[3.1.0]hexan-6-yl)propanamide | 493 | (5) |
| 85 | 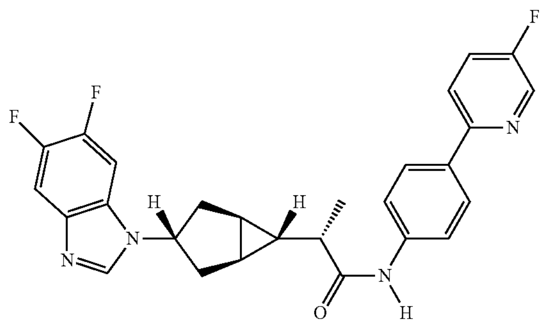 [SMILES: C[C@H](C(=O)Nc1ccc(-c2ccc(F)cn2)cc1)[C@H]1[C@@H]2C[C@@H](n3cnc4cc(F)c(F)cc43)C[C@@H]21] | (S)-2-((1R,3R,5S,6r)-3-(5,6-difluoro-1H-benzo[d]imidazol-1-yl)bicyclo[3.1.0]hexan-6-yl)-N-(4-(5-fluoropyridin-2-yl)phenyl)propanamide | 477 | (5) |
| 86 | 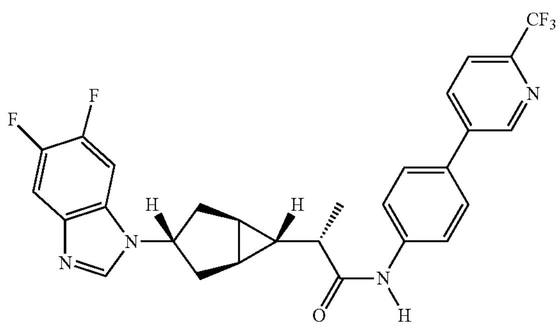 | (S)-2-((1R,3R,5S,6r)-3-(5,6-difluoro-1H-benzo[d]imidazol-1-yl)bicyclo[3.1.0]hexan-6-yl)-N-(4-(6-(trifluoromethyl)pyridin-3-yl)phenyl)propanamide | 527 | (5) |
| 87 | 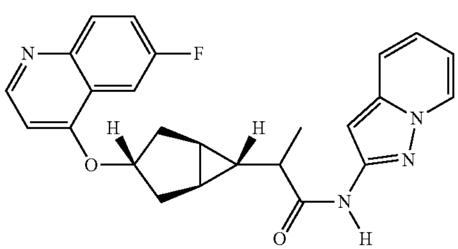 [SMILES: CC(C(=O)Nc1cc2ccccn2n1)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)bicyclo[3.1.0]hexan-6-yl)-N-(pyrazolo[1,5-a]pyridin-2-yl)propanamide | 430 | (1) |
| 88 | 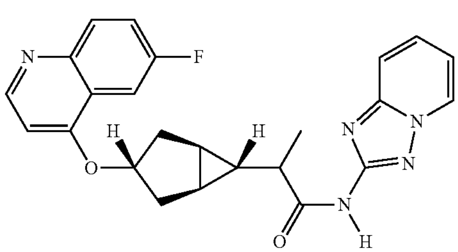 [SMILES: CC(C(=O)Nc1nc2ccccn2n1)[C@H]1[C@@H]2C[C@@H](Oc3ccnc4ccc(F)cc34)C[C@@H]21] | N-([1,2,4]triazolo[1,5-a]pyridin-2-yl)-2-((1R,3s,5S,6r)-3-((6-fluoroquinolin-4-yl)oxy)bicyclo[3.1.0]hexan-6-yl)propanamide | 432 | (1) |

TABLE 1-continued

Example compounds 12-151.

| Ex. | Structure | IUPAC Name | MWt | Notes |
|---|---|---|---|---|
| 89 | 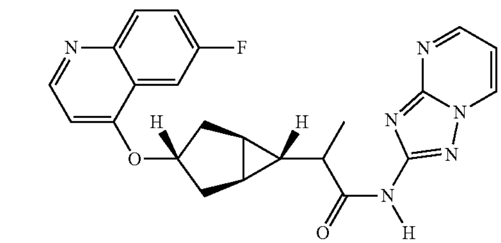 [SMILES: CC(C(=O)Nc1nc2ncccn2n1)[C@H]1[C@@H]2C[C@@H](Oc3ccnc4ccc(F)cc34)C[C@@H]21] | N-([1,2,4]triazolo[1,5-a]-pyrimidin-2-yl)-2-((1R,3s,5S,6r)-3-((6-fluoro-quinolin-4-yl)oxy)bicyclo-[3.1.0]hexan-6-yl)propanamide | 433 | (1) |
| 90 | 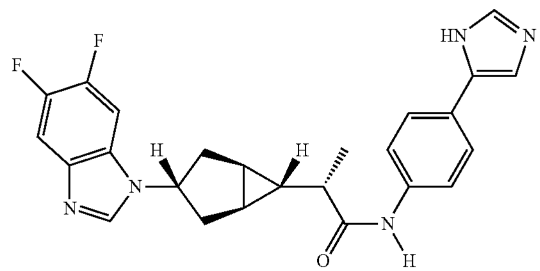 [SMILES: C[C@H](C(=O)Nc1ccc(-c2cnc[nH]2)cc1)[C@H]1[C@@H]2C[C@@H](n3cnc4cc(F)c(F)cc43)C[C@@H]21] | (S)-N-(4-(1H-imidazol-5-yl)phenyl)-2-((1R,3R,5S,6r)-3-(5,6-difluoro-1H-benzo[d]-imidazol-1-yl)bicyclo-[3.1.0]hexan-6-yl)-propanamide | 448 | (6) |
| 91 | 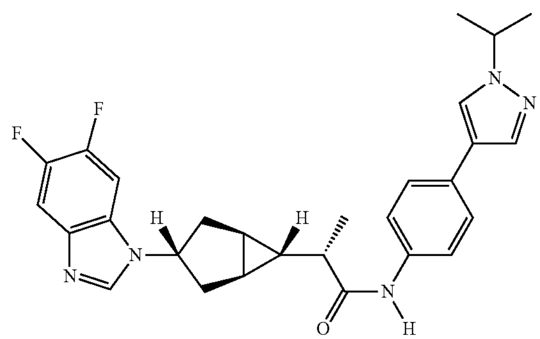 [SMILES: CC(C)n1cc(-c2ccc(NC(=O)[C@@H](C)[C@H]3[C@@H]4C[C@@H](n5cnc6cc(F)c(F)cc65)C[C@@H]43)cc2)cn1] | (S)-2-((1R,3R,5S,6r)-3-(5,6-difluoro-1H-benzo[d]-imidazol-1-yl)bicyclo-[3.1.0]hexan-6-yl)-N-(4-(1-isopropyl-1H-pyrazol-4-yl)phenyl)propanamide | 490 | (5) |
| 92 | 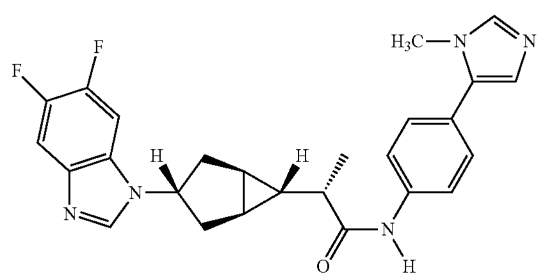 [SMILES: C[C@H](C(=O)Nc1ccc(-c2cncn2C)cc1)[C@H]1[C@@H]2C[C@@H](n3cnc4cc(F)c(F)cc43)C[C@@H]21] | (S)-2-((1R,3R,5S,6r)-3-(5,6-difluoro-1H-benzo[d]-imidazol-1-yl)bicyclo-[3.1.0]hexan-6-yl)-N-(4-(1-methyl-1H-imidazol-5-yl)-phenyl)propanamide | 462 | (5) |
| 93 | 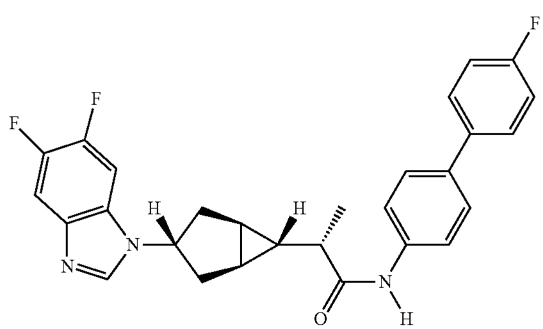 [SMILES: C[C@H](C(=O)Nc1ccc(-c2ccc(F)cc2)cc1)[C@H]1[C@@H]2C[C@@H](n3cnc4cc(F)c(F)cc43)C[C@@H]21] | (S)-2-((1R,3R,5S,6r)-3-(5,6-difluoro-1H-benzo[d]-imidazol-1-yl)bicyclo-[3.1.0]hexan-6-yl)-N-(4'-fluoro-[1,1'-biphenyl]-4-yl)propanamide | 476 | (5) |

TABLE 1-continued

Example compounds 12-151.

| Ex. | Structure | IUPAC Name | MWt | Notes |
|---|---|---|---|---|
| 94 | 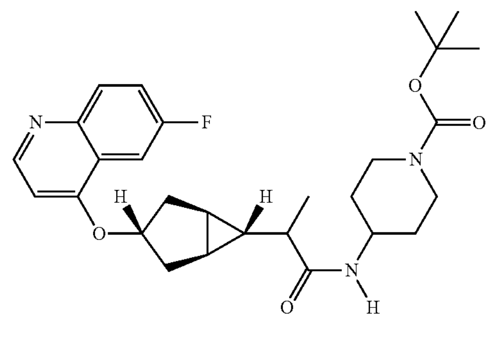 [SMILES: CC(C(=O)NC1CCN(C(=O)OC(C)(C)C)CC1)[C@H]1[C@@H]2C[C@@H](Oc3ccnc4ccc(F)cc34)C[C@@H]21] | tert-butyl 4-(2-((1R,3s,5S,6r)-3-((6-fluoroquinolin-4-yl)oxy)-bicyclo[3.1.0]hexan-6-yl)-propanamido)piperidine-1-carboxylate | 498 | (1) |
| 95 | 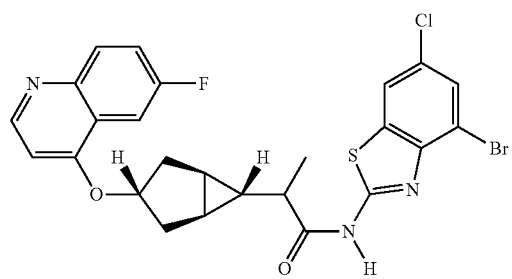 [SMILES: CC(C(=O)Nc1nc2c(Br)cc(Cl)cc2s1)[C@H]1[C@@H]2C[C@@H](Oc3ccnc4ccc(F)cc34)C[C@@H]21] | N-(4-bromo-6-chloro-benzo[d]thiazol-2-yl)-2-((1R,3s,5S,6r)-3-((6-fluoroquinolin-4-yl)-oxy)bicyclo[3.1.0]hexan-6-yl)propanamide | 561 | (1) |
| 96 | 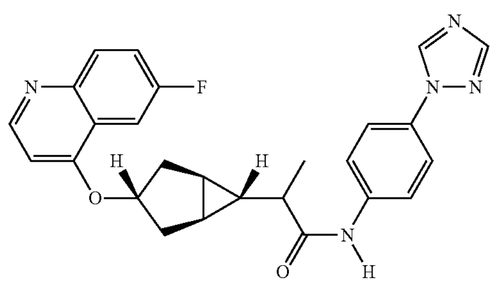 [SMILES: CC(C(=O)Nc1ccc(-n2cncn2)cc1)[C@H]1[C@@H]2C[C@@H](Oc3ccnc4ccc(F)cc34)C[C@@H]21] | N-(5-(1H-1,2,4-triazol-1-yl)pyridin-2-yl)-2-((1R,3s,5S,6r)-3-((6-fluoroquinolin-4-yl)-oxy)bicyclo[3.1.0]hexan-6-yl)propanamide | 459 | (1) |
| 97 | 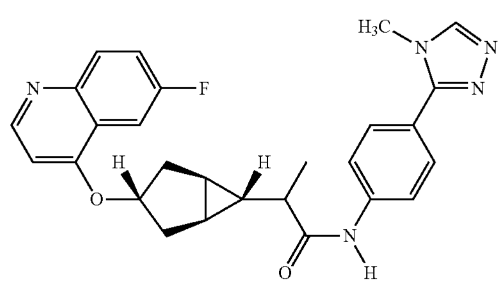 [SMILES: CC(C(=O)Nc1ccc(-c2nncn2C)cc1)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(5-(4-methyl-4H-1,2,4-triazol-3-yl)pyridin-2-yl)-propanamide | 473 | (1) |
| 98 | 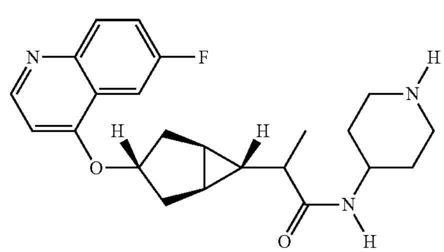 [SMILES: CC(C(=O)NC1CCNCC1)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(piperidin-4-yl)-propanamide | 398 | (1)(2) |

TABLE 1-continued

Example compounds 12-151.

| Ex. | Structure | IUPAC Name | MWt | Notes |
|---|---|---|---|---|
| 99 | 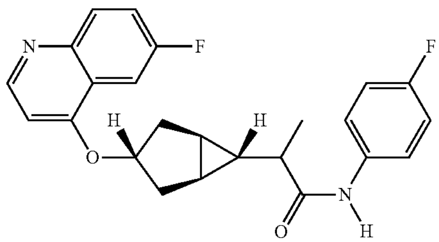 [SMILES: CC(C(=O)Nc1ccc(F)cc1)[C@H]1[C@@H]2C[C@@H](Oc3ccnc4ccc(F)cc34)C[C@@H]21] | N-(4-fluorophenyl)-2-((1R,3s,5S,6r)-3-((6-fluoroquinolin-4-yl)oxy)-bicyclo[3.1.0]hexan-6-yl)propanamide | 409 | (1) |
| 100 | 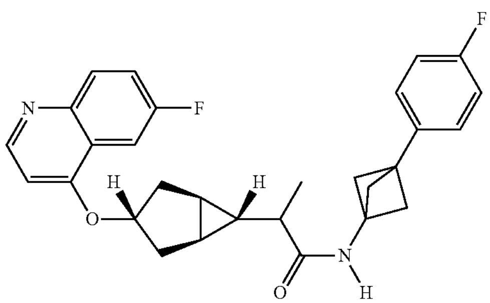 [SMILES: CC(C(=O)NC12CC(c3ccc(F)cc3)(C1)C2)[C@H]1[C@@H]2C[C@@H](Oc3ccnc4ccc(F)cc34)C[C@@H]21] | N-(3-(4-fluorophenyl)-bicyclo[1.1.1]pentan-1-yl)-2-((1R,3s,5S,6r)-3-((6-fluoroquinolin-4-yl)-oxy)bicyclo[3.1.0]hexan-6-yl)propanamide | 475 | (1) |
| 101 | 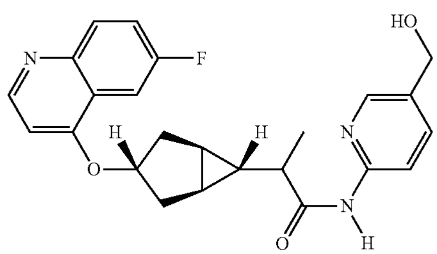 [SMILES: CC(C(=O)Nc1ccc(CO)cn1)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(5-(hydroxymethyl)-pyridin-2-yl)propanamide | 422 | (1) |
| 102 | 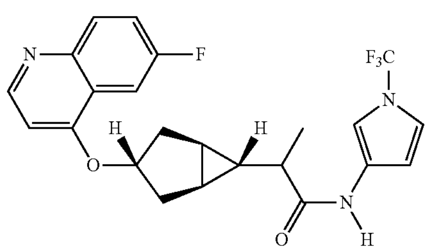 [SMILES: CC(C(=O)Nc1ccn(C(F)(F)F)c1)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(1-(trifluoromethyl)-1H-pyrazol-3-yl)propanamide | 449 | (1) |
| 103 | 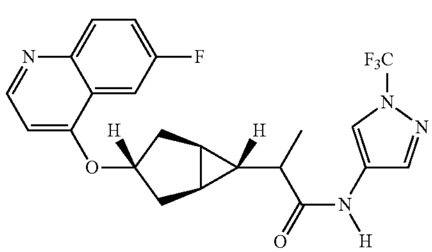 [SMILES: CC(C(=O)Nc1cnn(C(F)(F)F)c1)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(1-(trifluoromethyl)-1H-pyrazol-4-yl)propanamide | 449 | (1) |

TABLE 1-continued

Example compounds 12-151.

| Ex. | Structure | IUPAC Name | MWt | Notes |
|---|---|---|---|---|
| 104 | 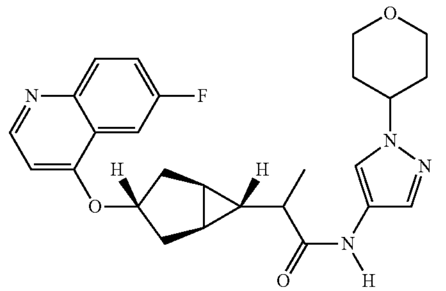 [SMILES: CC(C(=O)Nc1cnn(C2CCOCC2)c1)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(1-(tetrahydro-2H-pyran-4-yl)-1H-pyrazol-4-yl)-propanamide | 465 | (1) |
| 105 | 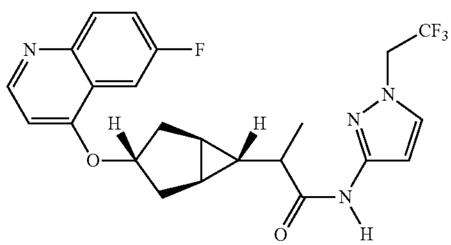 [SMILES: CC(C(=O)Nc1ccn(CC(F)(F)F)n1)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(1-(2,2,2-trifluoroethyl)-1H-pyrazol-3-yl)-propanamide | 463 | (1) |
| 106 | 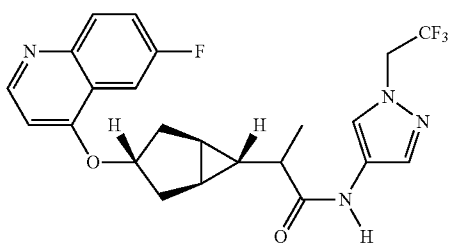 | 2-((1R,3s,5S,6r)-3-((6-fluoroquinolin-4-yl)oxy)-bicyclo[3.1.0]hexan-6-yl)-N-(1-(2,2,2-trifluoroethyl)-1H-pyrazol-4-yl)-propanamide | 463 | (1) |
| 107 | 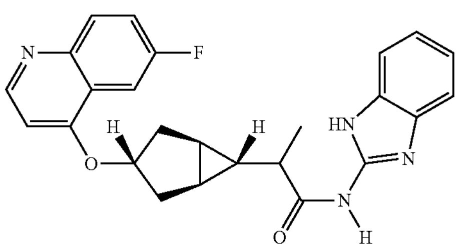 [SMILES: CC(C(=O)Nc1nc2ccccc2[nH]1)[C@H]1[C@@H]2C[C@@H](Oc3ccnc4ccc(F)cc34)C[C@@H]21] | N-(1H-benzo[d]imidazol-2-yl)-2-((1R,3s,5S,6r)-3-((6-fluoroquinolin-4-yl)oxy)-bicyclo[3.1.0]hexan-6-yl)propanamide | 431 | (1) |
| 108 | 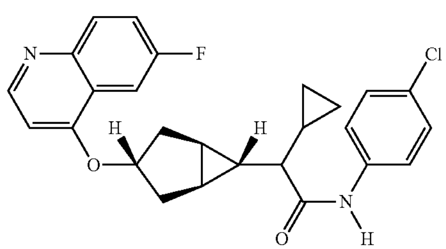 | N-(4-chlorophenyl)-2-cyclopropyl-2-((1R,3s,5S,6r)-3-((6-fluoro-quinolin-4-yl)oxy)-bicyclo[3.1.0]hexan-6-yl)-acetamide | 451 | (1) |
| 109 | 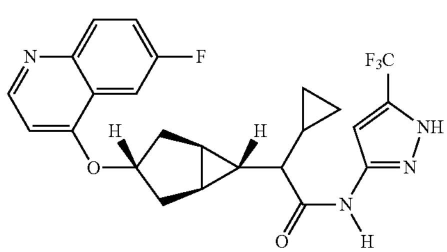 [SMILES: O=C(Nc1cc(C(F)(F)F)[nH]n1)C(C1CC1)[C@H]1[C@@H]2C[C@@H](Oc3ccnc4ccc(F)cc34)C[C@@H]21] | 2-cyclopropyl-2-((1R,3s,5S,6r)-3-((6-fluoroquinolin-4-yl)-oxy)bicyclo[3.1.0]hexan-6-yl)-N-(5-(trifluoromethyl)-1H-pyrazol-3-yl)acetamide | 475 | (1) |

TABLE 1-continued

Example compounds 12-151.

| Ex. | Structure | IUPAC Name | MWt | Notes |
| --- | --- | --- | --- | --- |
| 110 | 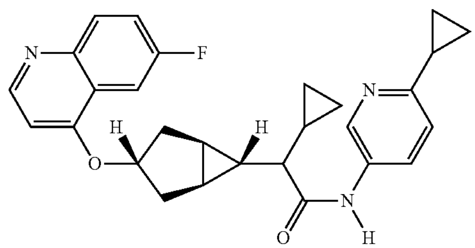 [SMILES: O=C(Nc1ccc(C2CC2)nc1)C(C1CC1)[C@H]1[C@@H]2C[C@@H](Oc3ccnc4ccc(F)cc34)C[C@@H]21] | 2-cyclopropyl-N-(6-cyclopropylpyridin-3-yl)-2-((1R,3s,5S,6r)-3-((6-fluoroquinolin-4-yl)oxy)-bicyclo[3.1.0]hexan-6-yl)-acetamide | 458 | (1) |
| 111 | 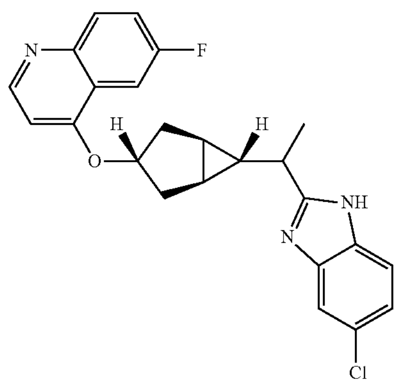 [SMILES: CC(c1nc2cc(Cl)ccc2[nH]1)[C@H]1[C@@H]2C[C@@H](Oc3ccnc4ccc(F)cc34)C[C@@H]21] | 4-(((1R,3s,5S,6r)-6-(1-(5-chloro-1H-benzo[d]-imidazol-2-yl)ethyl)-bicyclo[3.1.0]hexan-3-yl)-oxy)-6-fluoroquinoline | 422 | (10) |
| 112 | 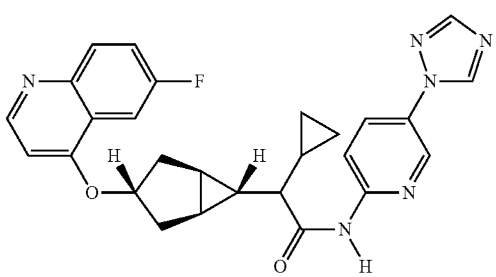 [SMILES: O=C(Nc1ccc(-n2cncn2)cn1)C(C1CC1)[C@H]1[C@@H]2C[C@@H](Oc3ccnc4ccc(F)cc34)C[C@@H]21] | N-(5-(1H-1,2,4-triazol-1-yl)pyridin-2-yl)-2-cyclopropyl-2-((1R,3s,5S,6r)-3-((6-fluoroquinolin-4-yl)oxy)-bicyclo[3.1.0]hexan-6-yl)acetamide | 485 | (1) |
| 113 | 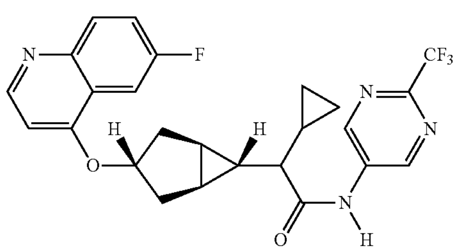 [SMILES: O=C(Nc1cnc(C(F)(F)F)nc1)C(C1CC1)[C@H]1[C@@H]2C[C@@H](Oc3ccnc4ccc(F)cc34)C[C@@H]21] | 2-cyclopropyl-2-((1R,3s,5S,6r)-3-((6-fluoroquinolin-4-yl)oxy)-bicyclo[3.1.0]hexan-6-yl)-N-(2-(trifluoromethyl)-pyrimidin-5-yl)acetamide | 487 | (1) |
| 114 | 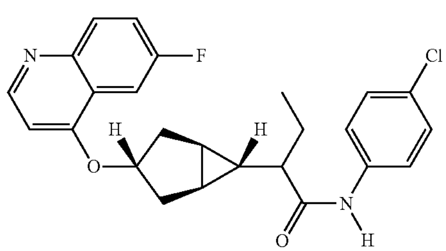 [SMILES: CCC(C(=O)Nc1ccc(Cl)cc1)[C@H]1[C@@H]2C[C@@H](Oc3ccnc4ccc(F)cc34)C[C@@H]21] | N-(4-chlorophenyl)-2-((1R,3s,5S,6r)-3-((6-fluoroquinolin-4-yl)oxy)-bicyclo[3.1.0]hexan-6-yl)-butanamide | 439 | (1) |

TABLE 1-continued

Example compounds 12-151.

| Ex. | Structure | IUPAC Name | MWt | Notes |
|---|---|---|---|---|
| 115 | 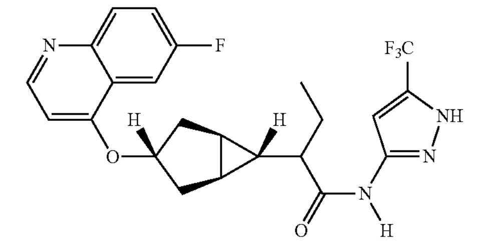 [SMILES: CCC(C(=O)Nc1cc(C(F)(F)F)[nH]n1)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(5-(trifluoromethyl)-1H-pyrazol-3-yl)butanamide | 463 | (1) |
| 116 | 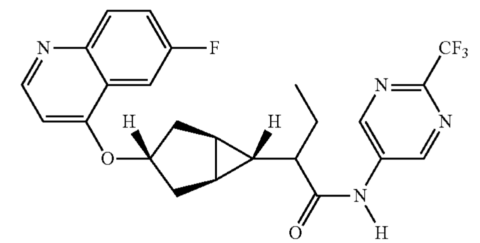 [SMILES: CCC(C(=O)Nc1cnc(C(F)(F)F)nc1)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(2-(trifluoromethyl)-pyrimidin-5-yl)butanamide | 475 | (1) |
| 117 | 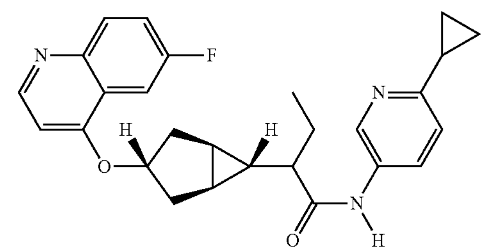 [SMILES: CCC(C(=O)Nc1ccc(C2CC2)nc1)[C@H]1[C@@H]2C[C@@H](Oc3ccnc4ccc(F)cc34)C[C@@H]21] | N-(6-cyclopropylpyridin-3-yl)-2-((1R,3s,5S,6r)-3-((6-fluoroquinolin-4-yl)oxy)-bicyclo[3.1.0]hexan-6-yl)-butanamide | 446 | (1) |
| 118 | 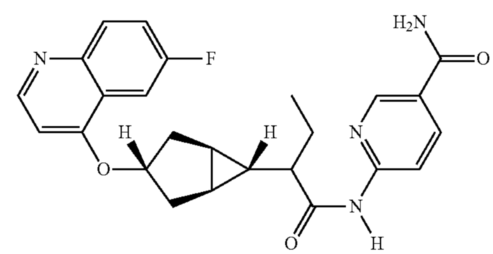 [SMILES: CCC(C(=O)Nc1ccc(C(N)=O)cn1)[C@H]1[C@@H]2C[C@@H](Oc3ccnc4ccc(F)cc34)C[C@@H]21] | 6-(2-((1R,3s,5S,6r)-3-((6-fluoroquinolin-4-yl)oxy)-bicyclo[3.1.0]hexan-6-yl)-butanamido)nicotinamide | 449 | (1) |
| 119 | 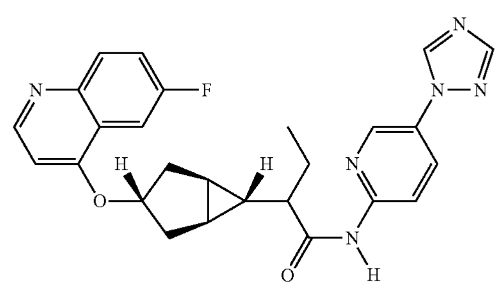 [SMILES: CCC(C(=O)Nc1ccc(-n2cncn2)cn1)[C@H]1[C@@H]2C[C@@H](Oc3ccnc4ccc(F)cc34)C[C@@H]21] | N-(5-(1H-1,2,4-triazol-1-yl)pyridin-2-yl)-2-((1R,3s,5S,6r)-3-((6-fluoro-quinolin-4-yl)oxy)-bicyclo[3.1.0]hexan-6-yl)butanamide | 473 | (1) |
| 120 | 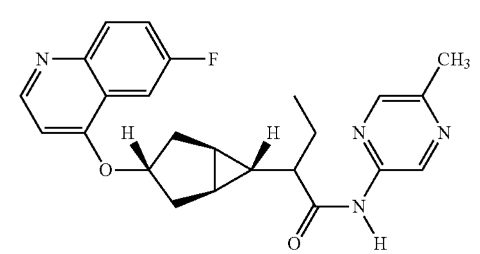 [SMILES: CCC(C(=O)Nc1cnc(C)cn1)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(5-methylpyrazin-2-yl)-butanamide | 421 | (1) |

TABLE 1-continued

Example compounds 12-151.

| Ex. | Structure | IUPAC Name | MWt | Notes |
|---|---|---|---|---|
| 121 | 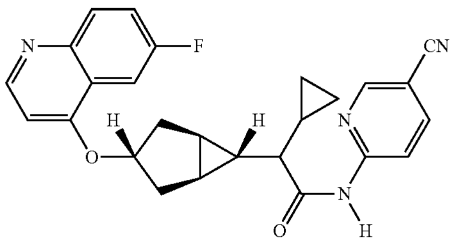 [SMILES: N#Cc1ccc(NC(=O)C(C2CC2)[C@H]2[C@@H]3C[C@@H](Oc4ccnc5ccc(F)cc45)C[C@@H]32)nc1] | N-(5-cyanopyridin-2-yl)-2-cyclopropyl-2-((1R,3s,5S,6r)-3-((6-fluoroquinolin-4-yl)oxy)bicyclo[3.1.0]hexan-6-yl)acetamide | 443 | (1) |
| 122 | 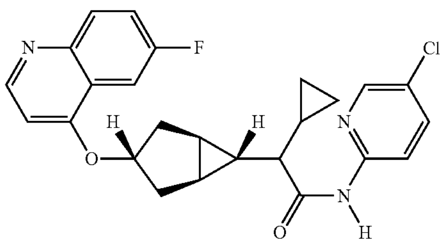 [SMILES: O=C(Nc1ccc(Cl)cn1)C(C1CC1)[C@H]1[C@@H]2C[C@@H](Oc3ccnc4ccc(F)cc34)C[C@@H]21] | N-(5-chloropyridin-2-yl)-2-cyclopropyl-2-((1R,3s,5S,6r)-3-((6-fluoroquinolin-4-yl)oxy)bicyclo[3.1.0]hexan-6-yl)acetamide | 452 | (1) |
| 123 | 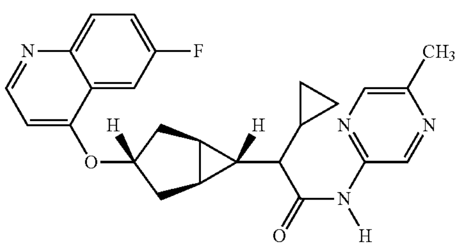 [SMILES: Cc1cnc(NC(=O)C(C2CC2)[C@H]2[C@@H]3C[C@@H](Oc4ccnc5ccc(F)cc45)C[C@@H]32)cn1] | 2-cyclopropyl-2-((1R,3s,5S,6r)-3-((6-fluoroquinolin-4-yl)oxy)bicyclo[3.1.0]hexan-6-yl)-N-(5-methylpyrazin-2-yl)acetamide | 433 | (1) |
| 124 | 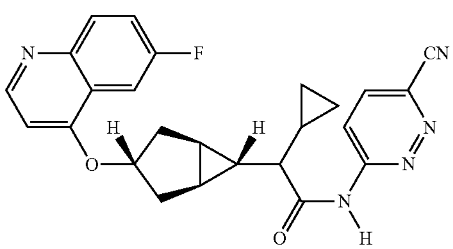 [SMILES: N#Cc1ccc(NC(=O)C(C2CC2)[C@H]2[C@@H]3C[C@@H](Oc4ccnc5ccc(F)cc45)C[C@@H]32)nn1] | N-(6-cyanopyridazin-3-yl)-2-cyclopropyl-2-((1R,3s,5S,6r)-3-((6-fluoroquinolin-4-yl)oxy)bicyclo[3.1.0]hexan-6-yl)acetamide | 444 | (1) |
| 125 | 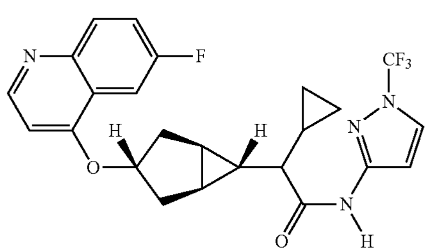 [SMILES: O=C(Nc1ccn(C(F)(F)F)n1)C(C1CC1)[C@H]1[C@@H]2C[C@@H](Oc3ccnc4ccc(F)cc34)C[C@@H]21] | 2-cyclopropyl-2-((1R,3s,5S,6r)-3-((6-fluoroquinolin-4-yl)oxy)bicyclo[3.1.0]hexan-6-yl)-N-(1-(trifluoromethyl)-1H-pyrazol-3-yl)acetamide | 475 | (1) |
| 126 | 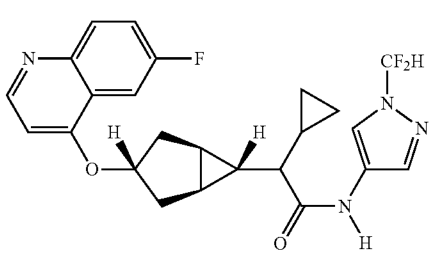 [SMILES: O=C(Nc1cnn(C(F)F)c1)C(C1CC1)[C@H]1[C@@H]2C[C@@H](Oc3ccnc4ccc(F)cc34)C[C@@H]21] | 2-cyclopropyl-N-(1-(difluoromethyl)-1H-pyrazol-4-yl)-2-((1R,3s,5S,6r)-3-((6-fluoroquinolin-4-yl)oxy)bicyclo[3.1.0]hexan-6-yl)acetamide | 457 | (1) |

TABLE 1-continued

Example compounds 12-151.

| Ex. | Structure | IUPAC Name | MWt | Notes |
| --- | --- | --- | --- | --- |
| 127 | 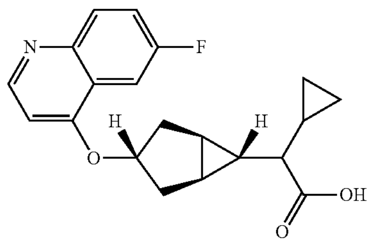 [SMILES: O=C(O)C(C1CC1)[C@H]1[C@@H]2C[C@@H](Oc3ccnc4ccc(F)cc34)C[C@@H]21] | 2-cyclopropyl-2-((1R,3s,5S,6r)-3-((6-fluoroquinolin-4-yl)oxy)-bicyclo[3.1.0]hexan-6-yl)acetic acid | 342 | |
| 128 | 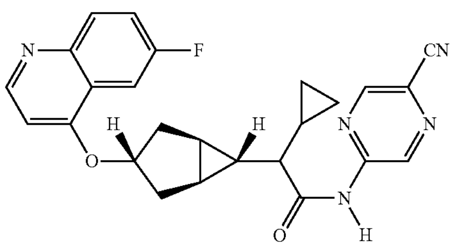 [SMILES: N#Cc1cnc(NC(=O)C(C2CC2)[C@H]2[C@@H]3C[C@@H](Oc4ccnc5ccc(F)cc45)C[C@@H]32)cn1] | N-(5-cyanopyrazin-2-yl)-2-cyclopropyl-2-((1R,3s,5S,6r)-3-((6-fluoroquinolin-4-yl)oxy)-bicyclo[3.1.0]hexan-6-yl)-acetamide | 444 | |
| 129 | 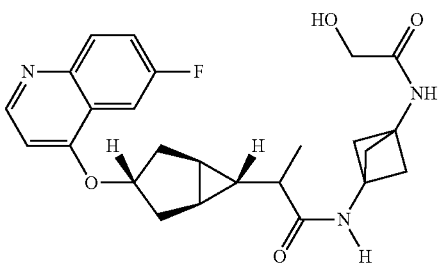 [SMILES: CC(C(=O)NC12CC(NC(=O)CO)(C1)C2)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(3-(2-hydroxy-acetamido)bicyclo-[1.1.1]pentan-1-yl)-propanamide | 454 | (8) |
| 130 | 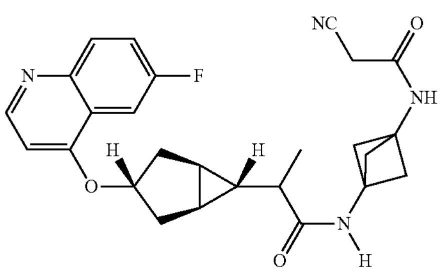 | N-(3-(2-cyanoacetamido)-bicyclo[1.1.1]pentan-1-yl)-2-((1R-((1R,3s,5S,6r)-, 3s,5S,6r)-3-((6-fluoroquinolin-4-yl)oxy)-bicyclo[3.1.0]hexan-6-yl)propanamide | 463 | (8) |
| 131 | 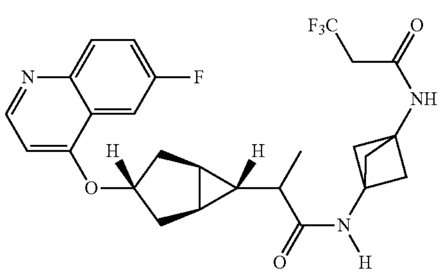 [SMILES: CC(C(=O)NC12CC(NC(=O)CC#N)(C1)C2)[C@H]1[C@@H]2C[C@@H](Oc3ccnc4ccc(F)cc34)C[C@@H]21] | 3,3,3-trifluoro-N-(3-(2-((1R,3s,5S,6r)-3-((6-fluoroquinolin-4-yl)oxy)-bicyclo[3.1.0]hexan-6-yl)-propanamido)bicyclo-[1.1.1]pentan-1-yl)-propanamide | 506 | (8) |
| 132 | 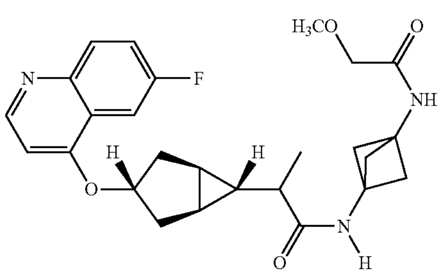 [SMILES: COCC(=O)NC12CC(NC(=O)C(C)[C@H]3[C@@H]4C[C@@H](Oc5ccnc6ccc(F)cc56)C[C@@H]43)(C1)C2] | 2-((1R,3s,5S,6r)-3-((6-fluoroquinolin-4-yl)oxy)-bicyclo[3.1.0]hexan-6-yl)-N-(3-(2-methoxyacetamido)-bicyclo[1.1.1]pentan-1-yl)-propanamide | 468 | (8) |

TABLE 1-continued

Example compounds 12-151.

| Ex. | Structure | IUPAC Name | MWt | Notes |
|---|---|---|---|---|
| 133 | 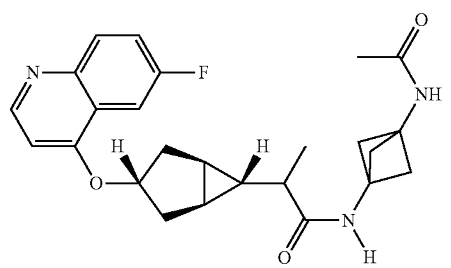 [SMILES: CC(=O)NC12CC(NC(=O)C(C)[C@H]3[C@@H]4C[C@@H](Oc5ccnc6ccc(F)cc56)C[C@@H]43)(C1)C2] | N-(3-acetamidobicyclo-[1.1.1]pentan-1-yl)-2-((1R,3s,5S,6r)-3-((6-fluoro-quinolin-4-yl)oxy)bicyclo-[3.1.0]hexan-6-yl)-propanamide | 438 | (8) |
| 134 | 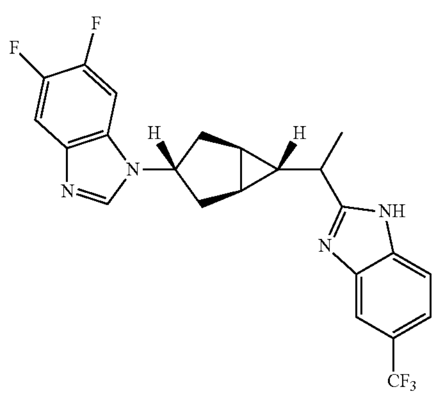 [SMILES: CC(c1nc2cc(C(F)(F)F)ccc2[nH]1)[C@H]1[C@@H]2C[C@@H](n3cnc4cc(F)c(F)cc43)C[C@@H]21] | 5,6-Difluoro-1-((1R,3s,5S,6r)-6-(1-(5-(trifluoromethyl)-1H-benzo[d]imidazol-2-yl)-ethyl)bicyclo[3.1.0]hexan-3-yl)-1H-benzo[d]imidazole | 447 | (9) |
| 135 | 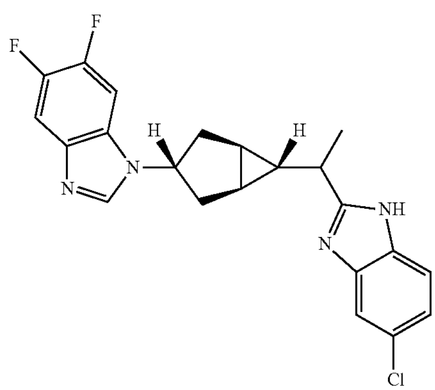 [SMILES: CC(c1nc2cc(Cl)ccc2[nH]1)[C@H]1[C@@H]2C[C@@H](n3cnc4cc(F)c(F)cc43)C[C@@H]21] | 1-((1R,3s,5S,6r)-6-(1-(5-chloro-1H-benzo[d]-imidazol-2-yl)ethyl)-bicyclo[3.1.0]hexan-3-yl)-5,6-difluoro-1H-benzo[d]imidazole | 413 | (9) |
| 136 | 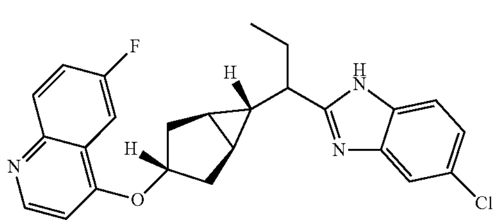 [SMILES: CCC(c1nc2cc(Cl)ccc2[nH]1)[C@H]1[C@@H]2C[C@@H](Oc3ccnc4ccc(F)cc34)C[C@@H]21] | 4-(((1R,3s,5S,6r)-6-(1-(5-chloro-1H-benzo[d]-imidazol-2-yl)propyl)-bicyclo[3.1.0]hexan-3-yl)oxy)-6-fluoroquinoline | 436 | (9) |

TABLE 1-continued

Example compounds 12-151.

| Ex. | Structure | IUPAC Name | MWt | Notes |
|---|---|---|---|---|
| 137 | 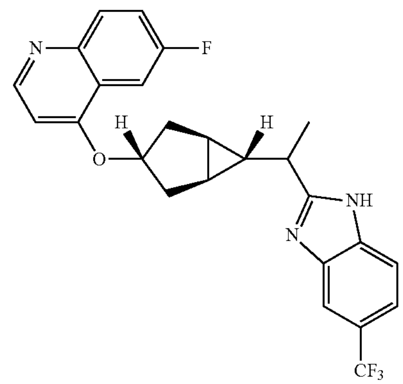 [SMILES: CC(c1nc2cc(C(F)(F)F)ccc2[nH]1)[C@H]1[C@@H]2C[C@@H](Oc3ccnc4ccc(F)cc34)C[C@@H]21] | 6-fluoro-4-(((1R,3s,5S,6r)-6-(1-(5-(trifluoromethyl)-1H-benzo[d]imidazol-2-yl)-ethyl)bicyclo[3.1.0]hexan-3-yl)oxy)quinoline | 456 | (9) |
| 138 | 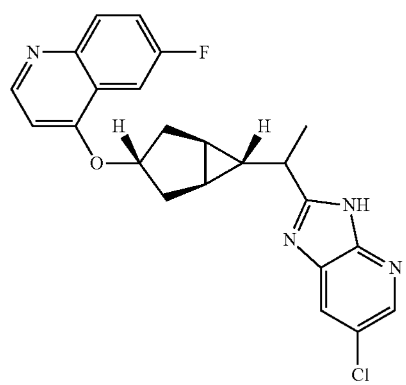 [SMILES: CC(c1nc2cc(Cl)cnc2[nH]1)[C@H]1[C@@H]2C[C@@H](Oc3ccnc4ccc(F)cc34)C[C@@H]21] | 4-(((1R,3s,5S,6r)-6-(1-(6-chloro-3H-imidazo[4,5-b]pyridin-2-yl)ethyl)-bicyclo[3.1.0]hexan-3-yl)oxy)-6-fluoroquinoline | 423 | (9) |
| 139 | 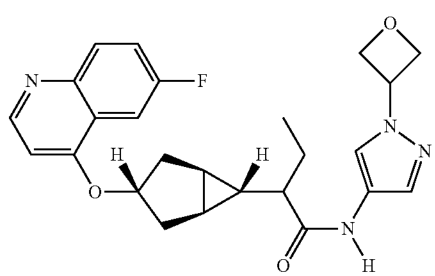 [SMILES: CCC(C(=O)Nc1cnn(C2COC2)c1)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(1-(oxetan-3-yl)-1H-pyrazol-4-yl)butanamide | 451 | (1) |
| 140 | 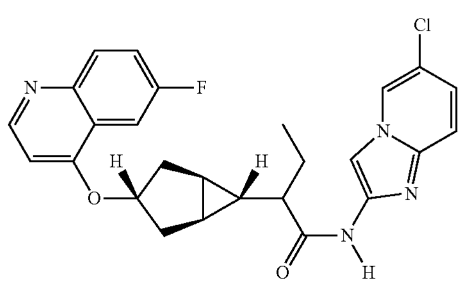 | N-(6-chloroimidazo[1,2-a]-pyridin-2-yl)-2-((1R,3s,5S,6r)-3-((6-fluoro-quinolin-4-yl)oxy)bicyclo-[3.1.0]hexan-6-yl)butanamide | 479 | (9) |

TABLE 1-continued

Example compounds 12-151.

| Ex. | Structure | IUPAC Name | MWt | Notes |
|---|---|---|---|---|
| 141 | 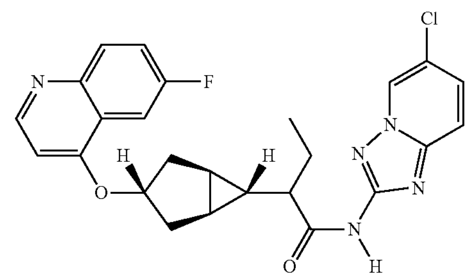 [SMILES: CCC(C(=O)Nc1cn2cc(Cl)ccc2n1)[C@H]1[C@@H]2C[C@@H](Oc3ccnc4ccc(F)cc34)C[C@@H]21] | N-(6-chloro-[1,2,4]-triazolo[1,5-a]pyridin-2-yl)-2-((1R,3s,5S,6r)-3-((6-fluoroquinolin-4-yl)oxy)bicyclo[3.1.0]hexan-6-yl)butanamide | 479 | (9) |
| 142 | 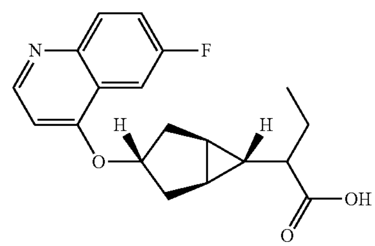 [SMILES: CCC(C(=O)O)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-butanoic acid | 330 | Similar to 70883 |
| 143 | 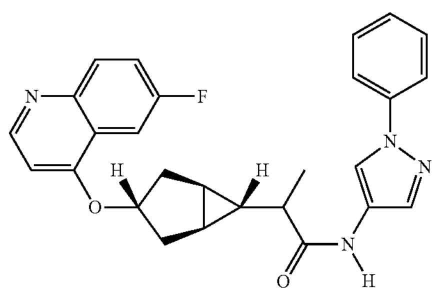 [SMILES: CC(C(=O)Nc1cnn(-c2ccccc2)c1)[C@H]1[C@@H]2C[C@@H](Oc3ccnc4ccc(F)cc34)C[C@@H]21] | 2-((1R,3s,5S,6r)-3-((6-fluoroquinolin-4-yl)-oxy)bicyclo[3.1.0]hexan-6-yl)-N-(1-phenyl-1H-pyrazol-4-yl)propanamide | 457 | (1) |
| 144 | 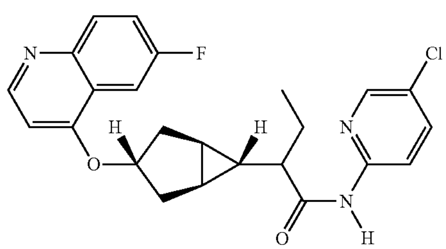 | N-(5-chloropyridin-2-yl)-2-((1R,3s,5S,6r)-3-((6-fluoroquinolin-4-yl)oxy)-bicyclo[3.1.0]hexan-6-yl)butanamide | 440 | (1) |
| 145 | 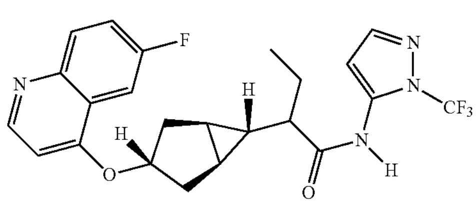 [SMILES: CCC(C(=O)Nc1ccnn1C(F)(F)F)[C@H]1[C@@H]2C[C@@H](Oc3ccnc4ccc(F)cc34)C[C@@H]21] | 2-((1R,3s,5S,6r)-3-((6-fluoroquinolin-4-yl)oxy)-bicyclo[3.1.0]hexan-6-yl)-N-(1-(trifluoromethyl)-1H-pyrazol-5-yl)butanamide | 463 | (1) |
| 146 | 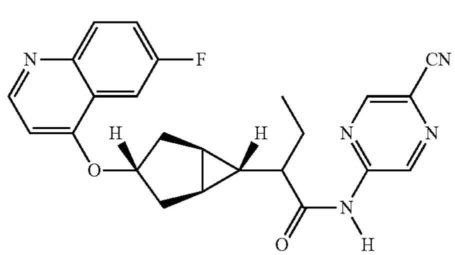 [SMILES: CCC(C(=O)Nc1cnc(C#N)cn1)[C@H]1[C@@H]2C[C@@H](Oc3ccnc4ccc(F)cc34)C[C@@H]21] | N-(5-cyanopyrazin-2-yl)-2-((1R,3s,5S,6r)-3-((6-fluoroquinolin-4-yl)oxy)-bicyclo[3.1.0]hexan-6-yl)-butanamide | 432 | (1) |

TABLE 1-continued

Example compounds 12-151.

| Ex. | Structure | IUPAC Name | MWt | Notes |
|---|---|---|---|---|
| 147 | 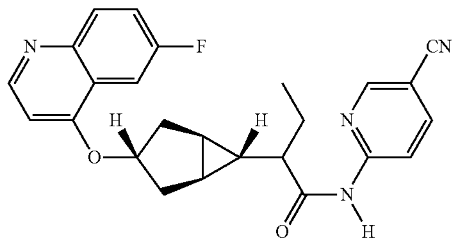 [SMILES: CCC(C(=O)Nc1ccc(C#N)cn1)[C@H]1[C@@H]2C[C@@H](Oc3ccnc4ccc(F)cc34)C[C@@H]21] | N-(5-cyanopyridin-2-yl)-2-((1R,3s,5S,6r)-3-((6-fluoroquinolin-4-yl)oxy)-bicyclo[3.1.0]hexan-6-yl)butanamide | 431 | (1) |
| 148 | 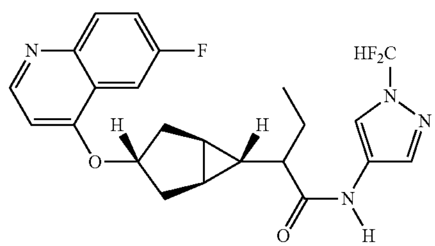 | N-(1-(difluoromethyl)-1H-pyrazol-4-yl)-2-((1R,3s,5S,6r)-3-((6-fluoroquinolin-4-yl)oxy)-bicyclo[3.1.0]hexan-6-yl)butanamide | 445 | (1) |
| 149 | 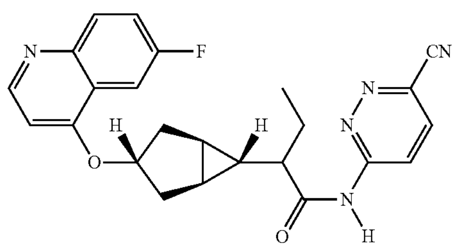 | N-(6-cyanopyridazin-3-yl)-2-((1R,3s,5S,6r)-3-((6-fluoroquinolin-4-yl)oxy)-bicyclo[3.1.0]hexan-6-yl)butanamide | 432 | (1) |

Notes:
(1) Scheme X, coupling with T3P
(2) Scheme IX, using General Procedure N
(3) General Procedure O: HATU coupling, using EDC
(4) Scheme X
(5) Scheme IV, Suzuki coupling of General Procedure S
(6) Scheme IV, Suzuki coupling of General Procedure S; using using 4-bromo-1-trityl-1H-imidazole followed by 4M HCl in dioxane.
(7) General Procedure O: HATU coupling
(8) General Procedure O: HATU coupling, followed by HCl deprotection
(9) General Procedure P.
(10) General Procedure P, using PyBroP The 1H NMR spectra for selected Example compounds is disclosed below.

| 65 | (600 MHz, methanol-d$_4$) δ ppm 1.19-1.24 (m, 1 H), 1.29-1.39 (m, 3 H), 1.49-1.68 (m, 2 H), 1.82-1.91 (m, 1 H), 2.25-2.45 (m, 2 H), 2.51-2.67 (m, 2 H), 3.88-3.95 (m, 3 H), 4.71-4.83 (m, 1 H), 7.48-7.54 (m, 2 H), 7.56-7.61 (m, 2 H), 7.73-7.80 (m, 2 H), 7.88-7.93 (m, 1 H), 7.98-8.05 (m, 1 H), 9.23-9.33 (m, 1 H) |
| 71 | (600 MHz, DMSO-d$_6$) δ ppm 0.83-0.90 (m, 1 H), 1.13-1.23 (m, 3 H), 1.29-1.53 (m, 2 H), 1.76-1.86 (m, 1 H), 1.90-2.06 (m, 2 H), 2.35-2.50 (m, 2 H), 4.79-4.96 (m, 1 H), 6.18-6.55 (m, 1 H), 7.03-7.18 (m, 1 H), 7.56-7.66 (m, 1 H), 7.70-7.80 (m, 1 H), 7.90-8.08 (m, 1 H), 8.57-8.77 (m, 1 H), 10.31-11.00 (m, 1 H), 13.05-13.71 (m, 1 H). |
| 111 | (600 MHz, DMSO-d$_6$) δ ppm 1.04-1.09 (m, 1 H) 1.46-1.53 (m, 3 H) 1.54-1.64 (m, 2 H) 1.98-2.05 (m, 1 H) 2.09-2.16 (m, 1 H) 2.43-2.50 (m, 3 H) 2.56-2.64 (m, 2 H) 4.97-5.07 (m, 1 H) 7.39-7.47 (m, 2 H) 7.71-7.76 (m, 1 H) 7.79-7.83 (m, 1 H) 7.87-7.94 (m, 1 H) 7.96-8.02 (m, 1 H) 8.11-8.17 (m, 1 H) 8.93-9.01 (m, 1 H). |

The following compounds can generally be made using the methods described above. It is expected that these compounds when made will have activity similar to those that have been made in the examples above.

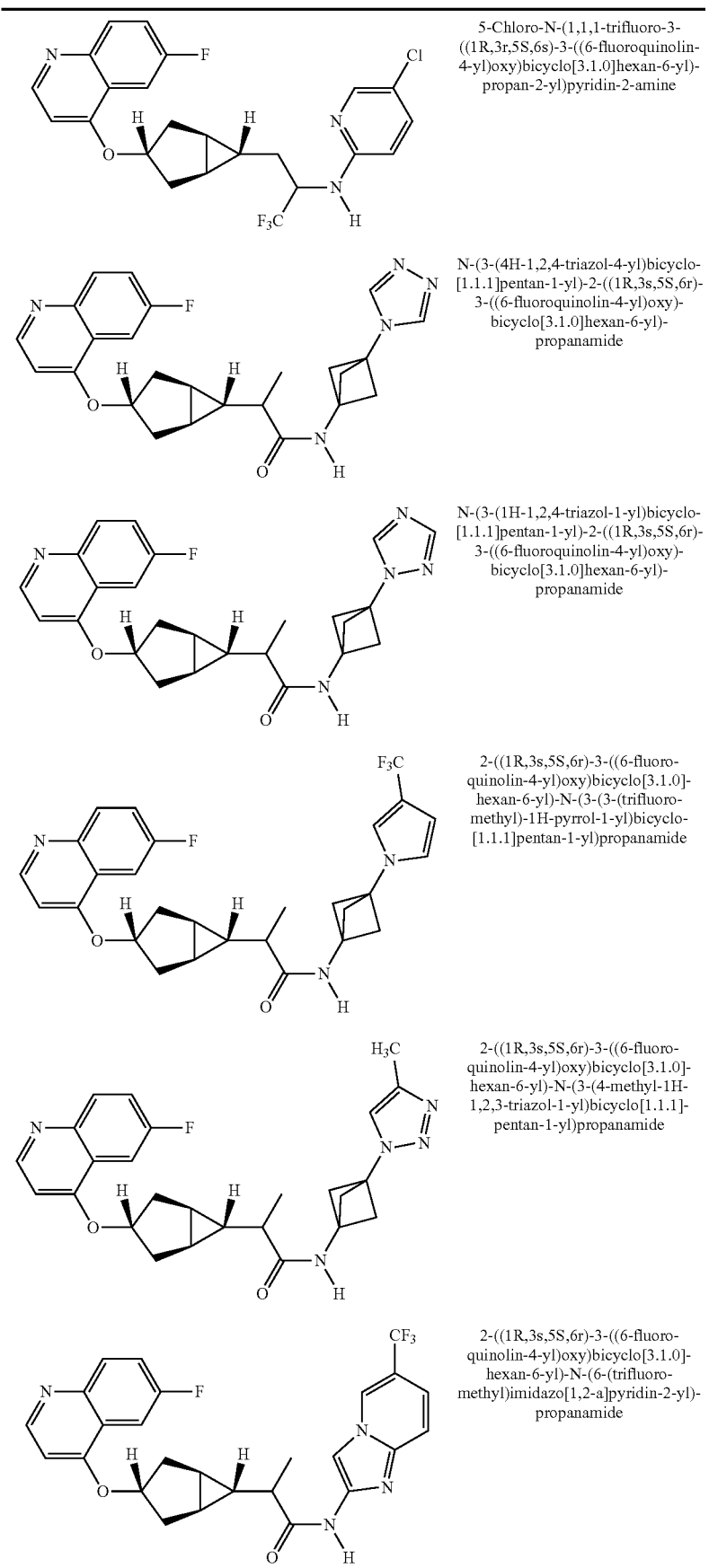

| | |
|---|---|
| | 5-Chloro-N-(1,1,1-trifluoro-3-((1R,3r,5S,6s)-3-((6-fluoroquinolin-4-yl)oxy)bicyclo[3.1.0]hexan-6-yl)-propan-2-yl)pyridin-2-amine |
| | N-(3-(4H-1,2,4-triazol-4-yl)bicyclo-[1.1.1]pentan-1-yl)-2-((1R,3s,5S,6r)-3-((6-fluoroquinolin-4-yl)oxy)-bicyclo[3.1.0]hexan-6-yl)-propanamide |
| | N-(3-(1H-1,2,4-triazol-1-yl)bicyclo-[1.1.1]pentan-1-yl)-2-((1R,3s,5S,6r)-3-((6-fluoroquinolin-4-yl)oxy)-bicyclo[3.1.0]hexan-6-yl)-propanamide |
| | 2-((1R,3s,5S,6r)-3-((6-fluoro-quinolin-4-yl)oxy)bicyclo[3.1.0]-hexan-6-yl)-N-(3-(3-(trifluoro-methyl)-1H-pyrrol-1-yl)bicyclo-[1.1.1]pentan-1-yl)propanamide |
| | 2-((1R,3s,5S,6r)-3-((6-fluoro-quinolin-4-yl)oxy)bicyclo[3.1.0]-hexan-6-yl)-N-(3-(4-methyl-1H-1,2,3-triazol-1-yl)bicyclo[1.1.1]-pentan-1-yl)propanamide |
| | 2-((1R,3s,5S,6r)-3-((6-fluoro-quinolin-4-yl)oxy)bicyclo[3.1.0]-hexan-6-yl)-N-(6-(trifluoro-methyl)imidazo[1,2-a]pyridin-2-yl)-propanamide |

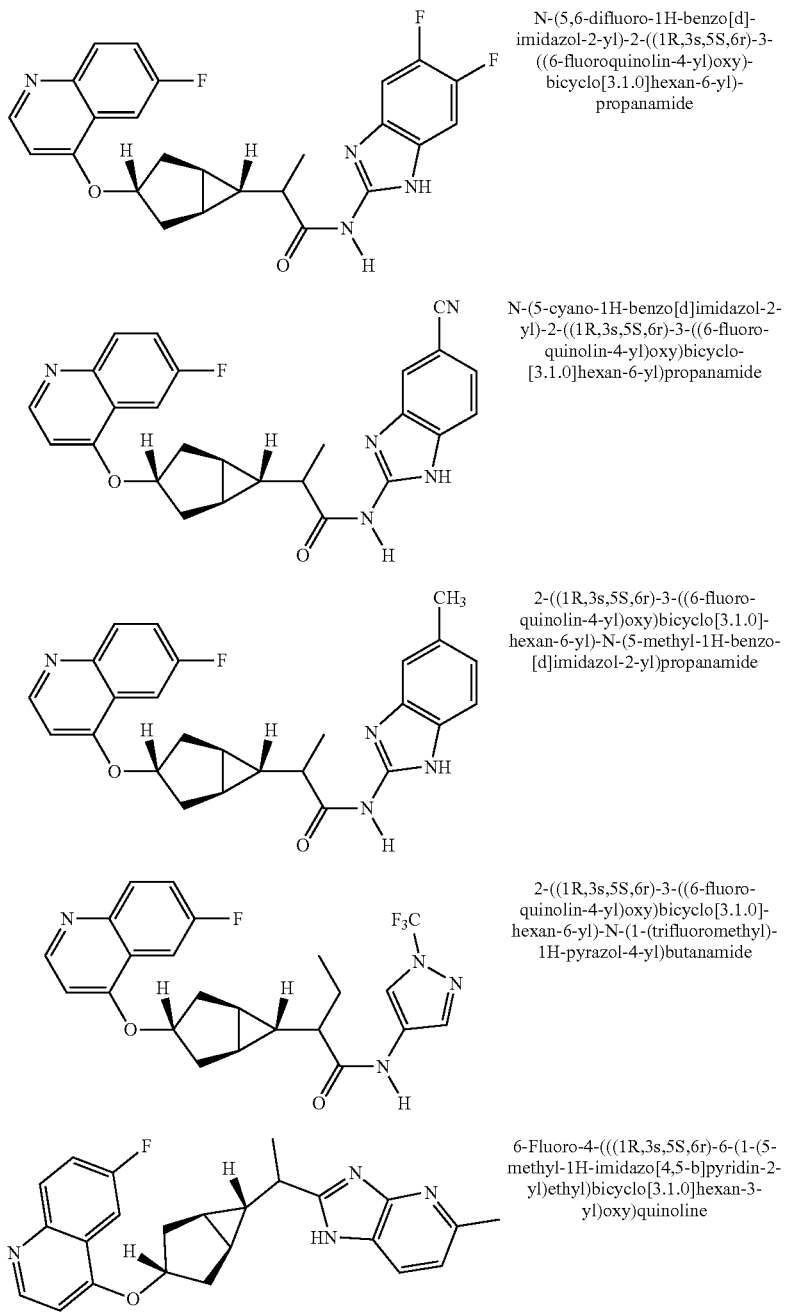

The activity of the compounds in Examples 1-118 as IDO1 inhibitors is illustrated in the following assay. The other compounds listed above, which have not yet been made and/or tested, are predicted to have activity in this assay as well.

Biological Activity Assay

IDO1 Cell-Based Assay

HeLa cells were obtained from the American Type Culture Collection (ATCC) and maintained in DMEM media containing 10% FBS. Cells (7,000/well) were seeded onto a 384 well plate in 50 μL of media and incubated at 37° C., 5% $CO_2$ overnight. Cell media was aspirated, fresh media containing 10 ng/mL IFNgamma was added, and cells were incubated in absence or presence of various concentrations of test compound (final 0.5% DMSO) for 24 hours. Aliquots of the cell conditioned media were removed from the cell plate, and mixed with an equal volume of 200 mM $ZnSO_4$ to precipitate media containing proteins. Two volumes of acetonitrile were added, mixed, and samples were then centrifuged at 2250 G for 20 minutes at 4° C. Aliquots of the supernatant were diluted 1:10 in 0.1% formic acid containing 3 μM of deuterated Tryptophan as an internal standard.

Samples were analyzed via RFMS to quantify N-Formyl Kynurenine (AUC) and L-tryptophan (AUC). A C18 cartridge was used with mobile phases of 0.1% Formic Acid and 80% ACN/0.1% Formic Acid under isocratic conditions. Dose-response curves were analyzed using $IC_{50}$ regression curve fitting (GeneData Screener). Curves were plotted as percent of control and normalized by high controls without inhibitor (100%), and low controls (0%) containing 1 μM of epacadostat, a potent cell-permeable IDO1 inhibitor. Cell viability was also assessed using the Cell Titer Glo Kit (Promega) following manufacturer recommendation.

Table 2 below summarises the results of the IDO1 cell-based assay, in which the $IC_{50}$ values are indicated for each compound as: (A) less than 200 nM; (B) 200 nM to 2 μM; (C) 2 μM to 5 μM; and (D) greater than 5 μM.

TABLE 2

| IDO1 Activity | |
| --- | --- |
| Ex. | IC50 |
| 1 | 5578 |
| 2 | 10000 |
| 3 | 2.2 |
| 4 | 5.1 |
| 5 | 471.5 |
| 6 | 329 |
| 7 | 468.5 |
| 8 | 51.3 |
| 9 | 55.0 |
| 10 | 259 |
| 11 | 1602 |
| 12 | 0.85 |
| 13 | 625.5 |
| 14 | 978.9 |
| 15 | 425.8 |
| 16 | 4.4 |
| 17 | 3.2 |
| 18 | 4.8 |
| 19 | 8.5 |
| 20 | 6.1 |
| 21 | 5.0 |
| 22 | 2.5 |
| 23 | 1648 |
| 24 | 116.7 |
| 25 | 3419 |
| 26 | 3.36 |
| 27 | 6.63 |
| 28 | 2519 |
| 29 | 10.9 |
| 30 | 1638 |
| 31 | 141.2 |
| 32 | 288.8 |
| 33 | 10000 |
| 34 | 179.4 |
| 35 | 1.92 |
| 36 | 2.1 |
| 37 | 3.6 |
| 38 | 1.37 |
| 39 | 12.9 |
| 40 | 109.6 |
| 41 | 7.8 |
| 42 | 77.8 |
| 43 | 191.6 |
| 44 | 6756 |
| 45 | 663.3 |
| 46 | 41.3 |
| 47 | 14.0 |
| 48 | 589.2 |
| 49 | 15.7 |
| 50 | 494.7 |
| 51 | 8.2 |
| 52 | 23.9 |
| 53 | 10.5 |
| 54 | 13.1 |
| 55 | 274.9 |
| 56 | 5.7 |
| 57 | 2.4 |
| 58 | 2 |
| 59 | 3.7 |
| 60 | 4.7 |
| 61 | 2.3 |
| 62 | 5.9 |
| 63 | 1.40 |
| 64 | 2.0 |
| 65 | 169.5 |
| 66 | 1139.5 |
| 67 | 260.6 |
| 68 | 10000 |
| 69 | 5546 |
| 70 | 238.1 |
| 71 | 1.16 |
| 72 | 1.51 |
| 73 | 4.7 |
| 74 | 156.3 |
| 75 | 1.58 |
| 76 | 4.6 |
| 77 | 111.3 |
| 78 | 3.3 |
| 79 | 877.8 |
| 80 | 539.1 |
| 81 | 710.0 |
| 82 | 8639 |
| 83 | 845.3 |
| 84 | 303.0 |
| 85 | 1911.5 |
| 86 | 568.2 |
| 87 | 3.0 |
| 88 | 7.4 |
| 89 | 38.7 |
| 90 | 550.5 |
| 91 | 504.4 |
| 92 | 1293.5 |
| 93 | 329.0 |
| 94 | 1090.0 |
| 95 | 231.2 |
| 96 | 7.1 |
| 97 | 817.5 |
| 98 | 7828 |
| 99 | 0.78 |
| 100 | 45.3 |
| 101 | 48.0 |
| 102 | 3.7 |
| 103 | 2.5 |
| 104 | 128.3 |
| 105 | 17.9 |
| 106 | 23.4 |
| 107 | 9.2 |
| 108 | 0.82 |
| 109 | 0.93 |
| 110 | 1.82 |
| 111 | 0.63 |
| 112 | 4.2 |
| 113 | 1.56 |
| 114 | 0.87 |
| 115 | 0.98 |
| 116 | 1.51 |
| 117 | 1.57 |
| 118 | 21.3 |
| 119 | 6.9 |
| 120 | 1.43 |
| 121 | 1.67 |
| 122 | 4 |
| 123 | 1.54 |
| 124 | 8.41 |
| 125 | 2.02 |
| 126 | 2.85 |
| 127 | 6309 |
| 128 | 2.14 |
| 129 | 597 |
| 130 | 635.6 |
| 131 | 745.3 |
| 132 | 511 |

TABLE 2-continued

IDO1 Activity

| Ex. | IC50 |
|---|---|
| 133 | 419.9 |
| 134 | 10.58 |
| 135 | 8.19 |
| 136 | 0.81 |
| 137 | 1.2 |
| 138 | 1.7 |
| 139 | 51.36 |
| 140 | 90.01 |
| 141 | 19.26 |
| 142 | 10000 |
| 143 | 2.77 |
| 144 | 1.15 |
| 145 | 0.78 |
| 146 | 0.69 |
| 147 | 0.66 |
| 148 | 0.97 |
| 149 | 5.49 |

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of structural Formula I

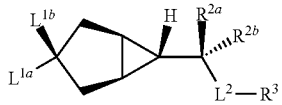
(I)

or a salt or tautomer thereof, wherein:
$L^{1a}$ is $L^1$-$R^1$ and $L^{1b}$ is H;
either $R^{2a}$ is $R^2$ and $R^{2b}$ is H, or $R^{2a}$ is H and $R^{2b}$ is $R^2$;
$L^1$ is chosen from a bond, —O—, —N($R^5$)—, C($R^{5a}$)($R^{5b}$)—, and —S—;
$L^2$ is chosen from —C(O)NH—, —C(N$R^4$)NH—, —NHC(O)—, —NHC(N$R^4$)—, —N($R^4$)CH($R^6$)—, and —CH($R^6$)N($R^4$)—,
or $L^2$ is

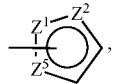, or $L^2$ is chosen from

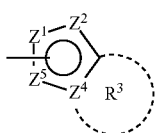 and 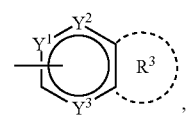, forming a bicyclic ring system with $R^3$ when $R^3$ is cyclic;
$Y^1$, $Y^2$, $Y^3$, $Z^1$, $Z^2$, and $Z^5$ are independently chosen from CH, C($R^9$), N, NH, N($R^9$), O, and S;
$Z^4$ is chosen from C and N;
$R^1$ is H or is chosen from alkyl, aryl, cycloalkyl, heteroaryl, and heterocycloalkyl, any of which is optionally substituted with one or more $R^7$ groups;
$R^2$ is H or is chosen from alkyl, aryl, cycloalkyl, heteroaryl, and heterocycloalkyl, any of which is optionally substituted with one or more $R^8$ groups;
$R^3$ is H or is chosen from alkyl, cycloalkyl, heterocycloalkyl, aryl, heteroaryl, (aryl)aryl, (aryl)heteroaryl, (heteroaryl)aryl, (heteroaryl)heteroaryl, (aryl)cycloalkyl, (heteroaryl)cycloalkyl, (cycloalkyl)aryl, and (heterocycloalkyl)aryl, any of which is optionally substituted with one or more $R^9$ groups;
$R^4$ is H or is chosen from alkyl, cycloalkyl, heterocycloalkyl, aryl, and heteroaryl, any one of which is optionally substituted with one or more $R^{10}$ groups;
or $R^3$ and $R^4$, together with the intervening atoms, form a first heteroaryl ring, which is optionally fused with a second aryl or heteroaryl ring to form a bicyclic heteroaryl system, said first heteroaryl ring or bicyclic heteroaryl system is optionally substituted with one or more $R^{10}$ groups;
each $R^5$, $R^{5a}$, and $R^{5b}$ is independently H or is chosen from alkyl, cycloalkyl, heterocycloalkyl, aryl, and heteroaryl;
$R^6$ is chosen from $CF_3$, $CF_2CF_3$, and $CF_2CH_3$;
each $R^7$, $R^8$, $R^9$, and $R^{10}$ is independently chosen from halo, haloalkyl, hydroxy, alkyl, amino, hydroxyalkyl, alkoxy, alkoxyalkyl, cyano, cyanoalkyl, NHC(O)$R^{11}$, NHS(O)$_2R^{12}$, NHC(O)NH$R^{12}$, C(O)O$R^{12}$, S(O)$_2$NH$R^{12}$, $C_{3-6}$cycloalkyl optionally substituted with one or two $R^{11}$, $C_{3-6}$heterocycloalkyl optionally substituted with one or two $R^{11}$, phenyl optionally substituted with one or two $R^{11}$, and 5-6 membered heteroaryl optionally substituted with one or two $R^{11}$;
each $R^{11}$ is independently chosen from halo, haloalkyl, hydroxy, alkyl, amino, $C_{3-6}$cycloalkyl, hydroxyalkyl, alkyl, alkoxy, and cyano; and
$R^{12}$ is chosen from H and alkyl.

2. The compound as recited in claim 1, or a salt or tautomer thereof, wherein $R^{2a}$ is $R^2$ and $R^{2b}$ is H.

3. The compound as recited in claim 1, or a salt or tautomer thereof, wherein $R^{2a}$ is H and $R^{2b}$ is $R^2$.

4. The compound as recited in claim 1, or a salt or tautomer thereof, wherein
$L^1$ is chosen from a bond, —O— and —N($R^5$)—;
$L^2$ is chosen from —C(O)NH— and NHC(O)—;
$R^1$ is aryl or heteroaryl, and is optionally substituted with one or more $R^7$ groups;
$R^2$ is H or is chosen from alkyl, cycloalkyl, and heterocycloalkyl, any of which is optionally substituted with one or more $R^8$ groups;
$R^3$ is H or is chosen from alkyl, cycloalkyl, heterocycloalkyl, aryl, heteroaryl, (aryl)aryl, (aryl)heteroaryl, (heteroaryl)aryl, (heteroaryl)heteroaryl, (aryl)cycloalkyl, and (heteroaryl)cycloalkyl, any of which is optionally substituted with one or more $R^9$ groups;
$R^4$ is H or is chosen from alkyl, cycloalkyl, heterocycloalkyl, aryl, and heteroaryl, any one of which is optionally substituted with one or more $R^{10}$ groups;
or $R^3$ and $R^4$, together with the intervening atoms, form a first heteroaryl ring, which is optionally fused with a second aryl or heteroaryl ring to form a bicyclic heteroaryl system, said first heteroaryl ring or bicyclic heteroaryl system is optionally substituted with one or more $R^{10}$ groups;

$R^5$ is H or is chosen from alkyl, cycloalkyl, heterocycloalkyl, aryl, and heteroaryl; and each $R^7$, $R^8$, $R^9$, and $R^{10}$ is independently chosen from alkyl, $C_{3-6}$cycloalkyl, halo, hydroxy, alkoxy, and cyano.

5. The compound as recited in claim 1, having structural Formula II:

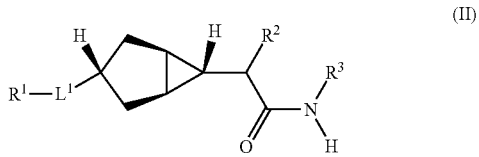

(II)

or a salt or tautomer thereof, wherein:

$L^1$ is chosen from a bond, —O—, —N($R^5$)—, C($R^{5a}$)($R^{5b}$)—, and —S—;

$R^1$ is H or is chosen from alkyl, aryl, cycloalkyl, heteroaryl, and heterocycloalkyl, any of which is optionally substituted with one or more $R^7$ groups;

$R^2$ is H or is chosen from alkyl, aryl, cycloalkyl, heteroaryl, and heterocycloalkyl, any of which is optionally substituted with one or more $R^8$ groups;

$R^3$ is H or is chosen from alkyl, cycloalkyl, heterocycloalkyl, aryl, heteroaryl, (aryl)aryl, (aryl)heteroaryl, (heteroaryl)aryl, (heteroaryl)heteroaryl, (aryl)cycloalkyl, and (heteroaryl)cycloalkyl, any of which is optionally substituted with one or more $R^9$ groups;

each $R^5$, $R^{5a}$, and $R^{5b}$ is independently H or is chosen from alkyl, cycloalkyl, heterocycloalkyl, aryl, and heteroaryl;

each $R^7$, $R^8$, and $R^9$ is independently chosen from halo, haloalkyl, hydroxy, alkyl, amino, $C_{3-6}$cycloalkyl, hydroxyalkyl, alkoxy, alkoxyalkyl, cyano, cyanoalkyl, NHC(O)$R^{11}$, NHS(O)$_2R^{12}$, NHC(O)NH$R^{12}$, C(O)O$R^{12}$, S(O)$_2$NH$R^{12}$, $C_{3-6}$cycloalkyl optionally substituted with one or two $R^{11}$, $C_{3-6}$heterocycloalkyl optionally substituted with one or two $R^{11}$, phenyl optionally substituted with one or two $R^{11}$, and 5-6 membered heteroaryl optionally substituted with one or two $R^{11}$;

each $R^{11}$ is independently chosen from halo, haloalkyl, hydroxy, alkyl, amino, $C_{3-6}$cycloalkyl, hydroxyalkyl, alkyl, alkoxy, and cyano; and $R^{12}$ is chosen from H and alkyl.

6. The compound as recited in claim 5, or a salt or tautomer thereof, wherein $L^1$ is chosen from a bond, —O—, and —N($R^5$)—;

$R^1$ is aryl or heteroaryl, and is optionally substituted with one or more $R^7$ groups;

$R^2$ is H or is chosen from alkyl, cycloalkyl, and heterocycloalkyl, any one of which is optionally substituted with one or more $R^8$ groups;

$R^3$ is H or is chosen from alkyl, cycloalkyl, heterocycloalkyl, aryl, and heteroaryl, any one of which is optionally substituted with one or more $R^9$ groups;

$R^5$ is H or is chosen from alkyl, cycloalkyl, heterocycloalkyl, aryl, and heteroaryl; and each $R^7$, $R^7$, and $R^9$ is independently chosen from alkyl, $C_{3-6}$cycloalkyl, halo, hydroxy, alkoxy, and cyano.

7. The compound as recited in claim 5, or a salt or tautomer thereof, wherein $R^3$ is chosen from cycloalkyl, (aryl)cycloalkyl, and (heteroaryl)cycloalkyl, any of which is optionally substituted with one or more $R^9$ groups;

each $R^9$ is independently chosen from halo, haloalkyl, hydroxy, alkyl, amino, $C_{3-6}$cycloalkyl, hydroxyalkyl, alkoxy, alkoxyalkyl, cyano, cyanoalkyl, C(O)O$R^{12}$; and $R^{12}$ is chosen from H and alkyl.

8. The compound as recited in claim 1, having structural Formula III:

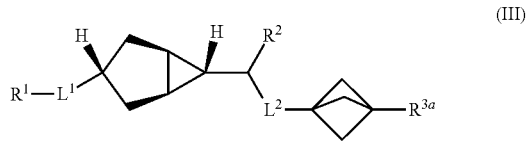

(III)

or a salt or tautomer thereof, wherein:

$L^1$ is chosen from a bond, —O—, —N($R^5$)—, C($R^{5a}$)($R^{5b}$)—, and —S—;

$L^2$ is chosen from —C(O)NH—, —C(N$R^4$)NH—, —NHC(O)—, —NHC(N$R^4$)—, —N($R^4$)CH($R^6$)—, and —CH($R^6$)N($R^4$)—;

$R^1$ is H or is chosen from alkyl, aryl, cycloalkyl, heteroaryl, and heterocycloalkyl, any of which is optionally substituted with one or more $R^7$ groups;

$R^{3a}$ a is chosen from H, halo, hydroxy, alkoxy, and cyano, or is chosen from aryl or heteroaryl, either of which is optionally substituted with one or more $R^9$ groups;

$R^4$ is H or is chosen from alkyl, cycloalkyl, heterocycloalkyl, aryl, and heteroaryl, any one of which is optionally substituted with one or more $R^{10}$ groups;

each $R^5$, $R^{5a}$, and $R^{5b}$ is independently H or is chosen from alkyl, cycloalkyl, heterocycloalkyl, aryl, and heteroaryl;

$R^6$ is chosen from $CF_3$, $CF_2CF_3$, and $CF_2CH_3$; and each $R^7$, $R^8$, and $R^9$ is independently chosen from halo, haloalkyl, hydroxy, alkyl, amino, $C_{3-6}$cycloalkyl, hydroxyalkyl, alkoxy, alkoxyalkyl, cyano, cyanoalkyl, NHC(O)$R^{11}$, NHS(O)$_2R^{12}$, NHC(O)NH$R^{12}$, C(O)O$R^{12}$, S(O)$_2$NH$R^{12}$, $C_{3-6}$cycloalkyl optionally substituted with one or two $R^{11}$, $C_{3-6}$heterocycloalkyl optionally substituted with one or two $R^{11}$, phenyl optionally substituted with one or two $R^{11}$, and 5-6 membered heteroaryl optionally substituted with one or two $R^{11}$;

each $R^{11}$ is independently chosen from halo, haloalkyl, hydroxy, alkyl, amino, $C_{3-6}$cycloalkyl, hydroxyalkyl, alkyl, alkoxy, and cyano; and $R^{12}$ is chosen from H and alkyl.

9. The compound as recited in claim 1, having structural Formula IV:

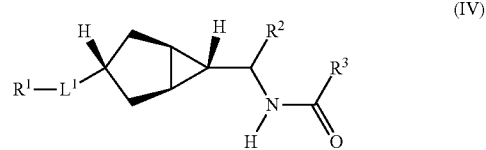

(IV)

or a salt or tautomer thereof, wherein:

$L^1$ is chosen from a bond, —O—, —N($R^5$)—, C($R^{5a}$a)($R^{5b}$)—, and —S—;

R¹ is H or is chosen from alkyl, aryl, cycloalkyl, heteroaryl, and heterocycloalkyl, any of which is optionally substituted with one or more R⁷ groups;

R² is H or is chosen from alkyl, aryl, cycloalkyl, heteroaryl, and heterocycloalkyl, any of which is optionally substituted with one or more R⁸ groups;

R³ is H or is chosen from alkyl, cycloalkyl, heterocycloalkyl, aryl, heteroaryl, (aryl)aryl, (aryl)heteroaryl, (heteroaryl)aryl, (heteroaryl)heteroaryl, (aryl)cycloalkyl, and (heteroaryl)cycloalkyl, any of which is optionally substituted with one or more R⁹ groups;

each R⁵, R⁵ᵃ, and R⁵ᵇ is independently H or is chosen from alkyl, cycloalkyl, heterocycloalkyl, aryl, and heteroaryl;

each R⁷, R⁸, and R⁹ is independently chosen from halo, haloalkyl, hydroxy, alkyl, amino, $C_{3-6}$cycloalkyl, hydroxyalkyl, alkoxy, alkoxyalkyl, cyano, cyanoalkyl, NHC(O)R¹¹, NHS(O)₂R¹², NHC(O)NHR¹², C(O)OR¹², S(O)₂NHR¹², $C_{3-6}$cycloalkyl optionally substituted with one or two R¹¹, $C_{3-6}$heterocycloalkyl optionally substituted with one or two R¹¹, phenyl optionally substituted with one or two R¹¹, and 5-6 membered heteroaryl optionally substituted with one or two R¹¹;

each R¹¹ is independently chosen from halo, haloalkyl, hydroxy, alkyl, amino, $C_{3-6}$cycloalkyl, hydroxyalkyl, alkyl, alkoxy, and cyano; and R¹² is chosen from H and alkyl.

10. The compound as recited in claim 9, or a salt or tautomer thereof, wherein
L¹ is chosen from a bond, —O—, and —N(R⁵);
R¹ is aryl or heteroaryl, and is optionally substituted with one or more R⁷ groups;
R² is H or is chosen from alkyl, cycloalkyl, and heterocycloalkyl, any one of which is optionally substituted with one or more R⁸ groups;
R³ is H or is chosen from alkyl, cycloalkyl, heterocycloalkyl, aryl, and heteroaryl, any one of which is optionally substituted with one or more R⁹ groups;
R⁵ is H or is chosen from alkyl, cycloalkyl, heterocycloalkyl, aryl, and heteroaryl; and
each R⁷, R⁸, and R⁹ is independently chosen from halo, hydroxy, alkoxy, and cyano.

11. The compound as recited in claim 1, having structural Formula V:

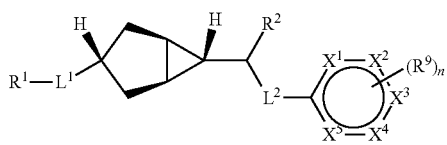

(V)

or a salt or tautomer thereof, wherein:
n is 0, 1, or 2;
X¹ is chosen from C(R⁹ᵃ), N, O, and S;
X² is chosen from C(R⁹ᵇ), N, O, and S;
X³ is chosen from C(R⁹ᶜ), N, O, and S;
X⁴ is chosen from C(R⁹ᵈ), N, O, and S;
X⁵ is chosen from a bond, C(R⁹ᵉ), N, O, and S;
L¹ is chosen from a bond, —O—, —N(R⁵)—, C(R⁵ᵃ)(R⁵ᵇ)—, and —S—;
L² is chosen from —C(O)NH—, —C(NR⁴)NH—, —NHC(O)—, —NHC(NR⁴)—, —N(R⁴)CH(R⁶)—, and —CH(R⁶)N(R⁴)—, or L² is

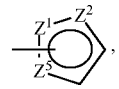

or L² is chosen from

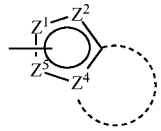 and 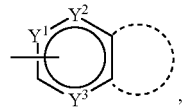, forming a bicyclic ring system with

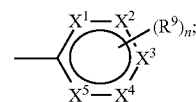

Y¹, Y², Y³, Z¹, Z², and Z⁵ are independently chosen from CH, C(R⁹), N, NH, N(R⁹), O, and S;

Z⁴ is chosen from C and N;

R¹ is H or is chosen from alkyl, aryl, cycloalkyl, heteroaryl, and heterocycloalkyl, any of which is optionally substituted with one or more R⁷ groups;

R² is H or is chosen from alkyl, aryl, cycloalkyl, heteroaryl, and heterocycloalkyl, any of which is optionally substituted with one or more R⁸ groups;

R⁴ is H or is chosen from alkyl, cycloalkyl, heterocycloalkyl, aryl, and heteroaryl, any one of which is optionally substituted with one or more R¹⁰ groups;

each R⁵, R⁵ᵃ, and R⁵ᵇ is independently H or is chosen from alkyl, cycloalkyl, heterocycloalkyl, aryl, and heteroaryl;

R⁶ is chosen from CF₃, CF₂CF₃, and CF₂CH₃;

R⁹ᵃ, R⁹ᵇ, R⁹ᶜ, R⁹ᵈ, and R⁹ᵉ are independently chosen from H, alkyl, halo, haloalkyl, hydroxy, amino, $C_{3-6}$cycloalkyl, hydroxyalkyl, alkoxy, and cyano;

each R⁷, R⁸, R⁹, and R¹⁰ is independently chosen from halo, haloalkyl, hydroxy, alkyl, amino, hydroxyalkyl, alkoxy, alkoxyalkyl, cyano, cyanoalkyl, NHC(O)R¹¹, NHS(O)₂R¹², NHC(O)NHR¹², C(O)OR¹², S(O)₂NHR¹², $C_{3-6}$cycloalkyl optionally substituted with one or two R¹¹, $C_{3-6}$heterocycloalkyl optionally substituted with one or two R¹¹, phenyl optionally substituted with one or two R¹¹, and 5-6 membered heteroaryl optionally substituted with one or two R¹¹;

each R¹¹ is independently chosen from halo, haloalkyl, hydroxy, alkyl, amino, $C_{3-6}$cycloalkyl, hydroxyalkyl, alkyl, alkoxy, and cyano; and R¹² is chosen from H and alkyl.

12. The compound as recited in claim 11, or a salt or tautomer thereof, wherein L² is —NHC(O)—.

13. The compound as recited in claim 12, having structural Formula VI:

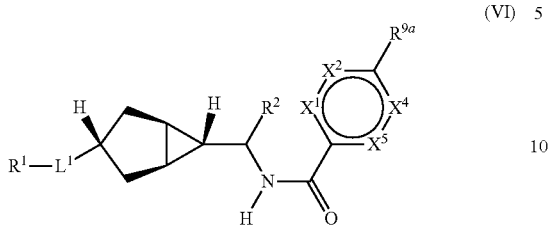

or a salt or tautomer thereof, wherein:
$X^1$, $X^2$, and $X^4$ are independently chosen from CH and N;
$X^5$ is chosen from a bond, CH and N;
at most two of $X^1$, $X^2$, $X^4$, and X are N;
$L^1$ is chosen from a bond, —O—, —N($R^5$)—, C($R^{5a}$)($R^{5b}$)—, and —S—;
$R^1$ is H or is chosen from alkyl, aryl, cycloalkyl, heteroaryl, and heterocycloalkyl, any of which is optionally substituted with one or more $R^7$ groups;
$R^2$ is H or is chosen from alkyl, aryl, cycloalkyl, heteroaryl, and heterocycloalkyl, any of which is optionally substituted with one or more $R^8$ groups;
each $R^5$, $R^{5a}$, and $R^{5b}$ is independently H or is chosen from alkyl, cycloalkyl, heterocycloalkyl, aryl, and heteroaryl;
$R^{9a}$ is chosen from H, alkyl, halo, haloalkyl, hydroxy, amino, $C_{3-6}$cycloalkyl, hydroxyalkyl, alkoxy, and cyano;
each $R^7$, $R^8$, and $R^{10}$ is independently chosen from halo, haloalkyl, hydroxy, alkyl, amino, hydroxyalkyl, alkoxy, alkoxyalkyl, cyano, cyanoalkyl, NHC(O)$R^{11}$, NHS(O)$_2R^{12}$, NHC(O)NH$R^{12}$, C(O)O$R^{12}$, S(O)$_2$NH$R^{12}$, $C_{3-6}$cycloalkyl optionally substituted with one or two $R^{11}$, $C_{3-6}$heterocycloalkyl optionally substituted with one or two $R^{11}$, phenyl optionally substituted with one or two $R^{11}$, and 5-6 membered heteroaryl optionally substituted with one or two $R^{11}$;
each $R^{11}$ is independently chosen from halo, haloalkyl, hydroxy, alkyl, amino, $C_{3-6}$cycloalkyl, hydroxyalkyl, alkyl, alkoxy, and cyano; and
$R^{12}$ is chosen from H and alkyl.

14. The compound as recited in claim 13, or a salt or tautomer thereof, wherein
$L^1$ is chosen from a bond, —O—, and —N($R^5$);
$R^1$ is aryl or heteroaryl, and is optionally substituted with one or more $R^7$ groups;
$R^2$ is H or is chosen from alkyl, cycloalkyl, and heterocycloalkyl, any one of which is optionally substituted with one or more $R^8$ groups;
$R^5$ is H or is chosen from alkyl, cycloalkyl, heterocycloalkyl, aryl, and heteroaryl; and
each $R^7$ and $R^8$ is independently chosen from halo, hydroxy, alkoxy, and cyano;
$R^9$ is chosen from H, halo, hydroxy, alkoxy, and cyano.

15. The compound as recited in claim 1, or a salt or tautomer thereof, wherein $L^2$ is chosen from —N($R^4$)CH($R^6$)— and —CH($R^6$)N($R^4$)—.

16. The compound as recited in claim 1, or a salt or tautomer thereof, wherein:
$L^2$ is

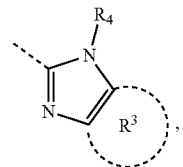

forming a bicyclic ring system with $R^3$;
$R^3$ is chosen from cycloalkyl, heterocycloalkyl, aryl, heteroaryl, any of which is optionally substituted with one or more $R^9$ groups; and
each $R^9$ is independently chosen from halo, haloalkyl, hydroxy, alkyl, amino, $C_{3-6}$cycloalkyl, hydroxyalkyl, alkoxy, alkoxyalkyl, cyano, cyanoalkyl, NHC(O)$R^{11}$, NHS(O)$_2R^{12}$, NHC(O)NH$R^{12}$, C(O)O$R^{12}$, S(O)$_2$NH$R^{12}$, $C_{3-6}$cycloalkyl optionally substituted with one or two $R^{11}$, $C_{3-6}$heterocycloalkyl optionally substituted with one or two $R^{11}$, phenyl optionally substituted with one or two $R^{11}$, and 5-6 membered heteroaryl optionally substituted with one or two $R^{11}$;
each $R^{11}$ is independently chosen from halo, haloalkyl, hydroxy, alkyl, amino, $C_{3-6}$cycloalkyl, hydroxyalkyl, alkyl, alkoxy, and cyano; and
$R^{12}$ is chosen from H and alkyl.

17. The compound as recited in claim 1, having structural Formula VII:

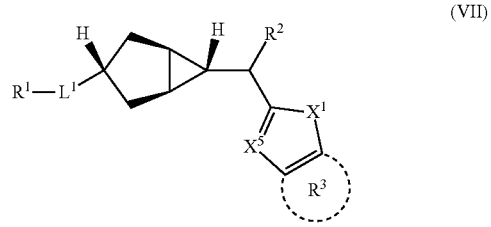

or a salt or tautomer thereof, wherein:
$L^1$ is chosen from a bond, —O—, —N($R^5$)—, C($R^{5a}$)($R^{5b}$)—, and —S—;
$X^1$ is chosen from NH, N$R^9$, O, and S;
$X^5$ is chosen from CH, C$R^9$, and N;
$R^1$ is H or is chosen from alkyl, aryl, cycloalkyl, heteroaryl, and heterocycloalkyl, any of which is optionally substituted with one or more $R^7$ groups;
$R^2$ is H or is chosen from alkyl, aryl, cycloalkyl, heteroaryl, and heterocycloalkyl, any of which is optionally substituted with one or more $R^8$ groups;
$R^3$ is chosen from cycloalkyl, heterocycloalkyl, aryl, heteroaryl, any of which is optionally substituted with one or more $R^9$ groups; and
$R^4$ is H or is chosen from alkyl, cycloalkyl, heterocycloalkyl, aryl, and heteroaryl, any one of which is optionally substituted with one or more $R^{10}$ groups;
each $R^5$, $R^{5a}$, and $R^{5b}$ is independently H or is chosen from alkyl, cycloalkyl, heterocycloalkyl, aryl, and heteroaryl;
each $R^7$, $R^8$, and $R^9$ is independently chosen from halo, haloalkyl, hydroxy, alkyl, amino, $C_{3-6}$cycloalkyl, hydroxyalkyl, alkoxy, alkoxyalkyl, cyano, cyanoalkyl, NHC(O)R$^{11}$, NHS(O)$_2$R$^{12}$, NHC(O)NHR$^{12}$, C(O)OR$^{12}$, S(O)$_2$NHR$^{12}$, C$_{3-6}$cycloalkyl optionally substituted with one or two R$^{11}$, C$_{3-6}$heterocycloalkyl optionally substituted with one or two R$^{11}$, phenyl optionally substituted with one or two R$^{11}$, and 5-6 membered heteroaryl optionally substituted with one or two R$^{11}$;

each R$^{11}$ is independently chosen from halo, haloalkyl, hydroxy, alkyl, amino, C$_{3-6}$cycloalkyl, hydroxyalkyl, alkyl, alkoxy, and cyano; and R$^{12}$ is chosen from H and alkyl.

18. The compound as recited in claim 17, or a salt or tautomer thereof, wherein:
L$^1$ is chosen from a bond, —O—, and —N(R$^5$);
R$^1$ is aryl or heteroaryl, and is optionally substituted with one or more R$^7$ groups;
R$^2$ is H or is chosen from alkyl, cycloalkyl, and heterocycloalkyl, any one of which is optionally substituted with one or more R$^8$ groups;
R$^3$ is H or is chosen from alkyl, cycloalkyl, heterocycloalkyl, aryl, and heteroaryl, any one of which is optionally substituted with one or more R$^9$ groups;
R$^5$ is H or is chosen from alkyl, cycloalkyl, heterocycloalkyl, aryl, and heteroaryl;
each R$^7$, R$^8$, and R$^9$ is independently chosen from halo, hydroxy, alkoxy, and cyano;
each R$^9$ is independently chosen from alkyl, C$_{3-6}$cycloalkyl, halo, hydroxy, alkoxy, and cyano.

19. A compound as recited in claim 1, chosen from:

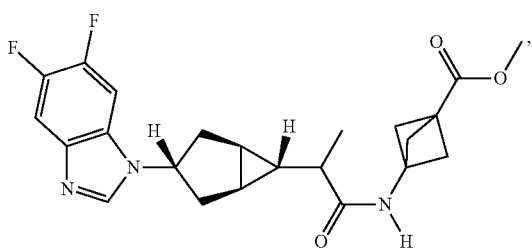

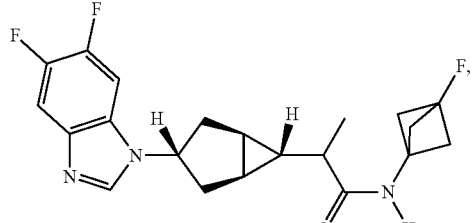

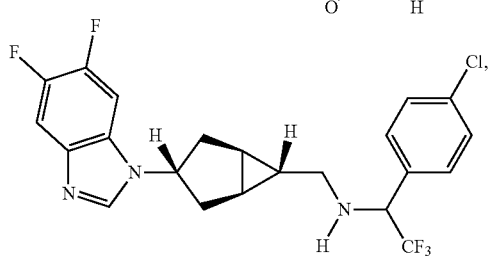

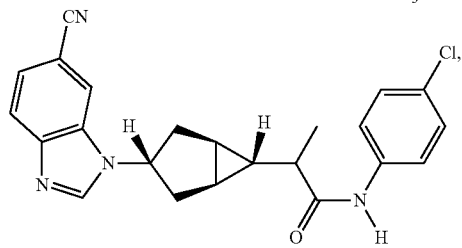

-continued

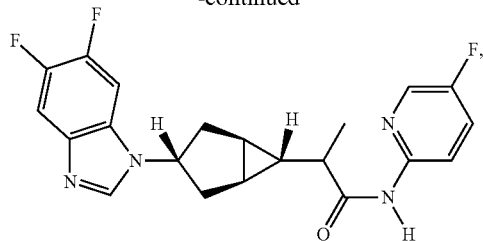

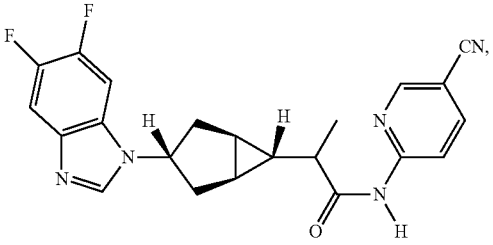

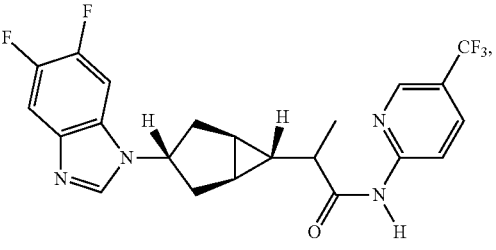

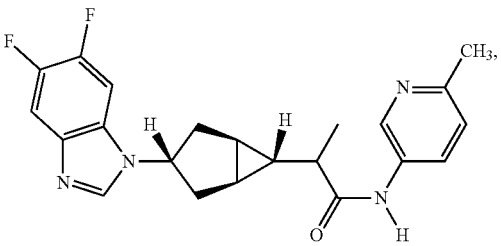

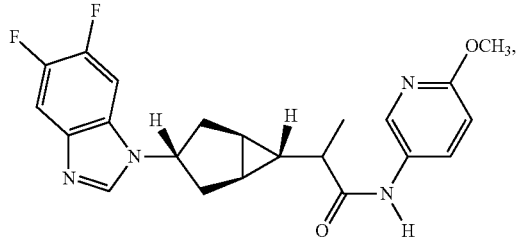

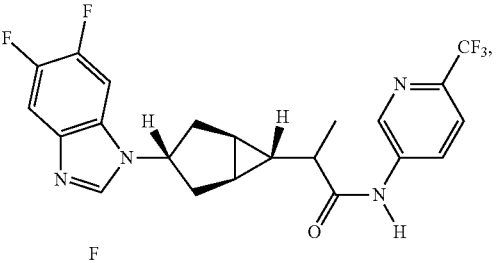

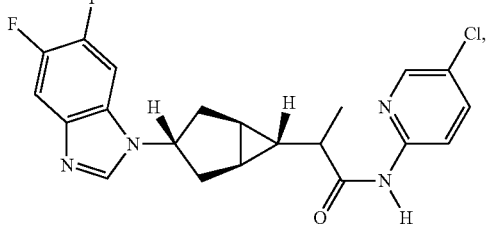

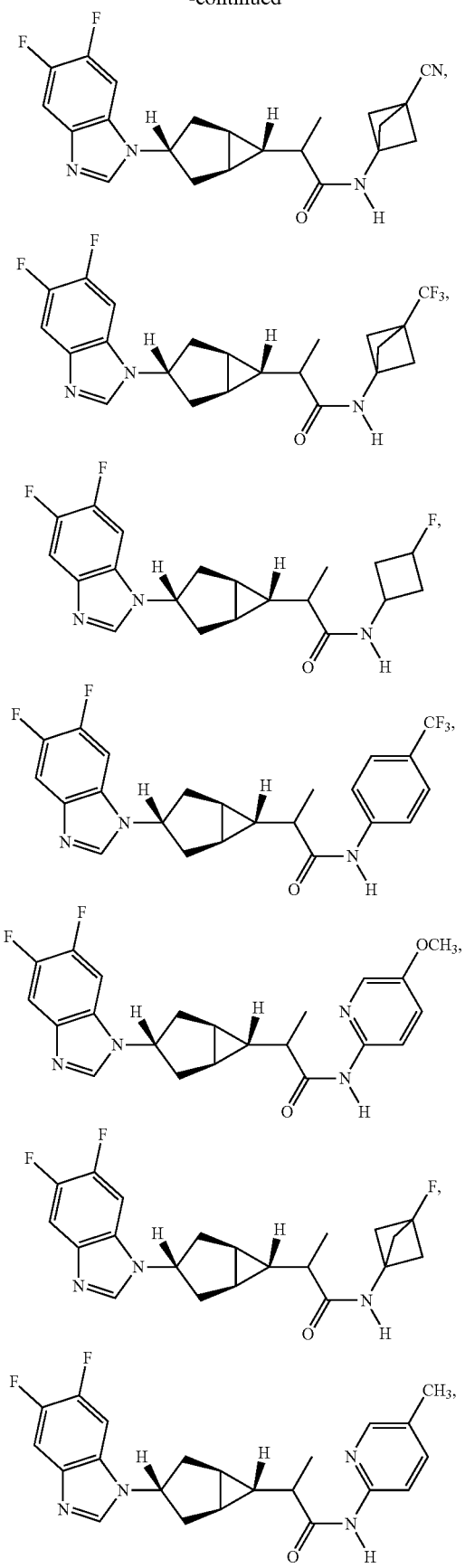
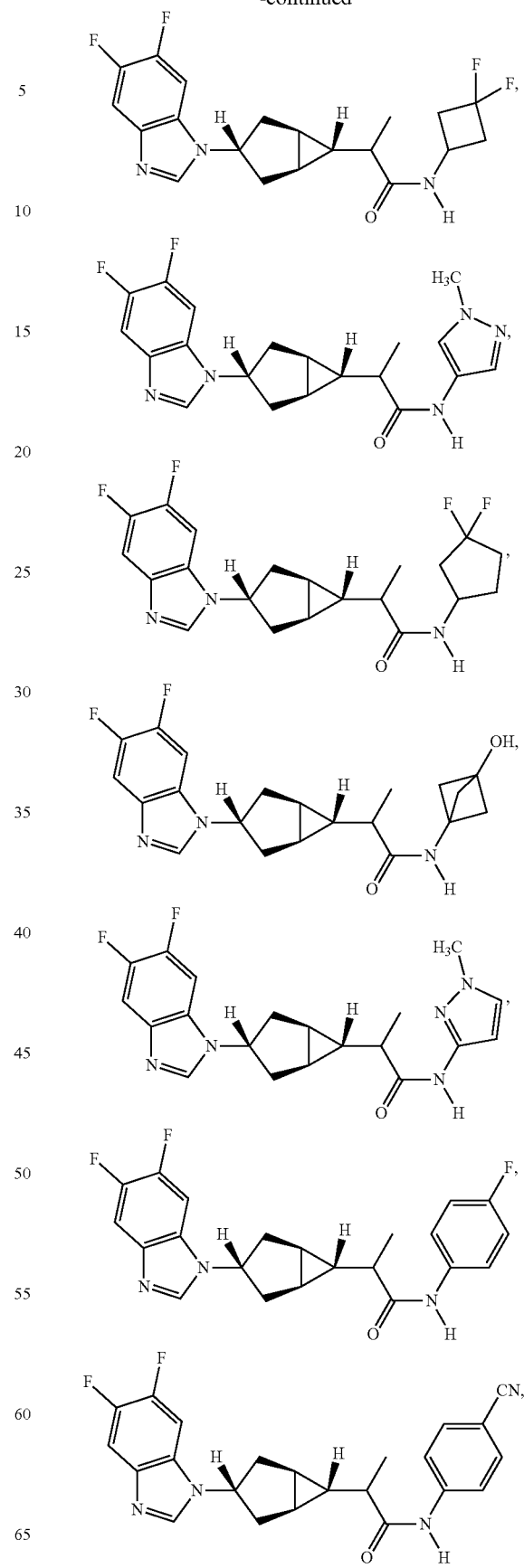

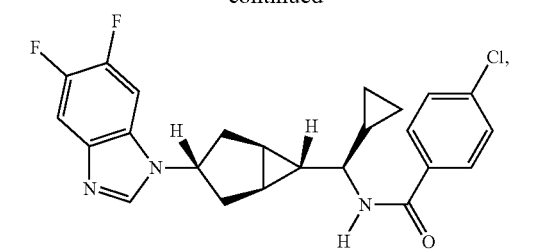
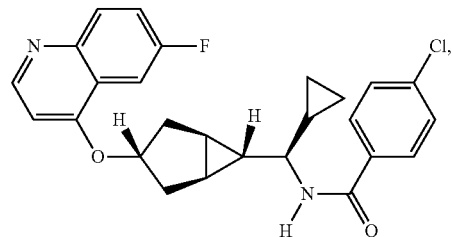
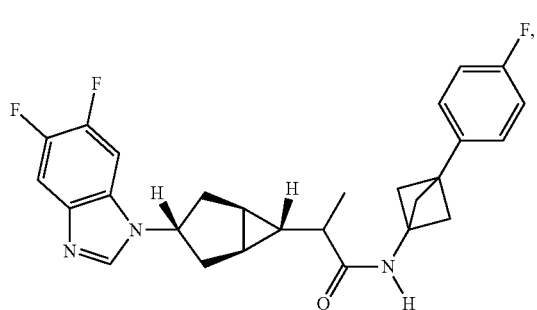
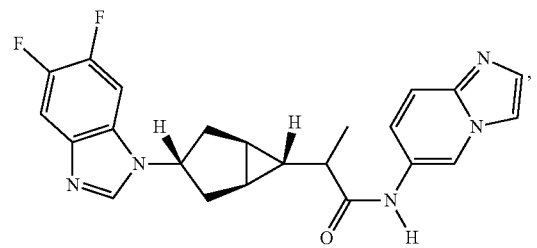
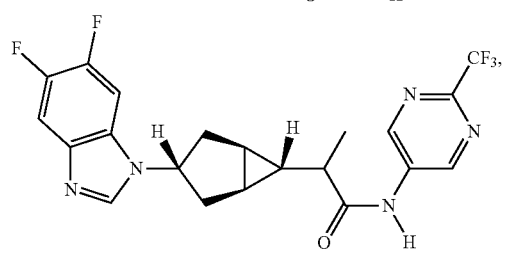
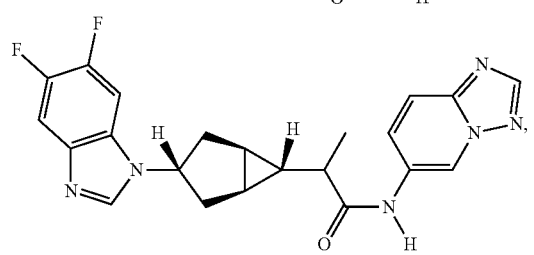
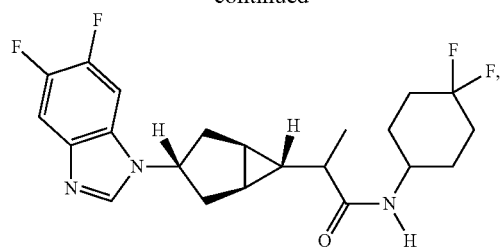
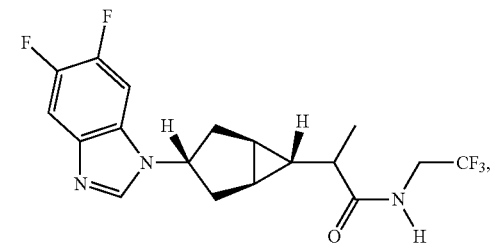
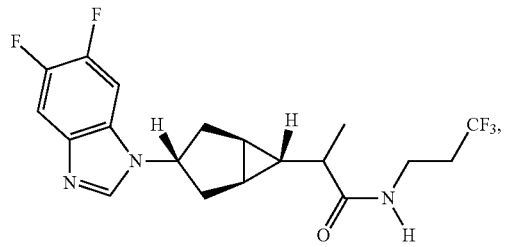
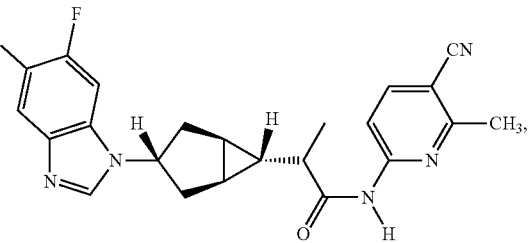
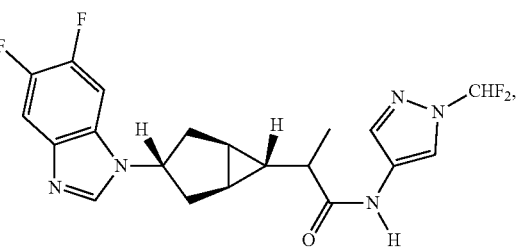
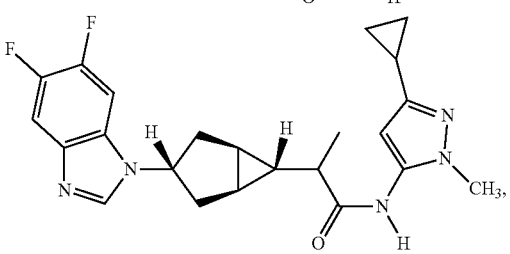
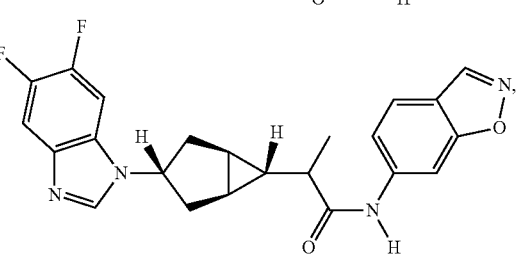

151
-continued
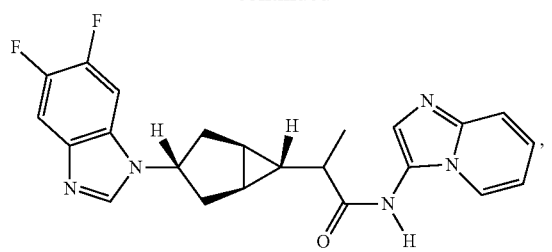
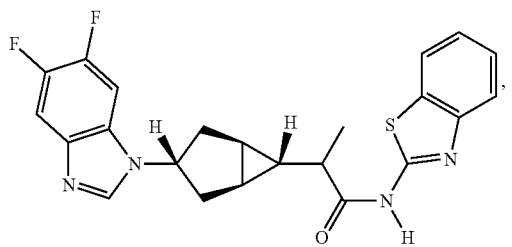
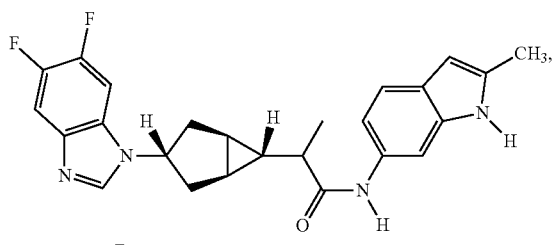
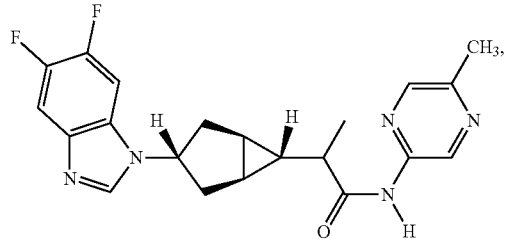
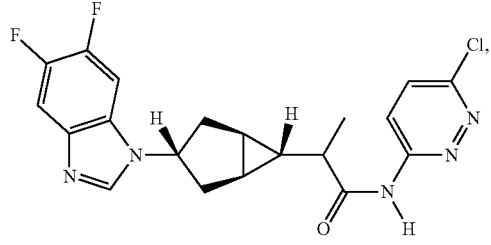
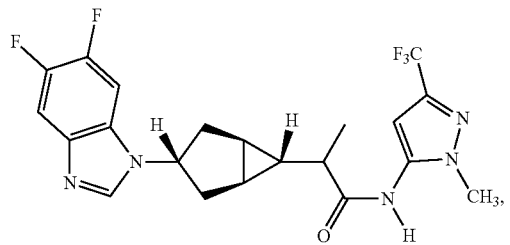
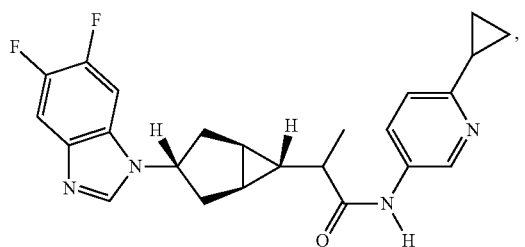
152
-continued
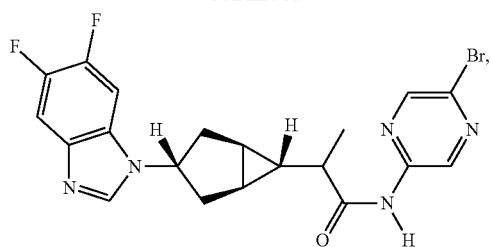
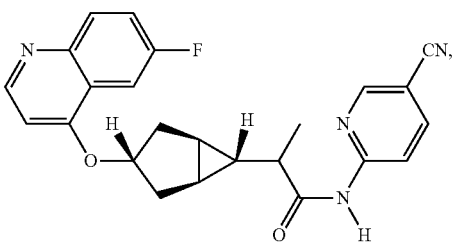
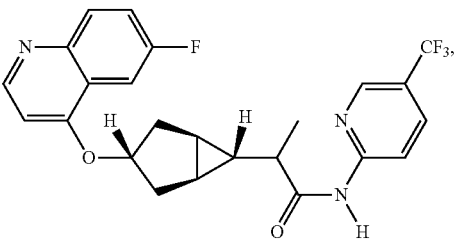
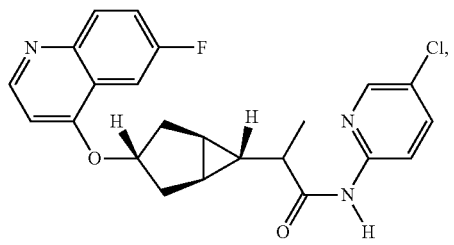
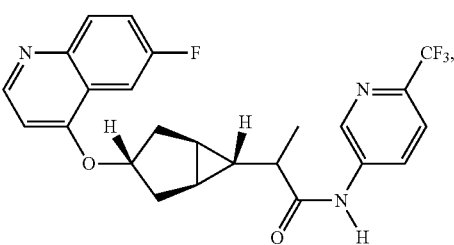
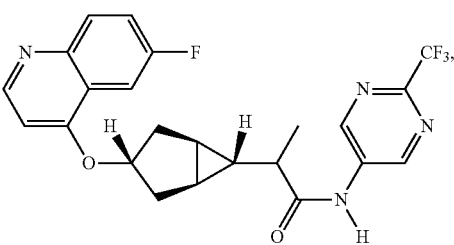
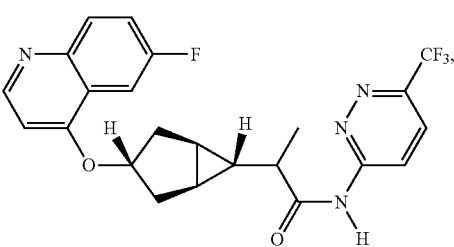

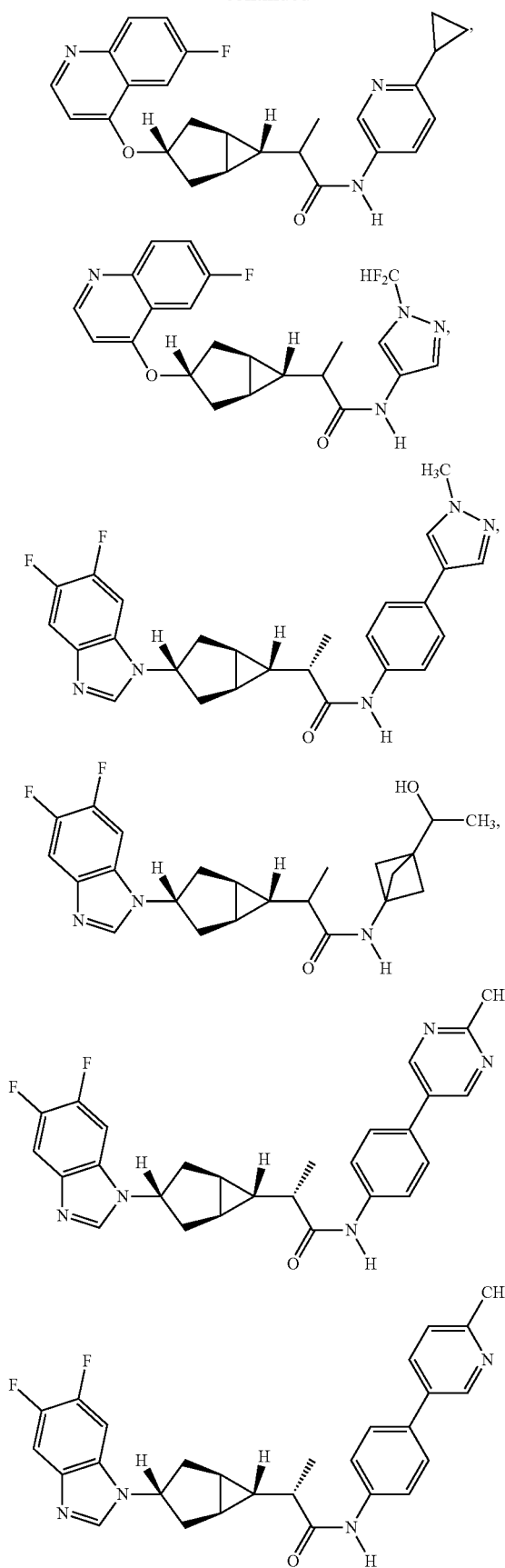
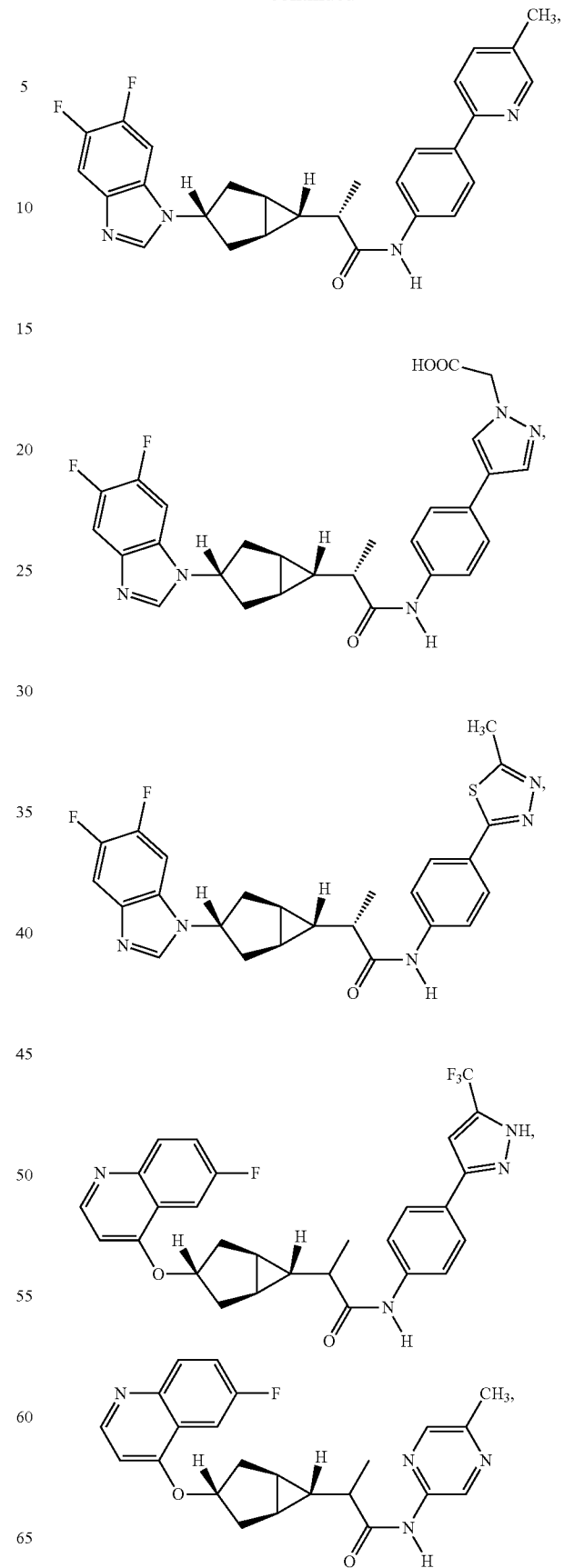

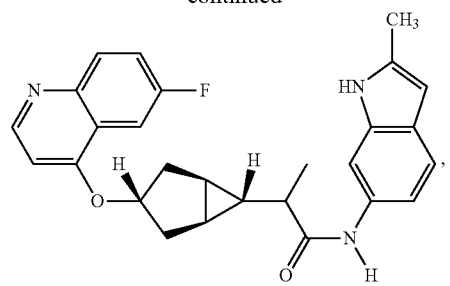
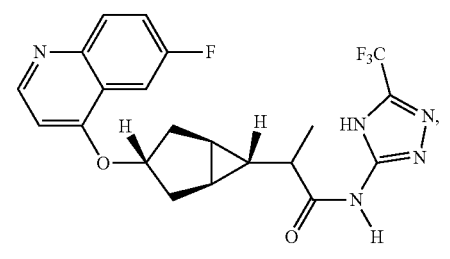
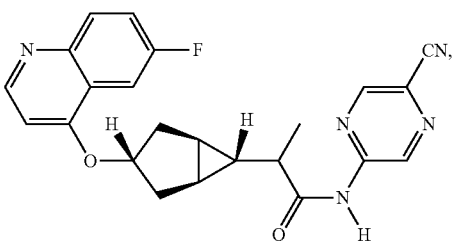
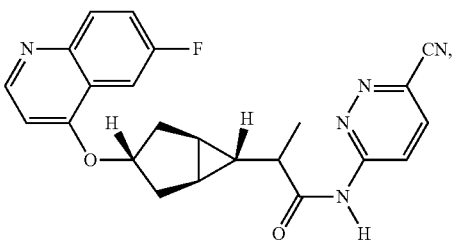
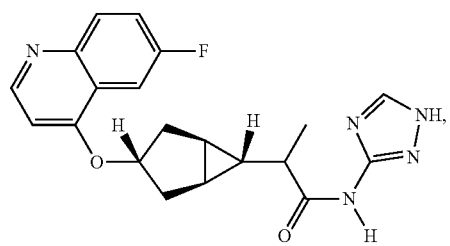
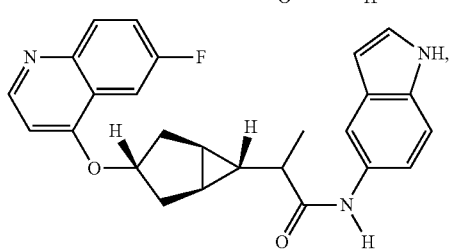
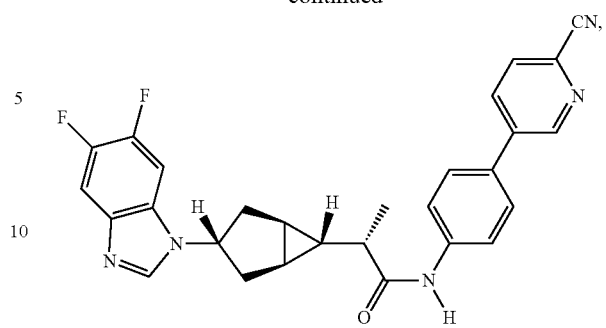
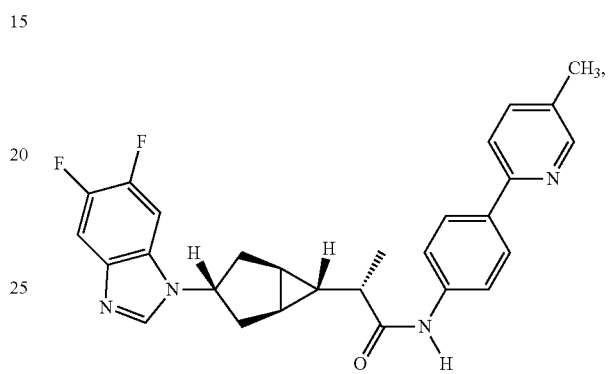
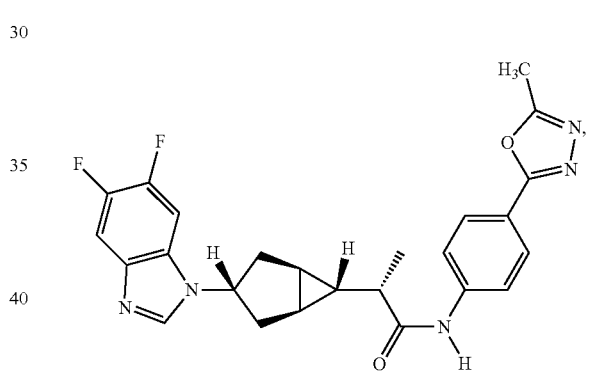
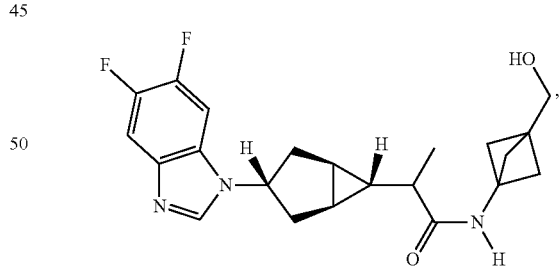
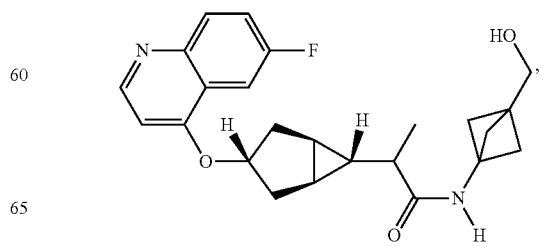

157
-continued
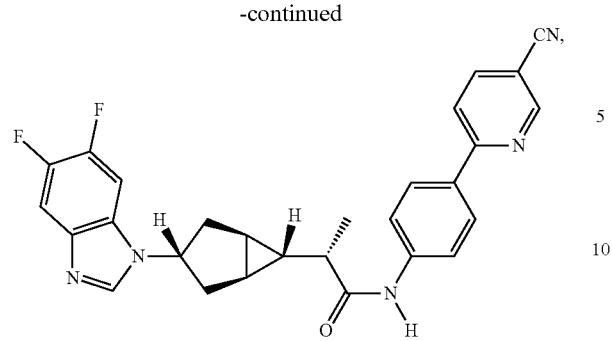
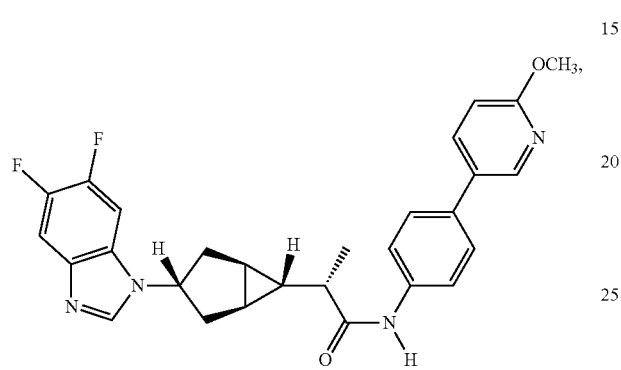
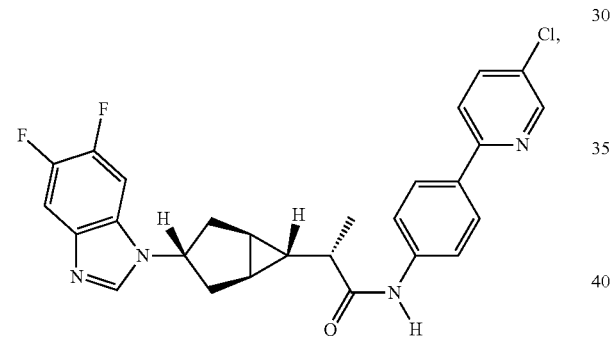
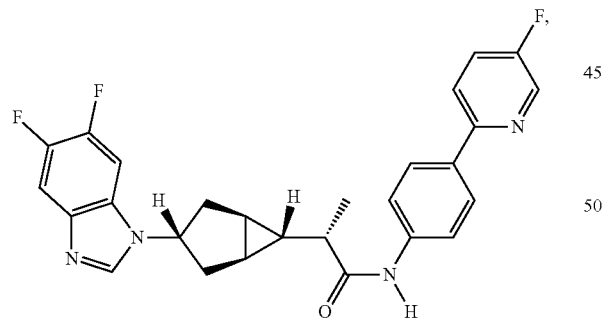
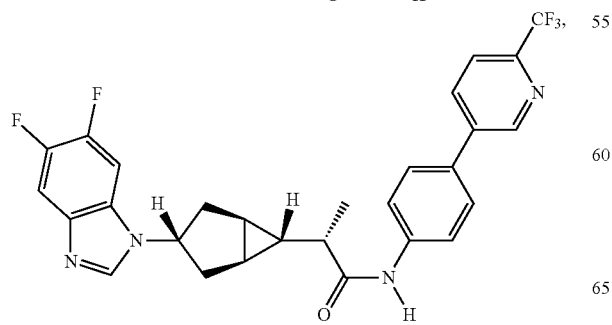
158
-continued
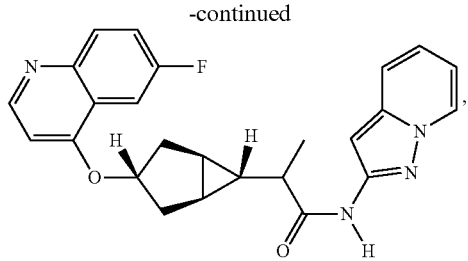
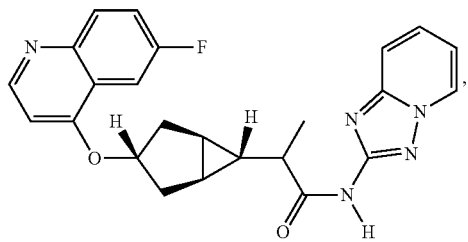
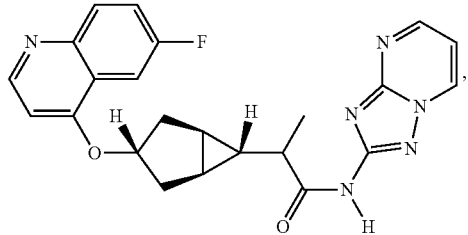
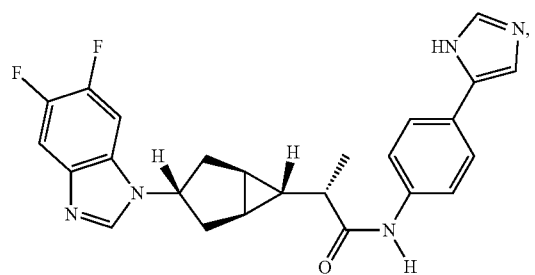
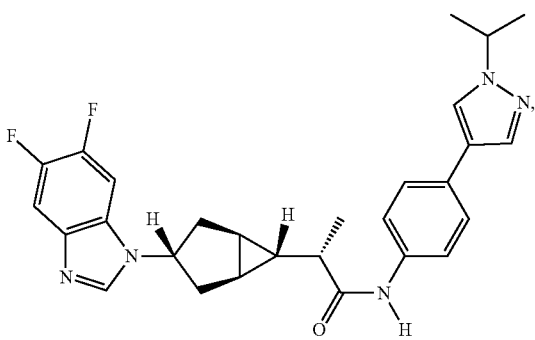
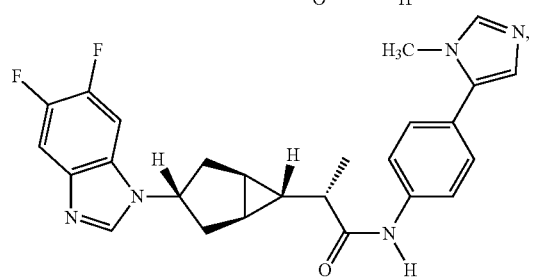

-continued
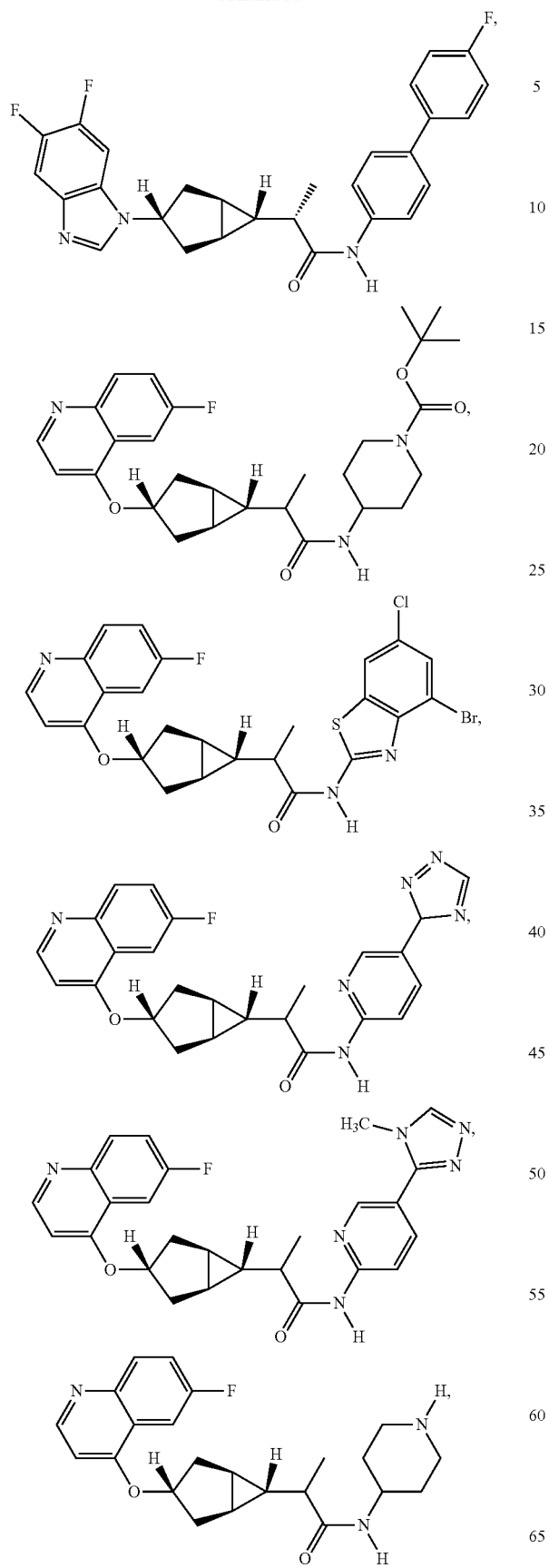
-continued
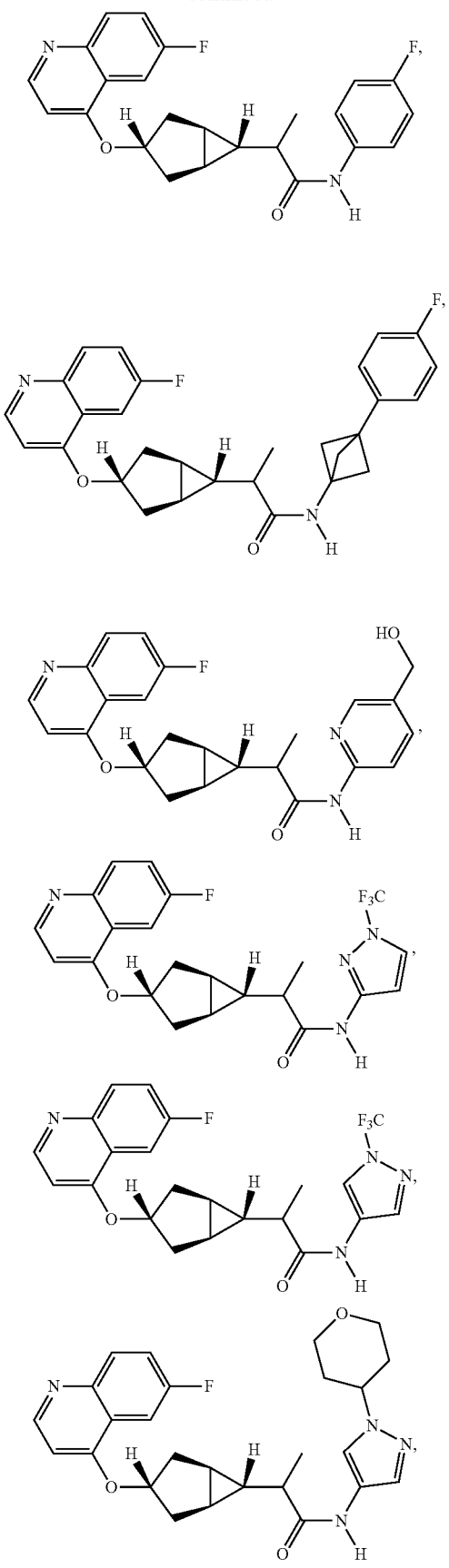

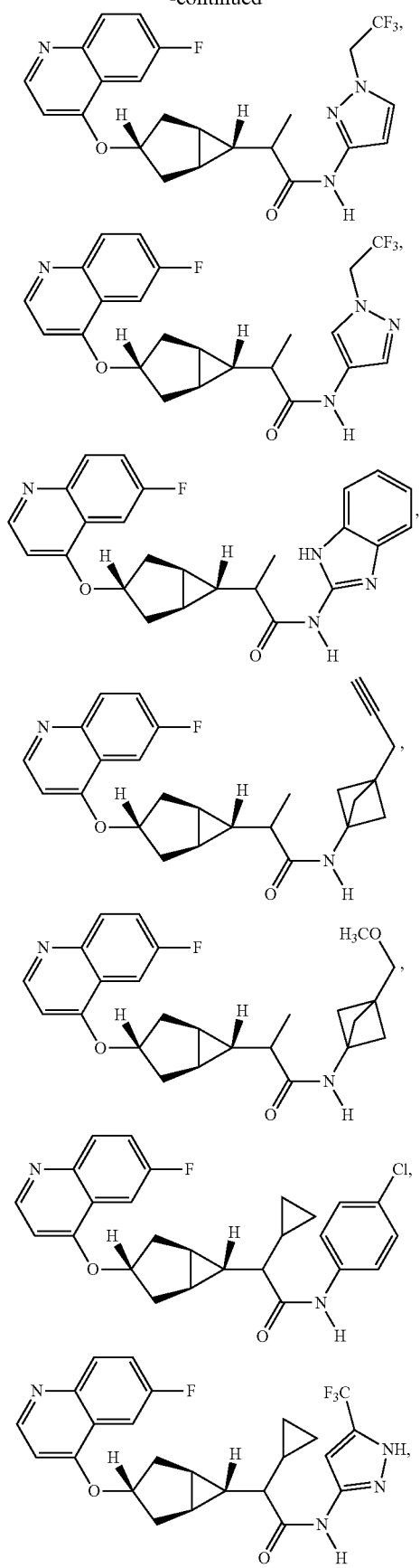
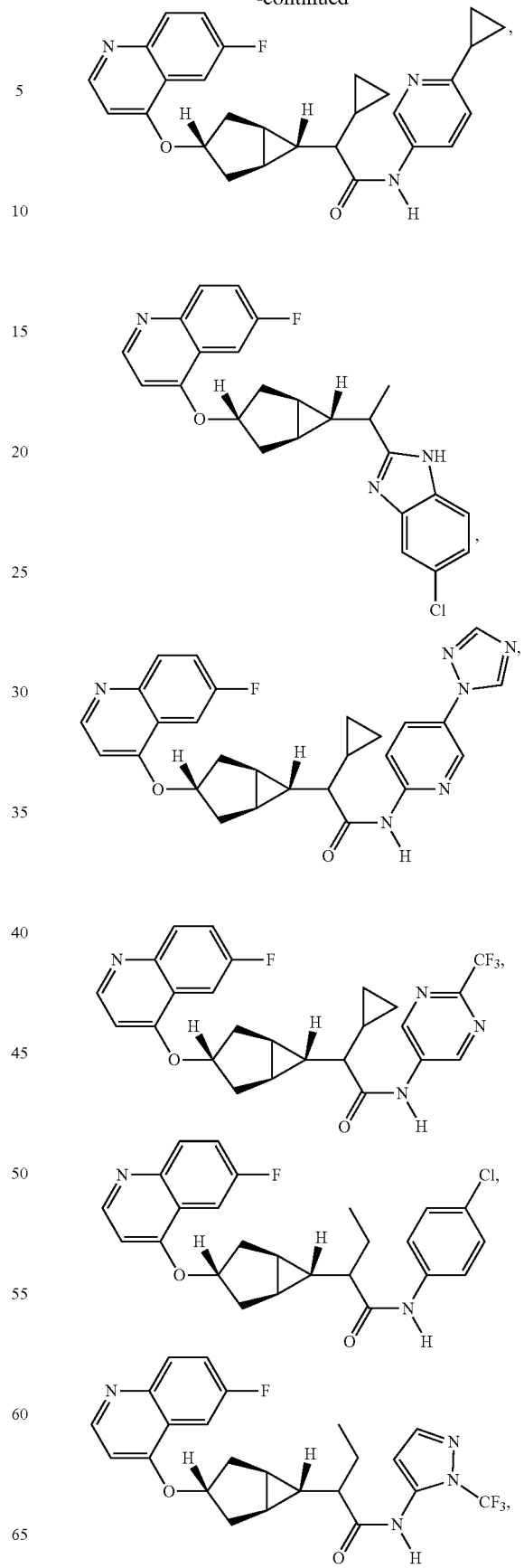

-continued
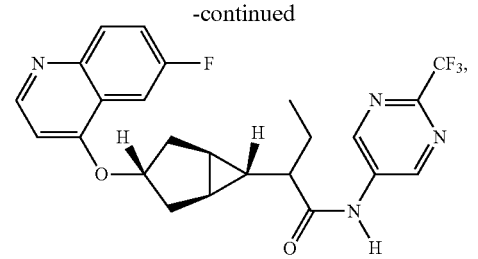
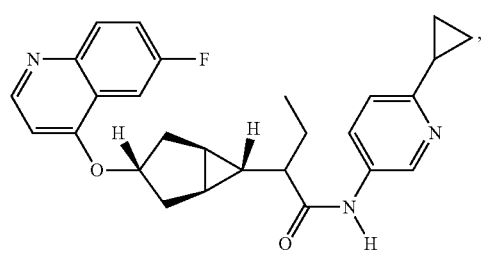
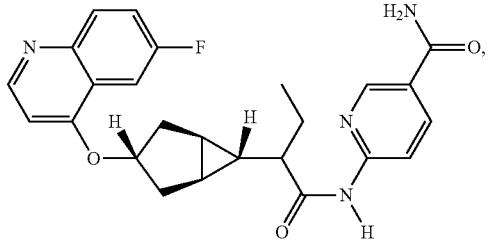
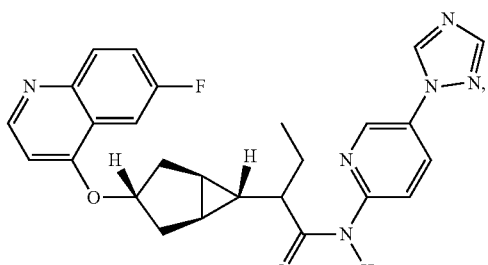
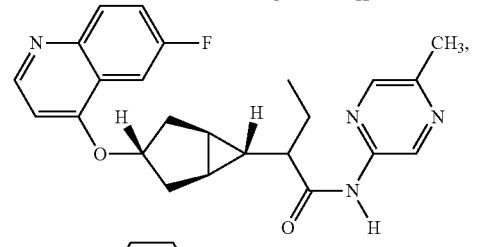
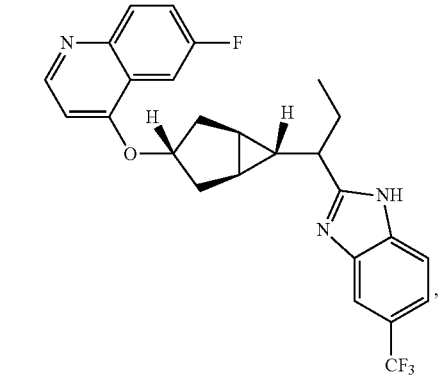
-continued
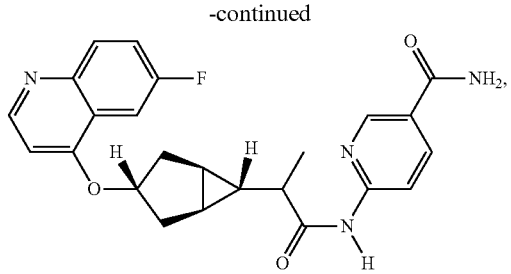
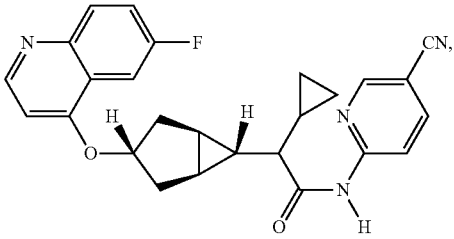
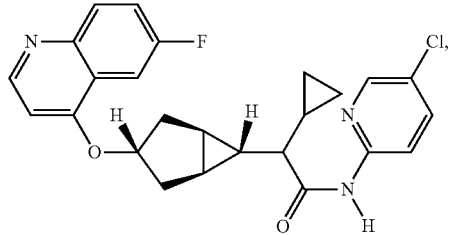
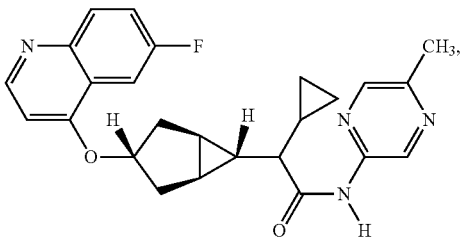
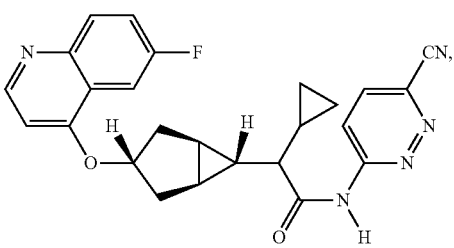
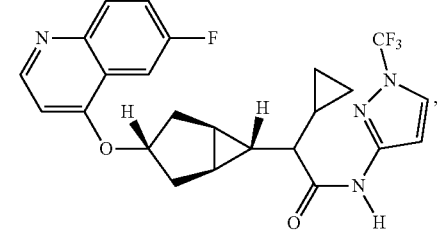
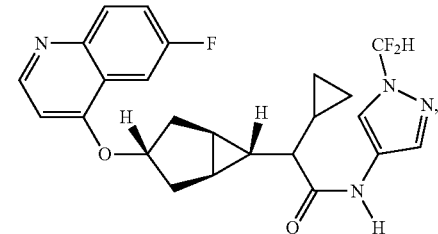

-continued
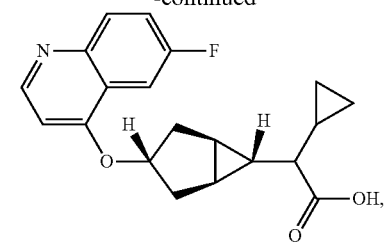
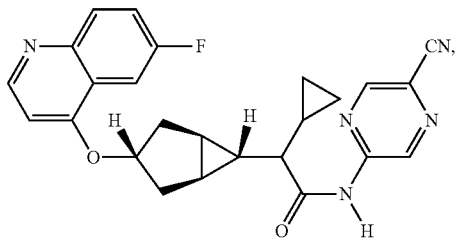
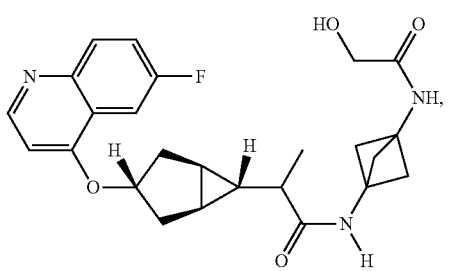
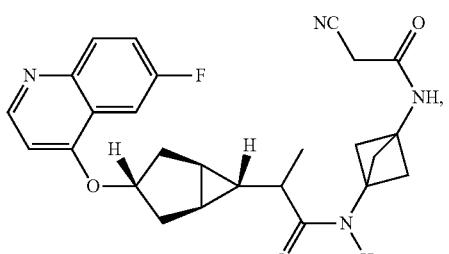
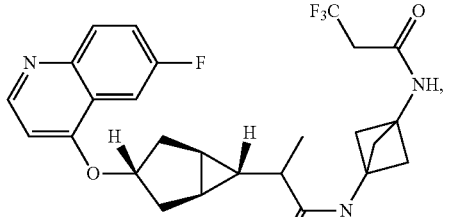
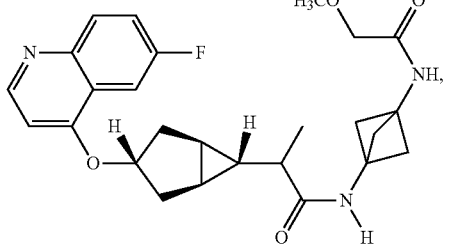
-continued
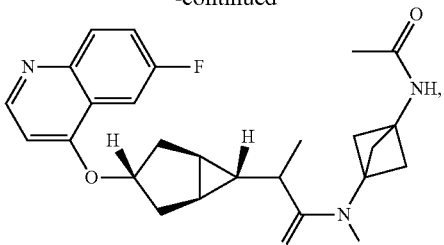
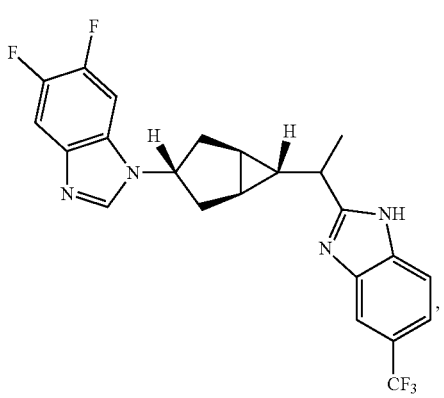
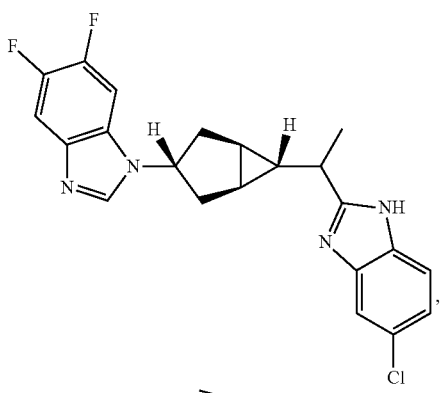
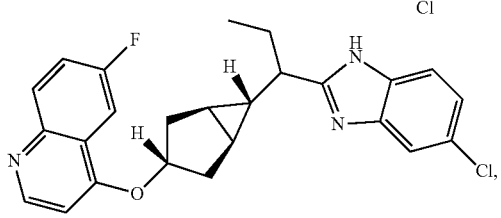
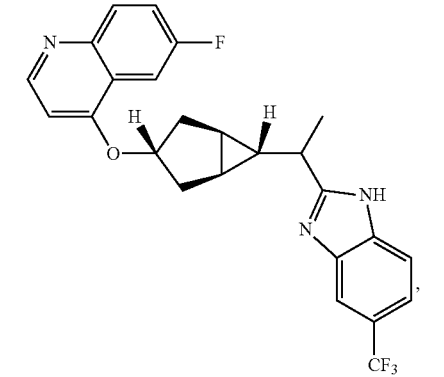

-continued

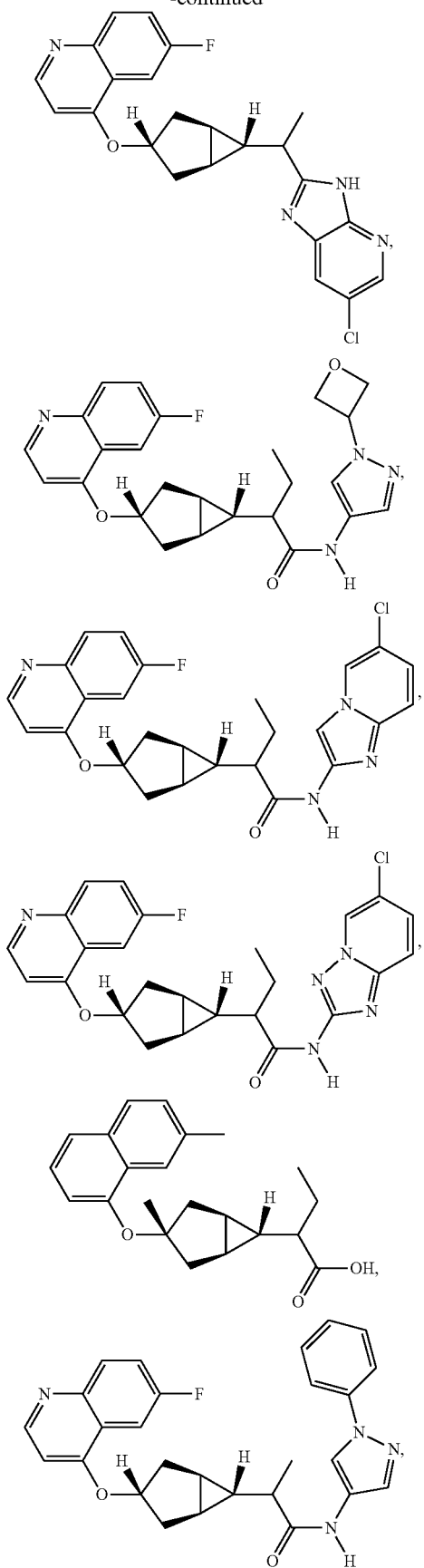

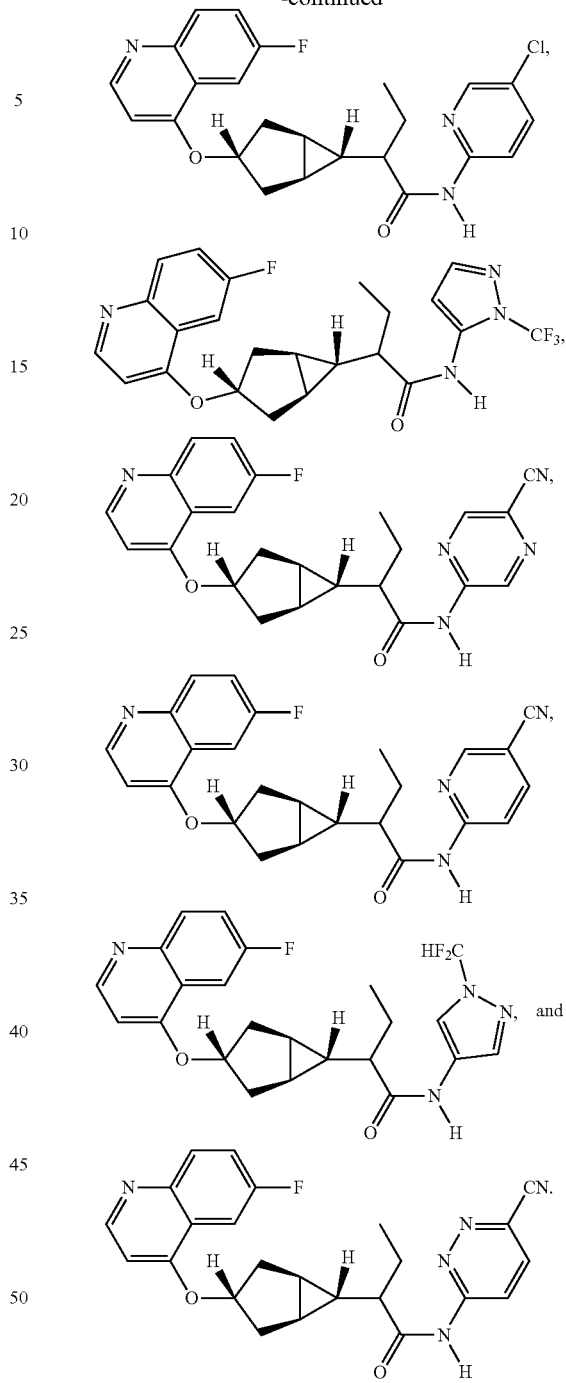

-continued or a salt or tautomer thereof.

20. A pharmaceutical composition comprising a compound as recited in claim 1, or a salt or tautomer thereof, together with a pharmaceutically acceptable carrier.

21. The pharmaceutical composition as recited in claim 20, comprising a further active agent selected from the group consisting of chemotherapeutic agents and immunotherapeutic agents.

22. A method of inhibition of IDO1, IDO2, and/or TDO comprising contacting IDO1, IDO2, and/or TDO with a compound as recited in claim 1, or a salt or tautomer thereof.

23. A method of treatment of a cancer associated with overexpression of IDO1, IDO2, and/or TDO comprising the administration of a therapeutically effective amount of a compound as recited in claim 1 to a patient in need of such treatment.

* * * * *